United States Patent
Safadi

(10) Patent No.: US 10,266,897 B2
(45) Date of Patent: Apr. 23, 2019

(54) MODULATION OF NLGN4 EXPRESSION, NK CELL ACTIVITY IN NON-ALCOHOLIC FATTY LIVER DISEASE (NAFLD)

(71) Applicant: HADASIT MEDICAL RESEARCH SERVICES AND DEVELOPMENT LTD., Jerusalem (IL)

(72) Inventor: Rifaat Safadi, Nazareth Elit (IL)

(73) Assignee: Hadasit Medical Research and Development Ltd., Jerusalem (IL)

( * ) Notice: Subject to any disclaimer, the term of this patent is extended or adjusted under 35 U.S.C. 154(b) by 0 days.

(21) Appl. No.: 15/914,112

(22) Filed: Mar. 7, 2018

(65) Prior Publication Data

US 2018/0202001 A1 Jul. 19, 2018

Related U.S. Application Data

(63) Continuation of application No. 15/256,781, filed on Sep. 6, 2016, now Pat. No. 9,944,988, which is a continuation of application No. 14/963,319, filed on Dec. 9, 2015, now Pat. No. 9,469,855, which is a continuation of application No. 14/501,160, filed on Sep. 30, 2014, now Pat. No. 9,243,294.

(60) Provisional application No. 61/884,153, filed on Sep. 30, 2013.

(51) Int. Cl.
| | |
|---|---|
| C07H 21/02 | (2006.01) |
| C07H 21/04 | (2006.01) |
| C12Q 1/6883 | (2018.01) |
| A61K 31/7088 | (2006.01) |
| A61K 45/06 | (2006.01) |
| C12N 15/113 | (2010.01) |
| A61K 31/713 | (2006.01) |
| A61K 31/7105 | (2006.01) |

(52) U.S. Cl.
CPC ........ *C12Q 1/6883* (2013.01); *A61K 31/7088* (2013.01); *A61K 31/713* (2013.01); *A61K 31/7105* (2013.01); *A61K 45/06* (2013.01); *C12N 15/1138* (2013.01); *C12N 2310/11* (2013.01); *C12N 2310/14* (2013.01); *C12Q 2600/158* (2013.01)

(58) Field of Classification Search
CPC .................................................. C12N 15/111
See application file for complete search history.

(56) References Cited

U.S. PATENT DOCUMENTS

| | | | |
|---|---|---|---|
| 4,816,567 | A | 3/1989 | Cabilly |
| 5,641,870 | A | 6/1997 | Rinderknecht |
| 5,910,573 | A | 6/1999 | Plueckthun |
| 7,579,392 | B2 | 8/2009 | Gan |
| 2014/0051597 | A1 | 2/2014 | Sarwal |

FOREIGN PATENT DOCUMENTS

| | | |
|---|---|---|
| EP | 0404097 | 12/1990 |
| WO | 93/11161 | 6/1993 |
| WO | 93/15210 | 8/1993 |
| WO | 96/13583 | 5/1996 |
| WO | 96/37621 | 11/1996 |

OTHER PUBLICATIONS

Abu-Tair et al., (2013) 1102 Neuroligin-4 receptor silencing increased human natural killer activity and decreased hepatic stellate cells activation. Journal of Hepatology 58: S450.
Bian and Ma (2012) Liver fibrogenesis in non-alcoholic steatohepatitis. Front Physiol 3: 248.
Bird et al., (1988) Single-chain antigen-binding proteins. Science 242(4877): 423-6.
Björkström et al., (2010) Expression patterns of NKG2A, Kir, and CD57 define a process of CD56dim NK-cell differentiation uncoupled from NK-cell education. Blood 116(19): 3853-64.
Bolliger et al., (2001) Identification of a novel neuroligin in humans which binds to PSD-95 and has a widespread expression. Biochem J 356(Pt 2): 581-8.
Bolliger et al., (2008) Unusually rapid evolution of Neuroligin-4 in mice. Proc Natl Acad Sci U S A 105(17): 6421-6.
Clackson et al., (1991) Making antibody fragments using phage display libraries. Nature 352(6336): 624-8.
Cooper et al., (2001) Human natural killer cells: a unique innate immunoregulatory role for the CD56 (bright) subset. Blood 97(10): 3146-51.
Holliger et al., (1993) "Diabodies": small bivalent and bispecific antibody fragments. Proc Natl Acad Sci U S A 90(14): 6444-8.
Huston et al., (1988) Protein engineering of antibody binding sites: recovery of specific activity in an anti-digoxin single-chain Fv analogue produced in *Escherichia coli*. Proc Natl Acad Sci U S A 85(16): 5879-83.
Kohler and Milstein (1975) Continuous cultures of fused cells secreting antibody of predefined specificity. Nature 256(5517): 495-7.
Leone et al., (2010) Structural insights into the exquisite selectivity of neurexin/neuroligin synaptic interactions. The EMBO journal 29(14): 2461-2471.
Lopez-Vergès et al., (2010) CD57 defines a functionally distinct population of mature NK cells in the human CD56dimCD16+ NK-cell subset Blood 116(19): 3865-74.
Marks et al., (1991) By-passing immunization. Human antibodies from V-gene libraries displayed on phage. J Mol Biol 222(3): 581-97.
Melhem et al., (2006) Anti-fibrotic activity of NK cells in experimental liver injury through killing of activated HSC. J Hepatol 45(1): 60-71.

(Continued)

*Primary Examiner* — Amy H Bowman
(74) *Attorney, Agent, or Firm* — Roach Brown McCarthy & Gruber, P.C.; Kevin D. McCarthy

(57) ABSTRACT

A kit having a means for isolating an immune cell population from a biological sample of a patient; and at least one agent capable of detecting NLGn4 gene product expression level.

16 Claims, 7 Drawing Sheets

Specification includes a Sequence Listing.

(56) References Cited

OTHER PUBLICATIONS

Moreira (2007) Hepatic stellate cells and liver fibrosis. Arch Pathol Lab Med 131(11): 1728-34.

Moretta (2010) Dissecting CD56dim human NK cells. Blood 116: 3689-3691.

Muhanna et al., (2007) Lymphocyte-hepatic stellate cell proximity suggests a direct interaction. Clin Exp Immunol 148 (2): 338-47.

Muller et al., (1998) A dimeric bispecific miniantibody combines two specificities with avidity. FEBS Letters 432(1-2): 45-49.

Sans et al., (2000) A developmental change in NMDA receptor-associated proteins at hippocampal synapses. J Neurosci 20(3): 1260-71.

Seki et al., (2011) Antitumor immunity produced by the liver Kupffer cells, NK cells, NKT cells, and CD8 CD122 T cells. Clin Dev Immunol 2011: 868345.

Wang et al., (2010) Delivery of siRNA therapeutics: barriers and carriers. AAPS J 12(4): 492-503.

Wittrup et al., (2015) Knocking down disease: a progress report on siRNA therapeutics, Nat Rev Genet 16(9):543-52 (10 pages).

Yanagi et al., (2012) Identification of four novel synonymous substitutions in the X-linked genes neuroligin 3 and neuroligin 4X in Japanese patients with autistic spectrum disorder. Autism research and treatment 2012: 724072; 5 pages.

Zapata et al., (1995) Engineering linear F(ab')2 fragments for efficient production in *Escherichia coli* and enhanced antiproliferative activity. Protein Eng 8(10): 1057-62.

Zelber-Sagi et al., (2011) Nutrition and physical activity in NAFLD: an overview of the epidemiological evidence. World J Gastroenterol 17(29): 3377-89.

Clinical Trial No. NCT01133184: Improved Prevention of Perinatal Hepatitis B Transmission. Updated May 27, 2010, http://www.clinicaltrials.gov/ct2/show/NCT01133184?term=nct01133184&rank=1.

https://en.wikipedia.org/wiki/Small_interfering_RNA—obtained Jul. 27, 2015; 6 pages.

Page 661 left column of Microbiol Mol Biol Rev. Dec. 2003; 67(4): 657-685 http://www.ncbi.nlm.nih.gov/pmc/articles/PMC309050/).

Agrawal et al., RNA Interference: Biology, Mechanism, and Applications, Microbil Mol Biol Rev. 2003 44 pages.

SEQUENCE LISTING

```
<160> NUMBER OF SEQ ID NOS: 20

<210> SEQ ID NO 1
<211> LENGTH: 338857
<212> TYPE: DNA
<213> ORGANISM: Homo sapiens

<400> SEQUENCE: 1
atctctcttt ttcttgcaga accgtctctc tcccttctct gtctcttagc acagagctct      60
tattcagcca ctagcttggc ccttcctgct tcaattgtaa tgcttgttct gcccgtccac     120
agactattgg cggcagaaac aacgaatttc ctccaaacta ggcggtgttg gtggctcttg     180
cattcctctg gatgaggaaa tctagttggg gggttccaga aggggaaggc tcctgggctt     240
tcaatacatc ctcctgaatc atacctcgtt tcgggttccc tagaaaaatc tggacgtgta     300 aaagaactc ttaacggccg atgcagctct tccaaagcta aggtaggtgc agttttaaga     360
cctgtctctg ggacattatt ctcattttaa aaagccgttt aaacattttg acttgcagca     420
```

```
aaggatggaa agcctcactg cagatacttg agcttcactt catctgatct ttatttttc      480 cttttatgat tattaatatt attttggaa aatttggaca ggactttctc ccatctgtct       540
cgctgcattt cttaggtgtg ggtgggagtg tagaccttca tacggttttt acatgcaacc      600
tctccacaga aatatttggt tttatttca cttaaagaga aaaatccaga ccaccgttgt       660
ttggaagcgt tttgctgcaa tcagctattt gaacggctct ggggccgtgt gtgatgtgtt     720
tacaaagtag cgctgccttc cacacaaata aacagaagac tgtggcgggg agaggaggaa    780
aaaaatatat atgtatctgc agtacaggga gaagaggag agaagcggcc agggctggag    840
atggtgaagg caggaagact tctgcaaact gtgaggcatg ggaggctttt cttttctttt    900
tctctccccc cccaccccc cccttattc tttaagaaaa ctgtcagcta ccaccgcctg      960
gggtgctttt ttgaggggtt gggggggtgc tgttaaccag aaagaaaaag ggaaaaccgg   1020
cttggttggg gtcgcattta agcgattttt ttcctcct tcatctccgg gcctcggata    1080
agatgacggc ttgggtgatg cacgaaataa cgcacgtgat tgattagacc tggcttggct   1140
tggctaggga acgatccagg cgcgctggag accccgcgtg aagatgaaat gacggtagct  1200
ccgggctgct tctgtaaacc ggggagcggg ctccatgcac ccctttccg tgtgtgtggg     1260 tttcgaggcg ggtgggaagg gtgaggcaag ccgcagaagg agggtagagc tggtggtttt   1320
gcttctttcg gagcctttga gtgtagtctg aacctttgag ggggcgcgg ggggcttgc    1380 agctgccgcc ctgggaacca tctctgaact gcccgctttt ccgaaggagc ggaaagttg    1440 gaagctgcga ggacagacta ccggagccct ggtctgggtc tcggggatc tggagcccta   1500 gtcggtgccc actgagaaca ccccttctcg gagcgagggt gtcgggggga gtgttaagcc    1560
tgcggggcgc acggtccgcc agtccccgag gtggggacgg gggaggaggc tgaggagtcg   1620
gttccaatag gcgcaccacc tctacagccc tggaaaacgc aaccgccacc ccctcttccc    1680
ttccatccca tcccaagcct ctctgctgtc ccgggccgat ttcatctcgt ctcttccccc    1740
gcctccccgc ttccccgcct cccaattccc gcgcggctcg gctcagcccc ttcccactcc   1800
agtgggcaga actgatggag aagatccgcc aagcgcgcag ccggcggcgg aggagacagt   1860
gcggggtggg cgaggggctt cgagaccacg cagagagaga gtgaacttca gtcctgaccc   1920
ctccccaagg ccgcggctgg ggcgcccaca gcccgcgctg gcacccgcgt ggcctgacct    1980
gcggaagcgc gagcggggat gaggtaggga gaggaggta ggtgccgctc ggctgcagat    2040
gatgcgtggg tgggggcttt gctgtgggag gagaggccca ggtcccggcc tgcgccctcc    2100
actccgcggc tgctccctcc gcctctggtt ttccaagagg ccggtcgcta ccccggagga    2160
cactctcatc cttcagtcag tctcctggac accccttcct cctcctgtcc ctcaacctga    2220
cctggctctt tcgcccctcc gagaaccggt aggctgggt ccctcggcgg ggttctcctg     2280
ggccgcaccc gaagctttgc gccccggta tccgggccca gtgctccgtg caaccctggg   2340
cccgagcgca cgattccggc gcctgctcgc cgccagacac agcgcccttt cttcccggag   2400
cggcgggggc gggagcaggg gggtcaggcc aaccctttgca ccccgaggc ctggcccggg   2460 ccaccctggg aacggatgtt ctgcatggag agcgaggggc agccggagga cgtcctccgc   2520 atcataccc tccccttccc cagaaggctt ttttttttc cggactgcgg gtttctttt     2580 ctctgccttc ttcctctgaa cctacggcag gtgtcagcct cttttgtgt atgtgctgct    2640 gctatctcgg ggatgcggg ggaggggtg caggaggcag cgtgaagggg tcctaggagg    2700
ttccggcggg gttttggccc ctgcggtgcg ccggggcttg caactcgccc gggtgctggg   2760
cgcgcgcgtc acgaattcag cctagggctt gggcgagtct gcggggagtg aggacagagg    2820
```

```
atcccgatct gtcatttgga cccaacttaa gaaatttggg gtgggggttg ggtgggggtt    2880
ttggaactaa gcaggtgatg ttcttgcgag ctggatccac aaggtggtag tatggcttct    2940
tttttatttt attttatttt atttctattt ggtcattttt tttgggggggg gcggtggttt    3000 gttgttgttg ttgttgctct tatcttatgc tttttgaagg catccgttgc ccgtaggggtt   3060 tacatcggag cgcgttgcat tatattttct tgaaaggggg tggtgtgcgt gagctcccat    3120
ctcagaatca gcccttccgg tgatgtgagg aaggcaaaag caaaaaaaaa aaaaaaaaa     3180 aaaaaaaaa aagaaaaaa agaaagaaaa aaaaggaaaa gaaaaagttt agggagacct     3240
cgttatcctg acgaagcaga attgccagtt tgtgtgggcg ttctgcgggc aacatagaag    3300
tgcatgctta agaaatccgg ggtagcttcc ttctccagct agaaattaaa tggccagggt    3360
gcaaacacct gactttgatg agaacaaagc ggcagaaact gcaagagacc tgcatggttt    3420
gaatggacgc actgagcctt ttcctagggg atggcagagc ggggtgaaat cagatagcaa    3480
agaaatctgc cgttttgtgg gggcagattt ggagagtgga gaattatttc atacctttag    3540
ttggctgtgg ggaagatgtt agcagtaatc cattaaatcc tcagcataga ttttcctgtg    3600
gaaatgagca aaatgttaag tggggagggg atggctaatg gcacatggtt gcattaatcc    3660
ctgtatttcc agaaaaaaat atggaatttc tgtgtatcct aaaattaaga atacaggaat    3720
ttcatggaga actctgcaag catgtatttt ctcagattag aaattcagta ttttattact    3780
caatgaaatg tagaatgcgt gtgtgtgtat gtgtgtatac agacatacac acacgcattc    3840
tacatttcta catatatgtg tgtgtgtgtg tatatatata tatatatata tatatatata   3900
tatatggcca ttttaaagag tattttcttt gacatgtaag aacataatca gggccagttg    3960
tagcaagtgg aaaattactt catcagtttt aagtcagtag attaaaatgg aaggcttcat    4020
ttttttttga aatcagaata ataattgcat tttcataata atgcctgtgc gtggatgcag    4080
ttttaaagat gctttgatgt tttcttctcc agtggaagaa ttgctacttt tctttgcgtt    4140
ttatttaaat aaactaatgc cgagtataca gttggccctc aaaccagtaa cctagctgat    4200
ttttacccaa acctgagaat gtaacagata cttgataagg gactggtggc tgcataaggt    4260
agataatgaa gttatcttga tgctgtgaaa tttacaagca gacttgaaag aatttgaaag    4320
ttcatagttg ttggcctgga atgtagccta atggtaaata tatagatttt ttaaaatttg    4380
tgaacttggc tatttcattg ttttgtgtgt agtaatttgt ggaaagctta tagtctctcc    4440
acaaagatga gagtgttgac tgactccgca acagagactt gcttttggaa gtgcaggggt    4500
ctctttaaaa gccatttgga atactgtgct tttatttcta gaccacaacc aaaaggttct    4560
caaaaaacta acattcaagt gcacgagggg aatgacctcc gtttaacatt ctttcttttt    4620
aattggtacg ccacatttca aacctttgt aatactgttg aatattgcca ataatgcaac     4680
ttgttgagcg aatgcattgc attcaaatga agtagcaata tacaaatatt ttaagtcctt    4740
tagtatcctc cttctaaaga taggcttatc tggttaaaat atacttatat tccaaataag    4800
gtgagagttg gtcttaagat gtgaatgtca agtgtaagag acacgatttt agtttgtaaa    4860
ccagaatgta ttcttttctgt actgcttcct gcctttaac aatatgtatt ctattcccaa    4920
atggggaaat atgttcagtt tagtttaaat ctgttgctct ttttgtgtgt gttttgtct    4980 gagtactgta cttttttcaga ggagagactt cgtctcctat ttaattatgt gaatggatat   5040
tcagacagat ttgaatagcc accactgatt tcttaaactc ctgagctacc agttttaaat    5100
caaagataca tctttttgcac agtcaattag aggaagtgag aatcaaaatt gaagcccagg   5160
```

```
ctgctgaggc aattaggtca tctgctgtgc tctctactac cattcactca acgaatattt    5220
tccagttctg tcattttct ctaaacaacc tacatttgga cttttgaaagg ctccactgtt    5280 ctttgttaag tgaacggcag tgtaggaagc ccttcctcat ttttcttgga gcacagtagc    5340
acacatgaac aagaaaaaaa agaaggtgat agctcctagc agtttgtcat tgtgccattt    5400
ataggctttg aataaatgta tagatgaaaa ggctttccct ctgcaggtgg ttacattaaa    5460
caaaaaataa gtaaataaaa gcctcataaa atcattacgg gagtgaaagg ttggtggtgg    5520
aaaacagccc atctacctcg ggctgagatt tcaaacttta gacatctcgt gttcagttca    5580
cgtgtcccag gtgtgtgcgg aacacctcca tacaccacat cttcccaagg cactctcatc    5640
ttcccagaaa tggtacctga aggagaacag acctaacccc aacaatacta aaatacgtat    5700
ataaaaaact atatatagta agatatgtat cctactatat aatatatata tggtaataca    5760
tattatagta aggtctgcat catgtatata aaaatacact atatatctta ttattatata    5820
tatagtgaga tgaggtgtat taatccattc tcaggctgct aaaaaagaca tacccaagac    5880
tgggtaattt gtaaaggaaa gaggtttaaa tgactcacag ttcagcatgg ctggagaggc    5940
ctcaggaaac ttacaatcat ggtggaaggg gaagcaaata cttccttctt cacatgatgg    6000
caggaaggag aggaatgaga accgagtgaa gggggaaacc ccttataaaa tcaacagatc    6060
ttgtgagaac ttactcacta tcataagaat agcatggggc aaactgcccc catgattcaa    6120
ttacttccca ccacatccct ccacgacacg tggggattat gggagctaca atccaagatg    6180
aggtttggtg gggacaaagc caaaccatat catgaggttt tattgaattt atttgagaca    6240
ggaaaagagt aatcctccat aatttagaaa ggagatgaag tacaatgaac atttaggtcc    6300
tcattagttg aggaatacat ttcaaagaga gaaatgttaa tttcagtata gtgctaatga    6360
aacgatctag gctttcactg ctctctggaa atgtggataa atgggcccaga attttgtttg    6420 ggttgtttta tttaaaatgt atattatata aagaaatcat ggtttgtcaa agtaacagag    6480
tgctattttt ggcttacaac aggactttct tagctccacc tgttaatatc ggtgatcatt    6540
ttggttttaa gaggctggta cctgattgga tgatgaaaac ttggatctca aagccatcac    6600
cccagacatg tgattttatt aacatctgtg gcatctgtc cggctcccac atcaacccttt    6660 catccaggct cattttctgt ttgttttttgt ttggttgttt gtatgctttg gttggggaga    6720
ggggacacgg attttgctaa gggcaccttt tcaggagtg aaacttagcc tgtcatataa    6780
gctgaaaagg aacttgggtt gtttcaagtt gcattacttg gtaagttttt ggatccttta    6840
aaaaagaaag gactgaggtt actaaaagtg ttattggcac tgataaaaga gctatggtga    6900
attgtggttt gttttttgtaa agtgcagaaa aggcctcttt ggttctgtga tgatggctgt    6960
ggtgaagttg catgcggtgc cattttccat gtttagtatt tcaacaccac caatatgtgg    7020
ctctggagta tgggacgggc aagtccaaga actcagtgag gcatgccgtg tgactccaat    7080
ggtcagagct gttcagcatg gaactgtggt ctcaaaagca tggggatgg gggcagaaga    7140 agctcgctgc aactgagtgc ctttaactta ttccactctt cagtactctc tgtgactata    7200
actctgtgaa tgggttaggt ggggaaactc acaaaagtaa atgcatgttt tcacaaacaa    7260
aatatgtcat tgttaactgt tttcctaagt gagacaatat gccctcatgc cctgaagcta    7320
catggtaaga atggcagtgt gtatgagcgg gtgtatacac atacatgtat gcatatgcta    7380
acacattaac taggaactag tctttgctga aaatgttttt ctcagccatt gcaacacatt    7440
agataaaagc aaatatatat atatatatat atatatatat atatatatat aatataagaa    7500
ggaaaaatgt ggttttccat tatttttcttt ttcttatcct catcattcac caaatctata    7560
```

```
ttaaacaact cataacatct ggcctgggta atagagtgag accccaactc cacaaagaaa    7620
caaaaattaa aaacaaatta gccgggcctg atggcaagta cctgtggttc cagctgaggt    7680
gggaggatca cttgagccca ggagttcagg gctgcagtga gctatgatta cgccagtgta    7740
ctccagcctg ggagacagag caagaccta tctctaaaaa tataaataaa taaataaata    7800
aataataaat aaaaatagaa aatgtacaat gaaagttata agttggcca ggcgtggtgg    7860 ctcacgcctg taatcccagc actttgggag gctgaggtgg gcgaatcacc tgaggtcagt    7920
agttcaagac tagcctggcc aacatggcga aatcctgtct ctactaaaaa tacaaaaact    7980
agctgggtgt ggtggtgtgt gcctgtaatc ccagctatac aggaggctga ggccggagaa    8040
ttgcttgaac ctgggagggg gaggttgcag tgagccaaga tcgtgccatt gcactgtagc    8100
ttgggtgaca gagcgagact ctgtctcaaa aaaaaaaaa aaaaaaaga agttataaaa    8160 gttacctatg atgggtctgg atgtactcct tatttaggag tgaagacatt cgttaacatg    8220
agacctaagt aagtagaaag tatgtgttta agggacaggt gtccatttc tctaggtctc    8280 ctggaagctt tttttttcta atttgagtac tagttccaaa aaggtgtta ccgcctatgt    8340 ttatagtgaa actatctatg tgtgacaaaa ttctaccctc tcttgtccat caatattgtg    8400
caatgttgtg tacttgtatg gagaaataga caacttttac aaagatcaaa ctaggcaccc    8460
tttaccaacg ctaaactcat aacccttta tctgcctttg tagaagattc tcacctttat    8520
ttctcttggt ccctctgaga aatattttcc tctgagacaa tgcaatctat gcctcatctt    8580
taagcaatcc tagctcacca gtatgagtaa tgttgtctat ttttaaggtt atctcattat    8640
tctaaaagac tttaaattgt tgaaaaataa attgtgtgag gggtggtaga gtttgaaaca    8700
attatctgtg atgttaccag atattttaga ctaaaatata ttagaatcca aggtattgtt    8760
catgccttaa aaatgctgaa atatctgact gttgcttatt aattttaaaa agaatatagg    8820
aaatagccat taattaatga ggctgtttcc actaccacat aaaaaaaaaa aaagctcaca    8880
ggtgcctgta tgttttttgtc gaatcaaagt aatctgcttt atgtatgcat ttattcatag    8940
aatttactaa aatcaaaatc aaggttttat aaatatagg tttgacaaag ttttaaaata    9000
taaccagcta tacaaatatg gcatgtggga aattctatta aattgtcatg aacatgcttc    9060
tttgtcattc caggagtctt tcttttcatt actctttcct atttgatctg ttattctata    9120
gaattatctt cattttctct ttaatacttt aaggatccct gagaccttgt cactcatcca    9180
aatagaataa aggaatgagg gaagaaagaa ggaagggaag aaggaaggaa gaaaggacgg    9240
aaggaagaag gaagggatgg aggaacgaag ggaggaaggg agggaaggaa agaaggaagg    9300
aaggaaggaa gaaagaaaga aagaaagaaa gaaagaaaag agaaaaggaa ggaagaaagg    9360
aagcaggagg ggagggagaa ggatgataga tcgaagggaa ggagagaagg agggaaggag    9420
ggaaagaaga aaggaaggaa agaagaagaa gaaaaaggaa ggagagaggg agggaatgaa    9480
ggaaagaagg aaagaaggaa ggaaagaaag aagagaaaaa gaaggaagga aggagggaag    9540
gaaggaagga aagaagaaag gaagggaaga gggaaggaag ctgtggtttc tgtgcaccat    9600
taactaacaa tagctcctgt gaaccagcct ggaagttcat tcaccacata caatatagtt    9660
tcttttggaa aatgcatgtc aaactatata tatggtttgt gtgtgtgtat atatatatat    9720
acacacacac acatacatat atatacgtat atatgtatat acatataaaa tttgcatgta    9780
cttttcatac aaaagaacaa gaactatata tatacaatat atatacattg gaatatattt    9840
attatagatg tatatggatt ttactatata ttatttcttg aaaaagtata agaactcccg    9900
```

```
aatcagggat tctttcttga agaggctgcc tggtccaata ttttggaaa accatatatc    9960
atttgcctct cttcaattat atcctgaaaa tggacacatt atggccttaa agtctcctgt   10020
actaatgggt ttagcagctg tgacggataa cttagggttc tttgtaatga gttttaacca   10080
aattaaccac aagagtgttg agaatacttc tgttgacaca gagcagaaag aagtactaac   10140
agggtatgaa gatacttgaa agtgtttaaa ttaccaagac tacttggaga tatgaacttg   10200
ttggtttttt tctttatttc acgaatttat tcaaaacttg ttgagtacca ataagtgggg   10260
tacaaagaag atgaaattgc ttatctttcc tatattaacc atacactaat gttattttgc   10320
acctctggtt ttatgtttaa gaacaaataa gttttaccag aattttctt ctggtgtgtg    10380
tgtgtgtgtg tgtgtgtgtg tgtgtgtggg tttaatctct catgtcctat ttcaaaagtt   10440
aaggaaaaca acagcttgat tcagtcttca tacatctttc ttaaatagtt aagggcaaaa   10500
tcatcagagc tacatagccc aaatattagg aattaggttc atgttcgaat ctcagaggg    10560
taattatata gttcgatttt aacttcttca acagaccgac tactacagtt gatgagcaag   10620
gagatgaaag tatttgataa acatcatgga gttaatatga ttcttgaggg aggggagaag   10680
gctgcttgtc ttaggtaatg cttttgaggg taggtttgtc ctagccttga ggtagcaggc   10740
ttgctctgtt ggctgaagaa gccttaacat gcatgcccgt attgcaaatt tacccacatg   10800
ccaactgtat gctgtgggaa gaaatgaata atgtagatgc cattacaggg aattaggcgg   10860
aacggataga cttagtgcat cagaaccaat gagaagtaga caagacattt agaaaatagc   10920
aacagcaatg aaaacaaata taagtaaacc acaatcaaaa cccttacatt tgggtttcta   10980
gttgcctgtt accacagagg gttctggtta ctagctaaaa tgtaacccag taggaaggtc   11040
aagacaaggc ccctcatgct gtctcaaaca gtaacaaaca gtaaggatga cccagggaga   11100
aagggtaaca agttacatgg aagttaaata ccagttacct gtgcagagac tgaaaacata   11160
aagcagacac aggaatggca gtagtagaaa gtggggaaaa tctgaatttg ttgcagcata   11220
aaaccaacca accaaccta gtgagggaat caataacctca aaaaaaaat cttctgacaa     11280
tctaggttca tggtagagat taaacggtac catattatga ggacagaaca ataaatcaca   11340
catggcttcc catagaattt gtgtgacagt ggttgtgtac tatgattcag tctgtcatga   11400
caatttcacc agtaaaataa ccttccagga tttatttgat atctcaattg ataagcctcc   11460
cgtaagtgaa taaccagaat atgacataat ttataaaaat taacttaaaa ttacacaaga   11520
agttatgtgt ctagtcattt cacaatcaaa tgtatttagg catttaatct agtaagatcc   11580
caaataataa aaaattgttt cttttctagac caacatgtat cctgatgtta taaatacata   11640
tgtaaattat atacatatat ttgtatatgt aaaatacaca tacatttaca tatgcataca   11700
tagctcactt tttattgggg agcacatctt cctgaaggtt tttcaaagaa taattattct   11760
acctgtaatg ctgtagcagt atttgtaaaa agttcaaatg tggctgggta cagtggctca   11820
tgcctgtaat tccagcattt tgagaggcca aggaaggagg gttacttgag cccaggactt   11880
tgagaccagt ctaggaaaca ccatccatac gaaaaaaatt taaaaataag tcaggtgtgg   11940
tggtgcatgt ctgtagtccc tgttactcag gaggctgagg tgtaaggctc acttgaggag   12000
tatatcagga gtttgaggct gcagtgagct atgacctcac tactgcattg cagcctgggc   12060
aacagagtga cactccatct cttaaaaaga attcaaatgc ctcatttatc tggacagaat   12120
ttgattggtg ttattctatt gctgaataat tccagggtat gcatttacct tttctctatt   12180
gactttaaac atagcttatg aaaaacaaac aaacaaaaac caaacagagg agtttgcaaa   12240
actatatttta aaagtaaacc atactccctc accccctgact ccacaaaaat actgtttaat  12300
```

```
gtagagaaac cacagacggt gcagccccca aatctggagc atcctcaggt acctggggc   12360 attctggagt gagggctga gcctcagagg catttggtca cacttgggtg gggatgcctc   12420
attggctagt gaagaagcag ctgtctcttc catgtagtgg tcagttgtgg cctctcctgg   12480
aagggaattt atccagcagt gtgtgttcct gaagatgcta atagcaaatt atgttcagtg   12540
aagccagctg catcctgttg gtcttgctag tcccgggatt cttgccacag caggtcagaa   12600
tggaagggag ctgcttatct ttcctcctta cttcctctcc ccatcccagc tctcatctga   12660
catccttcca acacctatat gacaggaaaa aaattctctc ttcaaattaa gaaaagggtc   12720
tggtctgggt acgatggctc atgcctgtaa tcccagcact tgggaggac gaggtgggtg    12780 gatcatatga ggtcaggagt tcaagtagtg aaaccccatc tctactaaaa atacaaaaat   12840
tagccaggtg tggtggcacg tgcctgtagt cccagctact caggaggctg aggcaggaga   12900
atggcttgaa ctcaggagtc ggaggttgca gtaagctgat atcacgccac tgcactccag   12960
cctgggcgac agagcaagac tctctctcaa aaaaaaaaaa aaagtgttt gagtatttac    13020 tctccacatc tttcagctat ttcacttcac tgggagtaga caggacagga tggctccagg   13080
gacagtgcta ttgttacctt gttatccact tccaatttgg aaaggtaaaa atatgcttca   13140
gtgtctacta aattgcctgc attgaatttg aagtacagtt tgttgggata ctcatgatga   13200
aattggaaaa cagaatcaca gattgttagg acttgaatgt acttgagcaa tcatttgtat   13260
tccctcatgt acacaaggaa attgagtcac agagagtttc agtgatttat cctcatcctt   13320
tttttttttt tttgagacgg agtttcgctt tcgttaccca cgctggagtg caatggcgca   13380
gtctcggctc accgcaacct ctgcctccca ggttcaagtg tttctcctgc ctcagtctcc   13440
caagtagctg ggattacagg cacacaccac cactgctggc taattttgta ttttagtag    13500 agacagggtt tctccatgtt ggtcagctgg tctcgaactc ccgacctcag gtgatccacc   13560
tgccttggcc tctcaaagtg ctgggattac aggcgtgagc caccatgccc ggccgtgatt   13620
tatctccata attttaaaca ctatccctgc aatgaaaaag gaatacccc aatttttaac    13680 atatctgctt acgccagttc atgacaagct tacaaaatta gaagtaaattt taaatgggca   13740 aaataaagca aagtgcatta tttaattttc aaaacagact tttctttatt atgcagcagc   13800
gatttaaaca gataaatcat ttctatgaaa gggactagca gagaaagcag gaaaagacat   13860
gtcccacatt aaaagctgaa cttgttggtg ggaactcatt ttgttttatg agttatgatg   13920
aatgcacctt agctgtttct aaccccgctc ccattccctg ttttatttg taagtcagaa    13980 cccagcattt ttacattttt tgaagtgtta attaattgcc tttgtttaat gcaccttgct   14040
gtgtctcaag cattgttaag aaaggataag atctttttca gggatgattc tttcctttcc   14100
ttacagggct ttgtctgtga tgagaacttt ctatacacat attttctttt ttaagagacg   14160
gggtctcact atgttgcgca ggctggtctc gaacgcctgg gctcaaggga tccttcggac   14220
tgacctcctg aaaatactggg attactggtg cgagccaccg cacttggctc tatctttctg   14280
caaaaactgg tggattctac ttctctctcc atctatgttt agtcctggga gatataatca   14340
agagaaaaga aacatctacc ttcattagat taagagtcaa acaaaagggc ctagaggcaa   14400
agaggctcca cgaccctctt ttgcgggtga gcctgtgcat tgaaatcctc agcttcaaag   14460
agacacagaa ggcaaaatag gaagttggat ttgcaggagt tagtctcttg gagggtcttg   14520
taaaattgaa gggttcacat atgccctgtc aactctccaa gagagagatg acttggtgaa   14580 atctgtatttt tgtgatgatt agtctttctc agagggctgg ttcaagggca aacgaagggc   14640
```

```
agaataagga cttgcagatg tgttaagaac agaacccgct gtgttgtgcg tcaacgacaa   14700
aagcccactc cactcctgac attcatattt tggggtaact gttttttgca gtgcagacct   14760
gtgaaacctg gagtattttc agtcacagct tttatcgaga tgctttctgt tgacctgaga   14820
attaattatg gttgtcaaa cagcttgacg accttgtcag tggtgttttt tggttttttac   14880 aactccccat ctaaggattt gagaatgccg cagtggataa aactgtgtga ctgacgttca   14940
ttattttttt ccacaatgct ttaaagtaag tgcgctggga atgctccatt tattatgtag   15000
aggagagaca tttccaaact ttaactttgt tgctgttgct tttgtacact gaggcattga   15060
ttctgcagga ttaaaagaag gtgctgatta ttccatttgg tggaaagttt caggagtgga   15120
agccagcaga attgttccac tgagatgata attctgactc tttgattctt acacattgac   15180
tacttttaca aaatacaaac ctgttttaat cttttttaaag acatttgtg cgctactgtt   15240 ttcatttttt aaaataacct tttaaaaatt ttaggatagt ttcaggtttg ctgaaaggtt   15300
gcaaagatag tacagagagt tactctttaa ctccacacgc atatcgcatc ttacgtgacc   15360
atctgttaca cttaaggaac caacattagt acgttactaa gaactgacat cacaatttgt   15420
ttggatttca ctggtgtcca cctaatgtcc ttttttctctt ctgaggtacc atctgaaata   15480
ccacactgca tggatttgcc ctattttctt agcctcatct agtctgtgac agtttctcag   15540 ttttccttg tttttcatga ccttaatagt tttgaggtat taatgtcatg agaatgtcc   15600 accaactaga gccagtctga tgttttagac aggggtatgt gtttggggga ggaaatccac   15660
agagatgaag gtttccttca tctcacccta gcaacggtga ctactgtcca gaagactttt   15720
gctgctggtg ttggctttga tcacctggct gacagagagt ttgtcacttt tctctgctgt   15780
aaagttgtac tctcccctcc ctgcccaagt ctagtctttg aaaccaagtc cctaaagtgg   15840
ggtgggggtg ggagaagagg cagaattaag ctccactttc cggatggtgg aatatcgata   15900
aattatttgg aattcttctc taagaaagat gggtctctcc cctttattta cttaatcaat   15960
catttatatc agtatggaca catggatatt ttagatatgc tttgggctac attgctgtga   16020
cttattccac tttatattcc ttgtggccat gatgtagaca ccagagagtc tattcacttg   16080
aatagcaagt aaatgagggg actcaatggt aaatgactct tagagaaact ctcagccctg   16140
ctggttcatg gatgctcagc ttgcaaaaac accttcttcc atcaggaaac ctcagtggat   16200
gggcaaacat tacagcgtcc ttgaatatgc ttcattgctt taatctacga acttcctatg   16260
cagtaagcaa aaccacccat accacagctt aagagtgggg ctttcctccc aacactcatc   16320
ctagtgtctt ttgataaaga ggtataaagt tgaaggaaca tgttactaac cagaagactt   16380
ccagaggacc ccattgatca gggtagatga atggctgtgt gcgtcttgtc acaaccatca   16440
gtatttcaaa aggtgatatc atcctcttaa ccttatgatg tgttttaaca taaaatttta   16500
atatgcatac aggcggttat tacttaagca ttgcttaaga agcagtcttt tttttttaat   16560
tcatgtaact ggatctattc tctgaataag gaatataagc aaatcgtagc catttcaagg   16620 actcttttt tttttttta aatggagtct tgctctgtcg cccaggctgg agtgcagtgg   16680
cgcgaccttg gctcactgca acctccacct cctggttcaa gccattctcc tgtctcagcc   16740
tcccaagtag ctgggattac aggtgcccac gagcacacca ggctgatttt tgtgttttta   16800
gtagagatgg tgtttcacca tgttagccag gctggtctcg aactcctgac ctcagatgag   16860
ccgcccacct caacctcctg acgtgctggg attacagaca tgagccactg tgcccagcct   16920
caaggaggct tttaagggca ggatgttttt ttttcttatg gtgaaggaat gaagagtagt   16980
atgggaaaga aatacagaaa ctttgaaaaa agaaatgtaa aactggatca tcattccata   17040
```

-continued

```
ggctagtagt taatagtaaa taactgtata gtttgttcaa gggattttgt gaatatttta    17100
aacacagatg ataattctct atctacatct acgtgtttac ctgcatttat atcatatgta    17160
cgtatggaca tatatatttg cctgtagatc acatctttgt atggtatctg taccaatatt    17220
agagtctata gctacagcat atcaataaca gtatctattc ttatctatat cttaatcata    17280 tctattttg tatctgtaca catatcttta ccgatattca cattatattt ctatgtctag     17340
atctatatat atctctatct ataccatttt gaactttaca tttcctacag tatgatagca    17400
taagctattt taggattatt aaaaatcttc ataagcattg ttttcatgg ttaattttct     17460 caaaagacta tgctttaaca tacccagttc tttatatatt ttttgacatt tggcttattt    17520
taatgttttt gctcctctaa tgtatttttc ttttttact ccacacccct cccgcctcta     17580
attttcaaat tgggcattct tcattatagg ggcattgctt attttctttt gtatgtttca    17640
aaaaacattc tgcattggtc tgtacacatt tttccctctt gtatcccttc tgtaaacatt    17700
tgtattcact tgaaaccttta tggaatattt tactacagaa aatttctggt tatgataaaa   17760
aaaggcagag aagatagaat aaaggatccc atgtgcccat cagttggctt cagcaattat    17820
gaatggatag cctaatcttt agtatctaac ttcattcata tttccattct tattatggca    17880
tgatgtaatt catttaaaga tatgtctgta cgttgctcta aaatatagga accatttat     17940 tttacacagc tgcagaatct tttccatgcc taaaattatc aacagtagtt cctctgtatc    18000
atccactata aagttgtaac tgtcaaaatg atcttctcgt agttttgtaa ctcacgcaag    18060
gtcaaggtct agcactgcaa taggttgatt tgtcttttac atttctttta attgatatag    18120
cttccctatc ttttatgca cattcttgtt gaaaaaactg ctcttttac tctacatgaa      18180 agtgggtttt agaattggaa aatgtagttg tcaagttatt ttagaaggaa cgtgtgtatt    18240
ttccgtaatg cacagtctta agttactaac tccttaggag caaacgctgt gtgacttggt    18300
agtgttctac ccagaaggaa tgctgctggg taaatttggc cagctacgtg acagctcttt    18360
ggactcagta tatctcagtt ttatctattt ttaacaaggt tttattttga agacagggtc    18420
tcgctctgtc gcccatgctg gagtgcagtg atgcaatcat agctcgatgc ggtcttgaac    18480
ttctgggctc aagcaatctt cccacctcag cctcatatta tctagtacct ggcagagata    18540
cagatctgat gagaagcaaa gatagagggg tgtcagaagg tagcttttgt tgcaccatta    18600
catacataca cacacacaca cacacacaca cacacacaca aacgggcgca cacgcacgca    18660
caaagaatca actgcaattt tttcctcttt gccaacccac agttaagtaa aattattagt    18720
tctattgaac tccacattgc atgtgatatt ttgaatgata gaggctaaag agaggccaaa    18780
gagggaggat tgcttgaggc caggagttca agacgagctt cgacaacata atgagaccgc    18840
gtttctacag aaaaaaagaa aaaaaatagc cagatgtgat ggctcgctcc tgtaatccca    18900
gctactggag aggctgagac aggaggatgg cttgagccga ggagttggag ctgcagtga    18960 actctgatag tgccactgca ctccagcctg ggtgacagag agattctgtc tctaaaaaac    19020
aggaaaaata tgactaaaga aaaccaaact aatctaatct atacagttat agatagttgg    19080
ctatcattct tatgctaatg taagtatgcc tcattttaag aagagttgtg tgtgtgtatg    19140
tgtgtgtatc tgtgagtgtg tgtgtatgca tgatataaat ccagacttct aagcgagtat    19200
cagggatggt gaactattat tagtagatca ttggaacctg ttacacaagg atgcactaga    19260
gaattttaca aactattaaa ttctgtataa tttaaaatgt gacttgattt actcagatat    19320
tttaaaagga tgcatgtctc ttacaaaaca agatttacta actttggtgc tcttgacgtt    19380
```

```
gaggctggat aattctttgt tgtggtggct gtcctgtgcc ttgcgtgatg ctgaatggta    19440
ttgctggact caagcttcta ggtgcccgtt gtatacacgt tcctgtttta aaaaaaactt    19500
atataaattt aacgggcaca agtgctgttt tgttacatgg atatattgca tagtgatgaa    19560
atctgggttt ttagtgtaac caccacccaa ataacataca ttgtatccat taagtaattt    19620
ctcattcctc atcatcctac caccctccca ccttttttgat tctccagggt ctattattcc    19680
actctctgtg tccatgtgta cacattattt agctcccact taggagtgag acatgtggt     19740
ttttgacttt ctgtttccga gttgtttcac ttaaggtaat ggcctccagt tccatccatg    19800
ctcctgcaaa agagatagtt tcgttctttt tatggctgaa taatatttcg ttattcatat    19860
ataccacatt ttctttattc atttatccat tgatggatgc ctagctggat tccatatctt    19920
tgctattgtg aatagtgcgg tattaaacgt atgcgtgcag gtatcctttt gacatagcga    19980
tttcttttta tttgcgtaga tacccagtag tgggattgct agataagatg gtagttctat    20040
ttttagttct ttgaggactc tccatactgt tttccataga acttatacta atttacattc    20100
ccatcaacag tgtatgtgga ttcccttctc tctgcatcct catcaacctc tgttatgttt    20160
tgagtttgac atccacaatg tctgcagaca gtctcagata tccccttggg agtaaaatcc    20220
atcccagtta aaaagctctg ttatgaaatg aggtgtactt attccaagtt ttacatgggg    20280
aatttcactg gttttttgggt tctagtagcc ccgacgtgta tactgggcat gaccagataa    20340
gataaactgg gcaaagagtg caatgagaga tagtaaccac attatttttgg aagatgtttt    20400
tcataaccag aatagacttt atgaattcta tcaattgtaa tgagaatcgg attgacattt    20460
ggggacagtt aatataacgc acgttatccg aaaggaggtg gcattgattt atataagtga    20520
gagcttacga gaaacaaag actggaaata aagaaaaaga aaatccttga taagtatctg    20580
atagaacaaa gtgcagaacg aaatgcagct agcttatcta aaattgggca aaatcatgtt    20640
ccaaatgaaa gctcagtaga tgggaagaga gtatttgaac atttgatgtg aaaaatgaga    20700
tttactgttc cacagatatg aacacattga tgagagctgt cagttattag aacttattaa    20760
catcaatggg aacaccagaa atgtgctgca cagaaaatta aatttaagac tgtttgaaaa    20820
tggtgttata ttttctgaac tgttacattg attgattaaa attagattat ccaacaaaat    20880
aagaactttt gatattctgt gagtgaatat gagatgaatt tatgtggcag atgtgttttt    20940
aaaagatgta ttattaaccg cagagattca gaattaatgt cgccaacccc aaagaatgca    21000
gtataacatt tgtcataagt gacctcataa taggttattt tataatatcg ttttttaattt    21060
tgataataaa tggacacctt ttacatcttt aataataaaa ggatatatgc aaaaccagtt    21120
attttttattc caatgttaat aaaatagcaa taagcctcat ttcatttgaa gcaccaactt    21180
tcactccata tcaaatttct aaaagtctgg gagatactca ccaactagtc aagaagattt    21240
tcattctata aaattgtata atgcagtgaa tcctgttctt ttcccatatg catttattta    21300
atatttatat ttgatacaag gaatctctat tattttcatt aagccactca taaacgtaag    21360
tgttttactt cttcttgggt acattttaa aaatttggtt acattttga gatgttgatg     21420
ccatggttaa aatattccaa ctaagtaatg ggatgggttt acaataagtt tttgctctac    21480
aaggaaatag gtcaataaat caggctccag ccaattatag gagaaaagga aaagttaact    21540
tattatacat tattgcacac agtgtttgat gtatgtatgc aaattgctcc caaatacagt    21600
ttggttgcag ttgtgctcca catttatggt ggatgcagtt ttgaatatgt gcagagagaa    21660
tatattctga cctcattcat caatgtgatg caaatgtgta gaaatggcaa ggtcattttt    21720
gtatgatgat aaaatgcctg tttgaaagta aactcatcca cccatccatc caaaggttgc    21780
```

```
attttctcaa ttcccaattc taaatatgtc tgtgtgtgtg tgtgtgtatg tgtgtgtgag   21840
agagagagag agagaatcta gtgcaatttt attgttctac tttgttccag gcttgacatt   21900
ttagtgattg aaactaaaat accttgattc ttaccctcta attttacaaa taaaatctgg   21960
tttactgtta tggattgaac tgtgttacag attgaattgt gttccccaaa aagatatatt   22020
gaaatcctaa tgcccagcac ctcagaatgt gatcttattt tgaaataagg tctttgcaga   22080
tgtaattaca atgaggtgat taaggtggcc cttattccgt acaactggtg tcgtaaccac   22140
catgtgaaga cacagacact cacagggtga agacggccat ctgatgatgg aaggttggca   22200
tgatgcagct acaaaaaggg aatgccaagg attactggca actccctgaa tttagaagag   22260
acaggaaagt atcctcacca agaaccctca gagggagcat ggccaacatc atgattttgg   22320
acttctagac ttcagaactt tgagagagta tattcctgtt tcctgagaca taagccttgt   22380
gattcttttt gatagtaact ctaggaaact catacaccaa gacacagagt tatttattta   22440
aattcatttt ttttcattta aaaatactta tttgacaaag actgtaatat ggaaagtgtc   22500
cagtgtgatg actggatgta cgtatacatt gtgtaacaat gatcacaatc aaattaatga   22560
acatatcact catagcccat gtggtacata atggatggac ctgaagttat gcagccagct   22620
tggggcagag ctgggtttga agggcagact cctcacccag ccacacttgt cttccagaat   22680
cactttcaca tcgtcatgag gattttagag actccactgc tccatgtcac tgcatcaaca   22740
cattgtggag tgggggtct cataattcat tgcaggtgtc tgaagatcaa cagttgggtt   22800
tcccttccct caactgtaaa atgagtgagt tggacctgtc tccagggcct ttctaagcta   22860
tatgatttga gaacaatgat cattgtaatt aagacgcttg acttgaatac tgctcatttt   22920
aaaccatgat tagggatatg agatgctccg tgtgttttct aaataaactt cattgtgacc   22980
tggttaagtg ttggatatga attggcaaga ggaggcttgc tagtagaaat ggtgtaattt   23040
aaaacccatt cacaagtatt tacacactgc aagacatcta gatcctcaga agtcaggtag   23100
tatcctaaaa gcacagtgtg taatttatgg tagataattg aaattgcact gaaattgaac   23160
ttggtggtgg ggagtacact tcatagtatt caattttgc cttcacttta ttctatgtct   23220
gactctcagg aaataggaac tgcaacgttg ggttctccca gtgtattttc aacttcaaac   23280
ttgtgaattg taaccatta aacaaatgat caaacactac atctttccct gctcttgtat   23340
ggacatagag ttttgttatt catgccttct cttttcttat ctgggaagag atctttctta   23400
acctttagaa attggattaa tgcgaccctc tttaacctca catttgatgt gaatgtcaga   23460 acttttgaa acttagctgt gcttttagta cactgatcac tgagtgcccg ttgactggca   23520
ggcactgggc tgctcagtga ggtaggtgaa gaagagacac cagctccctc ctggagtgtg   23580
tgctctgctg gaggataaag acacttatca agcaatagca taaatgcttc tgacaccatg   23640
actctaatca gagtggcaca gccaatgggc atggggctag gagaatatga gaattcgtag   23700
gtatggggat gctgtcaggg ttcatgaaag gtcttcccaa tgatgagaaa actgcaagtt   23760
gggaggaggt agaaataact gaaagaaatg gttgtagaga tgaatacatt gggggatgat   23820
cgtgttgcag ggtgacatct tttagtgata aaagggatag agtttgagct cctgctgcag   23880
accctcagcg atgtgttgta atggtaagaa ttggctcatg gtttcctggt ttgcctgatt   23940
gctgcatcca caaaaccatg ggttctgggg ttaattccca tccattttgt tgctgaattt   24000
ctcagaatga tagtcttcgg tacattgtta ctgaaaggag gtgctaaacc caatgtcttc   24060
attgcttttg aagcagatgg tccagtgtag tgtttctcaa acataagcat cagagtgtcc   24120
```

```
tagaggtctt gttaaaggca aattgctggg atccatccca ggagtttctg agtcagcaga   24180
tctgagatgg gacccataat tccccagttg aagttgccgt tactggtctt gggatcactc   24240
ttttagaact actgccttag ggtatttctg ggttacatgt gcacacatga cctgcttaag   24300
ttttgagctc aacattctgt tttattcctt cctgttcaga ggccggcatc cacagctctg   24360
ggtctcatca tttgcttttt gtcatccagt tgtgctctac tgatttataa gttatcttta   24420
tgttttcagt ttcccagtca attcaagcca atgcatattt attgggcatc taccatgtgc   24480
tatggactgt gagggactta aagattaata acaacaacca taaaaactca ttgacgtgct   24540
gggcattatt tatttcccca tggcccccaa atgctaggct tatcattcaa acactacag    24600
caacttgaag gcagcagatt gtttctcatt tcagggatcc acaggtatat ggcttctcaa   24660
acgaaggtct ggtaattcca ggctgcatgc agctattctt cctttaaaga ctgagaaacc   24720
atgcatacaa catctttcct tccttcttcg tttatacatt tgataactat gtactgacat   24780
cttactttga gaaggtcacc atgccagata ccgtcagtga tagaaacaca gataagattc   24840
aacctctgat cccagggaga ctctcagtaa ggaagagaaa atgagaaatg aaagtaccta   24900
tactacaagg catgcacgtc acacattcca taagtgggta aaaacacaga ccttggcagc   24960
acagaatctt gttttccatt tgtgtcattt aggacactgc attggttatc tattgctgca   25020
taaaaaattc ttctaaacct taggttaaaa ctgcaaacat ttatcatctc atgcatttct   25080
atacatcagg gatttaggag cagtgtagct ggccagttct agctcagggt ccgtcatgat   25140
gttgtggtca agttgtagac agggcttgca gttttatgac ggtgttggag aatctcactt   25200
atgtgtcact tggcaggagg cttcagttct tggccacatg ggcttctccc tagggctaga   25260
cgtgtgacat taacagctgg cttttctgaa agtgaggaga gaaagaggga ggctgaaaga   25320
gagtctaagg tgaaagccac acactcttag aacttgatct tggaggtgac accttgtcac   25380
ttttgcactt gatttggagg tgacaccttg tcacttttgc tacatgctat tggttgttca   25440
aatcaaatct ggcaccatgt ggatgaggat tccaggaagg tgttaattgc aggtgtcagt   25500
tggccatctc agaagctaga ctatcaccag aagctcttcc aaaggaggtg gcttatgagc   25560
tgcatagaat tttgtcataa ggacaaagga gaaagtgtga acaaacacat aggtacagca   25620
agtgttgagg aatgggctgt gttgtgttga gtgttgtctc aagggcatgt tgagtttggg   25680
tgatgaaatt gaaatcagat catttcaggt ggtgcaactt gatggtaagc catatagatg   25740
ttattctgta ggcaatgggg caatcatatt aggacttttg cagaattatt taaggaatag   25800
cagtttcatg atagtagagg tagggataga agacagaagg tcagtaatgc aagttggagat  25860
ctagttatag attcaactgt ggtagagatt gaggaaatgg ggatggcatg aggctctgca   25920
gaggcattgg aaggatgata ctgatagaat cttgcaaact attggataga ggccaagaca   25980
atgaataacc atccaaggtt gcagttatgg gtggagttgt ccagttaaga aaagggagag   26040
agttcagagg taggtgaagg tcagcattat tagatgcttt ggagacacat gagactgaca   26100
gagatgttta ctattttttt tggtgattat aaggtaatca atagactttg agagattact   26160
gttttttcagt cttccatatt atgttgcttg gatgcatttt tcttttttcc tgaaacttgg   26220
cagacatatc cattatcaag acgttttcag aggggcatgg tggctcatgc ctgtaaatcc   26280
agcactttgg gaggctgaag caggattgct tgagctcagg agttggagac cagccgggc    26340
aacatggtga aactccatct ctacacaaag tacaaaaatt agtcaggcat ggcagcatat   26400
gcctgtagtc ctacctactc gggaggctga ggttggagga ttgcttgagc ctgggaggcg   26460
gaggctgcag tgagcccaga tcacactact gcactccatc ttgggtgaca cagtgagacc   26520
```

```
ctgtctcaaa aaaaaaaaaa aaaagaaaat gaaaagacct tttcaaccat tctaatcata    26580
attccaagac ctatttgtgt cctgacttca agagcaggta ctcttattga gaaacatttc    26640
tgtaattgtt cccacttccc ttatacctt ttttctgaca gcaggtggca tcccctcagt     26700
tgtctagctg accactggaa gggctgaccc ctcaacaaac ccatatcctg cttggagttt    26760
ctctataggc cctgtcttat ttattgctcc tgctttgagt aactttctcc ttcctcaaat    26820
ctattcttct aattttcctt cactgcctat taattgaact gacttttctg attgtctgtt    26880
cctcctgcct ttgcagttac tgtcgctccc taaattccat cctcgaatca ctcctcttcc    26940
ttccgtactg tcctatgtag ctttgcatct actcatggtt tgatgattat ttccatcgga    27000
gagaccacag gggtctctat cttctgctct cacttctctt ccaagttcct tcctgcccctt   27060 acagctcccc tttcaacaac attgcctata tgctctggcc aaaactcaat tcagtgttcc    27120
caaaattgtc ccatcatctt tcttgccaag cttaccctgc tccctgctca tggcatcttc    27180
tcctctcaat tcctcatctt ggatttgaat cccctctctt tcccatcccc agtgtaaatc    27240
actttcagaa ataacaggtc ctgtcatttc ttcttctgag atacatctgt actttccttg    27300
gtcatcttct cactttatgt gttactattt taatcatatc ctgtctatga cttgtacact    27360
ctccaatcta ttttaaagc tattctttct tcatcttcac aaataattga ttatgtaaga     27420
ctactatctc gttcaaaatt cataaacaag catccactgt gcttcaccac ctgccccatc    27480
tccgccgtta caactgcagt catcatttta ctcctctggg tgttatactt catcctccac    27540
ccaacctgag tatggatagg aatcactgca tttcaccttg gtttcttgct ttttctcatt    27600
cttctcaggc tctctttcaa cctggaatac tgttattttc ccatctccac accttattca    27660
tgactgaggg ctaaaatgct gtttctttca ctgctctctc taacatgcat tgtttgtatt    27720
cctctgtggt agtcatcaat ttccattaca gaggccagga gacctgatac tttcttgagt    27780
gtgaatttca gtagttgacg tcttgtgtct cagtttcctc agctgttgag ggctgtgaga    27840
agagtaccta cctcgaggga tgtttgcaaa ataaataagt taaggtcagg cactgtggct    27900
catgcctgta atccaagcac tttgggaggc tgaggcagga ggactgcttg atcccaggag    27960
ttcgagacca gcctgggcaa catagggaga ccctgtctgt acaaagaata ataataataa    28020
taataaaaat taggcaggta tgatggcaca tgcctgtgat cccagctact tgggaagctg    28080
agacaggagg attgcttgag cctgggtatt caaggttata atgagctagg attgcaccat    28140
tgcactccag cgtgtgtgac agagcaagat cttgtaaaaa aaaaaaaaa aaaaagaaaa     28200 ggaaaggaat aaattaagca tataaagcac tttaaaacag gtatttagaa agtgttgaag    28260
gcggccttga cattacttat ctttggccca tccttgtctt tctccttcgt agtctaaaat    28320
gttttacaaa ggactgtttc tcatgacact gagaatgaac cccaaattcc tttcactgac    28380
ctattccact tttatacagt aagcctcttg ctcacttctc caccttcatc ccaggccatc    28440
ctcttctcac tgaactgctg tcccagtcct cttttggttt tgtgatctga gtggataccg    28500
tgttaggaca ttttttgtgtg ccactccctc tgcccagagc accctgtcct gttcccattt   28560
aaagtgggtt ccaccctcga ttgtgttctt atttaaccca ttatttactt tcttctctga    28620
gctcacctga tctcaaggc ttttttattc tttgtctact tatggatatg tgtggaggat     28680 ctgggggggtt agtgaatttt tctctgcatt ctctaaacat gtgtattgca tgaatctgga   28740
atagatcagc ccttactggg tatttattaa agaaatgagt agttgtaaga cactctatag    28800
atattcattt aatgaatgag aaaatcaaat gttgcctggt aaaaacaagt gttaagtcag    28860
```

```
ctatcacagt tttctgagat atgcagccaa gccagggaga ctgagggaag gatgtctttc    28920
attgtaaaat caacgcactg taggggaaag ttcctctctc acctaaggga atatcgatct    28980
tccttgattg tttgctttgg tatttctaaa ttagcatgat ttaccaaaaa tgtttggatc    29040
actcagtaca tgcatgtgat tttttctaaa tggctatctt taaaaaaact tcctcatctg    29100
tattaatgtc cctagagttt ttacattttt tgcctgtatt tcattaaaga tgatgtcata    29160
gaaaatttt gtcaaatttc tcattctggt ccgtgcctgg aagattgaca gtgatgcagt     29220
ctaagaaagt tcaggatttt gaggtttaat catttacatt ctaacactaa agctacaaat    29280
ctgccgtgca gtgttgctta cttctactgc tcactggatg gatgagtcta tgtgcttttt    29340
aaattcctta taaagatgtg ggtcaaaact agcagtgtgg tcaataaatt aatttcttga    29400
gagtttatca gaattgtggg atgatttggg aggagcaaaa ttgtgtaaaa tcaatcctct    29460
atttttaaac ttattcttct aaaattctaa atagaatttt tttattcatt aatattttct    29520
tgatttcata atgctaaaaa ttaagtaaga tgaatgttgt gttgagaaat gggagcaaat    29580
ccaagaccaa aaatcagatg atttattaaa tttgcaagtt aaaaaaataa atacagtttg    29640
aaagattgct ctgtttgagg aaaggacata caatttttgtt gagataactt agggtacaaa    29700
tcaaggtcat ttatgttcat ttgaacattc atattcacat ccggaaatat ccagaatgac    29760
tacactaaaa cctgcaggta aattctttc tcagctgagc ataccatatt gttgtagtta    29820
atcaagaaat ctaccaaaat taaatttgtc ctcctactt ttagtttaga aatttagggg     29880
gtcactggga ctcaaaagaa aattcaataa ataatggacc atcctagaga tacttctttt    29940
taacttaaaa atccctctga gatatcctca ggttttaaaa ataccttgtt atttcctgt     30000
ttttgtgtgt gtttgtgtag gcctacatct tcatattagt catcagtgtt gtcagaacct    30060
tggctagaat catagtctag acctcttgag gtcactgggg ggttggctac attttccacc    30120
tcttgctttt catgggtccc actctgagaa acatgctcct tctctctctc tcctcttttca   30180
aggtcatctt tgaggacatc ttctgaagct ttttctgaga tgctgcctct tctgagcacg    30240
acactgtcta ttcttgtatc accagtatag gagctcatgc aatttgtaag cacttgcctt    30300
aatgatgcgc tccctgaaag accctgagga gagggatcag gtggcgttca tctttaggat    30360
cccttccctg tcctcacagc acattcatgg tccacgttca gcaaacactt gtacaatgac    30420
atgacttagg gttctagac aatctgtatt gtaatttctg ttgatataaa gggataacat      30480
tagcatcata tgaaaagtca gagttctatc aatgtcatct tgatgaaaat atttatatcg    30540
ttatatctta tgtcctaggt gtcttcttga ctgactaccc agggcgagtt ggaatggcta    30600
tgtgcatctc tctgaacccc caaatcttta gttgtaatga tgaacttaca tggagaggct    30660
tattcgaaac gtcattatag tgtggatgat aaccttctta gtttccacag ctgatattcc    30720
tccaaagttt tgtatgcttt gactaatgta ttctctttat gctaagcttt ctttaaaatg    30780
atatgaatgt tccataaatg ctgatttttt ttgttttttg agacagggct tcactctgtc    30840
acccagggtg gagtgcagtg gcgtaactac agctcactgc agcctctgct cctgggctca    30900
agcaatcctc ccacctcagc ctgtggagta gctgggacta caggcgtgca ccaccaaacc    30960
tcgctaattt ttgtattttt ttgtagagac agagtttcgc catgttgccc aggctggtct    31020
caaattcctg agctgaagca atcctcctc ctcagcctcc cgaagtgctg ggattacagg     31080
catgagccac cacgcccggc cccataactg ttagtttaat tagcaccttt ctgctttagt    31140
tcatgttgac tattgaaaat ctatcatcct gtataattaa tgttttttaaa agatactttt   31200
agatagtgat caaaaactta tttattaagt agaatgtaaa ttattacaaa tgatatgaat    31260
```

```
accataggat aaagttttta tatgacaact tagattataa aatgcaattc tagccaggca    31320
cattggctca tgcctgtaat cccagcactt tgggaggccc agcaggcacc aaccgcttgc    31380
ttccaggagt tcgagagcaa ccagggcaac atagtgagac tccgtctcta taaaaaatac    31440
aaaaaaaaaa aaaatagct gagcatggtg gtgcatgcct gtagtcccag ctattcagga    31500
gactgaggtg agaggattgc ttgagcctgg gaggttgagg ctgcagtgat ccaaggttgc    31560
accgttgcac tccagtctag gcaacagata aatatgagta caaatggctg atcatcttca    31620
tattaatatg aaattgcatt ttttgataca ggatctcgtt ctgtcttgtg gccttctgta    31680
ataggttatc ttgtccaaat tctggaataa agtccagaag aattttaatc tagataattt    31740
attctttaac ctttgaaata ttgtatcagc tacatgacaa tggcttataa ctagctctaa    31800
ataaatgaaa taacgtttgc gagagtgaat cacatcactg agaaccaagg ggaaacatga    31860
aatagtgatt atttgaacag agagtgttag tggtctgcat tctgccttgc acccaaatgg    31920
catcacctat gggtgtgata aaagcccct gcctttctct ccctcctcag tgcttgggat     31980
ttccaacaac agcaaaagag aagccaggaa gaatgctgtg ttgtgagtac ccccaggaag    32040
ggttttcctt tatgaagagg cagacctagt taggaaatac ataaccatgg actgcaggaa    32100
agacagttga gtctgcatgg aggatagaga ccagggaccc cataaaagga gaggtggtga    32160
ccgaggcctg caggatgcat ggaaacattc ctgacctcaa gggcagcaac tgtgaacaca    32220
ctcctactag gcagaactag aatggatgaa cagagttctt ttcagggaga ctcaccaggt    32280
agatgactac acatgagaca cttttttttt tttttttttt tttttttttt tgagacagag    32340
tctcgctctg tcgcccaggc tggagtgcag tggcgccatc tcggctcact gcaagctccg    32400
cctcccgggt tcacgccatt ctcctgcctc agcctcctga gtagctgaga ctacaggcgc    32460
ccgccaccac gcccggctaa ttgttttgta tttttagtag agacagggtt aaaccgtgtt    32520
agccaggacg gtcttgatct cctgacctcg tgatccgccc acctcggcct cccgagtagc    32580
tgggattaca ggcgtgagcc accgaaacac tttcagtggg aatattttgt tccatcagat    32640
tttagcaata tcggatttga aaataggga agcacacaca gatacaatta gtttcaccat    32700
ctcacttgtg tatttaaaca aacctgtaaa caaagctaag cgaaccaaga aacaaacaaa    32760
acctcaaacc taatacagta ataataggct gggggtggtg gctcatgact attattaatc    32820
tcagcacttt ggtaggctaa tacagaagaa ttgcttgagc ccagagttcg agaccagcct    32880
gggcaaaata gtgagatcct atctctataa agattattta aaaaattagc caggtttcga    32940
ggcatccacc tgtagtccca ggtacttggg aggctgagag gcaggggat cacctgagcc      33000 taggaatttg agattacagc cagctgtgat cgtgccattg aattccagcc tgggtaaaag    33060
agtgaggtct gtctccaaag ttaataaata agtaaaataa taataataat ttttaccgta    33120
tcacaaaaaa tatagccagt cagatacaat gcacactaat tattgtaaaa ttttctgaaa    33180
cacacataca tcactaactt gataattgta aatttaacac tgattggagg gtgtgaacaa    33240
aggtatgatc aagtaaaata aatgtatagg caatttcaaa gtcttaataa tacaatttca    33300
agagctaata ttaattgagc atttactata tgcacactca tgcatcatgg gactgtgttt    33360
ggtgctaata tcacaaaact ttattttttc ttccactggt aattttgtc actgttgaaa     33420 actgtttcag ccatggatcc ccacagtgcg gagattgcgg gatgtgggag agaaatgatg    33480
gtctcaatcc ccacctgagc cagtgtccta tggcaggcag gtgaaagcca gccacccag     33540 cttgagttct ggctccactt ttatagttct gtggtgttgg gcaggttagc taatctgtcc    33600
```

-continued

```
ctgcattagt gttctcaact aatggggata aagctcacat ataccttata tgtttttgga    33660
gacaattaag agttagtata tgtaaagaat tcagcaagtt agatgctgac ccactatgta    33720
catattagct attataactt attattcgga caaacagcta atgcatgtgg agcttaatac    33780
ctaggtgacg ggttgatagg tgcagcaaac cactatggca cacgtttacc tatgtaagaa    33840
acctgcacat tctgaacatg tatcccggaa cttaaagtaa aataaaaata aaaataaaa     33900 aaataactat tattactact attattagaa ttgtttggat gaggaggtag cttgatatct    33960
tgaaaaaatg catggtcttt ggagtcaaga taggtcttac tccctgcttc agtgagctgc    34020
gttacttaac acctggatat cattttttc ccaatgtaaa ataagatgtc ataataactc      34080
ctgcccttgg ctgtagaagg gtcagtgaag atgaatgtta ttatgattgt tgttaaatat    34140
aaattcattt ttacaaatac agtttcatca acaatattta tgataatgcc tattaataac    34200
aaaatgtgct aggtgttatg agaaatcaaa aacatagtta aaatatgatc ttgtcttcct    34260
gtaatttaat aatgtgctgg ctcattagct atgaaaccca aaggccttat ctactttgta    34320
ttaatatttt ttcaagcatg gaagtaagcc cagaagggta ttgagtgatg tatcctcttc    34380
ttcccttacc atctttccta tagatgcaaa atcctgagtg tgaaaggcca cgtggtactc    34440
tgttagatat ctcgcaggtg ttacttatcg atggttcttg cttaaaagta gaaggaggag    34500
tgtcgcatga gacgcatcct ataaagagag cattccgggt gagatggcaa gaaaaactcc    34560
gaatggtcct gagatgataa ctgatccaat ggagatgata tatctgttca gttgacgcaa    34620
acataattgc ggtttatacc cgtgaatgta aggcaaaaac tgcaattacg cttgcaccaa    34680
cctaatatat atatcttttg gagacagggt cttgctctgt cgcccaggct gtagtgtagt    34740
ggtgcgatca cagctcactg cagcctcaac ctcccaggct caagtgatcc tcccacctca    34800
gcttcctgag tccgctggga ccatagacac atgccgccac atccagctaa ttttgagata    34860
agttttcttg cagtagagtc aatggcagtg ttgttctgac cttctgccac agcaaaacat    34920
ctctgcaggt tgaggattag ttcttgcaaa taagtgattt ctaaatgatt gattggttct    34980
tttcacacat tttgcagatt ttctttatta aacaagttat atctaatgga gaaatacagt    35040
gagttgatga tctccaacaa aactttaatg ccacccagat caatgccaac cagattatga    35100
gttgcccatt ggaaacctca aggagtcttc attgattttg tattctcaaa ctgcatgtgt    35160
gtgctaaaat ggttgcatag agattccaca tgcagccatg catgtgtgta ggtgctccca    35220
ctagactagt tccttgactt attagggaac aagttaagaa ttacttcatg tcatgatcgg    35280
ctagttcttg taactaccca taagaaagct tataaggaat gtcacattgg ttttgaaaca    35340
atatcatctc ttttactgat ggagagaggt atgttttct ttttttttt aaatagggaa       35400 caatgtgcta agatggaaaa aaaaaatcaa gtaggtttcc agggaggcat tttttttttt    35460 ttttttttt ttttgagacg gagtctcgtt ctgtcgccca ggcgggagtg ctgtggcgcg     35520
atctccgctc actgcaagct ctgccttccg ggttcacgcc attctcttgc ctcagcctcc    35580
cgagtagctg ggactacagg cgcccgccac tgcgcccggc taattttttg cattttagt     35640 agagacgggg tttcaccgtg gtctcgatct cctgacctcg tgatccgccc acctcggcct    35700
cccagagtgc tgggattaca ggcgtgagcc accgcgcccg gcccagggag gcatttttaa    35760
aggcaccatc tcagaaggac gaggcaatgg taagtatcag gaatagttat tggcgagtcc    35820
agcacagcag tcaatgactg tgttctggac tgcaccgttg gactcgggaa ccactgtgtg    35880
gccaggctgt gggctccggc agttgttcaa accctgaac ctggagctca gaccagaggg     35940
ttgtatggga ggctcactgt cattcattgt aaccctaaga acctcatcct tccttgagcc    36000
```

```
cgattgttcc catctgatca gagcttagat gcaagattgg gaagaaaggt ggtggagttg    36060
gggtctgcct ggaggacagc ccaggtgagt catgcatggc tgggagagca gtaggttcat    36120
tctcaccacc tcattttct aaggggaaac agatccacaa gggagggtca gccccagatc     36180
attggccaca cttatgggaa acatgtgctg ctgttacgca ggccccttca ttctgtttgc    36240
atgctctcct tgtaacccct gggcctatca ggacgccagg gtgtctgttg aagaggcat    36300 ccaagaagga tctttaggct gcaggatgga agcacacact acagcatgac cttaggtaga    36360
tggttcattc attacctttt aatatcttcc tctttctttg ctgtcaaaca tgggtaataa    36420
aatacctaac ctgtcatatt ataagaagta attgaggcca ggtgcagtgg gtcatgcctg    36480
taatcccaac acgttgggag gctgaggagg gagaatcact tgggttcagg agttcgagac    36540
cagcctgggc cacacagtga gacttcatct ctacaaaaaa tttaaaaatt agccagacat    36600
ggtgatgcac acctgtagtc ccagctactt gggaggctga ggtgggagga tcgcttgagc    36660
tcaggagttt gaggctgtgt agctgtgatt gctccactgc actccagcct ggccaacgag    36720
caagaccctg tctcaaagaa aaaaaaaatt aggtgaaaac aatgtctatg caacgctcag    36780
tgcctggtga tgtctaagga atgcccaaac tttctaggta aggggtaggg gatgcattgg    36840
gtgagagtcc cattggatga gcatgaatgg gaactcatca atattgctga aagtgcctga    36900
tccagaatta aaatatttca acagaaaatt cagaggaaac tttagaatgc tgaaaaatgc    36960
catattggtc agtcttactg gttaatcgac ttttctgaag tacatacaca ctttttttt    37020 atttgagata gaatctcgct ctttcatcca ggctgtagtg cagtggcaga atttcagctc    37080
actgcaacct ccacctccca ggttcaagtg attctcctgc ctcagcctcc cgagtagctg    37140
ggattacagg cacccactgc aacgctcagc tagtttttgt attttagta ggggtgaggt     37200 tttaccatgt tggccaggct ggtcttgaac tcctgacctc aggtgatctg cctgcttttg    37260
cctcccaaag tgctgggatt acaggtgtga gccacaactt ccttcccacc cagctaattt    37320
ttgtattttt agtagaggca gggtttcacc atgttgacca ggctggtctc gaactcctga    37380
cctcaagtga tccatccgct ttggcctcca aaagtgctgg gattacaggc atgagccact    37440
gtgcccagca cacacttcac tttggatcaa gccccctta gagcatctga acttcttttc      37500
cagtcccttg ttccacccag gcaatcccaa gcctggtgcc ttcctatctc tagcctttga    37560
tttaggctat tctgtctgcc tgtgtgcaac atttcctttc cctccttact gaagttctac    37620
cccatcctgt gttgcatgag ttgatggata attttgaaaa aataattatt ggtaatcatt    37680
aacctctact gacttatttc attgatgcat ttttgagcct ggttaaacca agtctagcag    37740
tgctttcgga ttactttggt ggtgaaaatt gtttacttaa aaaaaaaaaa acaatttgaa    37800
acaaataaaa gtagaaagca gtggtttcaa gctcatttgg agtgtccaaa gtgacatgcc    37860
tggaaattta ggattttgaa ataattgtct gctcctcctc atggccacac ttcggggtac    37920
atctcataaa gtagacaaac acagatgaag gtcacctgtc tgactcactg tatgtaaacc    37980
tctcagaaat tcacccttgg ctgcactgct caccggaagt ccattttctt ctagagtaaa    38040
gatttgcaat gatctaggac tcaaaaagtc catcttgggc catttgaatg accccagcat    38100 ctcatttac cctttgtatt tgtagcccct gcagagtggg gttcaaaatg tcagacaggt      38160
actactagta caggcagagg ggacactcag accatgagat ccttctcact gtctggacat    38220
tagaaagaga gcagagccca aggaaaagat atgggtagaa tacttttgtg atatacagct    38280
gtgagcccat gttagtggag atatttcaca attgaaaatc tggacccttc cccacaaact    38340
```

```
caaattttag aaaggttcat ctgatgcttt catacatctc aagtaaatgg ctctgtcttt    38400
tcatggttca gctgcaaatc tgaagtcttt acaatttgat tgcttaaata ttggttattg    38460
acaaattttc ttatcaattt gaatgttgta gcttccaaac ttttgtcaaa atttagacca    38520
caaaggcctt ttgagtatct ctttaatgat tgccagataa ttttcctatc catggctttc    38580
tctttacaga ataaaacttc agtatttttc cttgattcta gaagattgtc aaggtcatgt    38640
cctttatgga actcttgttt ccaacaaagt tgattttaa acatctctcc atatttcctg     38700
ccataaacaa atactaggtt tgttttttca aagataattt gtaatttata aagaaagatt    38760
aatgctgtcc cacctccccc atttgatcat taacatacaa atttggaagaa atcatactt    38820 ggaaaaatga ttgatcagct gtttgctatt tttatctagt atagatttat ttgtcttatc    38880
aaaggtaaaa cgaataaagg tacacatcat ttttcatcag catatacagc taaataatca    38940
ataatgatac attatgtaaa tcccttggc tcctgaatta cacgacttc ttttttttcca     39000 tttttctttt tttcaacctg gatgagtctt aataaataat caaggcctga agtctaagaa    39060
atgtttgtct tctctctcac acttacagcc tttggaacag gaacccaatg cagcattggt    39120
tgtaattatt tcagtagctg cagtgcaaag cacattcagg tgaatataat cagactgtcc    39180
tagttccaag gagaagcagt agtaacaggt ctggcatcag gctcagagct atagacgagt    39240
cacagcttat aatatgatag actcactta tgaaacccaa agggaacatt atataaagtg     39300
cacaatcatg agaaggaaat gagaacttct gaacctagga cttttttaaa attgttttac    39360
catatgcact taggttcaaa ctacatttga aaccactggg cattatcagt atgtctctgc    39420
aagagtcagc tactgctttt gcttaattgg tagctgcatt ttctcttaag gggggaatgc    39480
tttggagtgt gttttcctga taatttggag tggtctttgc tgaatggtga tcctaggttg    39540
gaatttccta cattgtacac caagaatcag ttggctggat gaaaaacaag tgacaaaggg    39600
tttttccttt cccagtattc tcaaaatcct cagtaagaac tgaaggcatc atgactcttc    39660
agtgacatca gttgtccttg aggaggggtg gaggatttcg tggagacaca cataggcctg    39720
ataatgagga catctatgct gtaatccagc tctgctgcta attagttgtt tgcaattact    39780
aggtttttgg tatgtttaaa gactgcagag acaggcattc attcctttc actatgaaga     39840 atgtgtgaat gtaaattaag aaccacagct agctgagaag tacaaataat ttgtgaagcc    39900
tatttaatac tcgaaaattt caatttatgt cagttcattc aattttttcta catacagttg    39960 actgaacact ttctggtttt gtaaccccta ttagggaaaa ttctttgcaa tggattttca    40020
tgataatctg gatagtctta gtgatcttat gttagaattt atttattgc taggatgact     40080 tagtccaatt caaaactgat gatcaagaaa aattcctttc atggcattcc tgaaaacata    40140
atttttaagt caagggatga tcaggataat tctaggggcc tgtaagtttg aacattgaga    40200 tgttgatac taagttctga acacatatta cccaaatgaa tctttatta aacatttgt       40260 ggtttcaaag gacatagagt agttatgcaa atcaatgtgg tgcagcaact acagtataac    40320
cttcagatgt tagggaatca acgactaaaa aaaaaaagg acagtatttg aatgttatta     40380
caaagacacc tgcgattctt gaaggacatt tcaaaggcag acaatggggt aaattgtgat    40440
tgaaatacac gcgcaatctc tatgatatgc tccttccact tagaaagtgg gatgaaagct    40500
catcaattga agagtaattg ctaaaaaaga tttctcctct atctagcttg ggagtattta    40560
ggagctaatc agagtatttc gtcttctcgg aaattaaaag agatgaacag agttgtgcag    40620
acatggggaa aataaagttt agtttaatat ttagatttta aaattagtac ttgatggaca    40680
ttttaaaaag tgtacaatta tcaaaacttc aatatctaat cctttttatgt aaactatggt   40740
```

```
ggatacatgg aaacaccagg gacgggtgct ggttcttgtt aacttttctt tctctgtcag   40800
ccacaagagt gcctgtccca tagcagtaaa ctaataagta tttgctaaat taagaagtgg   40860
gaagggcgtt gtaggttatt gatcaaacga aaataaatat attttgttgt ttattcaaaa   40920
atttccccga cttaattttt ttaaaatgta acttaattt ttaaagctca tctgtgtttc   40980
tttgttttgt gtcgagtcaa agattatttt atgtcaatta ccttttcatg ctgaggcaac   41040
agtttcagtt ttcccattct gcaaaactaa tttcctgatt cctctctcac cagggaccat   41100
tcccctccaa aatcctacaa ggtgggtcca tgacatctgc tagagaaaaa gagggacatg   41160
ttggagcgat aggattccca tgggcactga catactggcc tctggggata ggaagattaa   41220
tgcttagtac aagaaagaag gaaaagaagg ccttggcgag gactgtttta tctcagcatt   41280
tctcagaagc tccttcagtg gagacttcgc ctgggacctt cgccccacct tcttctaatg   41340
gcacttcctc cctgtggggc tccacgcggg acattacgtc ggtgatgcgt agggcatcgg   41400
gtgcggaaat gtgtgcgtgc ctcctggcgt gtgcgtgcct tctggcgtgt gcctgtgcgt   41460
gtacgtgcgc atgcgtccgc ctcccgggtt cacgccattc cctggcctca gcctccgggg   41520
tagctggggc tacgggcgct cgcttttttt tttttttttt gtattttag tagggacggg    41580
gtttcaccgt gttagccagg acggtctagg aaattttaa gccactctga ctaaagaagg    41640
tggagttggc cgggcgcggt ggctcaaacc tgtaatccca gcactttggg aggccgaggc   41700
gggcggatca ctaggtcagg agatggagac catcctggct aacgcggtga aaccccgtct   41760
ctactaaaaa tacaaaaaaa ttagccgggc gcggtggcgg gcgcctgtag tcccagctac   41820
tcgggaggct gaggcaggag aatggcgtga acccgggagg cggagcttgc agtgagctga   41880
gatcgtacca ctgtactcca gcctggttag agtttatatt ccttttaaat ttctagagaa   41940
aacagattgt catgtatttt tatagagaca aaatactgat gaaggtgata tacaggtagc   42000
ttaattatga tttttctaag atttaattag atggtaaatt tacagtaatt attaatatgt   42060
tcactgcttt tattaaaaac catcaattct gaatccacaa tgacacaaat ggtgagtaag   42120
gcttatgtct tgtatctgtg ttctttcagt gcttaaatgt caagagaaaa acaaagactt   42180
ttaacatgat ttttaaggaa cgttttcatt ctatggtggt ttctaatgta tgtgtttgtc   42240
tttagacttc ctttatcctt ttcctttcat ctctttctca aactcataag gtttcctttg   42300
tgcagatact ttttgcctg ttttttcctcc ctagtttatg ctgcttttct gtcaagaggc    42360
tatatttcag aatgggaaaa aagggcaagc atatatagtt aaatgaatca ttttacactg   42420
tttgtaagtt attatacata agctaatgtt tgatctctgg aggataaaaa tgagctcaag   42480
tttgagcaaa tgatggtgcc gcacacatgc cctaccttat ggtgagtcaa ctatggccta   42540
tgggtggtgg ccaattttg taataaaat gttttgcaac ccaaccacac acttaaattt     42600
acattttcat atatggttct tttatactac agtgccagag tggaatggtt gccccagaca   42660
ctgcatggcc tacaaagcct aaaatattta tcatgtgatc ctttaccaga aaacattggc   42720
aatgcatact ttggcaattc atggtgatca tcttgggcct atgagttaat gcatccgtgc   42780
atacatttta aattagaaat atgtaataca ttagcattaa caacagagca tatgcttttg   42840
tattaggaat tctatgaatg catgcactac aactcttaaa cacagagcaa gtttaaagcc   42900
tggcatctgg ggtgtatgga tgagtggggc ctgggaacac ccttgaattt tacctgtaaa   42960
atttatgtgc accagggaaa gattcagtgg cgttcaacaa cacaagaagc tgcagctggt   43020
tcgtgtgggt tttcattggt ggtctctagc tgctcaagtg atggattcca gttgctggtt   43080
```

```
gatctctctt agggctaagg ttcattattg cacagattga tcttggagaa acatcttgac   43140
tgttttttc  acactccaat ccatttgttt tatgatctag aagaaaggaa cgcttaaatg   43200
caaacaatta ttgtgatttt tattccgctt cactgaactt tttaatgaag tgcattttgt   43260
acagttaaaa ccaggggggtt cctggattct attttttgtg ggaattttg  agagagaagt   43320
aattctgact cagtacgctt ccttggagtg gataattaat attaatgggg aatggaattg   43380
ttttgtcttt cgctggcatg ttgttctctg ccacacctgg catgctgtgg acctgtagta   43440
aatattaact aaatatattt tagacacaga tgattaagga tcttttgctg aaaaacattc   43500
tcttaatctt ttatacttcc ctttccacag tgcctgctga aaacatgaat ttcaattgtg   43560
tttctaagtc ttggtcaatt taagtgtgac atggggtgat ggggaaatag cagttaggac   43620
taaaggtaga aggtaacatg atccatgtga attgtggtca gtgcaaaggc ctggaacagc   43680
ggtcactctt tcctgtccat gaacctttgt gctattcctc tttgtacaca gtttaaaata   43740
taaataagaa aatgtcatgc tgccaagtat gtatcacagt gcaggccacg tagaagatgc   43800
tttatatgtg ttggatgcag gccagtgttc tcaactcagc agtttcagag gaagtgaaac   43860
aagccctggc tggaaaccag tagccgtaag gtctaagtcc tggctgagca gtccaaatgg   43920
gttccctaac ctattgccca tcccctcagc taagaagggc aggcagtgcc cctgggcaat   43980
gctggtttta tccaactctc agaaggcgcc attctttgcc tacgctctcc cgtgtattgg   44040
tccaaagccc accaacttcc tgagtggagt tccttcacat tctgcagaaa accttctgtg   44100
gtgctttaac attggatggg aagatgaagt tatcttgggc tctgggctat gttagtcatg   44160
ttttggtaaa cgaagcattc tgttttcacc aggggatgag taggtataat tttccttctt   44220
gagttttgca aacctgggtg gagaagaaaa tcagtgcaat gtcttatgaa tttttttttt   44280
aatagaagat agcaacttgg aagcaattga gtgttgagtc taagagattc cccaccccccc  44340
ccagcatttg ttctgatctc atatatatgt acagaaaaat ataaattatt tagcattgac   44400
ttatctgtaa ttaagtcttc taaaaggact actgttttag ctgctatatt ttcttctcaa   44460
ttacttggaa aatttaaacc ttccttgggg aatgtttagt ctttcacttg tccttttaat   44520
ggtaattgat tggattgttc aaattatgct gttctgagaa gaagttaaca aataaaatct   44580
ggcaaagtaa taagcaaatg gcatcaggta aatgaaaaga acagcacact gtgtccagtg   44640
atatgtgtct tcactaattt cttacctttc aaaagttgaa gattgataat caaggtaaac   44700
tttaaaatgg aaaatttgcc agctacagat tttaaagttc ataaaaggtg gttttttgat   44760
agcttttgtt gctactattt ccatttagcc ttttataata attagttaaa aatctcaact   44820
aattcttttg ataagatatc ataggttgta ttttcaatg  tttaagccag atacttgctt   44880
aaaaatcagt taattaactg agagtgaata attgtcattt attattttat atttgaaata   44940
ttaggttata gtttaaacat tttacttaaa gtgtaactag aatactggac acattttgct   45000
aacactcagt gttttcaggt gttttttaaa tcatcaccat ttctatggtt aagtcttaga   45060
acaacactct gaaatgatgt ggcatcaacc atctgagaaa gtaattaaaa gggataaaat   45120
agtaccacat gagttgggat tccttgacta tccaaccaaa aaattaccga ttttaggaaa   45180
cattctattt aatctaatta tccttcaaag tgagtggacc tttgacgtca ttttcaacag   45240
cagtgccatc ttgttttttg tgtagttgaag atcagttcat tgatcttatg tctcaggaag   45300
aaattgcagt atttcttttt tgtctttttt tttttttgaga cggagtcttg ctctctcgtc   45360
caggctggag tgcagtggcg cgatctccgc tcactgcaaa ctccgcctcc cgtgttcatg   45420
catatctcct gcctcagcct cccaagtggc tgggactaca ggcgcccacc accactcctg   45480
```

```
gctaattttt tgtattttta gtagagacag ggtttcacca tgttagccag gatggtctcg    45540
atctcctgac ctcgtgatct gcccgcctca gcctcccaaa gtgctgggat tagaggcgtg    45600
agccaccgtg cccggccagt atttattttt ttggtgttta aaaggttaaa ctgctttgga    45660
aagaaatttc aaaatgattt gggttttccg ggcttagaaa gcagactcca gctctaatag    45720
tatatgcttt ttttctacaa atgttttcca ctagatggtt atagagaatc gtttcaattg    45780
atttctttct gatgtcttct ctatttggaa atgcagtcgt tcacatctaa tggacacttt    45840
ctagcagccc tgtttcatcc ctcctgtata cttcttaact aggattccag aaggagcagt    45900
cacatttgtt tttccttact ttccactcct tcttcagcat gttcatgttc tcagctgtaa    45960
cacataatca caaacttaat ggtttgaaga acactcattg gtaaacatgg ttctggaggc    46020
cactttctga aatggacctg gtggagctac aatcttagtg tcagcagggc tccttccttc    46080
ggaaggctcc aagggagaat ctttctcctt gtcgttttcc cccatggagg ctacctgcgt    46140
tccttagctg ttgtggcagg tcacatctcc ctctctgact ctgaccctcc tgcctccctc    46200
ttgtaagggc ccttgtaatg ccactgggct cacccagcta acccaggatc atctctttat    46260
ctcaaaatcc ttaacttaat cacatctgca aagtcccttt gccgtgaaag gtcacatatt    46320
cacagactct ggggattaag atgtggatag ctttggggac agtgcattat tcagcctcag    46380
gatgctataa tcgtatgatt gatgcatctc aggggtcatc ttagttggcc tctgcaacat    46440 cttttctccct cttgatacct ttcctgggat gctttcctca acatctttga caacactctt    46500
gttttccctt tttctccctg atggctgctt ttctctttat tttccttctt cccttgtctc    46560
tttccctcct ccttgctcca tctcccttgg gaatcccatt gtacattgta tactcgatgg    46620
aaggtatgtt tggaatatta tcacgtgtgt gaccaaagac tgatggccag tgaaatggtc    46680
ttaggtgatt tggccctaag ttccctttttc tatcccatttt catgacatct gtctacatat    46740
cctgtgtctc aggcatgttg aaggacacac aaccttctgg taccagcagt gtttagccac    46800
agacctccgt gtcactgtta ttgctacctt cctcccttgc ctgacttttc tccctgcagt    46860
ggaggtccta atgattccac attcacctga aagtcatttc tcaagggagc cttccatgac    46920
ctgctccccc tctataatca tgtatccaaa agagtacccc catgataacc ctctttcctc    46980
tcttgttaat ttcaatgcct tacttcccta ccagactaaa aattcccctg aatacaggaa    47040
atatcttacg ttattgtaat caccactccg tctaatgcag tgccccactg ctatggtttg    47100
aatatcccct ccgaaactta tgttgaaact taattctcag tgtggcagta ttaagaggtg    47160
ggcctttaag aggtgattgg atcaaggatt aatggattaa tgtgtaaaag gattaattgg    47220
ttaagaagaa ggagagagac ctgaggtagc actgagccct ttggctatgt gataacatgg    47280
gccacctcag gaatcagcag agagtcccta ttagcaagaa gcttctcatc agatgcagcc    47340
ccttaacctt ggacttctca gcccccagaa ctttaagaaa taaattcctt ttgttcataa    47400
agttactcag tttcagatgt tctcttataa gcagcgggaa acaggactac taagacacac    47460
agtcaaaaat tatttattaa attaataata ttaccataaa atcatagtag ttaaatctgt    47520
gtttagagat agtttcactc cttttagtct atcactttta aatctacgta ttcatgttag    47580
ttccgtggta tgagcgtctg tgtgcatagc tgtaattata gtgtaataga ttactaaagc    47640
agtcatgaaa cacttgaggg ttctttgtac caccgctcaa atttatttac atccatacac    47700
acttgtcaaa agaggtagag agtttcagat gcccttaact atccttattc cccacaggcc    47760
taccctcata tttctgatag cagctgatat accagggaga ctgaaaatta agttccatcc    47820
```

```
taagcacaga gacttaagag ttgctgtcac ttagagagag agagaagcaa actattggtg    47880
cctccgaatg caatattggt tttccccaaa gaatgcttta tcttcgcttt acttaaagaa    47940
aaaagcaggg cagggcagtg gaaatgaact gataaccttg tgtctgtgga tataactctg    48000
ctccagggaa gacattaaag ggtaatgctt tgaaaataac atcaagaaat gaaagttaac    48060
ataaaaaaaa aaaagctgtc agtactttag gtgttccaaa gtcctgtgga gagtggctta    48120
actggagttt atagcaactc tgagacattt tttttagta cagttctgcc actactttct    48180
atgtttataa acaatgaaca gatgcattca gtgctagtta cctagaatca actctcatac    48240
ccagcattac actcgaacgt tgaatgttgt attagtccgt tcttgcattg ctttaagaaa    48300
atacctgagg ctgggtaatt tataaaggaa agaggtttaa ttggttcatg gttctgcagg    48360
atgtacagga agcatagggg ttttttgcttc tggagagtcc tcaggaact tacaatcttg    48420 gcggaaggta aaggggagt gagctttctt acatggccgg agcaggagga agagagagag    48480
aggggcaagg tgctgcacac ttttaaacaa ccagatctca tgagaactca ctcactatac    48540
agtaccaagg gggccgatgc taaaccattc atgagaactc cgcccccatc atccagtctc    48600
ctcccaccag gccccacctc catcactggg aattacagtt cgacaggaga tttggatagg    48660
gacacatttt catcttaatt tgtatttgg tatagtttca taggaaagat ttaggttggt    48720
gttctctcgc atggaaattc acttagagct tttacttgct tgttacttgt tttaaagcct    48780
ttccaattga accaatttat taagggcatc tatttaattt tctatggtaa atgtactaaa    48840
aactagaaga gatcttactg ccttgatact agtttattgc ttgtttatta ggtgccctga    48900
aaagataact ttagcatcca ctgcttgcta accatccttg tcttcagcat cattagaaga    48960
tacgaaggag taaggaacgt gcttatgaga aaacagaagc tatggcatcc cccatcatag    49020
ccacatgagt cttgaatagg ccgcctgctt ctctgtcttc tttttgcaag tgggttgcat    49080
cctagctttg gtggtgtcct tgtaactttg gaattgcctt tgagagaaga ccagtctgtc    49140
tctttccagc tgctggacct gagagattgg gctgcaggtg gcaaatggtc gctactgaga    49200
aaactgaaag caatgacagc catataatat ggtgtgaaca ccatatggat caaactggga    49260
catcacagtc agcacacact catccaattc tcagaccaag gcacaccatg aaattctgac    49320
atttaggttt cctgcctctt aggaattcca tcaaaattat ataagtagca ctattctaaa    49380
ttttaaccta ctatcatttt aaaaaatgac ttactcacag ccctaacact catcggagca    49440
ggttgatatt gtagaaaact ctagccctat gcaactggag tgatcttgat gctaagacaa    49500
tatgacccaa agccttgtcc tttcctcttg gctatatgaa tattttctaa cttttgtgaa    49560
caaaatatgc ctcttttttcc tcatgatggt gtttcaaaat gagtcgatgg gtgttttca    49620 gttattagtg gataggagct ctcttagctt agtccttcaa aagcttgtgt ttgatgttgt    49680
agctttgtaa attatctcaa tgtatgcata cacacatact cccctaccaa aaaggtcaa    49740 tagatgctta gaattccttc cttccttcct tccttccttc cttttttttca gggtcttgct    49800 ttgtcgctca ggctggagtg tagtagtaca atcatagctc actgcagctt tgagttcctg    49860
ggctcaagta atcttcccat ctcacacctc agcctctcct gggaccacag gcatgcacca    49920
ccacacccag ctgatttaaa atttgttttt ttagagacac ggttttccta tgttgttcag    49980
gctggtctcg aactcctgga ctctagtgat cctcctgtct tgtgctcctt ggattacagg    50040
cataagccgc cacgcccagc cacgtagtat ttctatattt tacttttagc ataagtccgt    50100
gaaagaacta tatttctcat gctttgttca actgtgcaca tcatgatgtt gaaggatttg    50160
cacgatggct atgatggtgg ctgtcactgc actacaatac tttttttgaa aataagtgaa    50220
```

```
atattcattg ttcactagaa tagtcttaca ggcatttgtt tctttagaat ttggaaactt    50280 cttttatat tcatggtcgt atttcattct gctagcagtt taggcagatt caatctgtcc     50340
cactttccag tggtagaaac agtgtgaaga agtgaagtag ttgttggaaa atcactgtgg    50400
tttgcttccc aggggttgcc ttgtccactg attacaaaag tatcataaca catggcatct    50460
tcccacaagg agtttagagt ttgaaaagtc aatgtattaa tgtacatagg ggacccactt    50520
ccactcaaag caaacattga gtcaggtatc agagctcggt gggtgaacac gatggcattt    50580
aattatccta aattacttta tataatcaat atctactaac tgcctttgtt atgatgctac    50640
ccatcatttt tggagtcaca agctttcaac ctttgtctaa ctaaaagatg gatatctgca    50700 tttatatta ggtggtctgg aagccatagt aatattagag agcacatagg gaatgtttta     50760
gtccatttgg gctactataa ggaaatacca tagactgtgt agcttataaa caacagacat    50820
ttattgctca attctggagg ctgggagtcc aagatcaagg tatggcagat tcagtgtctg    50880
gtgagcaccc acatcctggt ttgtagatgg tgccttctcc ctgtatcctc atgtggtaga    50940
aggggtgagg gagctgagtt cccttttatg agggcactaa tcccattcat gaggctccaa    51000
cctcatgacc tcatcacctc ccaaggacct cgcctcctga taccatcatc ttgggggtca    51060
caatttcaac ataggaattt ggaggggcac aaacattcag atcatagcag ggagagagat    51120
gagccttgcc caactccatg aagccatcta gatttttttca gtctcagtcc tatttccatt    51180
ttttaatgtt gagttttgaa ctctattaat gtctcctggt attttcaaaa ctttgtagag    51240
ctttcatcat caatattaaa cctttcacat tcaaaggaca tgattatttt gtgtgagtag    51300
cgtgttgtta tttgacaaat gagtacaatt ataaataaat cttgaccatc ttgatagagg    51360
aaataaatgc acgtgtcaag atatactata atgcttttgt aatcaaaaca atgatggggc    51420
caggcgcagt ggctcacgcc tgtaatccca gcactttggg attacaccca ctgaggtggg    51480
tggatcactt gaggtcagga gttcgagacc accctggcca acatggtgaa accccatctc    51540
tactaaaaat acaaaaatta gccaggcatg gtggtgcacg cctgtaattc cagctactca    51600
ggaggctgag gcaggagaat cgcttgagcc caggaggcag aggttgcaat gagtcaagat    51660
ggtgtcactg cattctagcc tgggcaacag agtgagactc tgtctcaaaa acaaaacaat    51720
caaacaaaaa gcaatgatgg atagaacagg gtattattta aatgaaaact gtaaggggag    51780
ttgtatgctc tcaaatgtca ttatgcacag tctaatattt tcccttttac tttgtcactc    51840
tacctgctaa tttgcttcct taattcagag ttatgtcttt ggttattagt tataatatag    51900
gctgacagtt atgtagcgtt tcttctgtgc taggacctgt tccaagtgct ttttatatta    51960
actcattggt ctcaaccact ctacctgata gttaccatta gtattagttt cctatctgtg    52020
ctgcagtaac aagttactac agacttagtg gctgcttaca gctctagagg tcagaagtcc    52080
aaaatgagcc ttaggaggct aaaatcaagg tatcatcagg acaccgttct ttttggaggc    52140
tctaggagag gacagatttc cctgcctttt ccagattcta gagacttctt actctccttg    52200
gctcataagt tcctttctgc accttcaatg ccagtagatt gagtccttct cattctgtca    52260
tctttctggt tcttcctctt ttcttttttcc cttttctact tataaggatc cttgtgatta    52320
tgtggaccca ctggataacc tggaatcatc tccccatttc gaggtctgct gactgggaac    52380
cttaattcta cctgcctctt tcatttgaat ctcttttcca tgtaaggtca cacaaagtca    52440
caagttcttg tattaacaca tggtcatccc ggggggtccg ttattctgca gaccacacag    52500
ttgttatctt cattttacag acaagaaaga caaacagtga gagttaaatc acttactcag    52560
```

```
ggttgttggg ctgctaaatg gtagagccag ttaaaattag gagtgtacac agggaagcta   52620
ggcagtgttg tggtcaaggg ccttggcccc ctgaaggttc aatgaaaaat catggagaca   52680
aagtgatttt tactgtccac tcaactggat tgcacagagg gagagagaga ccaggagcct   52740
ggctggctgg tgagaaattc ttacccttg gccagcagtg tgggttcctg ggttctctgc   52800
actgtggctt ccaaaagagc agagcgtctt tgttgacccc gctcgctgtg tcataactgt   52860
aggggccaag gctctttact ccctaaaatt ttaatgaaaa atcactgact aggcagactg   52920
attaacagga gaaatgacat tacaagtgta tttaatgcag atacacagga gcctttggaa   52980
tgaagatcta ccctccaaat gaggtccaga agcttataca ccatcctgag gttacagaaa   53040
gagtgggggc ttggatccca gtaaaacagg tgatgggagg gggaggtgag gaattctgtt   53100
gaggagatta ttagaacaga gattaacttg taaagagttc tctttgaaaa ttaaatgatc   53160
cttggagaca cccttggaaa actgtctgct caggtgtggt tttatcttgt ttttttttt   53220 ttttttttctg taatagataa tgatataact tgaagggggtt gaaaaacaac tgtaggttgt   53280
caaatgtatc ccatatccta gccctcactt ctggttccat cttactttc tatgtaagtt   53340 ttcacttcta gttctatttc ttacttagaa attgtgttaa tcactggtat aagtagcatc   53400
tttgccagat aaaaggaaa aacaaaaaca atgctttat gacgatatgt gggagaaaag   53460
aatgtaatag tacttgagaa atattggaac tggttaaata ctagatggtg ttgggtagtg   53520
tttaataaaa tgattatatt tcatagagaa cattttctct acgctgaggc agaaatacag   53580
agataatttt atactatact catcctttct cctaatcata ttatttttta aaattcaagt   53640
tagaatttga gtgattgtat tgctgctgtg ctgtttttct cagaggaaaa atcatagcaa   53700
attatttcaa agatagatgg agaacatggt gtttctctat atccaggttg gattgaatgt   53760
tgtattagcc aatggaaacc ttcctcttca ccctctggag ggtcacggaa aatcatgtca   53820
caaaaggcag attaatagaa agcaatacat atttattaag ttgtagattt gtgtaacaca   53880
ggagccttca gaatgaggac acaaagatac aggggagact gtccaattt tttttattt    53940 caacttattt tagattcagg gggtacatgt gtaggtttgc tagatgggaa tattgcgtga   54000
tgctgaggta tagggtacaa ttgatcccaa tcaatggtgg taagcatagt gaccaccagc   54060 tagttttttca gtcctcaccc tactcacttc ccattctagt agtccctgt gcctattgct   54120 cccgtctttta ttccgtgtt ttctcaagct cccacttata agtgagaaca tgcagtattt   54180
ggttttctgt ttttatgttg actcacttag gataatggcc tccagcagta tccatgtttc   54240
tgcaagggac ctgattttgt tcttttttcat ggttgcatag tattccacag tgcatatgtg   54300
gagaccacat tttctttatt tattccaccc accactgatt ggcatctagg ttgattccat   54360
gtctgtcttt gctattgtga atagtactac agtgaacata caaatgcatg cgtctttttt   54420
gtagaacgat ttatttcct ttgagtatat acccagtaac gggattgctg ggtcaaatgg   54480
tagttttgtt tcatttaagt cctttgagaa atctccaaac tacttccac agtggctgaa   54540 ctaatttaca atctcagcaa gaatgtataa gtgttccctt tttctctgca aactcactgg   54600
catctgttat atattttttt ttttgactat ttaatgatgg ccttctgac tggtgtgaga   54660 tggtttctca ttgtggtttt gatttacatt tccctaatga tcaatgatgt ggagcatttt   54720
tcagatgttt attgattgct tatatgccct cttttgagaa gtgtgtgttc atgttctagg   54780
cacagttttt ttttgttttt tgttttgttt tgtttgttt tgtttgagac agagtctagc   54840
tctgttgccc aggctggagt gcagtagcac catctcggct cactgcaacc tctacctcct   54900
gggttcaaaa aatcctgcct cagcctccta agtaggtggg attacaggtg cccaccacca   54960
```

```
tgcctggcta attattttgt attttttag tagagacagg gtttcaccat gttggccagg    55020
ctagttttga gctcctgacc tcaagtgatc tgctgcctcg gcctcctgaa gtgctaggat    55080
tacaggcgtg agcgaccact accagcccct ggcacagttt ttaatggggt tatttggaaa    55140
ctcagttttt atgctaaggt tcaactaact gtggacaacc cagtagaaat agggttggac    55200
aaaaagggcc tgatctaaag ctaatggact gagtggggaa acccagccag tctgtctgc    55260 ctagattctt cttggcctct ctgagcagca ttccttctgg gtgtgaggta ggaccctctg    55320
tggaatgggg ggtcttagga cctacagtca aaaaggcagg tcagaggatt tatttatggc    55380
cagtgtttac agaaaggcag gggaaagttg aggtcatctt tttttggttt catgggtgct    55440
ttgtggggaa ggggtctggt ttgtatgacc tgctttaggg aggagggatt ccagttccta    55500
tggccagcct tcgggagaaa tggaattgag agacaacagg tcaggggagg gtcagagaaa    55560
aaccttttgc ctctgaggct gctgaagcct tcattttgtg gtatcattct ctgagcccca    55620
acaacacaaa ttttttaac ttcatgcaaa actcttaggt cagttgagcc tagaatacag    55680
gtttctacgc tgtgtggcta agtacggtc cttccctcct ctccacaggg agcagatgaa    55740
atttattttg gaggaagtta actcagaata aaggaccca gagatgtcag agagtggagt    55800
gggggcgaga gcccagactc cgtatctgtc ctgagaaagt taggacataa ggacccacag    55860
acatcagaga gtggagtagg ggtgagggcc cacgctctgt gtctgtaagg gaattgtcta    55920
cactctgcat actcacagcc atcagctttc ttgttcttcc ttccaagttg aaagtcactg    55980
gactccttca gtccatcct ggaggatccc tttcttggta aactgaactg gcagagaaaa    56040
gtattccata actggcattt ggaggccatt tgggcctatt acttatttac tgtacaatat    56100
gttcacctgc tgaggaagga cccctggcta tccacacaga cctgattctt aagtgagaaa    56160
agacagtctt acatcctaga tattttgag aagctttcaa taagaaattc ttttaaaaa    56220 ttgaaaaaag aatcatctgg aggtagcaca gacaacacca accaagaaaa caagagacaa    56280
aatttctaat ctgtaacttg taggagatat gatgaaatag tgactcataa aaaacatggg    56340
aattctatta aaatgtgaca tattaggcaa attaaataat cagattggag aacgattatg    56400
aggatatctc caatggacaa aactttaatg agagagagat agcaaaatgg aaaggaacga    56460
atatggagac tctaggaatc tgacattcga agagtatttt caggaaggac aacagaatac    56520
aaataagcaa aagtgactta tgaataattt ttaaaataat cccagcattg agggatctac    56580
acttccaggc ttatgaaaca acactcaggg ctcaccatag tgaatgaatt gaaactccaa    56640
actacaaaag cacattgcga gatttcagaa gaacaaatat atagggaaga tcctaagagc    56700
ttggaggctg tattaggccg ttcttgcatt gatataaaga aatacccgag actgggtaat    56760
ttacaaagaa aagaggttta attggctcat ggttctgcag gccgtacagg aagcatggcg    56820
gctcctgggg aggcctcagg aacgtgtcaa tcatgacaga aggtgaaggg aaagcaggca    56880
catcttacat ggctggagca cgaggaagag agagagagga cgtgctacag cctttcaaac    56940
caccaggtct cctgagaact cactcactat acagtaccaa ggggtgtgta cagtaccatt    57000
caagagaact ctgctcccca tgatgccatc acctcccacc aggcccatc tccaacactg    57060 gggattacaa ttcaatatga gatttgggca gggacacaga tccaaatcat atcagaggca    57120
aagaaaaaaa acttattaag aatcaagaat ttgtaatgtc atagaatgct tcatgtcttc    57180
actgaacgtt aaaagataga aactttcaca attctaagaa aaaacaattt actacgtaga    57240
actcttggag caaactgtcc atgggcaggc agggtcaagg catttacact gatgtagcat    57300
```

```
ttccgaaaat ttacctttg tgcaccctt cttggaaagc tgtgtgatta tgtcttcctt    57360
caaacagcgg aataaatgac aaatagaaag atggggaatc caaggaacag tggccttcac    57420
agaagagagc tgaaagaatg caggtctcag attaatgccc agagcaggct gggacagctg    57480
gaatcctaga gtgagacttc aaggagaaag tacataaaag aaaaggaaat gagccatttg    57540
accatgtaga aatagtactt gagatgggct ttagttccct tggaacattc agaaaaattg    57600
aacaatagac acacagaaaa gcatgaaatg aaaatgtgaa gttgttgttg tctccagata    57660
aaacaggagg caattcaatg aaggagattt aattagagta gaatgcttca ttcaggagtg    57720
attattaatt gcacagttac aataaagtta aagagagaag gccaggtgta gtggctcacg    57780
cctgtaatcc cagcactctg ggaggccaag ataggcagat ctcttgagtc caacagttcg    57840
agaccagcct gggcaatgtg gcgaaatccc acctctacaa aaaattcaaa aattatctgg    57900
gcatggtggt gtgtggctgt agtcccagtt actgcagagg ctgaggtggg aagattgctg    57960
gagcctggaa ggttgggct gcggtgagtt gtgactgtac cattgcactc cagcctgggc    58020
aacagagcaa gaccctgtct cgaaaaaaca aaaaggcaga aggggcaaat agagtggtgg    58080
ttgcccattg ataatttata ggtaatatct aaaaataata tatcaagaaa aaatagcata    58140
aactattact tagaaatatc atagagcata tatttggaga ggagaagcta agaaatctga    58200
aagcatttgc tttctaaagc aagtgtggtc atgggatgtt gtatgttggg caagaaagtg    58260
ctgtttgttg tgcaaataac acttgtagta gtttgacctt taaaacttca tgcatgcctt    58320
tctttattga aacaaaattt tttcaaaaga aaatgataa ggccaagatt gaatggtatg    58380
tgaatgtgaa tatgacagtt aaaagcatga tttctcaaat gtacctgccc attggaatca    58440
cctggagaat gtaataggta ttaatgcctg tgctgtggtc ctccagagat tctgacttgc    58500
tcggtctgca atgcagactg ggcagtgaaa ttttttcaatt ctccttaggg attctaagat    58560
gcagcagagt ttaggaagca tggatctagg tagctcagat tcttacttga atttaaaaat    58620
ctctagctgg gtgcagtggc tcatgcctgc aatcccagca ctttgtgctg ggctgaggtg    58680
ggaggattgc ttgagcccaa gagttccaga ccagcctggg caacatagcg tgcctgtgtt    58740
cccagctatt caggagactg aggtgggagg ttcgcttgag ccctggaggt caaggctgca    58800
gtgagctgag attataccgc tgcactcaag cctgggcaac agagtgagac cctgtttcaa    58860 aaaaaaaaa aatcttgtcc agtgttctct tcaccaagat acagtggttt cagtaataaa    58920
ctactactaa catgatgatt tagattgagc caacttcatc actcagtcat ttctttgtta    58980
tctgatatgt tctttatgga aaggcttaa ttgcttgaaa atgacctaat gcttctccca    59040
agcttcccat tttttttcc ctttcttaac tgaagtcaca gaatgttctc gtgtgtggaa    59100
tgctttgtct atcctacggg aagccaattg tgcatggctc atggcgccat gctggcttaa    59160
ttgttccaat tcctcctgtt tctccgacca cacatgaggt tgaattaaat ataatttcct    59220
cagtttgcat ttcccaggca gtcgtcctaa gtggcttctt ggaggagctc tgtgcattcc    59280
actggtctaa ttctgtgatg ccctttaact cgagggccaa ggacataatt accagctcta    59340
gaaattcgtt ccgtggtcaa ggatgcttgt gcagaggcca aattttcttt cattataatt    59400
tggcctttgc caagcttcaa agtgaagggg attgagttcc tactaaagag tattggcacc    59460
taggaagtga atgctttctc tatcttttgc agctagtgtg ttctacattt cttcaatgta    59520
ccttctgcct ggtaaatgtc agattatttg ttgatcatcc tcagggtgta gttctttgtg    59580
ttgttaaata agaacccagt ggcttaaaag cattggcttt tgagaagtca tttttatcct    59640
ggatgataac tcaaatccat gcagtgctga tatttacagc tgggaggtga catgatctta    59700
```

```
tcctttggtc tgttgctcaa attattgatt tcagtaggac ttactggctc ccttctgtct    59760
tggggatacc tttgatctgt cttgccttgg gggaccctcc ctctgacctg gaatagcagc    59820
ctatttccac aagaagggac cctctgagag aggacagtct tcataccgcc tcttccgatt    59880
ttcctttatc ttttatgggt tttggcttta aactttact cttagaatgt ccttaaagct    59940
aatgattttt taatgttctc tagtgtatta ctaaaagctc ttcatctact gaaagactg     60000 gggcaggaag attgcttgag cccaaaaggt cgaggctgca gtgagttgtg atcctgccac    60060
tgtattccag cctgggtgac agagcaagac cctgtctcaa aaaataaaa aggacaggtg     60120 cagtggctca cgcctataat cccagcactt gggaggctg aagcaggagg attgcttgaa     60180
gccagagttc tagaccagcc tgcaacatag agagacccat ctcttcaaaa ataaaaaaa     60240 aaatagctgg acatgatggc acaccctgt agtcccagct tcttgtgggg ctgagaccag     60300
caggaggact tctagagcct aggaattcca ggatgcagtg agcaatatgt atgtgttaat    60360
acatagtgaa accagttatt ggagaattag tatatgtcct cccacaaatt cagtatgttt    60420
tcctaattat ccaattaatt caaagggcat aaacataata gatgcaaatt attttacgtt    60480
ttttgtttaa aaacctttt gactgaatca gtctatgacg ctttagtatt tgaagttgcg     60540
gacagaactt agtcttaaga tagcactcgc tttgttgata gatttccatg gagggaattt    60600
ttgccagatg ataatttagc ttgaagatgt tatagatgtg gacagtcaca ccctctaagt    60660
tacacagtct ggggtgggcc aattgaaaag aacatgcaga aacacaggct tgttaaggga    60720
taattaaacg tgggggaaat agaacagtca tggcagagga tttaataggg tttaattggg    60780
ttaggaagaa taggccggag tgaaagaata gctcttaata ggaggtctag aaatagccaa    60840
ggaaagcatt aattgcagaa aatctgtgac atctgattac tgtagtgaaa gaaagatcca    60900
cctttaaaaa tcctatctat acagaaagaa gtgatagga gaaggaaatc ttcccacgga     60960
catatttaag aaaaacagtg gggaggtttg agatttcaaa gggccatggt tcaggttata    61020
attcaaaaga gaggcaaatg atagtcctac tcttcttgag tttcaggaag ggggaggatt    61080
ttgccacttg ctgtgaaata attttggagc ttctataacg ttgatccttt catcctattt    61140
tttcttggac ttgggatgtg gggagtggat aagatgggga tggagaagaa gcagggtttg    61200
aaatgcctct tttgattctg ttcattcccg gaattcttct ccatgggcct taaagagtag    61260
agactccttc ccggtgcatg acatccagtg gccaattaat gaaactttat ttcctcagat    61320
aagttccctt cctccattaa tttgtgggaa ttcagatgaa aacttacttg gactgtggtt    61380
ttctatgtgt ttgtgaatgg aaggacatgt ttgtctttga ccttccttta gtttcacgtc    61440
ttagtcttga tatttaagta gctttggttc agacagagaa ggaccatgtg tgcagttgct    61500
gggactgctc tctagcttgg aggttccctg gtcttgggaa agatctccct gcccatgca    61560 ggtggcatag atgtttaatt ttctacatga gagaagcgct agagtttttt tattcattac    61620
ttgtgtgcac agctgtggcc tctagggaag ctcagctgag gtggtctcag gttccaccaa    61680
aggttaccgg ggagagatga ctaggaagac aggaagacct gtctcacttg ggagggtatg    61740
gcaagagcta ggcaagacct cctggtggag atatttgcct tttattcttt ctttttttt     61800 tttttttttt tttgagacag tttcactctg tcacccgggc tgaagtgtag tggtgcgatc    61860
atggctcaca ccaacctccc cgtctcgagc tcaagccatc ctcccacctc agcctcttga    61920
gtagctaggg ctacaggcat gcaacaccat gtccagctaa tttttaaatt attttttagaa   61980 acaaggtttt gccatgttgc ccagactggt cttgaactct taggctcaag tgatcctccc    62040
```

```
gcctcagcct ccgaaagtgt tgggattata ggcatgagcc atgttgcctg acccatttat    62100
tctcaagtac ttatgctcag ggcaggtctt ccaagggaag agaacagcca gataagactc    62160
gtatgagata gctgaggagg tggcatttca tccttccatg cacatgctcc ttatccacaa    62220
gcagaaagct gtaacctttg ctgtccccac taggtcatga taggtagata cgcaggtgat    62280
gaccacagac tggcaattag ccaaggattc tcagctgtgc acgctacatg tgtgagtgtg    62340
tgtgacagat ccctttggcg gtttggtgga aaattgatac attttgtaaa aatgatatgt    62400
ttaagtcata caataaggta aataacgcat aaaaggaaat cggttttatt gaaatagtta    62460
ccaaggtata ttaatattaa tatttaaagt tggtgcagtg gctcatgcct gtaaacacca    62520
gcatttgggg aggctgaggt gagaggattg cttgaggcca ggagttcaag accagcctgg    62580
ccaacaaagt gagactctgt ttctacaatc aataaaataa aaaataaaaa taaaagata    62640
tatttaaact gggctacagt aatacatgtg catctttatt gtgtgctaag tacctggatc    62700
tacttaagag gttcgtaata gtcacaattt caaagtacaa taagcgtaaa cagtattttg    62760
ggatatctgt gataacagtg ttaagtgtcc tacctacacg ggtaatggaa gcaaatacta    62820
aatttcagtg catggtagtg aaactaaaga tgtaattact tttgcccatt gcaatttgta    62880
gaacccatgg aatctatcta aagactcctg ggtggcaaag gataaatgct tgagggtatg    62940
atacccatt cttcatgatg tgattattac atattgcatg cctgtatcaa aacaactcat    63000
gtgccccata tatatatata tgtatatgta tatacacctg ctatgtactc acaaaaaaat    63060
aaataaagac acctgggtgg gattgggggtt tttggactta gggtggagaa catctgcatt    63120
tagaattgtg tagaggaaag gttttgattt atttattata cctctgtttt ctttaaaaaa    63180
cctgcatgtg tagtaggaat tttgccagag gtgggaatgt gagagtcact agtttgcagc    63240
atagagcatt ctatactgag ataattattt ttatgtcaaa aagaaagtga agaatctggc    63300
agattagaat cttcatgtta ttttcattta aaaagcttgg aagtgtcaat atcaattaat    63360
attgactgct atttactgac attttttggca aaaaacattt catttaatg aattttgtct    63420
tgtttgaatg tttgtaaggc tttggaggta gttttaggag atagttgcct ttgattcctg    63480
aggtatattc ttgggtctac cctgattctg tctcttgact ttgcacctct ttccttcctg    63540
aaccctgttt aaaagagcct tccttttacg actcttttct tccatcctat tcttccttcc    63600
catgctaatg tgagacacag aggttttat gagaagcctg ttgtctatat gctggatctt    63660
ggaagccttg gttatttcct agagatggaa ggtctgatct cagttaagtt ctgaccccag    63720
gacaagaagc ctctctggag taactgactc actgggatag agcctgtttt cacaaattaa    63780
tattcctgtc tggggagggc agaggaaaca ttttggggag tgggtggagg tgatgaggtt    63840
caagcctgag gatgaagctt gccttttcctg ggagcttgta cagtgtcata ctcaggaaat    63900
aaactgtgtg ggaaaggtgg tgtttagtaa tctagagccg aacaccttgt aaggccctca    63960
ccttgtcatt ctgcactgtc agaagcacat gagaaaagag tgtaggctgc cagagcaagc    64020
atcacaccga aataggaact ctcagatag agccgtctgc ctaaaacaaa gtaaccttag    64080
caaataggat ctgtgctaca gaaaatggag cactctagcc agggttgtga gatggagctg    64140
gtcctgtggt cacaggtggt gtcttgggaa acgttctgaa gacactcagc ttttcggata    64200
ttgcacagtt cattaggaga ggtatgggca gtggttatga agctccttat gtaagagaca    64260
tagagataca ctcaacagta ttactccaga gggttctggc tcctgtcttg cacttgggag    64320
tacacacttt ttcttgtcca cattaacctc caactgtcca catgatcaac catctgcaga    64380
cccactgcca gttgagggtc gtgccaggtc agaagtacta actgcaggtt aaactgtgct    64440
```

```
atttagaaat tgagtgtttt ttcttactc aaactgacag ttttcctttg tagaagaact    64500
cactcagctt ccactctggc ttaaatattt cctttacatg atcaatatta tctctgtcca    64560
tcagatacag caatgagaaa gccttttaaa ggaaatgagg ttaaaagtga ctgggtatct    64620
agaattcttt attttgtttg ctaaattgca ggcaaatata ttcccagaac tagttgtgat    64680
acctttcag aaactggctt atttgacatt ggctgaaagt aatactctaa cactttactg     64740
ctgtgtcaat gagtgaaatt cctgcaggca aaaacaatag ggactacatc gtgaagccta    64800
tgagaatttt atggtggaaa catgagtgga gcaggtggtg gaagtagctc atcttctgtg    64860
gttgtggtac ccacaggaga tgagctaagg agaatgccct gaaacctaac cttgccaatt    64920
ttctgtcttc tgtgtcctgg ttccttctgg tttccttgtg tctctttttct tccttttaat   64980
ttaatagtgt ttactgaaga ccttctgtct tccaagttca agtattagtc atctctgggc    65040
tttgcccta gatacttatc atagtctagc aatgaatgta agcattgagg aagtaatggt     65100
gacataatgt gaatgttcag tgtggtatca tcttccccac tctttgtaaa tcttggtggt    65160
cttaattctt gaatgtcaat gcttacccc tctatgctgt ctttacagaa gtcctctggc     65220
ctagctctct ctacatgtct aaaattgtag aagcatcttc tgggcactcc attgcaaagt    65280
ccattctgca gaagcccacc atcccacaga aggagcaggt gggaggcagt ggaccacagg    65340
ctggctgcat ggtagcaatt gaaaagcaat ggagcacagg ctggcttcat ggtaacagtt    65400
gaaaagcaat ggagcacagg ctggcttaat tgtagcaatt gaaaggcaag cttcatctca    65460
tcagctggag tgtttactac ttgaggatgg gtacttgatt ggtgtatctt tacatttat     65520
caaaatgggt ttcaccttgg aagcattcag tggtacctca gtgaataatt gtaattagct    65580
aggatttctt tggggaatac ttattgttct aaatttatat gtgtttacat atatgtactg    65640
tattagtctt ttttcacact gctgataaag acataccgga gactgggtaa tttataaaga    65700
aaaagagatt taatggactc acagttccat gtggttgggg aggcttcaca attatggcaa    65760
aaggcaaggt aagaacaaag gcatgtctta catggcggaa ggcaaaaaga gagagcttgt    65820
tcaggggaac tcctcattat aaaaccatca gatctcatga gacttactat cacgagaaca    65880
gtatggggga aactgccctc ttgattcagt tatctcccac agggtccctc tccctatacg    65940
tgggaattat gggagctaca attcaagatg agatttgtgt ggggacacag tcaaaccata    66000
tcacatacat atgcatatct ttatgtaagg tgtgtgaata taggtgtgta tattcatata    66060
ctcttgtact ttctcaaaca caaaccatag cacgtgcaat aatatccttg agttacatct    66120
gctactctgc ccatttttaca cataagagat ggaagcattg atggttatat taggtagggt    66180
tctctagagg aacagaacta ataggacaga tagatatata aagggggagtt tatcaagtag   66240
tatttgttca cacgatcaca aggtcccaca acaggccatc tgcaagctga ggagcaagga    66300
agccagtccg aatcccaaag ctgaaggact tggagtctga tgtttgaggg caggaagcat    66360
ctagcacagg agaaagatgt agacttagag gctaagctag tctagtcttt tcatgttttt    66420
ctgtctctgc tttatatttg ctggcagctg attagatggt gcccacccag attaagggtg    66480
ggtctgcctt ccccagccct ctgactcaaa tattaatctc ctttggcaac accctcagag    66540
acacacccag gatcaatact ttgcattctt caatccaatg aagttgacac tcagcattaa    66600
ccatcacaat ggtgtataca cccttctctg gttgctgatg gagttaaagt gagagccagg    66660
atttgaatca tagtcataaa actgcacaaa acctctgccc catactacct cccagataca    66720
taatacacac atgagtaggt gtttttgtgc ctgttatagt gcatttgagc ctgttgttct    66780
```

```
tagtttgctc ttatgtagga ccatctctct gaaaacagat gatcagcatc atatgcaaca    66840
ggtagtattg attatctgta gcataaaggc atggaacacg ggattttcag ggaatggagt    66900
aggaaaaatt cctgaaccta agcagcttaa tagtttaata tttcacttgg ttagttcgaa    66960
tatatatgtt catatgcaca tgcatgaaat gacatggata aaataagttt taatgtattg    67020
tatctatata aatctcttta aacctcaaaa aatgtatata tccaaactaa ttatttgtca    67080
gtctctccct ctctttctcc ctctctctct ttccacgtat ttatatataa atatttctgc    67140
aaactaacca actgaaatat taagctccta tctatgtttt atatgtattt ctgcaaatag    67200
ccaaccaaaa tattaaagca attaaactcc taaatataat atttctttta tctattatat    67260
tatttcttca aactaaccaa ttgaaatatt aagcttctat gttttatata tataaagtat    67320
ttctccaaat aaccaagcaa atattgagg tattaagctc ctgtgaatgt tttatattat     67380
tctatgtata tagaataata tattttatat gttttttatt atattttata ttattctata    67440
tgtagaataa tatattttat atcctatatt atatatagaa taatatattt tatatccta t   67500 attatatata gaataatata ttatatatcc tatattatat atagaataat atattttata    67560
tcctatatta tatatagaat aatatatttt atatccctata taatatatag aataatatat   67620
tttatatcct ataaatata tagaataata tattttata cctatataat atatagaata      67680
atatatttta tatcctatat aatatataga ataatatatt ttatatccta tataatatat    67740
agaataatat attttatatc ctatataata tagaataa tatattttat atcctatatt      67800
atatatagaa taatatattt tatatccta t attatatata gaataatata ttttatatcc   67860
tatattatat atagaataat atattttata tcctatatta tatatagaat aatatatttt    67920 atttatatatt tatttttata atatattttg taatatatat gttttttata tagaataa     67980 tatatttat attattctct ctctatatat agcaggttag tttgaagata tctatacgta     68040
taatatatta aaatttattt ttggccaggc gcgttggctc acgcctgtaa tcccagcact    68100
ctgggaggcc aaggcgggcg gataatgagg tcaggagttc aagactagcc tggccaatat    68160
ggtgaaaccc tgtctctact aaaaatacaa aaaattagct gggcatgggg gcatatgctt    68220
gtagtcctgg ctactcagga ggctgaggca agataatccg ggaggcagaa gttgtagtga    68280
gccgagatct caccactgca ctccagcctg ggtgacagag tgaaactctg tctcaaaaaa    68340
aaaaaaaatt attttatega tataatttca tatatgataa gttaaagtac aaactcttga    68400
aacaactcct cttatatatg agggggaaaga agaagattat ttgtacagta caattagtac    68460
agtgaattct gggaaaaagt cagtaaatac tcatttcaaa tcctcatgta caattcaagt    68520
aaagaaaaat ctggtggcat ttttatatcc tgctaataaa ggttatctgg tgttggaaaa    68580
cataatttat ttttacatgt acatagtagg tgtatatatt tgtgggtaca tgagatattt    68640
tgatataggc atatgtgtaa aaatcacatt agaataaatg gagtatacat cacctgaagc    68700
atttatcatt tctttgtgtt acagactttc caattatgct tttagttatt taaaaatata    68760
cagtaaatta atgttgactg cagtcaccct gttgtgctat caaatactag atcttattca    68820
ttctgtctat attttgtgc ccattaacca tcctcacttc tctctctctc ccattaccct     68880
tcccagcctc tggtagccat cattctactc tctgtctccc tgactgcaac tgaaagaaat    68940 attttaaag aataggctgg aaggccacac tgactctcac tgtttctggc acactaaacc     69000
ttgccatttt ctgcagtagg gattgtctcg cttcagttat gccttgctac ttcagtgaag    69060
gactttctgt tcccactggg ctcctatact gagtctgctt tggagataat agtctgagat    69120
gtcagagcgt cttagtggtg aaagcaactt aagaggtcac tggcacaagc cctcgttttg    69180
```

```
cagtggaggg agttgatggc gagggcactt ggctaattag tgaccagggc tatagcaggc    69240
tcaggttcca tgactgtgct taccatggct ggcaggatcc cagggctttt ctgtgtaata    69300
tgtgggtgga tggtctattg ccttgggctt gtcgcataat catggagaaa acagtttata    69360
ttttcccttc aattttaaa tccaagatag tttgatagca catgggaaaa taaagtcatt    69420
gagtaaaact tatacggatg agaatctttt gattaaattt tcattgtaaa ataatcatag    69480 tcataaaag tgtatcaaaa tgtgtatttg gatattcatt ttaaagagta aaaataatc    69540 agatacatag tattgtaccc actgacagac aaggaaagag aacattccca ctgtttttat    69600
atatcagtgt gagttgcttc cctctctcct acctttcagt gaaatctaat cccccaagat    69660
ttggttttca tactgtcctt gctgtatatt tcaggacaaa catagctctg agcaatatat    69720
tgtttagttt tactattatg taaataaaat cacactattt gtagtcttct gtgacttgcc    69780
ttttatgttt gagatttttcc cattttcctc catatatctg tattttattc attttttgact    69840 gttttgtaaa gccttctgtt ttaatatgcc aacatttatt tattcattat cctatttatg    69900
gatatctgga ttgtggcaat attttttgca attataattg gggcttattt atcctcagca    69960
aactaacgca ggaacagaaa accaaacacc gcatgttctc actcataagt gggagctgaa    70020
tgatgagaac acatggacac atgggggagg gaaacaacac acagttgggc ctgtctgggg    70080
atgcccggag gggagagcat caggaagact agctaataga tgctgggctt aatacatagg    70140 tgatggggttg atttgtgcag caaaccacca tggcacatgt ttacctatgt cacaaacctg    70200
cacatcctgc acatgtacct tggaacttaa aagttgaaga aaaaaatg gggctgcagt    70260 ggacatttcc gtgcatgttt cctgatgcat gggagttcta gttgctccac atcgttgctc    70320
agtacttggt atcattgttt gtttgtattt ttattaatcc tattgtgatt tcatctgcat    70380
ttcaccaata atgaatgaca ttgagcctct tgtcctatgt tgaggctatc tgtagatttg    70440
aggactcctt cctggatgtg gatttatggt ggagaaacca acaaagatgg ctttgagtgt    70500
aggctgaatt actagaaaag taatgatcta gttatccaaa tatgaaacaa aagcatggaa    70560
gcagtttggg gattggagaa tgagattttt aggagcacca taagatgtct atctgactat    70620
attcttgaag agaaaatagt catggcacta caggcatggt ggcacatacc atgttatcag    70680
ctggcactac aggtgtatgc ctccatgacc ttgaggacat atgactttga gttcggtgag    70740
agagatgaac acaaagccta gagagatctg caaatcattt gatttagatt tagaaattgt    70800
gtctggaaaa catttaattt cacacagaaa atcaagcatt aacgcacttt tattatttgc    70860
cagtccttgt gctagcttta gatatgcaga agatgaataa aagaaaaaa tgcatcacag    70920 gtagggatag ataccttcat gagaatgtaa gctcctagtg ggcaggaact ccttctttac    70980
cccattacgt acccttacct agcatagtga tctttacggg atacttctgt ggtctgaagg    71040
cttgtgtctt tccagaatcc ccatgttgac gttgtaaccc caaagtgatg gtgctaggag    71100
gtagggcctt tggagctgat gagatcatga gggtggatgc cccagaatgg tattaatgac    71160
atttaaaaag ataccccagg gagattcctt gcccttttcc ccttttccaa agttataagg    71220
aaaatacagc cctctaggaa gcaggccctc accatacact gaatctacca tgccttgatc    71280
ttggacttcc agcctccaga gctgtgagca atgaatatct gtggtttata agcccccaa    71340 gctatgatat tttgttacag cagcctgaat ggactaagcc aacttctaag ttttggtgtt    71400
gtcttatttc tttggtcggt gtaggatctt tctgtccaca tagtttactc tagaaagatg    71460
tatgccctat tcctcatggt atatttgtct ttcctatctg tggaatatcc tcttatccaa    71520
```

```
ttcgtcttgg ctgggcaaca tataagccat taactctttta cccttgggtt tagtttgggt    71580
tctgctgagg cccctgctga aaattctggt ttctacaatt atggctcatg catgttcctg    71640
acccattaaa cttcagtgga agaacagaaa tggtgaggga ggtgatggag ttgataccct    71700
gagctgccat atggtgcaag atcatcttga agatagaaca tttggcatcc ttttttttt    71760 taagagatgg ggtcttgcta atttgcccag gctaaactca aactcctggg ctcaagtgat    71820
gctcctggct cagcctccca attacctggc aatacaggca tgtgccacca tgcctggcca    71880
catttttact ctccaattgc ttaatatata gtaaagataa tggttcaaaa tggtaaattt    71940
tttttgtgtg tataccaata acatttttt ttaccttaaa catattcaat ctttatttga    72000 caattttta aaatttcaac ttttttttt tattcatggg atatatctgc aggattttt    72060 acctgggtgt attggatggt gctgaggttt gaggtacagt tgattctgcc acacaggtat    72120
ggagtatagc acccaacagg tagttttct acctttcc cctccctctc cctgctgtag    72180
tagtcccaag tttgttattg ctttatgtcc atgagtaccc aatgtttagc tcccacttct    72240
aagtgagaac atgtggtatt tgattttctg tttctgcatt aattaactta aaataatggc    72300
ttccagctgc atccatgttg ctgcaaagga catgatttca tttgttttt tttgtttgtt    72360 tgttttgttt tttgagacg gagtctcgct ctgttccca ggctggagtg cagtggcgcg    72420
atcttggctc actgcaagct ccgcctcctg ggttcacgct attctcctgc ctcagcctcc    72480
tgagtagctg ggactacagg tgcccgccac cacgcccagc taattttttg tatttttagt    72540
agagatgggg tttcactgtg ttagccagga tggtctcgat ctcctgacct cgtgatccac    72600
ctgcctcggc ctcccaaagt gctgggatta caggcgtgag ccaccgcgcc ggctgatttg    72660
tttttatggc tgcatagtat tccgtggtat atacgcatca catttctttt attcaatcta    72720
ctgttgatgg actcttagat tgattccatg tctttgctat tgtgaatagt gctgtgatga    72780
gcatacatgt gcatgtgtct ttttggtaga acaatttatt ttcctttgta tatatacccca    72840 gtaatgtgat tgctaggtca aatggtagtt cctctttaa gttccttgag aaatctccat    72900
actgctttac acaatggctg aactaattga cgttctcacc aacggtgtat atagccttct    72960
cttttctctg cagccgcaac agcatctgtt gtttttgat gttttatgaa tagccattct    73020
gactagtgtg agatggtatc tcattgtggt tttgacttgc atttctctgg tgaaaaatgg    73080
tggattttta aatgggattt cattttaga tttaatagaa actgcatagg tgactgtgca    73140
aagaactctt aagatttgac aaaaggcaaa ttagattgta atctccttta tgtaggaggg    73200
gaaataaaaa ccagaatatt aaaatatcta catgtacaaa aatagacaaa gtggcagatt    73260
gctggtgttg gatggatgtt gagcagggat ggaggacttg tgtgtgcatg catgcatggc    73320
catgcgtgga gagtggtcat tcattttggt aacagcatag agctttgggc ttcagaacaa    73380
aagataagcc acatcccact caggtaccct aaaatgttgt ctccactaga cacaaaagaa    73440
aaggaagcca gagatgtctg tagcttatgc agagttttgg gaatagctat tctagacttt    73500
cttagtgaac agtatagaag gattattgta caagcccagt aatttgggca aggatcagat    73560
tctgttgctt ttgttttctg gatgctccgt aatgaatgtg agatggaagc ggatgtctca    73620
agtgcttctt gttctcagaa acctcctggc agcagacatc tcagtgggcc cagacgttca    73680
gcgtggctgg aagtaaaaca cagggaaggg tgctctttct cagttatcct atttttttt    73740 aaaagcatct acaaagcttc ctgttttcta atatattccc aggcctttga agacaaggc    73800 cataaacacc caggagatgt gactttattc ttttaaggt ccagatacca aaatgcctgt    73860
catcagggct caccttaatt aaatacgtat cttaaaatta aaccaatctc aatttaagga    73920
```

| | | | | |
|---|---|---|---|---|
| atgtatactt | tggggagaaa | tttattacaa | tttttattca | gaacacttta aattctgata | 73980 |
| ggcctgaaga | gtgtgagcct | caccttaatt | gcaacctgag | tcagaataac tgccctgcag | 74040 |
| agaatcattt | aaaataccca | atcaagttat | aaattagtca | aaatgccatt ctgagatatt | 74100 |
| attattttat | gcagtctttg | cagagaatac | atgctatata | gcccttcttc actcccaaag | 74160 |
| tatatgtata | tatttaatga | agttttcacc | tttttatta | aaattttttaa tccattaaca | 74220 |
| attttagaat | tcattttgta | gcatatcctc | tttatcttag | agatattaaa tatctaccta | 74280 |
| tttatgaata | actatcaata | accacgtttc | acccttgtg | aaatccttt cagttttga | 74340 |
| aactcacatg | ggagatcttg | tttttttttt | tccccacaag | gatgtaggtt ggttaaattt | 74400 |
| acagtggttc | tttaatgatg | ataatgcaca | tttgattgat | atcaataata aatattgata | 74460 |
| tcttcaatat | caacatttct | tgtaatgcta | aaaatttaca | agttgccaat ttttgaata | 74520 |
| tgactatatt | ttcacacaca | cacacataca | cgacagcact | aattatattc actaaatata | 74580 |
| cctacagata | cttaatcatt | tacacagcca | ctataatttt | atacttgatg ccttaaacca | 74640 |
| gtaattctcc | cttgagggtg | gttttggccc | ctgggctacc | tagcactatc tagagacatt | 74700 |
| ttccatagtt | aaaactgggt | aggaggtgcc | actatcatct | agtgagtaga ggtcagggat | 74760 |
| gctgcaaaat | actgtacatt | gtacaggcga | cgcccccaca | acaaagaatt atatggttca | 74820 |
| caatgtcatt | tatactgaga | tggggaaacg | ctgggcttta | attatagcaa ttttgtgcaa | 74880 |
| attagccaaa | tttcaaaaaa | caagggagtg | aaaaaagata | gctctcaacc tgtgaatatt | 74940 |
| gtgaatgccc | aatctagacc | tagtaagtgt | acagatgccc | ttgggcgcgt cttcttaggt | 75000 |
| tgctgctgct | tcataatcgc | tcactgccca | tcaggacctt | gtgggatgta gatttaggca | 75060 |
| gaggagggtt | ttgatcatac | agctggatca | gtcataacca | ataagtgact catagtctca | 75120 |
| ttcacattga | gtttgagaat | ttaaggtgtg | ggctggaatt | ccttatggaa ctaactttat | 75180 |
| ataccttgga | agaagtccac | ccactgaatt | ctacatttat | tgagctctgt gtttcaggga | 75240 |
| atgtgcaata | ccttgaggat | acatactatc | tcatttagtc | ccaagtagct tttaaatatt | 75300 |
| tgagagtggt | tttggccccc | aggctgaaag | taacagctac | ctctggttaa aaatctttca | 75360 |
| ggaaagaagc | aaccaaacag | gacatcacct | ctttgttttt | cttgtctgtc tcttaattat | 75420 |
| tcagaaatgg | gattgctgta | tggcagacat | ccaaatgttg | tctacagtag aattcagaga | 75480 |
| tagaagcaaa | cacctaaatc | agtcattggt | gagatgctat | ttgtcacttt caagttata | 75540 |
| atccagattt | tcagtgcgtt | ttcatccaac | tctggtgaac | ttttcccagg atgtcatgta | 75600 |
| ctatggaatt | tcccccccatt | gtattattgt | tctgtgataa | atccagctcc aatatgtttt | 75660 |
| atttaaaaaa | aaaaagccat | gtgatgtatt | ctgttcaact | gattacttaa atgaaatgga | 75720 |
| taattatttt | ctgatgcaga | tgctctgaat | aacccacaaa | atccttagaa acacattgt | 75780 |
| atattttgag | ttgaagaaca | tgctaaaggc | accctccttg | caacacctag tgaaatattt | 75840 |
| tctgttccta | ggggatcatt | taacaacata | atgtccattc | ctgcacagca ttcttttatt | 75900 |
| gtcacaggag | cagcgactta | tgtagggata | gttatattat | ctatgtaaag acaaattgag | 75960 |
| gtggtgaccc | tttaaaagtt | gactccaggc | tcaatgggaa | agtaactcaa atgcagcctc | 76020 |
| agcttttaa | atgggctgaa | gggtgaagag | gatacctct | aaggcatgca gtggcttact | 76080 |
| ggaaagtcag | gataattgta | tcaacacttt | taattatgaa | tgaagtcttc aagaaactag | 76140 |
| cactacagca | tgtacttgaa | atgcaccatc | ttgtatagtg | ttttacaagg aaactgagat | 76200 |
| tcagagcagt | gaagtgtgta | gcctaaatat | atatgcactt | gaccagacca aggagaattt | 76260 |

```
gtgtccaaag tctacactct tttcatttga tgatgttccc tttgtggcct gataaatatc   76320
cacatcatga tgccagattg acttggatgc atgcttccat ctttctccta ctggaaaact   76380
tttagagctc catgcatgtc tccttaggaa aatgtgacaa tttccttaaa catttgagaa   76440
acagtgtttt ggaagtaccc atgtattgat aaccagtctg gtaaacaata gcaaaactgg   76500
gaggtgttgt tactataatc tgcataacct gtataactct tgaacatctg tttgatcatt   76560
caacacagat ttgtttagtg ttttctaaat gtcaggcatt gttcatggtg ataggatgta   76620
cagaggaatt aagacaagtg gtggctgcta ggcatggtga ctcatgcctg taatcccaac   76680
actttgaaag gtcgagggt aggatccctt gaggccagcc tggacaacat agggtgaccc   76740
aatgtctaca aaaaaatcca acgaattagc cggacatagt ggtgcatgct tgtggtccca   76800
gctactcggg agggtgaggc gggaggatgg gttgagccca ggagttggag gctgcagtga   76860
gctatgacag caccactgca ctgcagcttg gcaatatag caagacacca tctctaaaaa   76920
aaacaaaata aataaagaca ggtgatgttc ttgctgttgc ctactatgtg gagatggcac   76980
tatacacatt tctatacaaa tgaataggaa tttcatagag gatgttgtg gatttcgtgg   77040 aagagccagc cagtgttcta ggtggtcgtt gtgtggcttc attattcttg tctgctttct   77100
tcctctttta ggctgccttg gagttttcat aagaaattgt ccctggaggt gttggatgat   77160
cacagcttcc ttggagcatt gcagttgctg gaatccagtt tcaggattaa gggagggctg   77220
cctccttgca atgggctgcc aagaaaacgg ctgtgcttgt tcttaacctc aggctctgtc   77280
tgtgatcagt ctgagagtct ctcccaggtc tactgctccc tggaaagccc tatctctctg   77340
caggctcgcc tctgggcttt gtctccttgg agccacatca ctgggacagc tgtggatgtg   77400
gatgcagatt tgaaccatgt cacggcccca gggactgcta tggcttcctt tgttgttcac   77460
cccggtctgc gtcatgttaa actccaatgt cctcctgtgg ttaactgctc ttgccatcaa   77520
gttcaccctc attgacagcc aagcacagta tccagttgtc aacacaaatt atggcaaaat   77580
ccggggccta agaacaccgt tacccaatga gatcttgggt ccagtggagc agtacttagg   77640
ggtcccctat gcctcacccc ccactggaga gaggcggttt cagcccccag aaccccgtc   77700 ctcctggact ggcatccgaa atactactca gtttgctgct gtgtgccccc agcacctgga   77760
tgagagatcc ttactgcatg acatgctgcc catctggttt accgccaatt tggatacttt   77820
gatgacctat gttcaagatc aaaatgaaga ctgcctttac ttaaacatct acgtgcccac   77880
ggaagatggt gagtacctca ctggaacaga aaacaatacc tcttgtgcag tgtgtagaga   77940
gatttgctag gagggtttta taatgtctca tgcatgatct cttctataac ccgtttattt   78000 tatttaatt tattttttcat attccaaatg caattcttgc agcaacttac cacatgttcc   78060
acttgtatgt attgggccat ctactgactg gacaaaacta taataataa ctttaattat   78120 tttcatatat tgccttctta acttttata atgcttattt gcagatgaaa ataaatatga   78180
gcatataatg ttgcatgtta tacctgaatc atctgtaaag gaatgaatct atagaaaaat   78240
aatagaatta agtacactat tatgctccag tttgcaaact gaaagataga gaaatggtt   78300 ctttctgcct taatgactta agatattagc acctttttg agttttcaaa gaaaaacttg   78360 attgtttta atatacaagt aggggatagt tcatacaatg gttggatttc attgtttaga   78420
atcggttttc ttaacgtaaa tttggatgtt cttttcttcc aatattcgct gcaatcaagt   78480
ggcaaaatgt aatcagatga ttctagctac attagagatg aatgcgtttg tatttttaaa   78540
aatttccttt tttatataaa acaacaatga aagtctgtag acacaataac gtttaatata   78600
ttaacctaat gttagtaaaa catgaatagt tttatgtctg tatagatttc aaattcagat   78660
```

```
ttccttggaa gaataaccag actaaagtat gccataatgg tatcacattt cccagttagc   78720
atttccatat gccgttttta gatgaggaga aagaacaaca gagaataaaa tatacctgga   78780
aagaaaggaa gttaatttgt gggaatgata gatgtatcta atgtagaaac tagagtgtgt   78840
cctttgtata aagttcttcg tggaaagtgt gataaatttc ttttatggag aaatttcttc   78900
ttcttctttt ttttttttt taaacttcaa tccctggaaa acattttca gtaagatttg      78960 gctgaaaata gtaaatcaac aacgacgtta atccactgat ctccaaaatt gttttgcatc   79020
tatcagatta ctctttctcc atataaatgc cagatagttt aagtagagtg tcatgaaaaa   79080
ccataccagg gttgtgtgtc actgaggtta caaattgtca ttgagattac aaagaacagc   79140
ccagagaaag aaattaaagg attctgcttc attatattag tggtttctgg catattgccc   79200
ttgtcgttat ggtgacagac ctctcaatta tctcataaag tccaggtctg aatgtgattc   79260
aaggagttaa actgacattt ggacgctgta cttccatggg gtgttctgag ctgtctccgt   79320
gcctaacagt ccctctttgt gtgtgtgtgt gagatgaata agagctctca aaagcaatta   79380
gggttctcat ttgagcagcc acctgggttg agatctttct cataatgaac tattcaaaca   79440
aaaaccaaaa agaaaggaag acaaaaatgg ggagaaaacc ccccaaacag gacaaagggt   79500
taaaattgct ttcataatac tttggatgtg ctagagtctg gtgattttgt agagctagcc   79560
ttggcaacaa tgaatgcact tcaaatagaa ggcctcctca tataggagtt ggacagaatg   79620
agaccaccca tgaaaagaa tcaatagcct ccctgactgc agagccctgt atgtacaatt     79680
gtgtggatgg agaccacaaa cggtgtggcc gtttcattgc aattcggtat tgaattaaaa   79740
tttgaggaat gtaaatatgt gaaaaatgct attcagtgaa aaagtaatcc aaacttcata   79800
ataaacccag ttccacttgt ttagatcttt aggcttttg aagcaatatg tgcatatgat     79860
cttgacaagg gaatcagaaa tctaatagtg actgaaaagg tagaatcgat ctccccacga   79920
tgtgtaaact ttagaatttt gctggtgaga gttcaaagct acagccctgc atgtttgtac   79980
catccacaag tcacagccta ttgggttagg agttttatt tttggttgct tgcttgtttt     80040
cttaactcta tcaacgaaga accagtgcag gccaggcgcg gtggctcacg cctgtaatcc   80100
cagtactttg ggaggccgag gcaggcagat cacgtggtta ggagatcgag accatcctgg   80160
ccaacatggt gaaaccccat ctctactaaa aatacaaaaa ttagctgggc atggtggcgc   80220
gtgtctgtaa tcccagctac tcaggaggct gaggcaggag aattgcttga accaaggagg   80280
tggaggttgc agtgagccac aatcgcgcca ttgcactcca gcctggcaac atagcaagac   80340
tccgtctcaa aaaaaacaa aaacaaaaa agaaccaatg cagagcttta gatgtttaat     80400
tattaattat tcactaaatg aatgaactcc gcatccacaa catattgaaa tgttggcatc   80460
atgctgattc tctccaaagg ccttctctta gggagtatct cagttcagat caatgctttt   80520
atttagcagg agagagagca atattattat ttggaattca aaattccact ctgaccagtc   80580
tgacaaagcc agaaagacaa atctaaacaa taacaacagc aaaaatctac ttttttgtt     80640 tagctttgtc tttctgcctt gatcagattg gctcaaattt ctatgtttct actttcataa   80700
aatgtgtagg tatattaaaa atacaaaaat agactatttt agatacgtac ttatccttac   80760
atttaagaac taacttgcat gaggaaaagt gttggaaatt tcttcgtagt acaatagttt   80820
atgaaacata tatttttttt ctgtagaaaa caatactttt tataattccc tttaaaataa   80880
atcaggtctt gctgaaggtg agtctttca tttaaactgg catcatgatc tactaaactt     80940
aggcttgggt ctttataact atttcctacc ttacaaattt ctttatttaa attttcatag   81000
```

```
gttattaatt tctctttgtt gttagacaac aggctaatta attaacttga attgcatatt    81060 taacctttig ataggtgctc aaataaggtc aaagtcagtc aagccagtcg gaagctctag    81120
taggacacgt gggccattgt tgacaaggaa cagttggaga ccgattgacc gaatctgcat    81180
ggtgtgtgtg tgtgtgtgta tgtgacagag agagagagag agagagatag cagagagagt    81240
gtgactgagt gactactttg aggaagcaat gcagaatatg gcttggtagc ttgattaaac    81300
ataaattgtg aaagtcaagc cgagaagttc cagtctcaca tactaagtcc acttgagttc    81360
atacatgagg ggatggcagt acagttcgtg attcgtcttg gtccccaagg agactgaaca    81420
cagaaagatg agttatggaa acacttaagg tttttaatga gaaccagtga tactgtttag    81480
aagtgaggtt aaaaagtaag ggaaaaataa aagacacatt ttgaaggagt tgctcagaca    81540
agatatcata ttaaatataa agcttggagg agaaagagcc acaagtgagt ccagattgcc    81600
ttgggaaatg gacagaccca tggaaccact tcctgagtga cctacacctg tgcttttttct   81660 ctggatcctt ggacatacat cttaaggtct tattcttgaa agatttcagg ggcgagaagc    81720
ccttccattc ttcatcatgg gactaaaaat actgggaaat ataaaggaaa atataaatga    81780
aagtcattat cgcccaggca cagtggctca tgcctctaat ccgagcactt gggaggtca    81840 tggtgggtgg atcacttgag gtcaggaatt cgtgaccagc ctggccaata tggtgaaacc    81900
ccgtctttac tacaaataca aaaaattagc tgggcatggt ggtgtgcgcc tgtaatctca    81960
gctacttagg aggctgaggc aggagaatga cctgaactcg agaggtggag ggaggttgca    82020
gtgagccgag atcgcaccac tgcactccag cctgggcaac agagtgagaa tccctctcaa    82080
aacaaaacaa agcaccactc attatcattg tattttcatt gtagcataac agcaaatgcc    82140
attatgattt ctagaaaagt gaaattttgg gttgtttttt ttttttgcta gcaatacaat    82200
tgaaaaagga agatattaaa aaagaacaga ttattggatg caaggtgtcc ctatcatctt    82260
tttcccccaa gatgacacct gactctttga atactatgac ttaagtaagc ttgctatgat    82320
tgttgattga ggacctattt ggtgaaaaca tggagcttta tgatgaaata taaacagaca    82380
cgacatggac aatgacctgt aggagtttgc acagttaata aacctagagg tagataataa    82440
gccagagcat cctagttagg gaacaaagaa agctctgtga cagctcaggg acaggctatt    82500
ttttgaggaa aaacttgatg gaagctgtta agttgttgag ctgtgccatg aagaatatat    82560
gggtgatgga agggattcat ctattaaagc atctgatgaa tggaacattt gaacacagaa    82620
atctatgtta agcagtttgg tgtcaatcgt tgctgttgtt actactgggg tgttaagtgt    82680
ggcgtggtaa cagaagctgt gctttagcat gggctgtttc tggcagtgcc atatcatgaa    82740
agttcttttt tttttttttt tccttttaga aacaggatct tgctctgtca tccagggtga    82800
agtacaatgg tgcactcata gctccctgca gcctcaacct cctgggctca agggatcctt    82860
ccatctcagc ttcctgagta gctgggacta caggtgcact ccaccatacc tggctaatct    82920
ttttagtttc tgtagagatg gggtgtcact atgttgctct ggctggtctt gggttcaagt    82980
gatcctccca cctcggcctc ccaaaatgct ggcattacca gcataagcca ttgcactggg    83040
cccataaact ttttatgtt atccacagct gctgacccta tactttctag ggtagacaag    83100
ctacctaaga tgaaagggtg gcaggagaac aacaggaaa gaagctggaa agtcaaccag    83160 cttttgctagc gattttacaa aaaaaaaatg tattcgcttc ttttatagat accactggat    83220
ctaattcaag atataatta tagcatggtt ttcatccttg aatagctccc atctttctg      83280 agggtcttac aaacttttct ggcattctgc attagtcaag agatatttgt gttcaaatgt    83340
tagaaggcaa cctagcctca atctgacttt gagggaaaaa atggaaattt attagaaggg    83400
```

```
ctatgggata tccaaactta ctgtaaaagt tgagaaatca gattggcaga atggcaggga    83460
tgcagctaga ctttagacac acctggaagc attgaatcca aggacatcac caatcttcat    83520
atctcgttct ttgcttcttt ctggaaatag gcttgcttta aatggcagta agagggttct    83580
ctgcagtttt tgttagttgc attttgtttt tctcagtacc accagtgagg acaaagttc     83640 cataattcca tactaaaaat cccagggcgg ggttttgatt ggcccacttg actcaggagt    83700
aagaagagat aaaactgggc tgttcttgtg tataccagtt ggcaggggga aaggacagt     83760 tctcaccata aggtgtctgg aatgagcagg cactacttca cttcactgtc caaatatttt    83820
ttgagcatcg attatatgcc agacatgcct tagaggctga gattgtgaga gatacaagca    83880
ttcctaattt tgagagatag gtacttgtag gcagaaaagt catggtccct gagagatgtg    83940
caagcaccgc cctccacccc taccccccag ccaactcgcc cattcctgga acctgggaat    84000
aggttggagg catggcacct gacttcttca atactctgcc ttaaataatg acttcaaatg    84060
gcaaagggga attaaggttg ccgattgaat taggtttgct aatcagcaga ccttccaata    84120
gggagaatct atcctggatt ctcatatata ttaacagaga ccctccactg tggatgcaga    84180
agactcaaaa ggagatcaga gttggtgtaa agcaacgtga gaaagagata cctggacatt    84240
gctggctttg aatatgagag agccaggaga aaggaacgca ggtggcagtc tctagaagcc    84300
ggaagagaca gggaaacaga tttttcctta gagcttccag caaggagccc gacagccctc    84360
ctgataccct tgattctagcc ccatggaaga aactctgacc ttagaactgt aaaagaataa    84420
atgtgtgctg ttctaagctt actaagtttg tggagatttg tcttagtggt aatagaaaac    84480
taaggaagag ttttatcacc ctgtaatatt atttgaaatt cataatgaag tattactctg    84540
aaaacaaaag ttcagagtct ctgaagttgt ttggtttcgg gccttctgga cccctctcca    84600
ttctgggatt ctacttccaa gaatttctag ttgaaaacac ccttgggcac ttagagcttt    84660
ctaccttgct caagcatgct aaggagatca tatcaattct tattttaggg cagacatttt    84720
tcagattttt aaaaatgtat tttttaaaaa tttgagagat aggtaccctg tctctgaatg    84780
gggtcttgca ctgtggccca tgctgcagtg cagtgtcaca gtcatagctc actgcagcct    84840
cgaactcctg gccgcaagtg atcccccaac ttcagcctcc tgagtgtctg ggactatagg    84900
ctgagactac tatattgagg ttcagagaag aagcatgtcc aggtgtctgc aaattagaaa    84960
atggtggcag attttttaaa aaagaaacga tgaaaaatta tccctgatta gatttacatt    85020
acaattttca gccaccatga ctggctagtt tttaaatttt taaagagttg gagccttcct    85080
atgttgccca gactggtctg gaaccctagc ctcaagtgat cctttcatct caaactccag    85140
agttctggga ttacaggtgt gagccaccac gcccagtgac attttgcaaa tttgacattt    85200
tgcatcatgt taatatagcc tcatggccaa ttgtcctaaa tggtatattc aaaagataat    85260
actgttttga cacagaaagg taccaaaggg tcatttagaa ttttttcagg aagctataac    85320
agatttccag agtagatggc tttgaatgac atataacaaa ataccgaaat tgttctttcc    85380
tcatctgtct ccacagagtt tcactcaaga tcgcggctgc acctttacat gtcttatttt    85440
cctacttaca aacactgctg acaaaatcct ctgtgttccc cactccttcc ggctacacct    85500
taagctgtgg tctcttctgg gcaaagtgat tctctgacct tttcaagcta caccttgttt    85560
cctcctccaa ccaaaacttg tttgctggag ttgaaatgcc agtttagccc cttagcagat    85620
cagtcattat gggcaagtga cccagcttgc ttgggccaca gtgtcctatt gtctaaaata    85680
gaggcggctg agaggtttaa ggttttaatc catataaagt gcttagtagc cagcacgtac    85740
```

```
aagcaccctg taatctgatg ttagtgcagc atcattaata acagaaaagg gaacccgaaa    85800
atttcagcaa aattgcatgt gcatagtggg tctggtatgt atattagtct aggcataata    85860
aatgttgaac gtctgtgaca taactattgt agtagtagag gggtaagctt aagaagtaag    85920
accaataaat agcccatcat ttctggcagt ttctagtatg gttttaacaa agggaatttt    85980
tgggaggaat aacatttta aaaagagccc actattatca ttctgcttta ttcctaactt    86040
tagtcctttt gagcctgtgt tatcaaatgg attttgagca tatgtgaatt agagaaatta    86100
atcactagga aaggattaga attaactttt ttggaaaagt tccttaaacc gtgaaaaggc    86160
agtaacacca ttctttgtgt gtgagattaa agagaaatta attttctttc tcttcttgtc    86220
tagacacaca aagtccaatt gtacgcatac agtcacaaaa tataggtgaa aaacgaaaac    86280
tgtgttaaca cggtgagaca gatgttttaa ccaatcaaca tcaacatgca actaggtgaa    86340
aataattaaa ttactccagt tttcatctgt cagttggatg tttgacattg tgtagacaca    86400
gcttataagt aaagataatt atgaaagatt attaaataaa gatctccctg acacggatta    86460
attgaaaagt atttagtatt ttttgtaagc acagttaaac tggagtggat ttccgatagc    86520
atgtgtctct cccccagctc aaaaagcttt cagcaatttg aatactgagt aataatctta    86580
ttgagggttt agaaattaca tatgtttgga ataaactat ttagtagtat gaattatgcc    86640
tgtttgaata attaagaaat atcttttcct aacaaagaac attttcccctt atgtacataa    86700 tcttccaata catgaatttt aattcaattc aatttgcaat ttagattctt gtcataattt    86760
gaacaaatac agattaccta gaatatatta aaaatcaaat tttcacatag tgcatatcat    86820
aagaattttt ttttagaaat tgtcagagat agaaacttta ggtacaacta gtccactgga    86880
atatttggcc atttaaaaca attagctcat tatttatttg tggagtcttg cttcctaaga    86940
tgttgtagtc ttatttgttg tcaattaata ttgctggttt gaacatggtt atttattttc    87000
cgtactattt tagccaagct attaattttt attatttatt tttttaattt tatttttttt    87060
atgtttgaga cagtcttgct ctgtcaccca ggctggagtg cagtggtatg atctctgctc    87120
actgcagcct ccacctccca ggttcaagtg attctcctgc ctcagcctgc cgagtacctg    87180
ggactatagg tgcccaccac cacacccagg taatttttgt attttagta gagatagggt    87240 ttcaccatgt tagccaggct caaactcctg acctcaggtg atcctcctgc cttggcctcc    87300
caaagtgctg ggattacagg tgtgagccac cgtgcctggc ctagccaagc catttaacct    87360
ttaaatattt agtgtcctca gctattaaaa ataagagtaa tatgattata catcctatga    87420
atttgtttta taattattgt gatttgggag taaacaacta tataagaaat aattataaaa    87480
gagataagat tagtgcatat taagactttg atgtcaggtt aattgaatgt taatcccatg    87540
actttatctt tcattgcaag attctttgcc tgagtggggt actggaagcc attgttgaga    87600
gtagatccga tcttactaga ctgttggctg gttctcctaa aaccaggctg ttttcataat    87660
gagttagttt aacattttgt ctttatgttt aagcacccct ttccttggtg cagtcacagc    87720
caaactgcaa acagaaatcg agaagttgtg agctccagat ttgagagcca cagagagttt    87780
gtgagatcaa aaacatccac tctcagtaaa taaatcagag ctacctaaat cacacagtca    87840
gcttaaaggc aagggaacca gagggaaaaa ctccaaagga gtgatctctt catgcaattg    87900
ctactggtaa aataaagcaa agatgagaca gtgtagtctc caccttatta tttcaatcta    87960
atattctata ttgaggttca gagaagcagg tccagatttc cacaaattag aaagtggtgg    88020
cttgctcttg taatcctagc acttgggag gtctaggtgg gtggattgct tgagcccagg    88080
agttaagacc agcctgggca acatgacaaa accctgtcct taccagaaaa aaaaaaaatt    88140
```

```
agctgggcat ggtggtgctg gcctgtagtc ccagctactt gagggatga ggcgggagga   88200 tcacttgtgc ttgggagatc aaggctatgg tgagctgaga tcacagcagt gcactccagc   88260
ctgggtgaca cagtgagacc ctgtatctaa aaaagaaata aaagagaaac atttccttgt   88320
tagactttac gtatctgacg atgacttttg atggtgaagg taggcattgg tatgtggtct   88380
gtggtgtgtg tgtgtgtgtg tgtgtgtgtg tgtgtgtgtg tgtgtctgtg tgtgaatgct   88440
attgaaggaa acccggtagg agaaatatcc acaattcagt taagatcaaa catgttacaa   88500
ttttctggga agtgccaagt tttacaacac ctaaactata tcctcttcct ctctgaaacc   88560
ccaaacatcc caaagtctcc ttcaagccag acatcctctt ggtctactgt gcatggtgtc   88620
tgcacggtcc tcaagtttgc ctcagggaaa gtgcctgttg ccatcagaaa gaagaatgc    88680 agcaggtact gatttatctc aggcaaagga gctcttgtgg tgggtttcaa caagatatga   88740
aaattgtagg ttcttgaaca ctccttttct tcttccttaa aatggatgtc tttagctaca   88800
ttctactctc ttctctgtct tttatgacat aatcagtcat tcactcaaca agggaacatc   88860
taatattcac ctaacatccc atttgcctgt cacatatgga ctttagcctc cagtcgggcc   88920
aatgacacta ttgatctcct aattccaatc tagactcttt gggtattttt ttctcttttc   88980
cattccttat tttctttaga ggcattttag ataactcatt taaaaattat tagtaaataa   89040
atcattattt gcaatcagca tagacaaggc cttgggtgag tctaagtgga tatctggaga   89100
gatctaaacc cgctgctgga aaagtgagtg ggaaagcccc attgatatgt gacccaacta   89160
aaccaacgtt tcatcaaaag cagtgtcttc agggactgct ttaggatttc agggaaaaga   89220
aaatggaggc aaatctgaaa gtggatgttt tctatggagg atccttgata gaaaagtttt   89280
cacccagcct tgagtgaata tgcagagcgt aaacacatgt ttgtgcagtg aggaaatgct   89340
gtctatgttt cctaaaatgg aagttcttgt ttattgcttc tttagctgca cggagacata   89400
aaagatgcaa aactgggag aagggagaga taaaactaag acaaaactgg aggagggtgc    89460
aatgatgttg taatttaaca tgcaaaatac tcacttgggt attttttaaa ttgttacatt    89520
gtgacattgg agggtcata aatgaattc catccaaact aattctaatg cctatctttt       89580
ctttttagca gactatagaa taaagttaaa tcaaagaaca tgaggtccca ttcttaccaa    89640
attcaaatat acttttatc acctggtgtt taaatcatta atacaaaagc tttcagtctc     89700
ctccaaattt ctattctagt aaagtacttt cataattta tattgaaat gtactaatcc       89760 agataactag tatgaaatca agttataata ctatttgca tgtttctaaa atgtttacat      89820
ttaaaaatag agaagtaagc cttagggaga aaacttcagc tttcccaaga atattaaaat    89880
gttaacaaat tatttcattt tgagctaaaa tcagataata atgagaacaa atttcaccat    89940
cgcacattct acagggatct ttgcatttta tactttttt tttgttttgc tttataagag      90000
gggattttgg tatattgaat atcatactgg aaatttacct ggacggaaac gatagagtca    90060
acttagactt taatcacaga atgataacat cttccaagga gaaggagctt tgaggtcat     90120 ttcaccaaaa ctctttcacc atacagtatt ttcccgttca ttaaccttt ggcactctaa      90180 gcagagatga agtatcctcc cctgagttcc tagaagttga atttaatcac cattttacga    90240
gtctgccctc cccagtagat ggtaaaccct ttgaagaccc agagcatttt tgagataaaa    90300
gaatgaatca tatacttcag tacatggaac aaatgaataa acctgtagtg cctggccacc    90360 cagcttttt tttgaacctg accgataaag acgtttacag cttttttaatt tcattatcag    90420 agaaagggtt ggcaatattt acctgagcac tctctacaaa cagagatgaa gaaatttgga   90480
```

```
atgtttcctt tctctcctaa tacatagctt tggaagtctt agaaaacatg ttggtatgtt   90540
ccttctaggt agtcttttgc aagcatcctc ttcagtgtca agcatctatt ctcatgcatc   90600
acattacagg ttatgaatat acccagagtt tatgtgagat cttttttgt caaatgcatt    90660 aaacccttgg cttatatata ttgagctgga agccacaagt ttttgtaata tttaaaagt    90720 aatatatttt ataatatgcc ttagaaatta aaagaaaat agaatacctc cacttcctat    90780
gacaaaatgt cagcatatac agcaaggcaa agccatttgt tgctgaagct cagttttcc    90840 caccggatgc tgaatgcaca acaatcacca gccaagccag gagtctgttt actgcacgtt   90900
tccctgaaat gccaagcccc tgaggtgtta caaggaggga aggcagcata catgtgtgat   90960
agaatggcca ataaactaat tggtttatag ttttgagaaa gcagctggtt gcctgttttt   91020
aaatgcagtg gtctataatt tgatagaatg cagaaggaat catttccaag aaattaatta   91080
aagttcatag gttggaaaat aatggagctc atcattaggg aaagcttatt ctaagactta   91140
ggataaaatg agcttcctct tgcatttcat tcaacttaag gtttgtagt tacttgtcat    91200 catcaaaaat atcatcagag tcatcgccat catcattatc taaatttgag tagctatgag   91260
aaggtattgt gaggtcctag ctttagagga atcaatttct ttgagatttg atattgttat   91320
tttaagactg cagagcatag gttagaatct gtgttttaaa aactttgaca ggccacgtca   91380
taggtagtaa agttttctct tggcatgagt tttgagttga cttgtgttat ggttgaattg   91440
tgtctctcaa aaaattgtt tatgtcttaa ctcctggtgc ctaggaattt cacttattt    91500 gaaatagga tttctgcaaa tgtaatcaag gtaagatgag ttcatactgt gttagggaag   91560
atcctaaacc caatataatt ggtgttcttg taagaagaga cacaacaaca aagacagaaa   91620
cagggagaac accatgtgag gatggaagca aacgttgaag tgattcatcc ctaagccagg   91680
gagcactgtt ggaaaccacc aggaaccaag aacaactcaa tccaagacag aagcatgaaa   91740 tggatttct ttaagagcct ctagaaggaa tcatcttaat tttggactct gccccagaac    91800
agtgagacaa tgcgttcttg tttcaagtca ccaagtttgt ggtaattagt tacaaagccc   91860
cagaaatgaa tgcagtctgg attaggtata ttctgcgtac atatgctgcc taagaatgcc   91920
agaagccaga agaggtgatg tctgcatttt tggttcctaa aatcctctct cagtacccac   91980
tgctctgtcc agggcaaagc tcccctgaca catttttagc ctttaggcta tgtcctatct   92040
cccctgctca ccagagaagt aggtcttgga ttccagtctc tcagggctgg cattttccaa   92100
gtgaaagaca ctgcctttgt gtaaatcctt cccccttgag tgtaggcagg acattggatt   92160
tgtttgtgtc tcatggaata tggtagagat aatggaacac cacttccatg attatgttac   92220
ataagcatat aaattgtgtc ttactagtat accctttttg ttgcattctt ggtttccatg   92280
ctttgatgaa agagcagcca tattaaacag gtgcatatgg caagaagctc agagctgcct   92340
ctgaaacaac agccagcaag gaacagaggc tttcagtcca gcagtccaca gggcattgaa   92400
tcctgccaac aaccacataa gtttggaagc gaaccttcct cagttattca gctttaaaat   92460 gagacccag ctcaggccaa caccttcatc agtgagagac ttcaaagcag tggaccctgc    92520
taaggttgtg cctggattcc tgatatgcag aaactcataa aataaataca ttacttgaaa   92580
ctgttaagtt ttggttattt gttacatagc agtcaataac taatgtggca taatatgcaa   92640
aacatggatt tcagctgagc acagtaatcc cagctccttg agaggctgag gtgggaggat   92700
tgcttgaggt caggaggtcg aggctgcagt gagctatgat agcaccattg caatcatagc   92760
tcatggcagc tatgagcctg ggagacagag caagaccttg tttctaaaaa aagacatgga   92820
tttcaaattt ggccagattg taacccaact tctacataga tattatgtct ccattggagg   92880
```

```
gatatatatt ttgagacttt gcaatcctta attacttagg aacaattagt tagcaagtga   92940
aagaaattca ggttgaattc acttaaggga aaagaagaga ttttcgggtt ccatttacta   93000
gcggtgcatt tagtttcgaa aatggtgtcc tcaggtctaa tcattgctgt taggaatctg   93060
gcactttggc gccatgtttc ttctttggct ttcttagaga ggcttgtccg tgtgtggtgg   93120
taggcagtca acagcatttc ctagtatgtc atccttttct cagagaagca cattggccta   93180
gcaactatgc gtactggcct aattttagtt gcatgccaac caatgtctat atccagtgga   93240
aagagatact tgaattgata tggactgctt gggttatgta tactcttcag aaatgagaag   93300
agattgggta agtccagtag gcttagggta gatggaagta agattgctcc ccagaggaaa   93360
attgaatgct aggtaagcaa aactcattga tgtccattgt tgcttatatt acaaatagta   93420
ccaaacaaga aagaatggca tggctgcttc atggaagagg agatgaactt ggggcaaaac   93480
cttacctagg atatttcctt ttttcagcta aaaagaggaa cttggacatt cagaaatgag   93540
aaaacttgta tatcagttgc tgttgttgtt ggtttgtaaa cagctgtagc tcttagtgac   93600
atagagagat aaagtgacag gaacagatga ggatatttct attaggatgt tatccaggca   93660
gttctatgtt gggagtcacc ctcctgggac actcctgggt ctggaagctg tcagctggtg   93720
gcaaatcaga gatagtctga gatttaatgc cagatgggaa acgtgacctc aaatgaatga   93780
ggctgtttag gagtgggcgc aacatgctgt gcttgccatc tcttttaaga gttctaactg   93840
aaaggttagg tttactgaag gataagccaa tttggggagc tgatctggtg aacatgaatt   93900
tggccaaact tcagcctaag cgtttagcag ggtgaaagtt tgggaagagt ttcgttgtag   93960
aacattaggc aaatggctga caaaagagct tccagttctc tcacaaggaa ttcttcaaaa   94020
agcaaaggag gtccttctca gtcagcctgc tctttctgct cagtagactt ctttgtgaga   94080
ctatgctgtg agtgagttct caggctggtg atataacctg gtcttcaatt cttgtgcagc   94140
tctgtaagtc cacgtaggca ccactaaata tccttacgac attaagtgtc attggattgt   94200
ttgctaacat ttgcttccat atgggcccca ggcattagca aacatgtagt ttattcattt   94260
atttattcac tcagtgaata tttattgaac ttattctaat tgtcaggcca ctttgctaaa   94320
tgttgttcca tcactttcct tgcagaacat acagggaaa atgcacaact aactggaatc   94380
atcatttagt gtaatccatg caatgatgca acaagttggg gagatgtgag aacatctggg   94440
agaagcatgt gtcccagact gagagggtga aaatgcacta aggagaaatt tgaagaatca   94500
gtaactgacc aaattgctgg gaggagagtc atttcagaca gacagaggag cacgttcaag   94560
gctgaagtcc acagcctgac attaatatcg attctcttag ctaagttttg ttaaagaaac   94620
caaatgacag tgaatttgaa gtcctgcact cagccaaccg tatgaagtgt agtcactgta   94680
tggtcagtta attacagggc agcatccttc agtcatcagt cgagctagag agaatattga   94740
cagatgtgct cttatgaaag ctgagaagct caaccaggac aagtatttag ctaaaagggg   94800
gtctgacctc cttttagaga tgggaagcaa gggtggacag cataacctgt agactaaatc   94860
tatcacactg ctgttttgt gaagggttta atggaacaca aataagccct tttatttatg   94920
tattgtctat gtctgctttc acactacaaa gacgaagttg agtagttgca aaagagacca   94980
tatggcctgc aaagtctaca atatgtacta tcttacccct tattttaaaa agttttctga   95040
cccctgatgt aaaggaccaa cttcatgaag tcgcatgtgg attttctagt taccatatag   95100
acatgaatgg aagagtacag aagttccatg tcagacagca attgttttca aacttgctat   95160
gaattttttc caaatgcaga ttcctgggct ccatccaggc ttccagtgac tcaaaatctg   95220
```

```
ggtatagatt ccaacaattt gccttttagt gaccttagag gtgatattga tggcaaaaat    95280
tttatatatg tacatattca tgaaacagaa aattggacgt gaaatatttt taatccacat    95340
ataaacagat actcctttct gtcattaaaa accaattagg aaaaaatgat aaaagcctga    95400
ttttaaaacc atggtccata tggcttatgc aagataattt tctgaagtga ccttcaagat    95460
gaaatagttg caaagtatat ctgtgttcag ttaaattagg aggtgtgtgt gcaacaagga    95520
attattagcc gtagatcttt aaaatcaaat caatgtaaac aaaacactgt cagcccagtg    95580
gccaaagaac acaatcaatc aaaatatgaa taaatataca caattataca ctactactac    95640
tagatgatga tgatgatggt gatgatgatg gttatgatgg tgatgatgag gatggtgatg    95700
gtgatagtga tgatggtgat aatgatgatg gtggttatcg tgatgacgat ggtgatgatg    95760
gtgatggtga tggttatgat gatgatagca atgaagataa caattattgt gatgataatt    95820 tatgcgata ataatgattg tggtgatggt ctgtttctat gcgtcaatct cagttgctcc    95880
cccagactcc atacaaacag aaccacctta gagatgtttc aaacttacca tgttcgaaac    95940
tcagctgctg cttttgacac aatgaatgcc ctcctgtctc cattttttacc atcttaggag    96000 aactcacacc atcccctcat cactcagtga gccaagtgtg ctagctgctg atccacatgt    96060
ctgaatggcc gccttgagga attgacatta ccttggggac ctacagggag caatgatgct    96120 ggactgggc aaggatgaat aaaggaggga taagtccaag ttgttggggg aagacagggc    96180
agccaactct atctggagct ctcagatggg tttagcggtt gtggagatat ttccaatggc    96240
attttgaaga cgtggaagaa tgttattagg catagcagag attcttaact aagagcaatt    96300
ttggccccac tgtaagggac atttgacaat gtctagagat attgttggtt gtcacagctg    96360
gggaggtgct actgacatgg agtaggtggt gaccagagat gctgctgaac atggtaaaat    96420
gcagaagaac gactcacaca gcagagaatt atctagtcca aaatatcagt agttctgata    96480
ttgagaaact tggctctgta ttgtgcatgt gtaatcgttt tttacttact gattctagat    96540
tcagctggca aggggggtgtc agcaatgtct ggagatattt tggattatcc catctgggca    96600
gtgtgtgctc ctgacatcta gaaggcagag gatgctgcta acatcctac aatgcacagt    96660 acagccctca caacaaacat aatcatccag ccccccaaatg cccacagtgc tgatgttgtg    96720
aaaccctgct ctaagtcaaa gcattgtctt actcaatttt taattcctag tgtatatcag    96780
tggttctcaa ctttggggag gggacaggtt tgcttccagt gtacatttgg caatgtggga    96840
agacattttt gtttgttgtg agtatggagt gtgttactgg gaatggaggc aagggatgcc    96900
actagacatc ttaacagtgc ataggacagc ctccacacct cagaatgatc tggcccctaa    96960
tgtgaacagt actgaggtag agaaaacatg aggtagactg tagaagccta tagaagaaga    97020
gaatctgaga aaattgttgt gcttggggaa cactgaagaa tgtggagcaa ttgaacaaat    97080
gcttgtgcag acagattggc accaaattgc aatggagcac caatgggaca gtgaaaaggg    97140
acaagtccta caatgcacag ttcttgacca tccccaaagt gctccaaagc tacagaagtt    97200
ggtgtgcatg tattatctca ttgatcctat ttgggaatta tcatgttgac agctggagtc    97260
ccatgaagga acattttta gcagcaaagt gacaagctct gatttgcctt ttgagattaa    97320
tgactcagag actgccagtt atttgttaac ttgcttgatt cagcctaagc agacatctag    97380
agggtgtaat ttgatttatt ctgcagaggg gtgattggcc cctacattat cttggcacac    97440
tgcctgaatt tctgaacacc aaagacttat ttatttagtg tatggccatc tcatttccaa    97500
gagtcaccaa agaagtgaga atggattaga tagggaacaa gctgaccatt ggattagttt    97560
atcagatgat tagcatgcca tgctaattta tcaagacatg gaacatttaa agaaggggag    97620
```

```
agtaacatat acagggaaga taggagatct ttgtcccaat tatttctttt tttttaatgc   97680
atgaatagtc ttttggtaaa tatagtttat gtttgtttct gctttctaag ttaggctgca   97740
aaatattatt tatcggtggt attctttgaa attgattggc atggcaagac tgtaaaagag   97800
tatccatagg tgtatttaaa ataaaaagat cgtcttttca tctttgcaga aaacatgta    97860
tttactattg cttggaatag aaagcagaat tttgctgtag ccattaggaa gtgacaaaca   97920
ctacgccata attatagtga gaagaaagca tcaaaaagaa atgttttggt ttttttata    97980
tacagttggc acaaaaatgt ccacatatat gaatactcta agaatgcac cataaaaaga    98040
accttccacc actattaaca ggattaatcc gtgctcatta ccatgggatt ggggatacat   98100
ttttacatgt tcttgattag attcaagagc caaagaataa ggcctaattg atgaaagtgg   98160
gctctaattt tgtgcttta aaataatggc ctctggccaa atatgggcaa agaaacagc     98220
acttgatttg ttactttaca tttgtttctt gcatcctgct cgaaaataga gatgatttac   98280
agttttaata tattttcat gcacaattaa catcattgtt gccagtttta tagaagaggc    98340
aggaaagtgg gccttctatg atttattgtg agtgcatgaa acagaagtaa tgctactagc   98400
aacagagttt tagtaggaaa aagttaaagc acacagtctt aaaaaggaaa ggttggtgtc   98460
aaaattatgt ttgctttagg taagctttat acctccatgg atggcttttt ttatagtaac   98520
aacaacagta actgtattta cattggggcc ttttctctgt ttcagaggct ttcatgtgga   98580
gtgccaaaat ggtaaaatat ataacattgt tatatgaagg agtgagggaa aatccaatca   98640
agattggcat ttttaaaaa agaaaaggag catgggaat atttttaaga tttgggccag     98700
agcctcgtgg ctgatgcctg taatcccagt gttttgagag gctgaggaag gagaatcact   98760
tgatccagga gtttgagacc agcctgggca catagcgag acctccacct ctataaaaaa    98820
gactaaaaag ttagctgagt gtgatggcac gtacctgtag tctcagttac taggaaggct   98880
gaggtgggag gatagcttga gcccaggagg gccaggcttc agtgagctgt aatcacatca   98940
ctgcactcca gcctgggcaa cagagcaaga cgctgtgtct caaagaaaaa aaaaaaaaa    99000
agatttggta tctttctttc ccccacagtt tgcatataca ttgaaaactg tgcatttaag   99060
ccaaaatagt tttttttttt aaacatttca ctataaaaaa ggagtctggc tttcacatgg   99120
gtacatgatt ttgctttggc ttcttcaatt cccacctgcc ctgttgtgag acccatgaag   99180
taagcaaagc attcttttg ccacggaaat gaaactccta acatattgt ttattgtcac     99240
ataatggaaa ggagaaacgt ttcaaaaata aggatacatg aagcccttat tgaaaagcaa   99300
tcatacattg gtgaatttaa tgttttggag caaaaactgt tatgttggat acctattagt   99360
cttttagct agtgaaatat gtacaaggca aaatcaagca tcaatagaag ggtctaacta    99420
agcttgtttc tcatatggtt tctctgccag ctcacacctc aagggtgcct cctgcctgca   99480
atgtgtactc tctggtccac acactgattt cccctttct gtttcatggg gtgacttgct    99540
gaccttctct gtgcatggct agtagtactc tattgactgg caaggttgt gtcttccact    99600
tgggtcttcc aagctgctga agaaagcaac acagaaagta tagctgacaa taattatctg   99660
tcaaatgtat gtgaatcaca gtgtggatgg tcgacctgtt gtttctttt tctctttgaa    99720
aggaagattt cagttttctc tgcagccatg gtactttata aattatttcc tcttccatct   99780
cttaaaagtc actgttattt accaccccat tagctgtgga tggggtgaaa tgcccactca   99840
tgcagcacag gaggatacac agattgtcac acatctttc aggagaccac acagcagtgg    99900
gtagtgtagt attaaataaa tgcctgaaat atgagctggg aatgcattgc acttcaagga   99960
```

```
attttatcca taggatgtaa ctgggaaagt gcagaagaat gcatatatat atagttgttc 100020
attgttacat gttttatgat agcaaaaaaa aattaaaaaa tattcaactt tcattttaga 100080
cacggatttg caggtttgct acatgggaat actgtgtgat gctgaagttt ggggtataga 100140
tcccattacc caggtagcga acatggtacc caacaggtag ttttcaacc cacatcccc 100200 tgtcttcctc cccttctagt agtccctagt gtggagtgtt cccatattta tgtccatgtg 100260
tactcagtgt ttagccccca cttataagcg agaacatgtg atattttgtt ttgttttcta 100320
ttcctccatt aagtaaccaa aattttaac aatgtagaat ccattacata attagagata 100380
caatacaagc attgaatacc agctgttaaa atggcattac aggataatat ttagtgatat 100440
ggaggaatat tcagagtgta ttatatacaa acattttcat catatcgttt tttactagag 100500
tggactgtca ttttcttgtg ggctcccttg tattatttac tctattgcat ctcagttttg 100560
ttgcatatta tgtaaaatag aagataatga tagcttggcg cattctctgc tgagactatt 100620
tacagtggtg taaaaagatg ttgccagggg tgtgtgcctc agtctgtccc agccttcgta 100680
gggccccatg tttcaactcc ctaatgaccc attgaagaca cacgggcaca caggggagaa 100740
tgctctggtt taaacagtca accataagcc agacacagtg gtgcaacctg tgttgcacct 100800
tgtggtagcc tcttgctacc caagaggctg agacagagga tctcttgagg tcaggagttc 100860
aagaccagcc tgggcaacat agcaaaactc ccattctaaa aaattaaagc aaactcaacc 100920
attttgagtt ttacatgttg taaatatctt ctcccactgg cacccaccca tcattcctgg 100980
ttttgattga aacaaaacca ttagttttaa tgtagcaaaa tgccatcaac atattttct 101040 ttctaacggt ttctcctacg tagtgcctgt taaagaaatc ctgttctacc ccaacatcac 101100
aaaaacattt tcctataagt atcagaattt cattgttcat acagacagtt tttaatccat 101160
gcagagttta tttttatata tgaaatgagg tgggaatctc atgttatttt tttccccaat 101220
aggggaacat tgctttgaca catgaaggaa gcaatgtatt cttttttttc ttttgagaca 101280
gagtcttgct ctgtagccca ggctggagtg caatggtgca gcctcagctc actgcaacct 101340
ctccctctca ggttcaagcg attctcctcc ctcagcctcc caagtagctg ggattacagg 101400
cacacgccac cacgcccagc taattttgt aattttagta gagatggggt ttcaccatgt 101460
tggccaggct ggcctcgaac tgctgacctt gtgatccacc ctcggcctcc caaagtactg 101520
ggattacagg catgaaccac tgtgcccagc tacaatgtat tctttcccaa tgatttgtgg 101580
tgtcagccag gaccttgata gggataaatg gcatgcaact tgagaaatgt aattaagatg 101640
gggacaggat agtggagtcc ttatgtgaag ttgctgatgc ccgctgaggt tgaactggac 101700
ctacctacca gggagggaac tggaggtcat atatacaggc cttactcgcc ttctgccctc 101760
cggattacct gctagtgtct tccttggctg aaacccagga gcagccagaa ggcaagagtg 101820
aacctgttta tttaccttcc acaccagaga ggagtggaga tgaggaaaag tcttgaaggg 101880
gacagactcc tccccccaca aaatagtaca agcttttaaa attcatcata tatacatcag 101940
ccaatccaag ggctttatat ttggtcttgt tgatttcctg atccattcct gcaagattaa 102000
agtatgactc aaatagtaca aatgcccata tattttcat cttcaacatt ctcgttgctt 102060
tttgtagaat ttattctttc atatacaata tggaatcaat gtatcaaaat ctgcaacatt 102120
cttctgtctt tgctgggaat tgtatttatt gaaatgttgg tttgaggaaa aataaacatc 102180
ttccaagctc atgttatctc atttgtaaac tggcatagtt cattacttgt tgagatctaa 102240
tcatagcttt attaaagact ttgagcatta tgtgttaatt gattattatt attatttgc 102300 aaatgatatc ttcaattaca ttttctactc ctggtataaa agaatgtcga tctttttat 102360
```

```
acattgatta tatgttcagc catctttttt gattccctat tatttctagt agcttttctg 102420
ttaaattaca tggtttccat aaaaatggtg acattatgta caaataatga ccattttctc 102480
tctttccttt caatacttgt aattttcatt tcctttataa cttgtaccat tgtatggccc 102540
actgacgtcc agtgcgagga tgaatactgt tggtacaaac ttttgttccc attcatgatt 102600
ttacaggaaa tgagtctaac atctttttg taaatgcagc gttgaggaga gattttaaag 102660
catgcagtca ttatcagata atatgaatta cttgcaattc ccagtttttt ctaagttttt 102720
aaaaaatgtt ttcttttgtt cataaatgtt gattatgacc aaataatcaa ctggcatttc 102780
tacagctggt tatatgattc ttctcttata attaatgtgc tctgaaaatt aatatatttt 102840
taaatatata ttcaatttcg ggaataacac attttaatc ttaaaagaaa cattttaaa 102900 atggccatta ttctattata gtggaatata ttgtatatga aaaatagcta ctattctact 102960
aagtttggtt tgtaaatatt ccacttaggt tgtctacatc taccttcata aatgaatttg 103020
atttataatt ttctgatgtt atacactcta tacttttgat atgaatgtta aactgtccat 103080
acaaaaggat ttgggtagct ttctttaatt gtatattttc tgaagaaaac ttaaataagt 103140
agaattacta aaattttgt gaaaattatc ttgggtggtg agttttatg tgggagattt 103200 ttagtgattc tttcattact acttatagct tttagtttat tcatttcttt gcgtaaagtt 103260
gctttgtttg ttttttttcct caaatatttc aatttctttt tttaatacca gggcttatac 103320
tattaaaata gtattttgta ttttttataa ctttgtttat ttgttatttt aaaaatgatt 103380 ttcctctta aagactattt gttctcatta tttgttgtat attatttgtt gtatattgtt 103440
gtatattatt tgtttcatta tttgttgtat atgttactct tccttggtca gtcttgccag 103500
aagtttgttt atattattaa gcttttcgat aaactagctt tcattttggt aattagctca 103560 actgttttt ctctgtttcg ctaatttctg ctcttacctt gatcatttcc tattttcaga 103620
tttatttgga tttattctgt tttctcttct tcctgtttct tgacttgcct ccatggctcg 103680
tttatttcca attcttcttg ttaccttgta aagatatttg aagttttaat tatccctttt 103740
aagcacttct tcagtcccat ctgacaaatt ttcacatgtg acatttgaac tatcactgga 103800
ctctgactgt tttgtgttta tacggtagca taaaggcaca tgcacacata tacatacaca 103860
catagatgtg tgtgtgtata tgtttagtgt tctatcatta ttttgaatgc tttttactat 103920
tgatttctaa ttctgttgac cgatagaata tagtgctgaa tgctgctgtt tctttaaagt 103980 actcttatg aaaggcagat tttgtaaacg ttcggtgtgt gcttgaaagc tatggacaca 104040
tttacacata catagacata ttcacaaata caaatacaga tatacgtgta tatgtgagaa 104100
tgtgtgtttt gaggagcata ggtttccata gatacccacc agatcacatg tatgggttac 104160
ttcagtcttc tatatcttat ttgttttggt gggtggggct agggacagag tctcgctctg 104220
ttgctcaggc tggagtgcag tggcctgatc tcggctcact gcaacctcgg cattctggct 104280
tcaagtggtt ctcctgcctc agccttccaa gtagctggga tcacaggtgc accaccacac 104340
gcccagctaa cttttgtatt tttagtagag acgcggtttc actttgttgg ccaggctggt 104400
ctccaactcc tggcctcaag tgatccacca gcctcggcct cccaaagtgc tgggattaca 104460
ggcgtgggcc actgcaactg gcctatatcc tcaattacat tttatttcct aagttttatca 104520 ctccaagaat gttgtgtttt attctactgt aacatttat cttttcttat ctgtcccttta 104580 tcttatatat ttaatgtata tggatatact atgttatata tatgtagtat gtatatataa 104640
aatgtactta tatacctttt acatgttttg aagctgtatt attaggatgt tacatgaaag 104700
```

```
tgtcagttac accttttta a tcttccattc cttttctagt atttattatc catttttgac 104760
atttacaatt tttgtttgat actaaatttg cttcctgtga tatttttca tttatatttt 104820 gttttatatt taaaattttt agtgtcttca ttttcaagtt tatgtatcca tttatttaa 104880 atatatcttt tcaacaatat gttgctaaaa gtatttaat caatatttta tctttattct 104940
aattttattt ctgcagttat cattattata gatttcactt ctgacatttt attttatatt 105000
ttatatttat caatcatgct ttttaaattt tacctttttt tttttttgct ttacctgact 105060
tccattatat aattttaaaa gtttctttta ctgaccttat tattatattt ttctttcttc 105120
tgtttttttt tccttatagt tgggattcat caaatttccc tcttcccatt ttatgctgca 105180
cttatatttt aatgaagatg tatctagtct tattagctat caaacatttc agtatccata 105240
attttcctca aaacaagata ttgatttagc attttctcta ctcttcggca tctctctctc 105300
tcaatcaccc cacactgtgt tagattctaa gagaatctgg gctctagatc atgttaaaaa 105360 tttgattta gatcattgtt tcttcggaat aattttttgt cgttacctgt attatgttgc 105420
tgtgttctgg gttcctctcc ttgcagaaat atattgtgtc aagatttctg tgatgtaagt 105480
ggatttggat ttaagctatc atttaaatga cagtttcact ggacataaaa tccaggctga 105540
ttttctttcc cttgtacttg ctgggggtga aagccactg cattttgtat cctacgttgc 105600
tttgcaatta gcctggtttt cattcctttg cacatcgcct gcttttctc cttgaaaaa 105660 ttagacatat tttgtttaca tttgaggtac tcaaaaattg gaatttgttt ttgctttgtt 105720
ctgttttaaa tcaacgtatt atttactttg tgagtacttt cactttaag ccttttttt 105780 tctttcattc tgggaaattc tcagccttc tgtctaatgt agttcttcct agtcttttc 105840 tctttgttct ctttctgggt catttttt tataggactg gtaacacttc tatttccatc 105900
ttccatactt tagcatttgg aggatgtttt tccaccattt tcatcccag atccattttg 105960 ggaaaatgta tctctgtctt ttggctccta tgtgcattgt ttgtgggtat ccttccattt 106020
cagtctgttc tttgtgctct ccagttcaac aatttcattt cttctcccg gtatctcgtg 106080 tgacttcctt tgaaacccct tgttccaact ttatatcgct atcattgtct ctctgtccat 106140
tggagggatc tgcttctttt gaatcccagt ttgtttactt gggtcatttt attattatta 106200 tttttttaaat aggatgttcc ttttctttta agtgctttgc tttttgactg gctcttaaaa 106260
atttcttggg agttcttta ttttcttgag gccggtagag gtcttggaag gtaccaagtg 106320
tccaatgggc aatcaaaagc ccacctctct gcctggcgcg gtggctcaca cctgtaatcc 106380
cagcactttg ggaggccgag gcaggtggat catctgaaga gttcaagacc agcctgacca 106440
atatggtgaa accccatctc tactaaaaat acaaaaatta cctgggcatg gaggcatgtg 106500
cctgtagtcc cagctacttg ggaagctgag gcaggagaat cacttgaacc cgggaggcag 106560
aggttgcagt gagcagagat tgtgccactg cactccagcc taggtgacag agtgtgactg 106620
catctcaaga aaaaataaa aaacaaaaaa taaaggccca cctctcgatt tcatgcctct 106680
gggtaaattg gagggaaaag agggtccctc tgtgaagagc ccttggaact cgagttctaa 106740
tttctaaacc aagaacttta tattctttcc tccctcccta tcacttccat ccactggctg 106800
gctcttatct gaaaactgtc gtgtgcagtt ataaatactc aacacttagg gaaggagaag 106860
gaattctgag agatttcgcc agcctgattc ttttcattgc cataaaattc cactgctta 106920 ccagaaaatcc ttggaatgtg gctttcctag ctttgcactg tgaccttctt cattcggaat 106980
aacgaagatg agaaaagcat tgatccgccc agacagtgag gagcgaagag caatacctag 107040
gtggaaagct ctatctcccc tgactgtcct gtgaaatgca cctgagtctc agaggactcc 107100
```

```
actgccatct gtctgtccag gaatttccca ttttgtatgg cgacttcaaa gtaggtaaat  107160
actttgatta aaggaataga gaacagaatt tgggtagctt gttcaaaaga tggcatggaa  107220
aattctgtga ctggagtagt tgtgaagcat cactcttccc gtaagaataa aggaggcatt  107280
tgccagatgt ctgaaaacac acagacacac acacaaagga attacttctg gctgcaagaa  107340
tattctctct cagcatcttc ctgcatctcc atgggcaaac agacccacaa cagcctggga  107400
ttttttaatt gccaacagtt ttcattgcat gagagcctga catgtctgtt gcatgatagg  107460
gtgtgttttt attttggct tcctattggt ttcaacatat ccctccttcc atgtcataat  107520
gacaattaca aagacctgag ttgaacctag aacgcttttt ttttgtcaga cacaacaatg  107580
cagtggatgt tagtcatagg gtaattcaaa cagagataat tttgtatatt ctagaatatt  107640
atgttttcaa acgtaggttt tgatgtacca taagatttct tctgccattg aggcgatata  107700
tatgtgtgtg tgtgtgtgtg tgtgtgtgtg tgtatgtata tatgtgtg tattttaaat  107760 ttaaattaga tattttttag aggccttagc ccttaagcag aattccctcc taatttaatg  107820
attttggacg aagctcattg tgaatcattt aaaaacacat tcatgcttct tcaaacagag  107880
gtaacaaagg atacagcacc ttgacttgtt gactaagtgc tgtcatggta gatgttattt  107940
agcatagaag atgcctgcag ggtcagttct actctctaaa gtttcttgag gctgtgttaa  108000
atgaaatcaa acacctgtgg attttttatt cttgttcacg ctttttatac ctctcctttc  108060
ttctccctgg gcaacctgct ttcacactag tgcctacctc tgttttccct tcagaatgtg  108120
atctatgcta cacaatctga ttaacaagct caacagagtt ctactggaca tagaataaag  108180
aaaccagtat agttttctct ctagggacaa ggcagtgagg aagccagttt gaatacaggt  108240
tcttgctctt gtaagcattg acattcagca ggttccttac tttctgaaca ctgcagttat  108300
atgatgggca gacagggact aagaataaca cctacctcaa cggggctgtt gtgaggatta  108360
ctgagataat ttatgtaaat ccctagcaca atgcctgact catgcgagat ctttaattca  108420
tggtagcagt tactaatttc atttatcata atgagctgcc tgagctacca aggagctctg  108480
ccactcccag tactgttcta cagttcttta attcaacaaa gaaattttc tttagttcca  108540 aataagtgcc aggcatcagg ctaggtgctg ggtgtatgat gatgatcaaa acagtgttcg  108600
tatgggggta gtcatcattt tgtcgatggg ccattttta tgatgtccct cttcattata  108660
ggtcttgatt cttgcctctg ttttgtatac atatgtgttg cggcaggggc ttgctataaa  108720
aatcagaatt gcccaggctg agcgcagtgg tgcaatcatg gctcattgca gcttcgggct  108780
tcagtgatcc tcccacctca gccttcttag tagctgggat tacaggcaca ctccaccaca  108840
cctgcctctg ttttgtgtag ctgtgattac gtagcaattt tctgaatcag tgacaagatg  108900
caatgcatat tttttcagt aggttaatta atttatctaa tctacatttg gagctatttt  108960
ttggagtgtt agtcatcata ataaatatgg tggcactgtc aatagtaata taaatataat  109020
ggtaccttaa ttccataata caaagatcac gtcttcatga ctgatgggcc attcaaacc  109080 cataggtaca tttgctcgct ctgtaaagta tacaaaagta agaattctgg acatctttaa  109140
aagttgtaaa tttttacatg aaaacttaca ttcacaccat ctttttgaata ttgaaaagat  109200 ttgggaacat ggggcctata tgtgactgtg gatgaggtgt ggctgttccc tttagacaca  109260
gcactcactt tgccatagtc acactcccca ccgctcccta ttgtgtctcc aaccccagg  109320 ctgttgtctg tttcttttcc aacgttatta cccactcata gatggtcaac cttatgatca  109380
ttgttacttt ctttcctca gaatctttct agtatttgtg atttttttca tgtggttatt  109440
```

```
ttgagctttt tgcattaaga atttgggatc acatactcaa aagtttagta tttaccagtt    109500
tgtattattg agcacttcag aaatttattt ctgttgctgt tatcaactca taaaatatct    109560
gtttaattat ccaactaaag actagatagg atagtgattc ctattttctc caagctcata    109620
tctgtgaact ccttgattgc ccaacatagg cattcaatca ttcattcaac aaatacccat    109680
tgaggaccta ctatgatctg ggcacttttc taggtgctga taattgtagt gaaatagtag    109740
accacagtgg acagtgtttc tttatggaat ttaagtgaat aaggaagtta ttttggagta    109800
tttcagatcg tgattcctgc tacgaagaaa aataattcag aataaagtag ataaggaata    109860
ataggaatgg acccacacag ttattatttt tattgctgtg gtcatactga tatctgaagc    109920
aagtaagaga agagtttcct atgaggatgg aatagcatgt gcaaagaccc tggagttgta    109980
gaatccttga tgcgtccaag gaatatggag aagaccagtt gggctagagt tgacaaaatg    110040
agggtgaagt gggggtataa aatagagag gtgctggaca gtaggccgtt gagagggctt    110100
tagcttttcc gtgatgaata ttggaaccca caatgtaatt ttgagcatga aaatgagagc    110160
cttgatttac atttttatca gatcaccctg agttctggtt ggagaatgag ctctaaggat    110220
ctgtgggtat atttagggag atacttaggt ggcctttgca ataatacgct caagggagga    110280
tgctggcttc accagagagc tgatagataa gccatggcca gattctggga atattttaaa    110340
ggaagatcca acaaatcgat tattcctaga atgcagaatg aatgagaaag agacaactta    110400
tggccaaccc caattccttt ggccgccgta actggaagaa ttgcgttgcc atgtgctgac    110460
aacagggaga ttgtgagagg agcactttag ggtgagggaa ttaggagact gcttttgttt    110520
aagttaagaa caaccaagga gagatagatg tcttagagac agctgggtac agtagtgtgg    110580
acatgaagag agaggtctac gctggagata caaggtcagg agacatgagc atgtagatga    110640
tatttacagt tgtgagactg aatcgcattt ccaacacaat gaatgtagat agagaggaga    110700
agtaagtgta ctagaagaaa aagaaggatg aagaggagga gagagagaag acagtgagga    110760
agaggaaaga agcagcgtgc atgtgtgcac ttgtatgaga aagagagaga gagagggaga    110820
aagtggaaga tatagataga aggagagaga gagagactgg gggaagaatt acatccaccc    110880
aaaacccaaa ttttaatgac ttacaatatg aaagcttcat ttttttttc tcttatgttg    110940 cacctcactg atggactatc atcagccca cttctcttcc aagtctttat tccagaatcc    111000
aggctggagg ccatgcctga actgaggaaa tggtgttcat gtacaacagt tctttcagct    111060
tctgctcaga tgtggcattg cacatccact catatgcgat tgtccaaagc attttctat    111120 tctctgggag atacttcaag gggcacaaca gtggctgggg attgagggg ctgtgaatag    111180 actttcagga aaaaggatca gctgtgctaa atgctgctga tgagtgcagt aacacaagga    111240
tgagtaactt gagtagcttg tagagaggta taggccattt gtttcatgcc caggaacaag    111300
gcaggaccag gaatcctggt tgagatgctg cagtttgggc tagttggagg tgggggcaag    111360
tttttctctc actgctggga cttactcagg ttaacagatg ggacgttgtg gaggagctgg    111420
agacggagga gaaagtgtag aagagttaac taggagatgg attgagagtg tttgatgtga    111480
gaggcagtag agcatgcatt gaacctaggc tgtatggttg gagggttttt ttccagccat    111540
gtcctgtctg ctcaggttca gaggaggtag gaggtagatt gaaccagcca caggtgatgc    111600
tccatgagta aagaagggtt gagagtcagg aattgaggag tccaaggcat taactgaaaa    111660
gatggttcat ggaatttaac aaagatgcgg acaaatatga ggagaggagg cagtcaaggg    111720
agagagaaag agtagggttg ggatacaggg aatgaaagtg agctcctaa gatgaatggc    111780 taatcccaca aaactggcca attcccataa ggtgaacggc taatcccatt agtgcattgt    111840
```

-continued

```
tgacatgaaa atgtcctcac caaataatga agaaaaattt gattttctta tgtggaaaaa    111900
gcaggaccaa aagcaatcaa ccaaaatcgt atctactacc tggcagtcca ttagaacaca    111960
ctaaacacac acataaagag aaaaatgaag tatgttaatt gtgaaacttg tatctccaaa    112020
aactggaaag cttcttggca cttaaaagca cttcttggca cttgggatta cttgcctgta    112080
atcccagcac tttgggaggc tgagacgggc ggatcacttg aggtcaggag ttccagacca    112140
gcctggccaa catggtgaaa ccctgtctct agtgaaaata taaaaattag ccgggcatgg    112200
tggcgcatgc ctatagttcc agctactcgg gaggctgagg cagaagaatc acttgaacct    112260
gggaggcggg ggctgaggta gaagaatcac ttgaacctgg gaggcggggg ctgaggccga    112320
agaatcactt gaacctggga ggcggggggct gaggcagaag aatcacttga acctgggagg    112380
cgggggctgc agtgaactga aatcgtgcca ttgcactcca gcctgggcga cagagtgaga    112440
cgctgtctca aaaaaaaaaa aaaaaaaaaa aaaaaaaaaa aaaaaaaaaa agaaagaaag    112500
gttcaatacc tacttgttga atgaaagtgg acgtgtgaat tcaaagtttc cgctctttca    112560
cagtgttttt ttttttttttt ttttttttttt ttgacagagt ctcggtctgt cgcccaggct    112620
ggagtgcagt ggcacaatct ggctcactg caaactctgc ctcccgggtt cacgccattc    112680
tcctgcctta gcctcccgag tagctgggac tgcaggcgcc caccaccacg cctggctaat    112740
ttttttgtatt ttgagtagag acggggtttc accgtgttag ccaggatggt ctccatctcc    112800
tgacctcctg atgcacccac cttggcctcc caaagtgctg ggattacaga catgagccac    112860
cgcgcccagc ctcattcagt tctttattac atttgtaaag gtaactctaa ctccgtgaga    112920
gcactttctc gctcacctct taattcttga gcaaacagag aagctgtgca tgataaagct    112980
ggagaattgg gtggtgtctt cctattaagc ttacaggaaa gcactgggca tttggaacag    113040
atgttgcatc ttgagagcca cagagtcagg tgtgcacgtt aaaacgatgc ttctaattgt    113100
tgcatagaga cagaagacaa tcacaaagat tctgccttga cctccttacc tctccagttc    113160
taaaaacatt tctcccacta cagaaagcat ccatctatgt gttttttgcc tccacgtggt    113220
cctattcctg aaatgctcct tccaagtctg tacttttcca agagctacta tttctggatc    113280
ttttgcagtt gcttcagcaa gaatcagttc tggcttcctt ggttctacca tgccaacttt    113340
accttctcgt ccctcagtgg gatgctaggg cttgggttaa ttcatctctc tccttcaagg    113400
cgacatgaag cccctgagaa caggggcata ttttgtgccca gccattacct acaatgatac    113460
aggagtcctg taatattcgt tagagaaatg tgtccactga acatgaattt cctatcctgt    113520
tccttctaaa aaggatgcat gagttatcct atattcccaa ggcacaacat gactttgttc    113580
tgatatgtgc caccgtgatc ctgtagaatt tgttttgttt ccagtcccta agaataaatg    113640
tctcttaaag tattgtagtc attcactcta catttttatg agttattact ggcccaccta    113700
caaccatatt tcctccgaaa ttcatccatc ctcctggaat tacctgattc tgaattatta    113760
agtggttctc ttggccatttt gctcaaaaaa agagcacact tattccaaca cacaggcatt    113820
gtttctaaat tattattgtt ttttcttcct agaaaccatt tagagatgaa gatccacttt    113880
agaacatgaa cccatttagt ttagactata acaattgaag atatggtgac tactgtttat    113940
ttctgttagg gatatatttt ttgtagattt cacaaaagac agaacctgct gtgtgacagc    114000
ttatctgcag gacaccgatg gtttgtagga cgatggtgag gctttgtgac aaggcagaaa    114060
tgtggaaggc tggcaagatt gtttactgag cttcccctaa ggatggaata attcaccaat    114120
cccacaactc ctccaccctc agtcactacc aatagctgtg cctcagtgtt ttcttttaa    114180
```

```
tgattgtatg tattaagaaa aaaatcctca tatgtagtgt ttagtttatc tgattttcgt    114240
tactaaaata ataaaggaga aaagtaaata attcatataa aagtaaactt tcttattcca    114300
agcaggtgta tgtgtgcatg tttgtgtgtg tgtgtgtgtg tgtgtgtgtg tgtgtgtgtg    114360
tttgccactt tgatggaaag aggctgactt tgcagagact attttttgtt aagaactttc    114420
cattaaatta gagctttaag ttataacact gattgcatag gccagggaaa atggtaggat    114480
gtggcttaaa aggcaatctc acaagaagta tgactttat cttatattat aaacaacagc     114540
acaaccttgg aatttgtccc aataaattcc ataagtataa aataaactaa ataagtaaag    114600
tgactaatat cctactaagt cttttccttc acacatgctt ttttgcctaa agccatttaa    114660
agtctctgag gatttaaatc tatgattctt tcatggagta gaagaaaccc agagaatata    114720
gaaatttaga aaaactttaa gacttattgg tttaacagaa gtaggccggg tgcggtggct    114780
catgcctcta atcccagcac tttgggatgc tgagctgggt ggatcacttg aggtaggagt    114840
tcaataccag cttggccaac atggtgaaac cccctctcta ctaaaaatac aaaaattagc    114900
cgggcgtagt ggtgcacacc tgtagttaca gctacttggg aagctgaggc aagagaatca    114960
cttgaaccca ggagacagag gctgcagtga gctgagattg cgccactgca cttccagcct    115020
gggtgacagg gcaagactcc atctcaaaaa caacagcaac aaacaaaaca aaacaaaaaa    115080
cccagaggta gatctaattc tgcagactgc aatcactcag ttatggatgg ataagtcagt    115140
ccttaagtcc atctgctatt tgtgtatcgt gcattttttt ttttttttga aacaagcacg    115200
ttcccacctg gattgaatgt taatattcac tgaaagccag ggcattgcaa cgagcccttta    115260 ggatgttata attctgggcc attttttacag ttcaggattt cagatttatt gcaatgttgt   115320 aagttttttag tttcttgtct ttctctaaca tctagtaagt tccaaaactt aaagaactac    115380
aggttttctt gataaatacc tgtgtcacta cttttttattt ttagattttt cttttttact    115440
acatgatctg agttaaaagt taaatatata tgaattattg ttttgaaaaa tattacctat    115500
aatagttttt taaaagaaac tttaattta gatttgtgct aaattggcga agattgtgta    115560
gagttttcct tataccccac cctcaaattc cactactaga aacaccttac atcattattg    115620
tacatttgac actattaatg agccaatatg tgtgcaattt tttactaaag cccacccatt    115680
cttctgattt cgttggtatt ttccttctgt cttttttctt tcctcaaatc ctatccagga    115740
tcccacatta catttagccg tcatgtctcc ttgagctcct cttgactgtg acagttttttc    115800 ttcttttgtc tttcatgacc ttaacagttt tgaggagggc tggtcacggg attggtacct    115860
tgtttggttt gtctgatgtt tttctcatgg ttatactggg gggctatgga ttgtgcagag    115920
gaagaccaga ggtgaagtgc cactttcatt acattgtatc aagggcacat actagcacca    115980
tgacattgca gttgatacta accttgatcc catggatgag gtgatgttgg ccagatatct    116040
ccagtatcac gttcgtcctc ctgcacacac actttctata ctgtaccctg tggaaagagg    116100
tcactacgtg cagcctacac ttaagaaagc aggaggccgg gtgtggtggc tcacacctgt    116160
aatcccagct actccagagg ctgaggcagg agaatcactt gaacccggga gaaggaaatt    116220
gcagtgagcc gagatcgcgc cattgcactc cagcctgggt gatagagcga gactccatct    116280
caaaaaaaca aaaataaatt aaaaaaaaaa aaaaagaaa gcggggacta taatcccctc     116340
cttgagggca gagtatctac agaaattatt tgaagttatt ttgcatgaga gatgtgccta    116400
ttctcgccta ctcatttatt tattccctca tttacatata tcagtatgga ctcatggata    116460 tttatttat actttgggtt gtaatctaat gtgatgttgt ttatctgcat agattttgtg     116520
tttacgtaac ttttttttcaa attcctgagg gatagctttt tagaaaatcc ctgttttac    116580
```

```
tttagatcca aggattacgt ctgcaggtgt gttacaaggg tatcttgtgt gttgctgagg  116640
ttcaggcttc cgttgatccc gtcactaggt tattctgtgc ccagataatg agcacaggaa  116700 gtttttagt  ccttgtcccc cctctgcaac agattgtagg aaataatctg agactgatca   116760
tttttaattt tcaagcactg aacatgcagt tattttatct agaaggtaga ccagcaaaac  116820
aaaattatat ttgacatttt agcatataag tattttctag ttaactttga catacaagaa  116880
gccaggttat gaatgtattt gttcatgact ctagcttgtt tggttaaaat tattctcctg  116940
ccaaccaaat gcttttttgc taccctgaat atttaaaaaa ttttacaat  atttcatctt  117000 taagagctat aaatgtatgt tttaatatcc cagggtaaga tatagggata ttttttagtc  117060
tgtcgaggct gctataacaa ataccttag  actgggtaat ttataaacaa tagacattta   117120
ttgttattat tatcattaag acagggtctc tttctgttgc tcaggctgga gtgcagtggc  117180
ttgatcatgg ttcactgtag ccttgacttc ctgggctcaa ctgatcctcc cacctcagcc  117240
tcctgagtag ctgggaccat acgtgtgtgc caccatccct ggctaatttt tatttttta   117300 attttagta gcgatgagga ctcactacgt tgaccagggt ggttttgaac tcctggcctt  117360
aaacatttct cctgccttga cctcctaaag tgttgggatt acaggtatga gccactttgc  117420
ccagctaaca acacacattt atttctcatg gtcctgggaa gtccaggatc aaggtgctag  117480
cagattcagt gtctagtgag ggcccattcc cccaaatggc atcttcttga tttatcctca  117540
catgttggaa gggacaaggt ggaagggcct gcagcctctt ttataaggac actcatccca  117600
ttcatgaggg tagagttatc atgttgtgta ttggatttca gcatatgaat tttgggagga  117660
cactaccatt cagactatat aacaagatac attaggtttg gggtgttctg cacttgagtg  117720
aatctatgta agcccttca  catatttta  ctttcactga aataaaacta aataaggaaa   117780
ccaatgctat cctatatctt aaaatgagaa tggtttgtaa cagctcattg ccttgcatca  117840
tggtctttta gggttagggt tcgggttagg gttaggatta gcttcgcttt gctgggcaga  117900
gtaggtattt ccgcctcgaa ccacctctaa gggcttcagc tttcagtaac gcacctgtca  117960
cttctaatgc aaaaccttga gtcctctgtc tgtgtgcaga ttcaggaaca ggtttgaggt  118020
ctaagaattt tcttattatt gccttccatt tcaatttcta gttcctccaa agtccttcac  118080
aatgatgacc gagaggagac actcaaaaat ttgttagcca gagtctcaaa gtacatagaa  118140
gctgtttctc ttgggtggat attacaagtg cctctacagg caactgcatt tctttctctt  118200
tccaggattt ttgcttattg tccagatatg ctcctcctag tgagagggac acttctgatt  118260
tttcctgcct ccatggaaca ggggcttcag agaagaaact ctctacagcc ccttcgttcc  118320
attaataatt tataattaaa tgcatttcca gcatgaaggc tgcctaggag tagaagagca  118380
tattagaaga accaatctgc tgcgtatctg cttatagggt ttgagcccag tcaaggaggg  118440
atgcacagaa actcaggatt ctgacagccc agccccttg  caattgggag ggtcgccaaa   118500
tttctttctt gcaaggggta cttactgtct gtgagtggga gcctcttgtg gataaggagt  118560
gagggcagag agggaacagc agagccctgg gaagttcttt ccacttgact ctgagcgtct  118620
agacagcagc ctgcccccac cccctagatt ggctttgtac ctgtgagcaa agtttctgac  118680
tgtgccatac atctctggaa tacatttagt tgctaatgga gatattacta taattccaca  118740
tatgttttta gtctctcctt ggggctgtgc ccttctgtgt ggcttggcag aagagaaagg  118800
agagaaagat tatacatggc agccttgctt tggagggagt gaaacctgtg attttccttt  118860
tctgtgtcag gaaagcgttt ttctgctgct tgactagcca cctcccaggc acattaacca  118920
```

```
gtcaggtgat gctgacattt gtaccccta atctggctta tttctgaaac cctcccttttg    118980 agccctaact gctataatta ggagactgga tcctaacagg tttggaaaaa ggtttgcaat    119040
ctcaaaataa agtagtgatt ttgaaagaga aatgtatagt agagttagct atggggtttg    119100
cacattctac atttatgttt gtttgttttt attttttcgc tcagactgct cacagatgca    119160
gtgagcacac ccaaatgcat gtgatcaatg catgtctgac ttctgcagct atggaaggtc    119220
tgggtttgta agatcactgc tgtagaccct tgtttgacct ttttggattg ctggatcaga    119280
aagtgagaga ttgcgaaagt tttcttaaaa gaacaagtca gtgaatcaat tcattaattc    119340
ttttgttcat taggattagt taatatactg ctacagtaaa accttttgtt attgtctgta    119400
ataataaaag ttggattatg gcatggctaa ccccaatctc catacaatct gctcatagtt    119460
ttgacctcat tctaatataa ccctgtattt cacgtgattg aatgttttgc accatattta    119520
taatattaca tccaggtatt acttggtttc tgaaggttta taaaattgta aatgcagtac    119580
atagggtatt agagattttg ttgttttatt tttttagaga ctgggtcttg ctctatcaac    119640
ccaggctgga gtgcagtggt gcaatcatag ctcactgtaa ccttgaactc ctgggctcaa    119700
acgaccctcc accctcagcc tctggagtag cttgtattat aggtgcatgc caccatatcc    119760
ggctaatttt ttattttgat ttttgtagcg atagcatctc agtgtattgc ccagattggt    119820
ctcaaaatcc tagcctcaag caatcttcct gcattggcct tccaaagtgc tgggattaca    119880
ggtgccagcc actgtgcttg gccattacct agagttttg ttagagataa tgaaataaga    119940
atgagattaa aatgaggtta gtctcatgct gcttaaaaca gtgatatgct taggagcagc    120000
tgcaggaaca tctgatccaa tcttggaggc agcctggagg gcttcccagg ggaagcacaa    120060
tgtagtccaa aacctgagag atgagcaggg attgactaac taaagagcag acctacacac    120120
caaattctgc catcagttcc ttgcatggca tggaaaattg atttctacaa ctacgcagta    120180 ttttcttcc ttttttttttg aaacagattc tcgctttgtc acccaggctg gagtgcagta    120240
gagcgatttt ggctcactgc agcctcgacc tcctgggctc aagtgatcct cccacctgag    120300
cttccctagt agagtagctg gtactacata tgcacaccac catgcccagc caattttttta    120360 tttatttatt tatttattttt tgtagaaaca gggttttgcc atgttggcca ggctgctctt    120420
gaactcctga gctcaagtga tcagcccacc tcggcctcct aaagtgctgg gattacaggc    120480
atgagccacc attttttattt ggtatgtgtg cattctacat tattctacaa aaataaatat    120540
ttaataataa ttcacagtat cctgcagatt ccaaaataaa gtaagcttaa gttctgttgg    120600
aaaatgaatt tctgtgagaa ggctttggtg ctttgacttg aagctgacat caacattagt    120660
gttgggcatt tggctacaca cctgtcacat tcaaaagcca attcactttg agtctttatt    120720
ttgttggcag taagggctgc acatttcgat ccactgtgta ttttcctagc ccagattcca    120780
ctcaaagcag aggtttagag aaaacccttg tttattgcaa atattatgcc aaaaatagg    120840 atgaggaacc agcactgtgt tgtgggaagg aacgagaaat aatcactatt tacaatagcc    120900
gagttgtgga atcaacctaa gtgtccatca acagtgcatt ggataaagaa aatgtagtac    120960
atctacaaca cagaatacta ggcagccata aaatagaatg gaatcatgtc ctttgcagca    121020
acatgaatgt ggctggaggc cattatccta ggtgaaataa ctcaaaaaca taaaatcaaa    121080
tatagcatgt tgtcacttat aactgggagc taaacaatgg gtacacatgg atataaagat    121140
ggaaacaatc aacactgggg actcaaacaa gggaaaggct gggaggggt gagggttgaa    121200 aaattaacct atgggtacaa tgttcactct ttgtgtgatt ggaaccctag aagtccatat    121260
gtcaccagtg tgcaatatac ccatgtaaga aacctgcaca tgcacccctg aatccaaatt    121320
```

```
aaaatttaaa aacaaacaaa aacacaaaaa agtgtattgg ccacagagga gtgactgctg   121380
cttgacccag tgaggttgtc tgaaaaccct tatgttatgt gtctccagac cacctttacc   121440
cggtgaaaat ggaggaccca tattcacacc atctttcacc tcttattagt ttactggggg   121500
taacctctcc aggctgcttg gggagtgcta agtaggtttt agtgtgcatc cactgtgagg   121560
catcagagaa acttcaggaa atcaagaaaa aggcaagttt gcaggtatga agtgaggctg   121620
cacctgcgtg aagctggctg aagtctaggc agagcagatc accacaagag cggctggaat   121680
aagccatgtg gccgaatggc atccagcaca acgatcaagt gaaacagagc tcctccagct   121740
gtggtagaac tagggccaaa gtatgtgaaa gtgttcaaag attcttcgca ttgaattcaa   121800
gctcatcatt gtccacaaat caatgagacc atgtctatat tggtaaagaa agaataaagc   121860
ataaattcat atttcaattt ttaggttatc tgaataaatg aatttcaaga gtgcttaagg   121920
tttttgctag atgtttgcag gttttttgcct ggagaggcac aggcagttct tgtcctatc   121980 attctagcct tccacttgta gggattccct ggaaagttga cataaccgct gattcctagt   122040
tctgttttgt gggaagtatc aagattaaga daccctctgg gtgaacaaga tgtctttcaa   122100
tagatgaatg ggtaaataaa ctatggtgta ttcagacaat ggaatattat tccatgctat   122160
aaagaaatga gctattaagc catgaaaaga catggaggaa aattaaatgc atattactaa   122220
gtgaaagaag ctgatgggaa aaggctacat acagtatgat tccaactata ggacattctg   122280
gaaaaagcag aactggggga caataaaaaa tccatcattg tcagagtttc ggttggggat   122340
ggggaaagaa aagataaata ggtggatcat agaggatttt tatggcaggg aagatattct   122400
gtgttatact gtaatggtgg atgcaaggag gttcttttttg tctaattaac tgttcacatt   122460
catcataatt gattccatac agtatgcatg gattttcagg gtccaagtgt taaccaactt   122520
cagtggactt aaaccactct gtaaatgggg tgctctttag tgtttgtttt gtttactgtt   122580
ctaggactgg ttaatagaaa tcagaggaca tacagatcca gagtccctta tctacaattt   122640
gaaagtcaaa aacagttcaa aactttacag tgatatcaaa actcatttgg gggcaaaacc   122700
tgatctgaca gatgactatt tgtgttcttt cttttccacc tcagggtgga catttagata   122760
ttttcctgca ggaatattaa tgagtttgat ttgggagtga tgttccatat tcctctgagg   122820
gtgctgcata aaacagatgt aaaaaaatta aaaagttctg agtccccttc ctcttgtcca   122880
caaaagcata ctcattccca agggtttcag atccccattg gtggatctgt gatatcaaag   122940
gtctcattga taatgttggt ggtcagtgga aaatagttgt gtggagagag atgtgttagt   123000
ctggacctca tgcaatgact gcagaaataa ttttatgatt tccaaagaac aacagacaat   123060
ctaaccacct cccttacctt taaagactga catctgtgtt gtgttcatgg atgattatgc   123120
aaatcaagaa aagtggcttc catcaaaata atgtcatttc tttttggaga aaagagcctg   123180
ggactgagtt gtgttatgtg tgcagtttgc cagctaaact cctggcttaa tgattgggat   123240
gggtttccaa gggctggttc tgagactcag tggcagttag ttaggtggta atttccccat   123300
taacattaat gagaaatgaa ataagttact taagaaaacg tgctagacga tagtctctaa   123360
gtactgaaaa gtaaatgaac ccacctacgt ttgttcacat aaaatttctt agtatatttt   123420
aaatttgcta atctaatgta ctttttttttt tgcttgtgct ttaactttgt taaattatgt   123480
cacgtaaaac attttattcc atattctaaa ttacataaat gtgtcacaca caatgtcatg   123540
aatcaagttt gtctaaagag gagataggcc aaggcaggtg gatcacttga ggtcgggagt   123600
tcaagaccag cctggccaac atggtgaaac cccatctcta ctaaaaatac aaaagttagt   123660
```

```
ggggcatggt ggtgcacacc tataatccca gctactcagg aggctgaggc aggagaatgg   123720
cttgaccctg aaaggtggaa gttgcagtga gtcaaaatca tgccactgca ttccagcctg   123780
ggagacggag tgggactcca tctcaaaaaa aaaaaaggag ataatacact ttcacgtttg   123840
taaaataatg ttgattaaat ggtctaatgt gattttatct tgctaatcca gttaccgtcc   123900
cagtatctga attatgataa cagtttacgc agcatagttt tctaacagtt ttggttccat   123960
ctctgctatt aaattcaggc cactggatct gtttggttca acttggatta gggtgtgagg   124020
ttctgttttc ctacctctaa ctccatatac attgtccgtg ctcctgacct tccatgcagg   124080
aggcttgcag gtatctcctt aatctgtctg tcatctgttt cttctgcca tctcagggac   124140
tcctgatctt tccagactgc ccatcctctc ctgtcccttt gactcttcct tttttgttca   124200
ctttctgtaa ctccagtctg atcatctaaa tagtctgagg ggaagatgag gtactgaagg   124260
cactcttgtg agaatatttc tcaggttcct aggtccaagt ttccgttgca tcttggtttc   124320
tatttcagtc tgagcagaga gagagagaga gagagcaaaa aagatcttca ggataaaagt   124380
gagagagaga gaagatggag aaataaatat aaatgaacaa ctgataaatg ccttgagcta   124440
taactctgcc aaatgaacac agaaactcat gtgcagttag atattatcca cctgagaatg   124500
tagttgataa catatttcat cataaataat atcgtctaaa gcccttactt gggaagatta   124560
tgaagcaagc caaatcttat gcagtatgtc cttctgttct cttgacaagc ataagtttct   124620
atttctgtat tgctagaaat ttttagtcac atgcaattcc aacagtgctt taagctggtt   124680
attactaagt agaaggtaaa tgtttgatga tggaagaatt tgcggtggag gtgaaattta   124740
ggataaatat tagcaacttt gaaaagtaag gtgtagatct gtgcggtacc agaaaacatt   124800
taacagattc agaagttagt ttatgtgtac ctatatgtgc acacacatac acacacaatg   124860
catgcacact tatgcaaatc acacacacat gcctcacgca caagtgcaac actcaggtgc   124920
acccaattgc acatacgtat tctattacta ttctttgcaa tgctttgaat gctcatcatg   124980
taccacaaag ttatggtcta attcataata ccataaggtg cgtgtgcttt agagatactg   125040
tgtatttcct ttcaacatcg aactagtgac tattaatgtt ttaaaatcaa atttgataac   125100
attctgaaat aaaatactga tgtattaagt accaatgcgt tgacatcagg tttcataggt   125160
gttgaactgt agcgaggaaa acagttatca ggtgtcctac tgtaactcta cccagcagga   125220
aagctctatg taatgatggt agaatatcca aatgatggtg tccacatctg cacaggtacg   125280
atttgagatt cactgactta tttaggagga ttcagtaaaa tttcgcagat gttgttatgt   125340
agtaatattt ggctcattca tattctgcac tcctagacat tgcagaaaga catgcaactg   125400
tgatttccat ctcatccctt tcaccctatt ttgaaacatt tagttatgtc tactagttac   125460
cctaagttgt attttttacc ctctaaaaag gaacaagaga agttggaatc catcccagct   125520
ttccttccag aaaatggagg ggaggaacaa ttggaatgga gaggaactcc agggagaaaa   125580
agacaaaagg cacatgagtg agtttgtcta ggctgggaga gtgggcgatc acatgagatt   125640
tgtgaactaa ttttgttctc cttctgtttc cactgataag cactttatga gtgccaccag   125700
tgtaagtaaa tattaaacct catctcaatt agtatctact cttttccaaa tatatgctta   125760
tgtcagaaaa tgagcagtag aaagcaacca caggatacca cctgcacacc cacgggctga   125820
gcattgcata cttttcaagga gtgctgttgt gttttcaaac ttagtaattt cccaaaacag   125880
agaattcaca gcttccctaa tcaccttcct cagaaccctg aatcttgtta attgagtcat   125940
ttttctgatg atcatgtact catacaattg actaaatgtc tcactatgcc ttcctgataa   126000
gtagtgtctc tacatgtgaa gtatctattt aatctatcta cccctctctc tctatctaat   126060
```

```
ctgttgattt cttatctatc taatttatat ctatcatctc tatgtatcta tgtatgtatg   126120
tatgcatata tgtatgtatc tatatatata tcgatctatc ttatctatat gtatctatca   126180
tctctatgca tctatgtatc tatctgtcta tgtatgtatg tatgtatgta tgtatgtata   126240
tatctatcaa tcctctctct ctctcttagt tcagcaaatt acttacaggt ttttgttatg   126300
taactgagca aaattatata cacacacata agaaggctgg aagttcaaga tcaaagtgct   126360
tacagattca gtgtctggtg gggacccact tcctgattca tagacagcgc cttctcactg   126420
tgtcctcaca tagtggaaag ggcaagggag ctctgtggga tccctttat aagggcactg   126480 atcccattca tgaaactcca ctgtcatgac ctcattacct ccaaaaggcg cccacctcct   126540
aatactgtcc cgttggggat taagatttat atatttttc tttttaattt ctaattttg    126600 tgggtacatg gtaggtatat atatttatgg agtacatgag atattttggt gtagacatgc   126660
aatgcataat aatcatatca tagaaaatgg ggtgtccatc tcctcaagca tttatctttt   126720
gtgttacaaa caatcaaatt atattatttt agttatttta aaatgtacaa ttaggccagg   126780
cacggtggct cacgcctgta atcccatcac tttgggaggc tgaggcaggc ggatcacgag   126840
gtcgggagat tgagaccagc ctggctaaca cagtgaaatc ccatctctac taaaaataca   126900
aaaaaattag ctaggtgtgg tggcgggcac ctgtagtccc agctactcag gaggctgagg   126960
caggagaatg gcgtgaacct gggaagcaga ggttgcagtg agccgagatc atgccactgc   127020
actccagcct gggcgacaga gcgagactca gtctcaaaaa aaaaaaagt acaattaaat    127080 tactattgac tatagtattg actatagtca ccctgttgtg ctagcaaata ctaggtctta   127140
tttattcttt ctgactataa ttttttgtacc cattaaccac cccacttccc cacatcccac   127200
ccccactacc ctttccagtg cctgataacc cttttttgac tctctatgca catgagttca   127260
atctttttga tttttagctc ccacaaataa gtgagaacat atgataacag tctttctgtc   127320
cctggcttat ttcacttaac ataatgatct ccagttttat ctatgttgta aatgacagga   127380
tctgattctt ttttatagct gaacaatact ccattgtgta tatgtaccac attttccttt   127440
atccattcac ctgttgatgg acagttagtt tgcttccaaa tcttggctat tgtgaacaaa   127500
gctgcaacaa acatgggggt gtggatatct ctttgatata ctgatttcct ttcttgggg    127560 gtttggatat aaacatatga attttgagag gacagaactt tcagactata gcatactgta   127620
ccatctatct atctgtccat ccatctgttt atctgtctcc cattcctgaa tattgcatgg   127680 catatttgt taattatttc caatgtcata ttgagttttta agtaagatt acatttctga    127740 gaggcctcac gtgggggcat cctgaaaagt acattctctt tatagtttaa atgttttggt   127800 tttttcttt attttttca tatttaatta tatttctttc aagtgactcc tttgggagac     127860
atgattttcc tacctcctgg gactgccaca attccctgc ctcttggaat gcaatcgatc    127920
tctagtctgc ctcaagtata aagatgatat tcatgttgat gacattgaga aggatgagga   127980
gaaaggagtt gatcagagat ctatattcat ggtatatatg tttatcgtat atatatttat   128040
ctgcttatcg tcttcagaat ataaactcca agactgtggg tctttgtttt cttcagtact   128100
accttgcaga gtctaggcct atttattcaa agcttaatat tgtgaagtg catgaatgaa    128160 taaatgaatt ctaatgttat cactgccgtt ggtatggtat ctgtttctct atctgtattg   128220
tcctctctac ttttcattat ttgtttaatt cccactcatt gagacagatt gcagaagatt   128280
cctttgccaa ctacttctgg gtagagataa atttccctcc acggagctcc cactggactc   128340
tacctgcagc tatatgttat cttgtatttt ccaacactca gctgtaccac ataagacttg   128400
```

```
attgagtgaa gaccctgact tagctttgca taaaaccaaa gtaaatgctt tccacacata   128460
gccattcaca gacattttca cattttatac agcaactgat gaactaggct agtgttggga   128520
acaggccccc taaaatctgg ccataaactt gcccccaaac tggccaaaac aaaatctctg   128580
cagcactgtg acatgttcat gatggccatg accccatgc tggaaggctg tgggtttacc    128640
agaatgaggg caaggaacac ctggcccacc cagggcggaa aaccgcttaa aggtgttctt   128700
aaaccacaaa caatagcatg agcgatctgt gccttaagga catgctcctg ctgcagataa   128760
ctagccagag cccatccctt tatttcagcc catccctttg tttcccataa agaatacttt   128820
tagttatcta taatctataa aaacaatgct tatcactggc ttgctgttaa caaatatgtg   128880
ggtgaactgt ttgaggctct cacctctgaa ggctgtgaga cccctgattt cccactccac   128940
acctctatat ttctgtgtgt ctttaattcc tctagcgctg ctgggttagg gtctcccgga   129000
ccgagctggt cttggcaggc tataaagaca ttttctactg gcttaacaga gaagaaaaac   129060
aaagcttagg gagactgatt atgcagaatt taatttgcaa caagcaaaga caagtctatt   129120
gacttcaaat ggacatcatc acattgtcat ctgataattt ttccagcatc ctttgcctcc   129180
tctgtgttaa attataaatt aatgctgatt tatacagttc agttcagctt cacaaatatt   129240
taatgagcac ttgctgtgta ccaggtatta ttatataagt agttctttat ggtgtaagaa   129300
tggatagtag atactttttt atccattcaa ctttaaaagg ttgatgccta gtcatagata   129360
ccaggaaaca cttaagtgaa tgaggacaag ttttctgctg tcaaagagag agatcagaca   129420
ccaactagag tccaagaaag aacaaagtaa ttttgatcaa caaaactcat agaagaaaat   129480
aagcattctt tgttgttaca tatacttcag agccatttta gtgctcaaag tttgatagaa   129540
attgatacac aggacttgct gctctgaatt ggctatccca gaatattcta cgagctacaa   129600
ccagacctga cattaacctg tagttacttg tggtttattc atctatccat ctaaatgtta   129660
tgagcatctc ctatgtactc ttcatggtac tagactttag acattgaata cggagcaaaa   129720
aagacatagt ttcttattta atgtggctta tactctgatg tagcatttct tcaccagggg   129780
taattttgcc tcaggggaca tttggcgatg tctaaggaca gtgtaggttg tcatgactga   129840
gatttgttgc tgatgtctag tgggaagagg ccagaccccc ttcacaataa agaattatct   129900
gaccaaaaaa ggtcagcagt gccaaggttg agaaactctt ccagcagttg aagaaaaata   129960
atcatcagat cacccacaag tataattaca aactgaaata catgttagat gctggtagag   130020
ctggtttcca aagtttctga tccagttgtg aggatacata ttgatattga aacgggcgg    130080
ttgaaggggc agtagtaagt tattagggta agaaggtctt ggtgagcaga gggactttca   130140
tgcgaagact ccagggctcg aaggagccca gtgcagtcag gatctgaagt gacaggtgtg   130200
gcttgagaac agcggcaatg gggagttagg caggagggga agctggaaat gcaggcaggg   130260
gtagacaata aaagtacgca ggccgtttat attatacaat cctgtagact tctttcttct   130320
ttcattcttg atacttttct ataataacat tcaagcattg gatcagcacc ctttgttgtc   130380
ttctgtcatg tagcccaaag gtttaccttg agacacaaa ggcaactaag acaatggttt    130440
ctgcactagg gagatcatat tctcactcag aagacatttg cagggtgtga ttagtgagtc   130500
tcacatacat gtcaatttct tcctaagacc ttgtgctttt ctagttttta tttttttatt   130560
attattttta tttatgtatt ttatttgaga gagcctcgct ctgccaccca cactggagtg   130620
cagtggtgtg atcatagata gctcactgca gcctccaact cctgggctca agcaatcctc   130680
ttccctcagc ctcccaagta gctagaacta caaacatcca caaccacacc cagcttattt   130740
tattttttgt agaggcaagg ctgtctctac aaattccgtt gcccaggctg gtctcaaatg   130800
```

```
cctgggctca agcgatcctc cggcctgggc ctaccaaagt gctgggattc caggtgcgag    130860
ccatcgcgcc ccaccctcta gttttaatt ggtttatttt cttctcatat ttcagttgag    130920
cattattcat ttattgctgt tgaggtttta ctttttttt tcttcccaaa ggtagattgt    130980
agacagctca cctttgttac caatttgaaa tgctagatgt taattcttaa tgttgtagct    131040
gtaaagggcc atgatttgag gacgtgttat ttttttaagc ctgagtttgg attggtctga    131100
gttgaatgca gttgctaagc catcgaatga gggagtgtcc ctgaactaat gagtgacatg    131160 gacctttct tataggtgag agtccatttg tgataaaggc attgttttag gatacataag    131220
ggtcatggtg tatattctta gcaagtgtta tgaatacatt cgatctattt cttttgaatt    131280
ttagtgtttc tctactctcc atcttactaa accaggtgtc ccagatttcg ggttcagcac    131340
atttgtgtct gggttcacat agagggacta actaggtgga gtttagggta aggggggtatt    131400 cagagtcctg ccctcctgca accacagcaa cacccccaag tctctctcat tagattgtat    131460
ttgttctcct acttatgttc tttggcctct gctataaaca ttttcaaaaa agtatccaat    131520
gaaaacaatg ttgtcaatga ctgtctttag taagtctgta gtcagattca tatctttaaa    131580
atatgtacac tgtgtgaata tttcaaagta tgtatcatga aaacaaataa ggaaaaaaaa    131640
aaaaaagcca agaaagctga gatggctcta ttaatatcag gcaaagatac cttcaagata    131700
aggattattt ccaaaataaa agagagacat ttcataatga tacaaggaag aattcaccta    131760
agagaactaa taatgttaat ttgtgtacac ctaataagag agctgttaat tatacaatta    131820
gcaataaatg caaagaaaga ctcatcaata atgacagttg gagatgttaa gatgttacca    131880
caatagatga aagatgaaga tagaaaacac acacacacac acacacacac acacgata    131940 tgaaaatttt caacagcacc atcaatgtcc ttggcaactt cgtacttcga gtccaacctc    132000
ccttcacaat ctaatacaga aacaaacaac ccatgatttt tctgcatttc gtggttaggt    132060
tccctgtggc tcaaggcctc tggcgcaaat gatgttgtct tttagatttt catgctaaga    132120
agatactcat gttcgtatgt gtgtgctttt tcctctatag catccttaat gttggcctcc    132180
agatgagagt ctctgacaat ggggctttaa catcaaacag ccaaagtctc tcagcgagtt    132240
aacctctttg gccttaaatt tctcacataa tgacatacaa cagtccgctc ttcttcaagt    132300
ggcctttgag gagtctaggg acacttgtga attcacttcc acaactcagc tgcattgcga    132360
attcaattat tgtgctggga gatgttgtac cattattttt ttttaaaggt gcatattcta    132420
aaggttaatc ttgaggctat cacattaagg gttaacattt tatcgggggc attatagagt    132480
gcatttttga tggctgtgat ttcagataac aagcttgttg tttctatttt tcagctctag    132540
cttggcctct aatctgtagg gaaggctggt tcctaaatgc aggaaatgag gctcaataga    132600
acatgaaaag ccagtgttaa tacaccattc aatctcaaga aagagtggga ggaagaatga    132660
cagagctgtt ttttgacaga tgagtggtta ggcatccccc tagctctcca agtcaccact    132720
aggatgaact ttcaggatgc agtgtcctgt ggaatttggc tctgaaacat aacttcttca    132780
taaggcagat attgtaacgc agttctggat tttgtaccta cagacagctc tgtgttatgg    132840
taactgtttt ctgttggcac aacaaacaat tagttagctt catgctgtag aatatttcca    132900
gatgccctga tactccaaac cattggtcat tgcagcctcc atattcagat gtagcggcta    132960
taaacaggtg atgcatgcat cctggccagg gaccatttg atttttccac cttttctttt    133020
cccaaattca gggtttgtcc acattagcac tattaaaact ttgggggcgc ttcctgtgcg    133080
ttgtaagatg tttagcagca ctcctggcgt ctacccactc caagtcttta acacctaacg    133140
```

```
cccatcctta attgtgacaa ccaaaactac ctgcaggcat tgccaagtgg ctcctgaggg 133200
ggcagcattg tcttcattga gcaccagtat ggtaatccta gcctaatcta ttgtgttacc 133260
ttattgttcc ttaacatata tggggtagaa tcagaattac aggaacgtga atttctttca 133320
acaattattt ctttacaatt atgtaataaa atcataaaag gtaaaactgt atcttttttag 133380 aagccaagaa gcaacagttt atgaaacaaa acctctttta gtatttcata ttaatcaata 133440
gatattgtgg aaaggctagt tcttctttaa ggtaacagtt gcttaagagt tgaagtgcag 133500
cttatgagtt ttacaagccc tgatttatgc acagcttgag gcattgttgt tttgcaacta 133560 ttgtttttcca gcagcactgc tattttataa agcatgtat cagcaatagt atagaattgc 133620
atatatgctt cagagtcaat gcaatcatta aatagcatgc aatctgagta gagtctaccc 133680
aaagctggaa ttcagagcgc atatttatgc acttagcaac attgccataa ttacacacac 133740
acacacacac acacacacac acacacacac acacacacac gcacgcacgt acttaaagcc 133800
ttagccattt aaaaatagaa ttcaacaact aaggctcgta cacatggaac tcttttcata 133860
gcaggatttc caatgtgcaa atttgataaa attactcttt taaaaaaaa aattgctgca 133920 acgttttttca ttaacaccat aaacatttac acatgattca ccccaaattg caccctagat 133980
gtatttaccc tgacttggca atttcatact tcatgtctct acttcccttc atgcttcaat 134040
acagaaacag acaaccgatg acttttctgt atttctgtgg ctcaagtcct ctggccaacc 134100
tgataaatgg cttaggctat tcgataacct gcagcagatc ctctgagatc ttctttagaa 134160
atttcctcca agatcctaac tacattcatt tgtagaaata tttgagatgc aatgcatacc 134220
ctgtctagta tccccccacc ccataacaga aatgtgaagt agggtgatct gtcatctttg 134280
tgcaggtcat tgccagctct agcaccagaa tctcctcacc tggggaatat ctcagtccca 134340
ggccaactgg gacttggata ctctaattct aggtgtggtt gaagcatcgg tgggttccta 134400
taacactggc acagggaaaa acattaacag tgggacagaa tagagagtcc agaagccaga 134460
agtgcatatg aatagagaag ctggtcccag ctgggaccag cttttttaacc ttgccaaatc 134520 ttgctattgc atctttagct tttcttcttt cctttttata ccttcttcct tctactttct 134580
gtttagtttc ttctgttttt ctccactaat ttcttaagtg ggatgattca ctcattactt 134640
tttgcccttg tgtttgttac tgatgtcagt atttatggct ttaaattttc tctactgcta 134700
attttcctgc ctcctgtaaa ttctaaaaca cagtatttca gtatttgtct attaagtgtt 134760
aagtgagatt tgtgtgacgt tctaataaac agttaatttt taagtgtttt gtgtgtattt 134820
tctaatgatg agatacaaaa ttatgtaatt gtctatcaaa tcatcggtta actgtttatg 134880
gcatctgttt ttcctatttt ttgatctatt aaaattgaaa ataggtttct ttgtatcttc 134940
cattaatgaa tgaatttata aattcttcct ataatactac tgatttgggg ttttttaaag 135000
aacgtatgtg gcataaaata tataacaagt tatctccttg aagaatgaaa tattttacta 135060
tgtaatattc ttgctatctc ttaaaatgct ttctgtttta caatagatat ccaatattag 135120
tagaaatatg cttgtttctt ttttactttt gggttggcta ttgctgagaa tatattttt 135180 atattttcac ctttagtaat ttcagatatt atggttgtat catttcatat gacagatatc 135240
tataatttct ttttttcaat gtgacagttt cagtctagta attgcataac ttatgctatt 135300
tatgagtttg aagatatttg atataattca acgtattta atctttcgga tttccttttt 135360
tatgcattcc ttttaataaa tgagtttgtt cttttttctgt attttcttct taatttgcca 135420
tttacttgat ttctactttt caagaaaagc ttgcagttgt aaaactcaca tttaagtcat 135480
taaagtctaa aattaagcaa gaccttagct ccattctaga aaataccaat cacctgtctc 135540
```

```
cctagttaca ggctattatt atgtatcatg aatatttgtt ataaactctt tcagttttg   135600 tttgattgaa taccttttgtt ccctgctcat tcctgaaaga taattttgct tattatgcaa  135660
atccaggtgg accattattt cacatttcac tgtcttctgg ctatacagat gtcagttggt  135720
tttgagttaa actttatgca caggttgtct ttggcaaggg ctaaaattta agatctcctg  135780 tttattttg gcattcatca gtttcatgtc aatattgatt ttttttttgc tttatccatt   135840 cttctatgg tttctgtgcc tttggattca tatatttaat cattatttga agatcttagg   135900
gatcaccttt caaatactga cacttctcca ttcttcctgt tttctcaaat tttgatttga  135960
tatatgagat tctcattttt gcacccatgt ctcctaaatt gactttata ttattagttt   136020 ctgtcttctg ttttttgtaa gattttccca gacatatctt tttttattgt cttttcttct  136080
gtgtctaatc tctttagcta atccattaat ttctatttat ttcaacaaat acagttttta  136140
tttatttcat ttctatgtgg tcattttca aatcttcctt gtcctttcca gtaatttcct   136200
gttttttgtt tattgtttcc tgtttcaaac tttattttt aaatagctat tttaatacca   136260
caagttttgt gtgcagcacc tataatacct cagtgttcat gggcttagtg atctttgact  136320
gtgaactcat gtttgtttga tcttaatctg tgggaatttt ctggcctatg ctggcattct  136380
ttccccaggc aggtaggttc gctttccttc tgatagaagc tagagtgtaa gacttgagcc  136440
ctttcaaggg tccaaattct ccaccttact ggaagccaag cttgggtttc tgccccagc   136500 cccttgtctt acacatctgg ctgcccttcc agctacctgc tcccttttgtc tgaggtcagt  136560 gctactatgg gtgtgttaca taagggcaga cttcccttag gtccagtttt ccctttgctc  136620
aggacaccca aatattcttt tgcttacact gttggaggag ctttatgtgg gaaagcttaa  136680
ttttggatat ttctcttact tccttgtgcc cagaagttca ctagcaagtg catcttatca  136740
ggaggtaatt gttttgttca gggaaggtct cccagagtga tgtgttacct gctgatgata  136800
ggagtggaag cttttccttt gagaaggttt caccaatgga aaaacaggaa ggaatgaggg  136860
agggagggag ggaggaaggg gggaagaaag aaaggaagaa aggaaggaag agagagaagg  136920
aaggagtaaa aaaagaaagg gaggaaggga gagagggaag gagtgaaaaa agaacaaagg  136980
aagaaaggaa ggaaggaagt aaagaaggag aggaggaaga agtactgagg aacatcttac  137040
tcaatggtga gacccagttc gtacatgttc ttatcctatg agctaatttt ttctcttttg  137100
tttttcttaa gagaattggc tgtctcttac tctgtaatac agatctgtga gaaaatagct  137160
tttataaaaa gagattttgt agtattacac acttggcagg aatatagttg tctgttgtaa  137220
taatgaatac taatctagaa taggaggctg agaagaaaaa tataattaaa atggtaatgg  137280
cttttttttt atgtgaatga aactcatcca gtattggttt tgaaagatat ctaagttcta  137340
ggagcagact gtagcagaat ctcctttaat actctaagga aaggacgctt ttagaaagta  137400
ggcattgcct ccttatgtga aaactgcatt cctttcatga gggttccatt ttctggaaca  137460
caggatgtaa gacaggagac ataagaaggg atcttgtagc agtgcagatg aatcaagtca  137520
ctgcactttc ttatttgatc ttatttaaa aagatgcttc cagggaagca ggaccttgga  137580
acccacaaag tctggagcaa gtcattgacc tcgcaaggta ttcacgtcct cacagtaaaa  137640
tggagaataa aattgctagt ttttaaggat actcttagga ataaataact tgttatagca  137700
catatcagac catcagtcat gccagcctgt tttcctttct ctcttactct ctccctctgt  137760
tcattttctc catcttctct ccaactattc ctccctctct accactgttg ctccctcct   137820 ccctccctcc cttccttcct tccattttt ccttccttcc tttctacatc cctccttccc  137880
```

```
ctctctttct tttcctttgc ttcctttttct ttttcttcct ctctcttttt cctacaaaac 137940
agtatttgtc aactttggca ctcatgacat gtggagctga tcaccccgtc tttgttgtag 138000
gaggtgtcct atgcattgta ggaggtttag tttagcagca tgcctgggct ctgcccagta 138060
gatgacagtg gcaccactac cacaagttat gaaaaccaaa aatatctcca gacattgtca 138120
aatattgcct ctgaggcgaa accaccctg gttgtgaacc accactcaaa aatacacttc 138180
atatcaataa aaatcctgct ttatatat atgttttttg ctcagttcag ggttattaag 138240
attgtaagac actagtgttt ttacaagatt tctagggatg ttctttgatt gagtcttaaa 138300
atcttactgt tgatgaaaaa ttgaaattat gttgttattt ttatattcct tcatatagca 138360
gcataaaact tggtatttta tgggaatgag tatgcatctt gttctgattc tatggtctac 138420
ttttatgtgt ctcaaaatga gattcagatc aagaaaatt aaaacgagag caaaagtgaa 138480
tattaaggta aaggtatagc attctgatta tctgctgctt gtccatctca ggtatgcaat 138540
actgacactg tgccactagt agcttcttga cattcttaag atgaaaatag tttagttttt 138600
atctaaatat attaatagag aatatacaat atatatttat tcatatatta atactggaac 138660
aatagagtaa ggttaaacac tcaaaattta gctcaaccct gagattatta tgaagtactt 138720
acaaaaataa aaactaaaaa gacattagta gcgtacttcc cagcttcatc tctgcaggag 138780
gtgttacctt agctcagggc ttggagaata ggacatgtgt ttacgtgatt gactcttgtt 138840
gggattgttc tcagagctct cctgaccttg gtccacacac ttgggagcac atgattccta 138900
atactgataa ccacagtctc atgaattttt ctcattttgc agaggaggga attgaggcac 138960
tagatggtaa tatcttttc atttcacata gttgctggtg gctaagggaa gctggtctc 139020 agcttgtccc aggccatatc taagacattt gtctggcccc ttgctttcct tcctttcatg 139080
catacagcaa gcatatccaa cttttctatg ctggtctatt tctagaaggt gttatttgac 139140
atggcatcac ctcctttgta gccctctgac tatgagaatg atagaatgac ctctcttta 139200 aacctatctc cttatccgcc ccaacacata cccctttggg gtggggtcat aaggggggtat 139260 cccttctcca cactaacttt accgacttct ctcttcattg tctctctgca gcagataatg 139320
taagcaagaa aaagattaag ttaattacat gcacctcaag tttcagtagg aatatcccac 139380
aattcctctg tctcttaatt taactgttat ttattgaaca cctgctgtgt tcttgggaaa 139440
attccaggtg ctggatggaa ttagtttatg atgatagcta agacttgcag agacattaat 139500
gtgctgttct tcttcttct cagaaagtat agccatgtac aaactactaa agggcgatat 139560
caaatgttgg ggagataaat atcaaaatac agagcttcca tacctgtagt tttggttagt 139620
ttaataggcg ttaacattta ctcatttca gctacctaca tttattgagc agtgcctata 139680
ccactcattg taatttaatt gcataataaa ttacactgta tttgctgttt atagaaattt 139740
agaaatttag tttaacgata tgtttataat tttcttacta ctatggataa tacatttaat 139800
gactataatt aaaattcttgc aaaattttttg aattgttttt agtaatttgc caatgatttt 139860
cccaggtatt aatttaatat attgaaattt tgtctttata gcatagaggt ttttatttc 139920 attcatttat ttaacaggca tttatcattc atctgcttta tgcaaggaaa aaatggtca 139980 agacaaggat gccaagtctt taacctcagg gaacttacag tttatgtaca gggacacata 140040
cttatcaaat aaacagagaa aggaatgtat attcatatga actcggcatc atatattctt 140100
ctttatgtta tcattaataa catccaaatg tcaacaacac atctattgtt actttggtta 140160
aaaagctaca cagacagtag tagatatggt acttggatga agaaagctga agtttattat 140220
tttctctttc tagttttaat ccctaagggt cattgataaa agacttacac aaacccccct 140280
```

```
ttagtaacct aataatgtat aataatcctg ttcttaaaat ggtgatagag atttgcttgg  140340
tttctactac ataacaccat aataccatat taagacttga atctctttat atcatggaac  140400
aactcaggta gtgttacaaa ctgctgttac tgaataaatg cggagaagaa caagctctcc  140460
agagcagtgc catgcctgtg tctgatgttt cccaggatag aaaactgcgc agatgttgat  140520
ggtttgtttc aggtgctttg acagcctgat catgggctct agccgtggac catgaaaaat  140580
ggcttctgca ggggcttaag aaagacaatg aagagcttcg cattttctct ggcatttcc   140640 tgctattgtt taaaaggtca catatgcaat ttaaaatgtt ccatgcatgg agcatgacaa  140700
atgccacgta gaaaatgaaa ctgctttcgt tgacattttt ggccaatttc caaagggtac  140760
cattttccgc cttttcccct ttgtggattt gcaaatttg gcttgtgcaa aatgcgtgcc   140820
ccacggtgca ctctaggttg ggaagtgcca catgttaggt agaaaatcgt gtgtagatga  140880
gaatggcaca ttcagaataa aagtgagaaa ttaaatgaca tcaaaaaaat agagaaaaat  140940
agagaaaaac ttgtaaatga gtccatcaga actatcagaa gctcaaaaag aaagaaaggc  141000
ttagaactca tcaataacaa tgtccagtct cattcatatg taaagaaagt gaaatcaact  141060
ttattttagt taattttact ttattttatt ttattatcct tttacctagc tgaatggcaa   141120
aactcagttc agttatcttt gggcatggaa aaatgagcac tctcacagtt tgctagttgg  141180
aggaagaatt gaagtagagt tttagaagac attgggtatt atacaacaaa atttagaaag  141240
agacccactt tactcctctg gaagcatttt tgcttccagg aatctatctt acagatatat  141300
acacaaagat atatgtacat aggtgatcat tgcaactgaa attttctca tcaggaagat   141360 gagtgaatta ttttaagcac ttagaatatt aaaactatct ttcccttgaa attgaagagg  141420
cagagcaaaa tgtgaggaca cagagtaata ttcacataaa ctccttaaac ctatgtatgc  141480
acgtatagat acttgtatat atacatagat atgaatgcac aatagtatcc atacacatat  141540
gtgtacatat gtgtgcatgt gggtgaatgc ttatgtgtag atttgtatac aaatgtgtgt  141600
atgttgctgt attaaaaaaa gtcaaaaaat aaacaaatta ttaacaatgt ttgcctctta  141660
gaaggtgact atggtacggt gcccttagag agaggctttg attggcagag aaaatgaaaa  141720
accataactg cacctatatt taagatttta aaaaattctt tgtagtgagt ttgagtaact  141780
tttaaaagta cattgacatt tcatttatgc agatcttcta ggtgtgtata aaaagccatg  141840
agaaaaagat gatttcatgt gatagagaaa actagcacag gttagaattt ggactcagct  141900
gatgagacag tatctgccca aaccaattta atcaaagctt tgttgcatga gccgggtgtg  141960
gtgagtcaca cctgtgactg cagcgctttg ggagaccgag gagtgaggat cacttgaggc  142020
caggagttca agaccaggct gggcaacata atgagatccc ttctctacaa aaagtttaaa  142080
aaatctagcc aggcgtggtg actcaggcct gtggtctcag ctactcagaa gactgaggtg  142140
ggagggttgc atgagcccat gagtttgagg ctgcagtgag ctatgatcac accactacac  142200
tccagcctgg gggacagaac aagacccgt ccttaaaaaa atttgtttta aacacttcat   142260
tgtgtggaag aaagctgtat atttaaacaa atataaccaa acccgtaata ctgggagaa   142320 agattgatgg attgttgaaa ggattatacc cgttaggcca attttgagat gtaggcaagg  142380
aatctcagaa gttccaaaaa gttctgctgt ggttcagtgt tacagggaaa tctactcaag  142440
ggaataatat atggcttgca atcattttgc tttttgtta catttcctat tattcattgc   142500
ttcattgggc ttgagagaag ccccacagag gaataagaaa taccctacat cattcacatc  142560
ttcttggctt ttgaaaatta aattttatat acttaaaagc agccatgaca catgaaaaca  142620
```

```
ttttctttct tcctcaaacc atctttacct agcctcaccc aaaccaaact ttaattttta 142680
cattaatttt tcttttccaa agctatgcag ctgacactca tctgctcact tggcataatt 142740
catttggtat ccagtaagtt taagaaattc tgtctgggct tcatgcaatc ataacctaca 142800
tccaaatagc aacacttata ataacagtaa taatagtatt ttttagtgtt cacatggatt 142860
ttctcccta attttcatga catctcaaca aaatagacaa aatacatggg cttctcctca 142920
gccctgagct ttgcctatcg ttaacccctt gaagaaaaat ggcgctgagc tatcagtcag 142980
tcattccctg gcagaaaggg aacagaatca gtatagatgg ctttctgaag acattgactt 143040
gatttctgtc accaacaatg gcatattcag gctgtgctcc atgccaggtg ccgtgtgggc 143100
atggagtcca ccacaccagg ggaattctca gaagcagtat tgaaaacaca taggaaagca 143160
ttacttaagc ctgtataaac ataagctctg tccagacatg gaatacagtg ggagttcttc 143220
ctaggataat cccaaaaact aatacatcag aaagcttacc tataacatga gaattcaagg 143280
caaaggcatt tttggtatgt aagtaaaata ttaggttgaa tccatctctt aatgcggatg 143340
ttgaagaatt aatgttatat ccatgaagcc agtgttgact ggaaggactc aaaaaaatct 143400
gaagaatata aattccttga ccttctttat tgaagacttc agctccatta cacgaccacc 143460
tcacagtcct cattcggttg ccttttgcct gtttctgact tactgaagga caatggtgtg 143520
gagctacgat ttatcaccca gaaaatgatt actaaagtcc gtattctact ctgaatactg 143580
aaaactctga gtaatgacc ctaacctaaa cctcctcttc ttctggctat cacttcttcc 143640
ttcccacttt gatcactctt ccatgaatcc tggcaaacct cctagtactg agtatccttc 143700
cagccaccaa acgtctgaca tagatcgctg gatctgactt taattctctc actaagaccc 143760
tcaatttcct cctctgcttg tggtgggctc accctgttgt ttctcagcta agggtgcatc 143820
cagatatcaa tttcttgtgt cccatagcac tgctagcatt aagtgaatta ctgcatggtt 143880
tggtctcatt agtgtgtggt ttccagaaac acttgagatc ttactgttgg cttgtaatct 143940
gtcttagtcc attttgtgct gctataacag aatacctgaa actgggttgt aaaacatata 144000
aatttatttc tcctagttcc agaggctggc aagtccaaga tcaaggcacc atgatctggc 144060
aagacctct tgaacatcat caaatggcag aagggcaaag agcttaagag agtgaaccca 144120
ctcctgcaag cccttttat aattacactc atctgttcat gagggcagag cctttgttac 144180
ctaaacacct gccattgtcc cctctcctgc aacactgtct tactagggtt taataatatt 144240
catgtcaacg catgaattcg gggaacacat tcacaccata ggacaaccca tttacactct 144300
ctcctcatcg gggtcaaagg gcatcaattt aaggtttttt gacctttttt gttttcatta 144360
tatctcattt ttatactaac agattcattt gttcgtataa ctctcctgtc ttccagaatc 144420
tgggacagtt ttccacctcc caagtgggat ctaggagtta acccccacca tcaacccaag 144480
tactcctcct gtgtccaatg gccagtcagc ctcaatcctg tcttctcttg agttatgaca 144540
tatttttctc cttccattaa tagtgaccat tactgtaata ggaatttata gttctttgtc 144600
ctccagttct ccaaaactgg ttctctatcc tttcaatttt atgctaacaa atctcattaa 144660
agtatgacca gtgatttcta cattgccaaa acccagtggt gtctttttag tgatgatcct 144720
atatcaattt gatgggcact ttatcacttg cagaattctt attccttttc attttatcac 144780
tatgttctgg ttttattcta caattgtgag aagctcttct gtatttttctt tcttattat 144840
tcttaaatgt tgactttttcc taggatttgt tcttgacttc attctgtata ttgtatgtct 144900
aggtaattca ttgcatcttc ttatcttcaa ctatctgcct ctatgtggat gattctcaag 144960
tcttttatttc cagctcaggc cactagcttc agttacagtg tttgtaattt tagcccctat 145020
```

```
tagaaatctc tagttgagtg tcacatagac actccaaaca caacacattc aaatattaag    145080
agatgctctt cctctaaaac ctattcctct ctgcaccctc ctgttagtta aaggtgcccc    145140
atataccagt gtgtccaaga tacaaactct gttggatttt acttctcttt tctcagcact    145200
tatgtaaatg gatgtctact tctcatttct gccctgcaga acattcctag ctatgtgctg    145260
tcttcctgtg gcccactgtg acagcttcct tatctcagtt tagattgtta tgcagtccat    145320
tactcttctg cctcctacct tcaagctact attggagtca tcttcctgat tctcacatct    145380
gatggctttc agtggctaag tgatgcattc caatctttct tagttcattt tatgctgcta    145440
caacaaaaca cctgaaactg ggttataaaa aatagaaatg tatttctcat agttctagag    145500
gctgggaagt ccaggatcaa ggcaccatca tctggcaaga ccattttgca catcatcaaa    145560
tggcacaggg gcaaagagct caagagagtg aacccactcc tgcaagccgt taaaaacgca    145620
tcatgggccg ggcgcggtgg ctcacgcctg taatcccagc actttgggag gctgaggcag    145680
gcggatcatg aggtcaggag atcaagacca tcctggctaa cacggtgaaa ccccgtctct    145740
actaaaaata caaaaaatta gccgggcgag gtggcgggca cctgtagtcc cagctactcg    145800
ggaggctgag gcaggagaat ggcgtgaacc ccaggggggcg gagcctgcag tgagccgaga    145860
ttgcgccacc gcactccagc ctgggcgaca gcgagactcc gtctcaaaaa aaaaaaaaaa    145920
aaaaaagaaa aaaacgcatc atggcaaaat ctctttttt accacctggg aaaacctaag    145980
acccttggga cagcacagaa gactccttaa tctgcccatg tgtcccttc cagtgttagc    146040 ttcttttact ttttcttgta cacctcgtgc ccttgcccct tggaacaaac agctcacagt    146100
tccctcagca cacccaccct tctacctgcc cgggagctgc cttccgataa gttgtatctc    146160
gatgacttcc tccccactct ccatctggga agatcccagt cattcatttg ttaaggccca    146220
gtgaaaaaga tttttatttat tttccttcat ataatatttt tatgtataca tatatatgca    146280
tatgtatgct atctatctat tagatacatc ttgttttggc ttatttttat tttttatgtt    146340
ttgagacaga gtctcagtct gtcacccagg ctggattgca gtggcatgat cacagctcac    146400
tgcaacctcg acctcctggg ctcaagcaat cctcccacct cagcctcccg agtatctggg    146460
actacaggtg cataccacca tgcccagcta attttgtat ttttttttt gtggagacac     146520 agtcccacta tattgcccag gctgtttttg aattcctggg ctcaagcaat ccacctgcgt    146580
cagccttcta tagtgctggg attgcatgcc tgtgcccctg tgtctgacgt tatccttgtt    146640
attttaatgc ctacctcatt tgtctttttc aaataataat caacaaatga tttctggatt    146700
gataaatgca tgaatgaaat gatagtttgc caaaatacag aatattaaaa ccatagggta    146760
accttgagac aatttaggta aaaaatagg gattatttta tattagaaga ttattcaatg     146820
tattattaaa atgtttgttt attgcatgtg ttttaagtgt tgagaattta acagagaacg    146880
agacatgaat ggtctaagtg tttatgcatc ataataaagt tgaagaaatg tagggttccc    146940
atggtgtttc ttttcaaact ttgataataa cacttcttta ttgatcgcaa ctgtacattg    147000
gcagcaccgc ctccagactg gaaaataaga tcgatttctc ctttgtgttt cttttataac    147060
cttgcaattt tattcctctt gggcttactg ttatgagttt ggtttctagt ttctagagca    147120
tgagttctaa gaagtggaaa tcaagatgga aggaagttac tatagtgaga gggtgtcatg    147180
ccctgcaggc taggtatctt agagtctgac tgcaactccc ttgacacagg cagttctttt    147240
tcttgcctgc agccctttcc aaacaaatat caccagcctc atattcccct ccccttata     147300 gatggagccc ctttgtcaag caggccagtt tactgggaaa aggcccttct cagacatgct    147360
```

```
ttctcatcct gatgctttgc ctttaccagg agtgaggcca gaaccttcag catgcattta   147420
tatcaaaaaa gagagatgtg ctgttttcat ttaaattccg catttccact gggcatagtg   147480
gctcatgcct gtaatcccag cactttggga ggctagggca ggaaaatcgc ttgagaccag   147540
gagatcatga ccagcccagg caacataatg agacccgtc tctacaattt tttttgagaa    147600
agggtctcag tctgtcaccc aggctggatt gcagtggcat gtccacagct ccctgcagcc   147660
tcaacctcct aggctcaagc aatcctccca cctcagcctc tggagtagct tggaccacag   147720
gtgtgcacca ccatgcctgg ataattttg ttttttggta gagacagggt tttgccatgt    147780
tggtcaggtt ggtcttgaac tcctgacctc aggtgatctg cctgccttgg cctcccaaag   147840
tgctgggatt acaggtgcga atcactgcgc tcagcctcta tattttttt tttttaatta    147900 gtgtgctagt agtctcagct acttagaagg ctgaagcaga aggattgcct gagcccagga   147960
gtttgaggat acaatgagcc atgatcacat tccaccctgg gtgacatagt gagacgctgt   148020
ctctattaaa aaaataaata aacaaattat aaattttcac atagtcgtaa acctctgaag   148080
atgtggatac ttcatttgtc acatttaggt ctttaataca ctaataccttt ctcttgggaa  148140 acagtgtttc tcagtctctc ccgtattgat aatgtttcca cttttgcct gaagattttg    148200 tgggttatgg ggaaacagtt tatggggtgt ctttcagcag aaccacaacc cttttttagga 148260 agaagctaat tatggtgtga aagggacagg tgctcttatt aggtagtgat agtaagagtt   148320
aaaacccagt tctcttgagc tgttacttgg attcttcaac tgagggtgat tttgcatctt   148380
tggcactaga tgtcattcaa ctgacagtca tggactccca ggggacccccc aaactctatg  148440 tcacctttat gagtaggcga gaatggattt ttccttggga ggagtgtctc ctcaaagaag   148500
tctgtgacct agaagaaaag atgaaaaatc tctgctttgg attcggaatg tcaggactgt   148560
tcacttggaa cttaaggaga gtttcttcct agtatatacg agactgaacc ttatgggtt    148620 gccattttct tagacccaaa gctttcaaat acagtcattt tcatatgact tctacttaga   148680
caataagatc atcatgtatt ccttttttcc tctttcagca tctggcattt ttctcctctt   148740
gggcttgttg ttctggtttt tttttttttt ctggtttcta gaccataagc attcatgcat   148800
tcacattatg ttgcctccta agttgtaagc tctccaaaga gagggaatat agctgcttta  148860
tgtcttcacc caactttgag tagagatgat ggcaggaaac agagagcatt ttcacagaga   148920
agatggagtc catttgagtc aggggatctt gtttgaaatc ttacctgtgt gatctggggt   148980
gaattaatac agctgtctgg aaaatttaga acagagacct cagaggattg cagtaaggag   149040
tcctagaagt taggatctcc tcagtaaata taaatactta ttctcttggg taatgaagct   149100
gacccacagg atgatgccaa ttatttcctt ggtattataa gcacataaac aatagttcac   149160
atttattgag tgcttactat gtgtaagata caattatgtg ctttgggata tgggttcaca   149220
catgaaacaa gtgtttattt agtgcctact ctgtgcccaa cactggagat gcagctgtca   149280
tgagcactaa caccatccca atatcatggt gctcatgtac ccatgtggga aaaagtaaag   149340
acaggctcaa gcatataaaa tagggaaggt ggtcttagga taattcaagc tggattggga   149400
tcagtagtga ttgaagggct agattaaatg aggagtttag gacatgcatc tctgcaagat   149460
ggcatttgag caagaaacat aggcaagact tatctacttt aattttcaca gtagggtcat   149520
gagattacac tgtttattaa ctctgttaca gagatgtgga aactgagatt aggatgattg   149580 ataacagcc agattagtaa tagggctggt agtcttaat gcaagtctca tgggctatgc    149640
tgcacacagt cttaacaact tgccaccttc cgtggtataa gagaggaacc aacccaattc   149700
ccgttgcctg ccttccctgc tatattagtc tattcttaca ctgctataaa aaatacctga   149760
```

```
gactgggtaa tttataaagg aagaggttta attgactcac agttccgcat agctgggaag 149820
gcctcaggaa atttacaatc atggcaaaag gtgaaaggga aggaaagcac cttcttcaca 149880
gggcagcagg aaggagagaa gtgctgagca aggaggaaga accccatata aaaccatcag 149940
atctcatgag aactcactcg ctatcatgag aacatcgtgg gggaactgtc ctcatgatct 150000
aatcaccccc catgaggtcc ctcccccaac acgtggggat tacaatttgg attacaattc 150060
aagatgagat ttgggtggag acacagagcc agaccatatc acttgccatc taattacctt 150120
gatcaactac cctgcaacca ttccttagtg agtaataggg ccacactcag gaatggtttt 150180
aatagaattt aaaagttatc agtattgtag tttaattgta attttaaaaa tggtgaacct 150240
cacatcagtg gctaggatca gcacatgata tgctgcatct tggggtcaat aattgccgca 150300
agcacattat tagagttgct gttaatagtc atggaaacca ccctgtacct tcttccccca 150360
gtgcaaccaa cctggcagtg attgacctac tcggtagcga gttgctagac atcaggagaa 150420
gtcagaagta agtggaagaa ggccaggtgt ctagaagacc ccccactac ccatagcagt 150480
agcaacacat atgcatagga ataggttaaa tgagtcttca ctcattgatc cattcattca 150540
tctttcatcc atgaattaac tattcatgac ccattgttgt tgactctgaa gatacgtag 150600
caaacaggat gcacaaattg tcctgctgtt actttagtta tggggacaga agataaagca 150660
gtgatcaaat gcatgaagga cagaattgct gatggtgatc atagctttga gggaaatgaa 150720
gcaacgataa catctaatgt gggttatgag gatctttgag atggagtggc cagggcatgt 150780
ctttatgagg gtgaggaatt taagcatccc agacacaagt tctgactcaa acatcagcct 150840
tttaattatg tgaaagggtc tcgcaaaatt taataaactt agtggtagga gttcaggtaa 150900
cactacaaga aaccaagctt tctttgtgaa tggtgaggtt agaaggggtt tgttgctgaa 150960
aatcccattt gcaggttcta aggctgggga tgaagtagaa ggaacaatct cttgtcattt 151020
gccaatcaaa gaacaatccc tgtatctggc aaaagagaca tacctttcta tgaatcctgg 151080
ttttggtcat aagccaaact tctatattag ttttcccttt ttggttgagt tagtgaacaa 151140
ttggatgatt agctaaatgt tgctgaaata ggaggaaggc agattaaaaa tacagaaagt 151200
aactcttatt taatgatttg aaaaaatgag gttaatccga caaaattta aggaaaagtg 151260
agataatttt ggtgtataaa actatgaaat tttaggctgg gcatggtggc tgacacctgt 151320
agtcatagca ctttgggaag ctgaggcagg aggattgctt gacccagga gttcgagacc 151380
agcctgggca acatagtgaa accccgtctc tacaaaaatt acagaaatta gctaggcatc 151440
ctggtgtgtg cctatggtcc cagctatgag ggaggctgag gcaaggagaa ttgcttgaac 151500
ctgagagttc aaggcctcgg tgcactctgt cctggcttgt agagtgagac cctgtcacac 151560
acacacacac accacacaca cacacagaca cacacacaca cacacacaca caaaataaaa 151620
ttttggaatg taataacatt gatgctgaag tgaattgtgg aaaaatatca tataaaatat 151680
attttaatca catagtataa atttctctct gtgcattagt taccaaaatt tgaacataaa 151740
cattttcaaa tacacacttg tgcaaatgtc agggatagca ggtggtatat cactttttat 151800
attaaaatg catgtaggaa tgaaaggaaa aaggtaaaaa tatgttaagt gtagaattct 151860
aatgaaagaa catattggaa ctatgaaaac attatggagg actttgttca tttatggtct 151920
gagcacagat gatgctaaac atggtccttc aactttagct ggcagccatt tgaaatgaac 151980
acactaaaca ccatgagaag caactgcatg aaaagcaaag agagttatcc aagtgaactt 152040
catatctcat catttgcctg tgtttatgta atagtaaaga cccaaggaat tggtctaatt 152100
```

```
aattggtatt ttattttagt gatgaaataa tgagtgcggt tgagcatgcc agatgtattc   152160
atctgataca ttcttccagt cacatggtag gctgcattag gtgataatgc ttcaccctgc   152220
attcatttat aagttagtga agggaagtcc acaactctgg tctcagagca tttatcccat   152280
tgttgatcag ctaagctgtt gctcttactt agctgctaag gaatgaagct aattggacca   152340
ttccagcatg taaaatatgt aaaatatgtc ctttcatgga actctgaaac aaacaatgag   152400
aacaaccaga aaaattgcca gagtcataca aaagctgtct atttctaaat gatcattcct   152460
caagctcttg tcatctactg ggagcccta gatggatgta tagttgttgc tgttgtggct    152520
gattttgata ggactaacat aggaccagtg tatggagctg tttattaaga tgcttttgtt   152580
gctgagtatt tacattttgg gtgttctcgg ataacatacg ttaattccta ctgcagtatt   152640
taataaagtg taactagtgc ctgtctcacc tgtctgaaga cattcaaata tggagcgttt   152700
gtttctttct ctagtgcaga tactaaatat catattgtaa ttagagctat acagagattt   152760
agcatatagg actggcaagt cttggaggcc aattttatg atgtgggaag aggggggcgt    152820
gatttagagt ggacaaataa agtgtgggaa aattttgtgt ttctggcttg agtgaccagc   152880
tcttacctct cctccccata ttctcttcct tgcctcagtg caaattcaca ctgtcttcat   152940
tttgtatgat caccctctgt cttagtccat ttagttttgc aattaaggaa tctctgagac   153000
tgggtgacat atagaggaaa gagatttatt tggctatgat tctgcaggct gtacatgaat   153060
cacggcatca ggatctgctt ctggtgaggg tgtcaggaag cttccactca tggtggaagg   153120
tgaagaagag ctggtgtatg caaagatcac gtggcaagag aagaagcaag agaatggggg   153180
gaaggaggtg ctaggctctt ttaaacagtc agctcttggg ggaatgaaca gagcaagaat   153240
tcagtcatta ctgcaaggct ggcaccaagc tgctcatgag ggatccacct ccatgactca   153300
aacacctccc actaggcttc atctccaaca ttgggaatca aatgtcagct tgatacttgg   153360
agaggacaaa catccaaact atagcactct gtctccttag gtgcaccttt cttcttcagt   153420
gactaatcta gagttctctt tggaaaatgc aaatgtagtt atgtttcttt tttgcttta    153480 tgccttactg gttccctgtt ctttatagca tcaggttgca tcttcatcaa ctggggaacc   153540
agttgatgaa gagaagatca gcatcctgaa gtatcttgta acttcttgaa gtatcttgaa   153600
gtatcttcaa gattcagaat gcatgttacc ttctctgcaa agtgctcttt gcaccttgtc   153660
cagtgtagct gtgttaactc cagtgcacct tcctgatgat cttcctaagg ctcttacctt   153720
cttgtcatta gtcgtttctg tgaccatctt gcctatagga atgtgggcta ctgtgggcaa   153780
gtacaatgcc tggcatgcag caggctttcc agaaatgctt gtttggcttc tagagttctc   153840
tttgctgtta ccacatccat cccctttatca tccttttttc cctagtcatc tttcctctgt   153900
acctttgccg ttggttcttt ctccatgaat caatataaat aatacaagct tgtgcatag   153960 cagaccttca ctcttgtctc atgatttcat ttctttcttc ggcatactga aaggcaagta   154020
cctttctctc tctgactctc aatttactca tctgtataat tttgatggtt ctttcaattg   154080
tctgctattg ctgatgatgg cacgaactca gatatgcaaa gtatcagact ttcactcttg   154140
tctcatgatt tcattgcttt cttctgcata cttaaaggcc attaccttcc tctctatgac   154200
tctcaagttc ctcatctgta aattttgat agttgtttct actgcctgcc attgctacga   154260
caatggcaca aactcagata tgcaaagtac ctctgggtta aatgtgaaca aaaccttcaa   154320
cctgctgcaa gataatctga cctctgcttg actgtctagc tctgtttcc tggcagttgg    154380 atgaagaaca tggcaacaat attcttggcc acattgctta caatacaaac gatcccctat   154440
ttgtaaatag catcatgacc aggagaaacc ataaagacct gaaagaacct agtggtaata   154500
```

```
ccaccccacc tcaggcttcc cggagggcaa gttttggagt cactttgcag ctgctctgtt   154560
cactctagga accatggaaa ctctgctcat ggagtattta cagggaatat tggctgctgt   154620
gaaggctggg acttcaatgc caaggaatac ccaattcccg tggatatgga ccttgtaggg   154680
atctttgcat ctcagctgtc ctttgtggag cagatggttc ccatatgcct gctgcagcct   154740
tcctgatgag ctgagcttct tgtctgtatt gttttgagtc ggttggcacc atggtaactt   154800
tgggggggtc ttgtgattct gcatgtttaa tggaacctga aagacccctt actgggcatt   154860
aaagaacaaa gacaaatgtc cctgtgacag aatactggct caacaattgg ttttctctct   154920
gatgcctctt ccctgcttgg aaagcccttt tcttttatcc ttcataatca cttcttacat   154980
ctggcacagc cttcagcttt gcattattcc ttcattatct tttctcatcc cacattaaaa   155040
aaaattcttt aaattgtggc caaatgaaca tgacataaaa tgtaccattt tcacatgtgc   155100
agttcaagag tattaagtac attcacattg ttgtgcaaac atgcttttt tcactctgtg    155160 ccctcatttt gctctttcct ggtttccaat gcagtatctt atatatgatc taataaatgt   155220
gtcctgggca tctcagtctt gtatattttg gtcctctgtt atatcaggta cacccttaagg 155280 atagacattg tgccctacta atcttcctcc ttcatcacat gaaatattgt gcttgcatag   155340
tacattttct tcactcccct ccctgttatt ttttatgtat atcatgacac ttatttgcca   155400
aggatggctt tggccctcta tgcaaaatgt caccaatggg aacaatgcta aagtctgcat   155460
aaatcttaag tttaattcta atttaaata tttgaatata gtgctagtgt tgtcattcta    155520
taggattcat taattcatcc catcaacaaa cacttattga gttccaaatt tgttcaaaac   155580
atggccgtat gtgctgctgt agaaaaaatg taaaaagtca gtttctagtg taagggaaat   155640
aaaatatgga tatcattaag tcctggagaa ggcaggggt gactgatttc aggcttgtac    155700
catagggatt cccaggagga ataagtaggt tgcagcattt aagaagggat catgaaagac   155760
atgccacttt aactagttcc aaatggaatt ttggaagcag agccattgga tgttatagct   155820
gaagtaatat tttaagcaag gtgtcagaac aggattgagg cataatttca gaagaacatg   155880
aagtccttgt ttactaatgc agaatatgtt ttatgatagg ctggaaagtg aatctgtgac   155940
tagatttggg agtgattcag tgtacaatga atatggcagt aaagagcttg gacttaattc   156000
gggctgctgg tctggtcagc ccttgtgttt ggagagatga gtaacatttg caaaggtgga   156060
gagaaggaat tggagattct agttaggtgc tttgggcata tgttcagtga gggatgaggc   156120
attaatgttc atcaaggcag cattcacaag ggctatggcg gcactgaatg ggagagcaga   156180
cagacacagg tgtcatccca gaggtggact ccgtatggca cagcggcaag ggagtgtgaa   156240
gggttatgac agatgctgag taggtgctag caacatattt tttaaaatag tggcaaaatg   156300
tatgtaagat ctataatttt tgcatgtaca gtttagggat attaacaata ttcacactgt   156360
tgtgcaaaca tgcttttttc actctgtcct cattttactc tttcctcatt tacagtgcag   156420
tatcttatat atgatctaat aactgtcccc taagcatctc agtcttgtat attttggccc   156480
actgttctat cacgtacact ttgaggggc attttcagat aattccaggt aaaacgtaaa    156540
cctcacgatg gcagctaaga aaacaggggc gttctctgca ttggttagtt gcagggctat   156600
tagtcaaaat tccaaatctc atatgcagaa ggccaggatc tgcagtctta agtagttcag   156660
tttgtttcac ggaggtaaat aaaagaaaaa aggcatgctg aagatacata tccctggcct   156720
ctagataatc agacagtaag atctctccca cacaccagag aaatctattt ccagctttct   156780
gttgcagtcc atgaaaatga cagaaaatac atgccctgct tggaccacag cctagctcat   156840
```

```
gggaaaaaaa aggaaaataa aaaagaaccc gagcttgctg tggatggttc ctatggagtg 156900
tttttggcac tgtcagagtg cacactctga caggctgggc atggtggctg acacctgtag 156960
tcgtagcact ccatggcact gaatttacgg tggaaggatc acattggcaa gtcaaatcct 157020
tgggctacag gaaagactcc catgtgctgc ttttatgctc cccagcagcc aggctgtcgt 157080
tcacaaagca ctctccaagc atcttcattt aatgttgttg ggcacaaggc cctggtgacc 157140
ccgttaaaat ttaaatcttg ctcatacaaa gtgagggcag gttttcagtt gacatttgga 157200
ggtttctcca gccatgttag aaacaaaatg catttaagtg atgagccctt gatacataag 157260
aaggtgtaga gccagctgga tttctccggg accatgaggg gatccatctg attagggctt 157320
ctgaagccga aggaaactac agagagatgt aacttggctg actctcagtt cattattttc 157380
tcttggtaag agcacttctc atattggaca atctttctt cactgattta gatattattt 157440
tagatgcacc ttttctttt gttatggaag ctttatttta aaataaagtt aacctaaaat 157500
gggcgtatta ctctccccc gccccaccgc taatgattta gaacatgaaa ataatccaca 157560
agaccatggg tgctgtcttc agctacaatt actactttct taattgtcat ggaaacatga 157620
tttattattg gatggttttt tactgtctta tgcaaagatt tcatatgagc cgcaatacac 157680
actgtttcat atgggtaagt ctcaatatta tctgacaaag agagcttctc tgcccaagtt 157740
tatgaaaagt acatttttt ttaagtcact gtcttgccca ggctgcagtg cagtggtacc 157800
atcatagctc actgcagcct caacctcctg ggctcaagca gtccgctcac ctcagcttcc 157860
ttagtagcta ggtgtttgg tttggctttt tatccccact tgaatatcat cttgaattgt 157920
aatccccaga tgttgaggga ggaatctggc gggagatgat tggatcatgg gggtggtctc 157980
ccttattctg ttctaatgat agtgagtgag ttctcacgag atctgatggt tttaaaagtg 158040
tctggcaggt tcctccttcg cacattcttc tctctcttcc caccatgtga aaaaggtcct 158100
tgcttccatc ccgccaccct ctgccatgct tgtaagtttc ctgaggcccc ccatgccatg 158160
cggaggtcaa ttaaacctct ttccttctta aattacccag tctcgggtat ttatttatag 158220
aagtgtgaaa acaaactagg acactaggac tacaggcaca tgccatcacg ccagctagt 158280 ttatgtttat ttttaattt tgtagagat ggggtctcac tatgttgctc aggctagtct 158340 caaactttg gccttgagca gtcttccac ctagacctcc caaagtgttg ggattacagg 158400
catgatccac tgcacctggc tgaaaagttt ctattgaatg gaaagaacaa tgctgtgaaa 158460
atatatttta ttaatgttca ggaaattgtg gaacttgaaa aactctagct ttttagcagt 158520
tttaatggct actatgtgct tctaaaattt gtacctgctt ttttgaagtg ttatatgcat 158580
ttttgtttgt tgatggtggt gatgtttttg ccgttgatct cacctgctaa cgtggaaaca 158640
tttcaagaag tggaaaaatg tcttatttta gtacatacta tggtgtcagc tacattaaaa 158700
aaaaaagcct taagaatgt agcttgaatt gagggttgct atgacttttt gttgtagtag 158760
atttatgaat tgtgtatcat cattttcctt cagtggaaaa ttcagtaact agtatgttac 158820
tggttcctgg attccaaggg aggagaacat gaaacattgc aatggaatta aactccaatg 158880
agcttgaccc agctacgatg ttgaagtgag ggaatacata aagacttggg tgtatgtgtg 158940
tgatctgttg gtattaaagt gccaggatta aacattcta tgaaaatggc taatcatatt 159000
caatatttat ttgagacgct taagatgcat ggtttgggtg gaactagggt taggggctg 159060 ctgttttgaa cagccaaact agaattctgc tcaattatct cacacaggca cacttctgag 159120
gcatttttta catgatgcct caagaaagct ttgctcccatt ttgtatttca gcatgaatac 159180
aaatttttga aatttccaca gtaaagtgtt tagacttacc aaaaggtagg ccttgttata 159240
```

```
ataacaccag taggaccgat gtagtcattt ctaaaatgat tcaagcactt tatgtttctg 159300
gatgagctat tagatcttac cttatgtgtc tggataagct attagatcat tacatatttt 159360
aaagtgaatt tttgaaattg ttggttcatt gtttaaattt tcaattttgt ttctgttgca 159420
ttaatctctg agatttgaaa atgagaaaag aaaaaagatg gatacacatt aatgctttta 159480
taccttcctt tgtaacagca attgattgtg cacttgcttt tggctgtagt tagtccttt  159540
cttaaattag tttctggtat ggatgtctac ttttatttaa tttttttttt tttttgagac 159600
ggagtcttgc tctgtcaccc tggctagagt gcagtggcgc gatctcggct cactgcaagc 159660
tccaccccg aggttcaagc aattctcctg cctcagccag ctgagtagct gggactacag 159720
gcacctgcca ccacgccagg ctaactttg tattttagt aaagacgggg tttcactgtg 159780
ttagccagga tggtctcaat ctcctgacct cttgatccac cgcctcagt ctcccaaagt 159840
gctgggatta caggcgtgag ccaccgtacc cggccccact tttatttaat ttttattcaa 159900
ttttacattt tatatgcctt gttacttcat ttcttagcac cagaactaca agtttaattc 159960
ttcagacatc ttctctagca cctcataagg tattctttgt tacttggtga tagagaacta 160020
tgtaatttga ttttcttctt ttgcaatgga gtgttcaaat acgtcgttgc ttttaggtga 160080
gggatgtgat taattagaaa aatgagtgga tcttagctca atgaaattta atcagcagaa 160140
tggaattttc cattcagagc aaatgagttc ctaggactgg acacacctag atctgctgac 160200
ccaaacccct ttatagattt catttctgaa tgagctatta gatcattgta tattttcagg 160260
tgaattttta caattgttga ttcatcgttt aattttagt tttattttct gttgcattaa 160320
tctctgagat ttgacatata gaagaaactc tcatgccagc cccaaacgct ttccctatct 160380
cctcctccca tgccttcctg gagtggaggg aacgtcaggc ataagcagag cccaggagac 160440
actcatagac attctgagaa agcttttctc tgtagaaggg accaacacat cttgcaccct 160500
ctccctctct tgcccctgc ctgcatgtgg gtgcaggtgc ttttgtcagg accccactgc 160560
ttatctcagg tcaggagctg gcaaacctat gaacaagatg gaaacccaac tgctgaccag 160620
ggtggtgttc tgacaggaga gaagacttga gcccttatag acactgttga atcactaagc 160680
tgtaaacaat tttctttggt cttcttgtct ggtaaaatca attctctttc atcctttta  160740
aagacctcag tttgggcttt agaatccata ctggcaaatg cttcctcact aatattgtga 160800
gatttaatta gagatagcat tttatgtgct cacctaaaac tatacggtag acacaaagga 160860
gtctgggtct cagatcccaa cacgtggatt atagagaagg cagaatgcta taatgccttg 160920
agggtgagcc atccattatt tggggatttg aaaaaggaca atttctgttt tatgtttctg 160980
tcctcctaaa tggagttgag agacagcttc ttttctcctt agcatttggg caagaacaga 161040
atccagtaaa accactgagg aaggtcatca ttgcagcgtt tatttaacat gagtaattct 161100
agcatgagct ggcatgccat ttacatccat ctgttttaag tgtttgcaag cagaatggta 161160
ataagaaact ggggtaagtg ttaaaaataa ttatatggaa tatagattgc cccagatgca 161220
ctatctaatg ctgatgggaa aggagagagc aggggggtacc tggaacctgg acttctcctt 161280
ggaaacatgc catgaccggg tatgttactg gattgcatag gtgcagaaca tggaacattg 161340
cagtggaatt gaactccaat gagctcagcc caactacgat attggagtga ggaatgcatg 161400
aagacaaaac ctttattata agtctgtgtg tgtgtgtgtg tgatctgttg ggattaaagt 161460
gccaggatta cagcattcta tgaaaatggt agtggagaaa aggaaggta gaggaaaaga 161520
gaaaaaccaa agcaagagga aaccactgg aagaaaagaa gatgggaagg agaaagggca 161580
```

```
tctctgaaga atgtaaggag tacaagatcc cttacaggca gtgaacacat aagaaggcat   161640
cattcaccag aaagtcatac cagtttatgt attaaaactg ggaatggcaa tgataggcat   161700
tagttagaga ttatgcttta aattgtatgc atttgcatat ttttatatgt tttatttaat   161760
tttgttttgg ggggggggact gtatctcact ctgttgccca ggctgatgtg cagtggtaca   161820
atcctagttt actgcaacct tgaactcctg gcttaagtg accctctcac ctcagcctcc    161880
caagtagctg ggactacagg catgtgctac tatgtccaac taattttgtt attttttgt    161940
agagacaggg tctcaatgta ttgcccaggc tggtctggaa ctcctgggct caagtgatcc   162000
tcctgccttg gcctcccaaa gtgctgggat tacaggcgtg agccactgtg accagccctt   162060
ttgcatattt attgttttg tttgtttgtt tgtttttga cacagagtct cactctgtca     162120
cccaggctgg agtgcaatga cgcgatcttg gctcactgca acctctgcct gctgcgttca   162180
cgcgattctc ctgcctcagc ctcccaagta gctgggatta caggtgccca ccaccaaacc   162240
cggctaattt tttgtatttt tagtagagac aggatttcac tatgttgggc agactggtct   162300
cgaactcctg acctcatgat ccgcctgcct catcctccca aagggctggg attacaggtg   162360
tgagccactg tgaccagccc atttgcacat ttagtgttta ttttcttaat cagtatcgaa   162420
actgtgaaag ggaatgttaa aacggtggag ccaggtgaaa aagaaaatcc aagagtcaga   162480
agagagcatc caaagaagaa ggcagaggca ataacaagta gactctgaga ctgaaattaa   162540
actgtatggc tagaagatgg gctagcatag gacaagatga ggtaacatgc taacatggaa   162600
gattgagaag aattgcaaat gagaaatcac ggataaaaca ctgaccgcct aataggataa   162660
aagcagagga tgttcataag cagctgtcat caccaaggaa gaggaaaaca tgggaaaggt   162720
tttgccctct gagcagaaca atcctgcatg tcaaggggga gcctcatata ccatgtaacc   162780
tcatgttaaa ccataaatac ttaccaatac ctcttacagt gtgacaggac acaaactatt   162840
aaacctgatg cagataatgc cttttaaaat gagtattata tttgattatt atttctaata   162900
atgttataac tatgtttaaa ccatccactt tattccctag atgaaatata attgaattaa   162960
atgttaaaca tatttgacat gcatttctcg gggcttttga tttaacattt taaaatatgc   163020
aatttagcta ttttaaaaaa cagtcttaaa aaataacata gtatatcaag ataggcaaa    163080
ggaaaattta ggcaccaaat aatagagtac atgtttccta ttatgtgttt tggttgggag   163140
atgatctttg gaaagtgctg attctgtttt tgtttccata aaacaaaatt tccagagatt   163200
atatattgga ttctgcttga aagagttcag tagacattgc acttctatca cactgatagc   163260
ccaggaggaa ttttaactat gtaattattt aaccgcaaaa ttttccacct tctcccctta   163320
aacatttggc ggataaatta tgataaaagc agtcatgata tgcagttcgg tttcatagtt   163380
tcctttctct tccttttgc tatatttcct aaagttctat tatggagaga taccagtttt    163440
aaatgtcaag caatgttaac atctttgcat ctttatcttt tcctatccac tcttctctct   163500
tttcttttct tttttttttt aagggccaga gagtgacact tagccaatac ttaaccagta   163560
ctctctttct gtttgtttgt gggaatttta tatctatttt ttcttttttca attttttatt  163620
taggttcaga gggtacatgt gcaggtttgt tacatgggta aattgggtgt cgctggggtt   163680
tggtgtacag atgattttgt cacgcaggta gtgagcatag tacctgatag gtagtttttt   163740
gaccctcagc cttttcccac ccaccacttt gaagtagacc cttgtgttta ttgttcccct   163800
ttttgggccc gtgcgtcctc aatgtttaga tcccacttgt aagtgagaat atgcagtact   163860
tgcttttctg tttctgcatt agttctctta agataatggc ctccagcgtc actcttgttg    163920
cttcaaagaa catgattttg ttctttttat ggctatatag tattccatga tgtatattac   163980
```

```
accacatttt ctttatccag ttcaccgttg atggccatct aggtggattc catgtctttg   164040
ctgttgtgaa tagtgctgtg ctgaacatgc aggtgcatgt gtctgtttgg tagaatgatt   164100
tatattcctt tggatagata tccagtaatg agaatgctgg gtcgaatggt agcgacttgt   164160
ctcttaatag ttttttacttt gcctcgatct cctgattctc tccctttttt tcctggccat   164220
tcccgctgca cttgcctcat ttgctattga tgacatgctt gtccctgct tccatagatg     164280 tgtccacaaa tgcatgtgca cacgtgcttc agctaaagat tcctcagcta aagattctcc   164340
ctctccatca gggtttctct ctttagctca cctgcccttc tctacatggt tttaaagtga   164400
gatgattgta aatgtgtttt tcacaatgga aattctccca gcgggcgggg aggaaaaaag   164460
acatcttgaa atattttctg agaactatga ggaccggcag agtttgacat gttttgagg    164520 cgataaagtc atgtgtccat ctgtgaaaga caggcattgg ctttatccac atccacacag   164580
ccttccccgc tgtgtggctt cattattgat ttgctgtcat gtagagtcga taatgagaaa   164640
acctaggtag ccttgaaccc aactttgcaa gaaccttta ggactctggg acttctaacc     164700
ctctaggaag gtggagttaa ggggatatag gcacagaatg gggcagaagg gaaagacatt   164760
aagagacagc ctttagcaga ccagagaata catgccgttt atcaaattgt tagatgtctg   164820
tgcaccagga atgttgattc aattatggta tctaaaaata ggacagaaat aaggaggaaa   164880
taaaaggaaa tgaaatagca gtttacctct ggcaaaaaca aagagcccaa tcagaaaaac   164940
tagacaaagc cacctgtagg actggaagaa accatgtgag ttaggtatca ctaaccttgg   165000
aaggacaagg acttcctagt attttttgtat tttgtgaagc actttctctg cattttctta    165060
atttgtcctt aagtgattat ctctcaacca accccaaaat ttgactcttc aaatcattta   165120
ttctctaaga tttttaagca ttcaactgta atggcttatg tatcagcata gtcttatata   165180
attctaaaac aacattcata gcatggtatc ttgtaatatt tgactttcac tattaattct   165240
ttcagttatt atttgagtgc ctgtcacatg ccaggtattg ttctaagctt cagggatgca   165300
tccatgtaca aaataaataa aatttcctcc cttgtgccac tgatattcta taggtggatg   165360
gaaaacaaac ttaagagtta aataaattag gttttattta aagacagggt cttgccctgt   165420
cattcaggct gggtgcagtg tttaatcata gctcaccgta ctctccaact cccgggctca   165480
agcagtactc tcacatcagc ctcccaagta cctaggacta caggtgttgc caccatgccc   165540
agctatttat tttctgtatg ttttttctttt tgtagagatt gggtcttgct atgttgccca   165600
agctggtctg gaactcctag gttcaagcaa ccctccctcc ttggcccct aaattactag     165660 gatcacagac atgagccacc atacgtggcc aaagttttgt attattttat aaggtgatga   165720
gtgctgtgaa gaaaactaga agaggataag tggaattaga attgctaggg aagttgcagt   165780
attttaagta gggtggtcaa tgacaacctc aatgaaaagg ggatgtggga gtagagaatt   165840
gaaatagcta agggaaaaag ccatgatgat atatgagaag gatgttccag gcagagggaa   165900
cagccagtgc caaggctctg gggtaggaac atccctgttc tgtttagggc agagcagtgt   165960
attagtctgt tctcaagctg ccaataaaga tatgctcaag acttgggaat ttataaagga   166020
aagagtttta gtggactcac agttccacat ggttggggag gccttacaat catagcagag   166080
ggcaaggagg agcaaagtca tgtcttacat ggatggcagc aggcaagaga gagcgtgtgc   166140
agtcccttta caaaaccatc aggttttgtg atacttactc actatcacca gaacagcatg   166200
ggaaagacac accccatga ttcagttacc tcccatcagg tccctcccac gattatgaga      166260
gctacaattt aagatgagat ttgggtgggg acacagccaa accatatcaa gcagtaagat   166320
```

```
ccacatttct agagtatcag agtatgccat cagaatggca ggtatcagag tagggtggtg   166380
ctatcgagaa ctttgtaatt ctgagaacca gggagaacaa atggaaggat ttcaacagat   166440
aattcatgtg tcaaggtgtg ttttaaagga gcactttgct tagctgaggc ttgtctgtag   166500
gggcaaaggt ggaatgtggg agaccagtta gaaggctgat gtaagagtca agataagaac   166560
ctacagctgg gaggtgagaa gtggttggag ttttttatac atttgaagta agatttgcta   166620
gttatatgga tgtggagtgt gggagatcga aggaagtcca gagttttggg cctaaacact   166680
ggaaaaggta gaggtggtca caggtgacat tggaggatgg gctagtagag acattcttaa   166740
gttatcatca aagtttaaat gtttgagttt gaaatgtcta tgagacatca aacggaagat   166800
atcccataag gagatggatg tcagagtctg aagttcaagg cagaaatctg tgctgaagag   166860
aaaaaatgtc agcctagata gtgtcgatgg tatctaaagc tatgaggcgg aataaaatta   166920
tcaagagagt tctgtggaca gagaagagaa aggaccaagg ctggagcttg ccaacaattt   166980
gagattggta ataatacgag gaacctggaa aggaaatgaa cataattgtc cagggtgtaa   167040
aagaaagtct ggtaatgtgg aagtgaaggg gggaaaaagg catttcaatg acagagaggt   167100
agtcaactgg gtgtaattca ataggtcat aaaatgcaca tctgctgcta tggtttccac    167160
tacagatgca aggaaaaagt gtcctcgtcc ttttgtctgt ctgattgtgg cagttgagat   167220
tgaatagagg tagacagagg ggaaaaaaga atgaggaaaa ttgagaacat agcaatgcaa   167280
atgtcatttt tgacctttag tagaaaagta ataattttgg tggagtgttg ggggtaaaag   167340
ccccaattgg ggcaggtttc agagagaata agagcaataa aattggaatc aatatcaata   167400
aatattttca aggatatttt cagaaaagga acaatataga cacacttttt tttttaagat   167460
gagaaaattg ttttattgct tttaagatgg aaaatctaac cacatttctg tgtgctgtag   167520
ggttgatcta gaggcgtggt gttatcaatc agtacagtgt atagtgtgct acattaacaa   167580
atatccctaa aatggcagcg acatccacag ccactaaagt tgatttctcg ctcatgttca   167640
aagttcgcta agggttgact gtggctgttt tctgtgtatt cttaattctg ggacccgggc   167700
tgatggagaa gactcattta ttcttattat tactaattat ttttgttatt ttagcaaagg   167760
gggaaaatgg gcagaaccac attatagctc ttaaggtttt cgcttggaag tagccccact   167820
aatttctgtt catgtttcat ctgccaaagc aagtcaatta gctataactg aagtcatgga   167880
agtgagtcag tgaaattctt tcgagttagg gacaggggaaa gtcttgcaag tgtgtatttg   167940
tccccttgag aggtgtggac agttttttac acaataatac aacatacaag aggaagacaa   168000
ttctgaggat atagcaagag caaggtgttc tattgttggg ttgtcaagag ttgatggagt   168060
ttgatgggtg agagtcagcc ttatattggg ttcctatcat tattctctta tgaaaagagg   168120
aggcacaaaa gatggggcca ttattgtcac atgggtaaat gggttagtgg tggtttgtgc   168180
atgttttctt gagatagaat ttcttcagtg tagtaagaag ccaggtcata ttctaacagt   168240
gaagatggag cacgagggat tggggattag aagaggaaga agaaggtgct atttagcaga   168300
gcctttaagg gaattcatca gagaaattta gtatgatata caggcatctc gattaaccta   168360
ctggaggttt gtgttcatga atttaatgtg agataagtca gcatgattaa atatcttctt   168420
tcatctgtgc tgatcagtaa aggtgaggcg gatgcatgct gggtggggag gtggatttca   168480
ccagggttgg agttttgcca aggaagaatc aagaattaag gctggattag aattgagggt   168540
gtctaaagga tcgtggatct gctatgactc cacaactcta agaaaagaag attcggtacc   168600
accatcctca ttatggaaat aacaaacgaa tgaaacaaaa ccatttgtca ctttctacaa   168660
gattcagagg gcttgtatgt ctatgatctc aggcctcaaa aagagtaaat cagttaccct   168720
```

```
tttcccacat aactctgtgt gtgtgttagt acaattttgt atgtttgccc tagaatgtga    168780
accatgaatt tgtgaaatga aagcagtgaa taggaaaaaa ggtaaagata cagttttgta    168840
ttatctgtag caaaaatatt accacagcta tgtaatccac aaaaatggaa gaaatttatt    168900
aggtatttaa tttttatcca agagtagtaa aatgaaggca gctatataat tatgtaggtg    168960
actgttaaaa tattagactt tttgttgaaa ttttttggct cagaaaacag gtttcatgcc    169020
atgctgaaaa attacttagt ttgatgaaaa agtaaacaag acatgacagt gaatcatac    169080 agtgttgaaa caggaaatag ctaaaatgta ttttctcag taaataagtg gctggcataa    169140
gttgtcctca ttttggggtc aagatcttat tttggtgtct cagctgaaga tgacctcttc    169200
acaatccatt aggtattgtg acactgatta attattatca agcagaaagt attttttgga    169260
agtactttgc actaggcagg taaggcagtc gctaccacag gggcacaggt tcgaagcag    169320 ttcaggagga gccaacgtct tgctgagaaa cccaaggcag acagcaatta gaggataaga    169380
taatgtataa ttaactgcca ccgtgtgtgg ggtagacaat tagagaacaa ggcaacacag    169440
atgttgtaag gtgctgatta tgggttttaa caataatgaa aaatggaaga caacatcatc    169500
agcgtgggct gacgctgtca ggggtggtgt gttttctcat gtgctgttac cctctaatca    169560
gtgttgagtt ggatagtatt cccaggaatg gctgtttggc ttcgcttctc ttaccagaga    169620
attgctctgc cttataaatg tagagactga catgtagaca cacttggatc atgaatttcc    169680
attctactct acaagaagta cagctgcaaa gaaaatcaaa tcatgttcag taccttttctg    169740 gaattttccc aagtactcag tagtcattct agctcacatc ttaactctgc tagggttcaa    169800
taagtatacc aaatgcatat ttttttttag ctaattccaa aatctaattc actttgatca    169860
atagtcatct cctatgaatt ccttgtgttt tcttcactat aaaatatttt tgtgattcat    169920
ctttcagtag acgaaaggtg aggtactttg agattatatt tctactaaat catgaatgat    169980
tcattatttt actgaaagta aacacatcca tcatattaaa tccatatcat gttctgttgt    170040
atattgtcac ttaagtgttt ttattatttt taaacaggtt gtataattgc atagagcttc    170100
aggctatcta catagacaaa atatctgaat aaaagtacaa cgatcatatt ttatcttgtc    170160
agtttaaatt atgtttaatg attttaattc cagggaaaac tctaatgtac caagttacca    170220
actgaaatgt gcccagtatc aatcctttat ttttaaatat aacattgtaa gttgttaagt    170280
aagttgttaa ctcttatccc taaaaagaca taatgttccc ttttcttatc atatgctaaa    170340
ataaaaattt ctaacaatga atgtgccatt tttataagcc agcaaactat gcaagtaagg    170400
atctcaatag aagatttaaa caaaataatt attttgctcc atattctgtt gcttttgttt    170460
tttgatgaga taattaattt tcatggaatt ttaaatgatc aatttgtagt aaattttggg    170520
aaatatgtcc attatttaat cacagattta gtatcttaaa cacattgaca acgtcaaact    170580
tgtctgcagc aaatggttac tgttaaaaat ttgccatagg ggtgagaact gcaatttata    170640
ctatttctaa gctatcaatg cttcaattat tacatgtgtt tatatatata tgtgtgtatg    170700
aacatgtgtg tgtgtgtgtg catgtataca caaattttaa agtaatggct tactgaaagg    170760 ccttttttttc tcttcatatg actaagatat ctgaaattct gcccaaaatt gctaagatta    170820
tatacccttc tgaaaaattg caatgtgttt atgacgtatt tttatgatat ttcagtaccg    170880
gatatgttca ttaccccatg tatgaagtct tatcttgtga tgatgagttg atcagaccta    170940
ttacattgag aatattttta ggtataaact ttatatagtc tctgatggtg agtgtgtagg    171000
taaattgctt tgggctcacc tgattgtatt ttcattgttg ttgactttca ttatttcact    171060
```

```
aatttgggag caagggcttc tttttttatgg tctatttcta gatcatcttc ccttagatta   171120
catcatgtaa tgaactggca gaagatatta agtagatctt attcaaacaa gaactttgaa   171180
cctaaatgga gatttatcaa gctaaattag cctaattgtc tgtaacaatg accacagcat   171240
attaataaaa cctgtgaccc ttacatatat acatgtgcat tttaatgttc ttccactatg   171300
aaaggcattt tgtgatttaa tctgcttgat gaacgattaa tatgatattc actaattttt   171360
actcatctta ttcttaattc atctaattta tctaattctt agtaatctaa atgattcaag   171420
cctcttacag atttttatct ctacccagtt tttcatccag ctgtccgtgt ggtcatctct   171480
gccttggtgt gcttgagaat tatttctgat tctatgacac caatgcactt tgcagtcttt   171540
gaacttgaat tggcagaatc aagcttcctc tagacaaatc actgaatctc ttttctcacg   171600
ttaaggtttg taggaaccct attctcaaag ctgccaaaac actactgctt agtctatgca   171660
aatcaacaac tacaaatgca cgtcactcaa tcaacattat gaaactcctt tttggaatga   171720
ttgatgatca caaatgtga tcttgtgaca atatgatata ttcatttaag ccacattgag   171780
gtttcaaatt ggcaccattg acaacgtacc tctttcatgc taagtgtaat aatttgttgc   171840
ctctcatttt cctatgctgc ttcacttcat taaatctgaa taattaaaaa ttttcgtagc   171900
atcgccaaag tcacttccca ggagctaggg aatgtgtcga tctgtacact gatccagttc   171960
ctgctgacgt ttgcttggat gcagaggcca tccatcgctt tccattgatt tttgtcaatt   172020
gatgcttttc ttccttcttt cctggtgact taggaaatgt tctgaaactg tgcattcaag   172080
tcaacacatg ttagattcat aactaggatt caccttcaca gtggactggt cccaatttgc   172140
tgtattttta ttcagcctgt caactcacac tatctgacta aaagacgcta atgcagtgtt   172200
ggccagtccc ctgtcatctc tttctaattg tttggtctca agcaatggt gcatgttaca   172260 catatccatt taactgtcca attaacgcat gtttctagac aattctgata gaaagggtct   172320
cttttcttcc ttcagcccaa acaaagcaaa acaaaacaaa agggcactta cacgatgttg   172380
atctatgttt tatctttttt ttttttttgag atggaatctc cctctatcac cctggctgga   172440
gtgcagtggc gcgatccccg ctccctacaa cctccgcctc ccaggttcaa acagttctcc   172500
tgcctcagcc ttccgagtag ctgggactac aggcatgcac caccacaccc ggctaagttt   172560
tgtattttta atagagatgg ggttttgcca tgttggccag gctggtctca aactcctgac   172620
ctcaagtgat ccacacacct tggcctccca aaatgctggg attacaggtg tgagccacca   172680
cccctggcct gttttttgttt tatcttaaat ctcttaggct gagactcata tggtcccact   172740
tacccatctt tttacagcat gaaattgtcc agttaaaatt acagctcttt attaatggcc   172800
ttaagactct tcattttgaa tggataaaat agtaataggc tgtgagcacc aacagtatta   172860
atgtatcatt catgcatgat atagtagtgt tgacatcttt cttttccttt tctgttttta   172920
aatgaagttc aggaaaccaa tatgaaaggt aagaaattgc caacatcttg gactatcaaa   172980
tcatggcaga caatgaatta aagaattcaa caaatctttg gcagcatcag tttcaaaggt   173040
atttagatac aaccaccgtg taattctaca caatttaatt aaatcattta tcaaatcctc   173100
tacaacttga ataatttaac tgatatcaga ataatccatt tttcagataa ttatttttat   173160
atttaatgtg ttaaatataa aaatatgaca cttctcttgc ataatttgca gaatgttatt   173220
tatttcatta tttttattatt atttttaaaa tttcaacttt tatttgatac atgtacagat   173280
ttattaaatg gaaatattgc ctgatgctgg ggtttgcagg aaggatcctg tcacccaggt   173340
agtgagcata acatccaata ggtagttttg taagcccccc cacaaccagc acctatagt   173400 agttctcagt gtcttgctct tttgcccagg tgcaatcaaa gctcaccaca gcctccaact   173460
```

```
cctggactca agtgatcctc ctgcctcagc ttcctgagta aataggacta cagatgccac   173520
catggccaac taatttttta atttttactt tgtagagatg gagtattgct atgttgacta   173580
ggatgatcat ccactcctgg cctcaaatga tcctcccggc taggccttcc aatgtgccag   173640
gattagaagt gtgagccacc tcgcccagcc ccaatgcttg atctttaaga gcttcaggca   173700
gttgaagggt tttgtctgcc tgccacagcc ttccatcttt ttgagatgtg tttacctgag   173760
acagctaagt aggtgacaac ctgaactacg gttgctggca attggaaaac agaagattgc   173820
tctgttgatc cattgggaga agtacagtag tctgtagagg aacagaatcc cagggttttt   173880
ttctggcatg gaatcactct agagagccac attaaaaatt taattcctgc tgagcacagt   173940
ggcttacgcc tgtaatccca gcactttggg aggccgagga gggcggatca tgaggtcagg   174000
agttcgagac tagcctgacc aacatggtga acgctgtct ctactaaaaa tacaaaaatt   174060
agctgggtgt ggtggcgtgc acctgtaatc ccagctactc gggaggctga ggcaggagaa   174120
ttgcttgaac ccgggagatg gaggttgcag tgagccaagt ttacaccatt gcactccacc   174180
ttgggcaaaa caagcaaaaa actccatctc aaaaaaaaat taattcccct ttgactgttg   174240
atttttattta tttattatta ttttttttaga gacagggtct tgctctgtct ttcagattgg   174300
agtggtatga tcatagctca ctgcaacctt gaaatcctga ggtcaagtga tcctcccacc   174360
tcagcttccc aagtagcttg gttgacaggc atgcaccact acacctagct aattttttcta   174420
ttttttatttt tgtagaaaca gggtctcgct ctgctgccca gtctggtctt gaactcctgg   174480
cctcatacga tcctcccacc tagttcttcc gaagtgctgg gtttataggt gtgatagtgc   174540
cgagccattt ggctgctgtt tttacattta taccattatc ttcatcctaa ataggaattc   174600
tgatagtatt gttggcagaa tagggtcaac tggaacacac attttttgttc tctaggtaaa   174660
gatgatgaaa cttaaaatgt agctaatgtt attcctgcaa tgaatatgtc aatttctaat   174720
ctggggacaa aaataaataa aaaaaaagtt gcacgtatta aacaccttct tgactaagtg   174780
gcagctgtaa tgatttcact tggggatagc cattgcttct taactcatgc taacagtgca   174840
ttaaagctat tgattttttag tggctgctgt gctttcgtga ttgtagatca tttctctctt   174900
tggaaactct atttgatgac aaagctggct ctgttgcaga gtaatgataa aagaaaggac   174960
ctaccagaat ttcaagtgaa atgtataaca tatgtgataa tgcatggtga ctgcaatgat   175020
tatttcccga tgttgctgtt taatagccat gaaagcatcc tactgaaata gagtatttct   175080
gctttgaatg gcttagttag ctcaaaaatt ttgaaagctt tctcagtaaa gcatggtgcc   175140
aggcactgaa agattccttt tggaggagcc agagtcaatt tggatgatgt ttataaaatg   175200
ctgctggaaa attgggtggt gttttctaaa tgatcttcct agtaatgatt tatgctgtaa   175260
atcagaaagg ttgccatctc tctggatgga aatgcatagt catatgcccg taatgcagg   175320
gatttgacct cctataaaaa agctctctct tccccctcat ttatgtgatg attgtatacc   175380
atctgagcgc tgagaaaccc attggccatc ttccacttgt gtgtggctgg aggtgcttgc   175440
tgcagctctg tgatgccctg agccagcatg ctcgtggagt tccagtctgc tgcatgaaca   175500
agtggagaaa catgatcttc ctaaactgct cacaagctgc taaatgagtg atttgtgttc   175560
cctttgaatt catgctgtaa atggaaatgc ttgctccttc ccgggttatt actctgtgta   175620
cacgccattt gaggatgcag ataattgttg catcttcact gaagcatccc atcttagtcc   175680
agatttccgt tttcacagac caaagggca aagtcagact tggcagacag cgcagcttca   175740
gtctcatggg gggatttctt tgtctcatca gcctcagtca tgggctttcc agccattata   175800
```

```
atttcacatg taatatggtg ggtgtccatc tgagcaagtg tggtgcctca gtagggttgg    175860
aggaggcact tggagctgat gtagagaaag gagagtgaat taaaagtgga aggaggcaaa    175920
ttaaaagaag cgaggaaaca ttcttttcca caccagagaa acgttttcaa aacaccaggg    175980
aagcctcaga accaatccag gtactgcttt tatttctgaa ctctgttata atttgtgatg    176040
tcagaagctt ctatggaatc tactgatatg tgcagaaata atgtgctgct gtgcccattc    176100
tgtgttatac atttagaagc agttgcggta tcatgggata cataatattc tttaatccca    176160
atagggcttt caattctaaa tataacaaaa acagttggga aaggcacaca tacacaggtt    176220
ggcctgtaga gatggaggtg gccaatttgg tgtgttttga acagacgggg atgctctctg    176280
cgtactgccc ccacaccaca ggacagctga caggcagccc aaatgcccgt gcagactgct    176340
gaactccaga tggcttgctg gtgctggctg gcacgccttc aagtcctgcc tttcttgggt    176400
ccctaacaga attcacatta cctgaaattt cagggaattt gtgggctgg ctaaacagat     176460 tccttacata actggtgatg tgcggtcaga aagagaatag atgagtaaga ttgcattggc    176520
tgcctgtgtg tattagtttt cttttgctgc atattgaatt actgcaaact cagtggctta    176580
aaatcacaca catttattat gtcacaattt ctgtggtcag gcgtctgggc atgtctgagc    176640
tggatttcct cctcagtgcc acacagagat gctatcaagg tgtcggctgg gcagcatgac    176700
tctcgggagg ctcatggtcc ttttccaagg tcactcaggt attggcagaa tctggtttat    176760
tttggttgta ggattgaggt ccctctcttc ttggtggatg tcagcagggg tcgatgtcag    176820
ctcctagagg tcccccaggc agcttcttgc catgaagcca tctcagggac tgtctcccaa    176880
tacggcgaca cgtatcttca agtccagcag gagaatctct tacttccagt cggctaataa    176940
aataatctta gataacataa cctaatcaag gcaatggcat cccatcctat ttcctaggta    177000
atgtaataca ctcaagggat gacttctatc aacctcatag gtccggctca aattcaactt    177060
cctgggatta cgggagggca tggcttatta ggtccttctg agtcataaat gctctaatgt    177120
ataaacttcc tagggtttct ataatatatt aacactgggt ggtaaatggt gtaaactggg    177180
tgacttacaa caacagaaat atattctctc ccggttctgg aggccagaag accaaaatca    177240
aggtgttggc atggttggtt tcttctggag cctccgaggg agaatttgtt ccttgtctct    177300
ctcctacttt ctgggggget gccggttaac ttttggcttt tcttggaagc gtcacttcaa    177360
tgtctgtctt catctttaca aggccttctt ctctccatat gtttctggat cctctcctct    177420
tcttaaaagg atactagtca ttgggtctag ggaccactgc aaatctgtga tgatttatc    177480 tccaaagaaa ttacgtgatc acatctgcaa agaccctgca gtagtacctt tttatccatg    177540
gttttgcttt ccagggtttc agttccctgt gatcatttaa tctctaggct tagtcagtta    177600
actcttgaga tattaagagt taatctcttg ctgtgtataa tttataaatt aaactttatc    177660
atagacatta atacatagga gacaacatag tatctataca atttgatact agctgcagtt    177720
tcaggccttg aaacatatcc tcatagataa ggatgtgggg tgttatatat ttccacatag    177780
gaacacattc tgagattctg gtggatgtga attttttggga cattattcaa cacagtacac    177840
cccgtcaagc tttgcccatg acctgacact gcccaatcct ctggtctcat cttgtgggga    177900
ctctccttca ccttttctgg aatatttcct tacaacttcc tttctaactc cttaactcct    177960
aattcagatc atcttgggct aggagtaata ttcagtactc aatcattaga gaagatgggg    178020
tcaccaggag ataaataggt aagcagatag gtaggttgat agatatagat agttagatag    178080
atagatagat agatagatag atagatggac agacagacag acatgggtga atagatgatg    178140
gagatggata gatagaaagg tagatagatg atatatgtgt aagaatagat agataaatag    178200
```

```
atagatatga ataggtggat agatgataga tcgatggata gatacatgga tagagatgat  178260
agatataggt agatagagat ggatagataa atgatagaaa ggcagataga tacatagatg  178320
catagacaga tatggataca tggatagatg atagatagag atgggtagac aggtagatat  178380
atggtagata taaagatgtt agagatggat agatgataga gatggataga taggtaggta  178440
aataagtaga tataaattta gatagagatg aatagacagg tagataggta aatagacaga  178500
caggtaggta ggtagaggac agagatggat agatagacag gtagatgata gatggtagag  178560
atggatagat agacctctta atccctatgt atcaatccat ctctatagct atctgtaatc  178620
acacatgtat atgtctacat gctcattaat aacattttca cagcaggaat tcagtgattt  178680
agtgattatt gaattaattg ttgcataagg ctccctgagg gcaacactgg gtcttcttgt  178740
tcactatcct cagtgctatc attttacagt gggaggaagc ttaccttcct accaaaagca  178800
ttctgtggct ctgaagtggg agaaagatag attctctgcc acctttccca aaccagggat  178860
cctggttcca acatcaggat ttacctggcg ctgaaaggat tcattccatt gcattaattg  178920
tattcatgca catgagtatt ttctgagcat ctctgaggaa ggcaacagtt tctatggtga  178980
acggtgtgga gagcacagtc actcctcatt acagcactgg aagtaatcac aatgatgata  179040 acatacccctg cattctatcc agagccattt ttaagattta aaaaatttac ttggcattat  179100
tttcttcatt tgagtagctc tttaaggtat tttgtgaccg ccccccccccc ccatttatt  179160 tttccttttg tagagaaggc ataatttttac tttcaccctc ttaagagttt tttctgatgg  179220
tcctgagaat taaatggaca aaggacagat cagcaggaga aaaacataca aacccatgta  179280
atttaaggtt tctgtgacat gagaaaaccc tcagatggaa acgaagactc aaagaagtgg  179340
cgacacttca gtgcttttag agaaggttga acaaagacag acgatgatgg aaaagtagct  179400
aacctatgtg gaggctaaag aaatatgtgg tttattttaa catggtcttt tagtacacaa  179460
ttctcttatt tcagcctccc cttctcaatg acaagaatgc ttttttccttc tggtataggg  179520 agggcacagt ccatacagga gtttcatctc ttgctttcag aaaggaaaac aggatcagag  179580
cagctttctt gtacctgctg ttttttttcct cccctcccct cccctcccct cccctcccct  179640
cccctcccct ccccttttcct ggcctggagc ttaaatgacc atacaccaac atagcatttc  179700
tggggtggca gattctgcca gccttttcact ttacatcctc ctgttatcat ctgaattttt  179760
gaattatcac tcacaacttt tgtacatggt ttcttaatat tttacaaata tctatatgca  179820
aaaataatgt tcatttggca tacccttatt cttttttaaa attttatttt atttttatttt  179880 attttaagtt ctgggatcca tgtgcaggac atgcaggtgt gttgcatagg taaacgtgtg  179940 ccatggggt ttgctgcccc taccaatcca tcacctaggt attaagcccc gcatccatta  180000
gctatttatg ctaatgctct cccttccccc cgccctccct gacagaccct agtgtgtgtt  180060
gtttccctcc ctgtgtccat gtgttccaat tgttcagctc ccacttatac gtgagaacat  180120
gtggtgtttg gttctctgtt cctgcattag tttgctgagg ataatggctt ccacctccat  180180
ccatgtctct gcaaaggaca tgatcttgtt ctgttttatg gctgcatagt attccatggt  180240
gtatatgtac cacatttgct ttatccagtc aatcattgat gggcatttgg gttgattcca  180300 tgtcttttgcg attgtgaata gcgctgcaat gaacatacac ttgcatgtcc acattgagaa  180360
accatctcac gcaagtcaga atggcgatta ttagaaaact catattcttt aataacatct  180420
ttgaaatgat gattcttcag tcttgaatca tcagtgcttc caggccatac cttccccatt  180480
cttaacttga atcctgactt cattcttgag cttgttggag ttgccctgag cttgatttct  180540
```

```
tagagtgaat tatcctgtga tttttactct atgcctaagt tagatggact ttcttagcat   180600
gctaatctct aaaaatacct tttcaaagga gagattggga aaggttttgt accaaaacat   180660
ggtagatctt gttccattat caactgcgtc tcgtgtcaga gagttctaag gtgagtgaaa   180720
ttgtgcgtgt ttgtagcgtg gtcataaaga catttcacag agtggatcgc aaacaaacca   180780
acagagcaca gagggcttga gagcaatggc agctggtgga agcacaggac agggcacagc   180840
gggaatttca tgggaccacg aaccaagaac agaacccatg accaggctgt ttttccttcc   180900
aggggcccag gctttctcag ctcagccttc acttgcatgc tgctttgagc atgtttggct   180960
tctttgagaa aatgagccac ccaagaggcc tacatccaag tcacctgcac tcagatccca   181020
gccaggagta tggagggccc atgtggggtg gagtggtgca cgtcctcacc accttagaca   181080
cagggaccac ctacctcatt ttagatggag tgggcagata atctgcacac atacctccaa   181140
aggtgtcctc tattgtagag acaccttttg ttttctccc tcaatcctgg acattttgtt   181200
tgtttttctt tatttcacta attttacaat aaactgccag gatatgtctc catgtctagc   181260 tcttttgtg aattattctg gaaataacag cctctgcaag gctgctaaag tgacaaaggt   181320 attttcaat cgcgtctgat tccttcaga tatttccatc ttcctactcc atcatccatc   181380 tcttttaaa aattttgttt tgttttgag acaaggcctt gctctgtcac ccagattgga   181440
gtgcagtagc atgatcgtag ctcgctgcag ccttggtccc gggcttaggt gatcctccca   181500
cctcagcgcc cccaagtagc tgggactgca ggtgcacacc ccacgaccag ctaattttg   181560 tgttgttagt agatactggg ttttaccatg ttgcccaggc tggtctcgaa ctccggggct   181620
caagtgatcc gcctgcctca gccttcatgt tttctttacc agttggttcc ctctctttcc   181680
cacacttgct aagaccacta ctggttcact gtcacgatgt cacttacttt tttgactacc   181740
ttcagtgatc tttcttttct gatttatgta tatatttcct gagtaatgtc attctttatt   181800
aaaaatgtat atgtatatat gtgtacacaa agtatacat atatgtgtat atatcctaaa   181860
tgattctatt atttattgaa ataaataatg tatgtataat tatatattta tatataatgt   181920
aagcattagt atataatgta tattatggat acattatata tacatttat acacaattag   181980 gttctgtgta tactatatat gtatgtatac agacatgtgt atatatatat gtgtttataa   182040
tatatacaaa tgattgtaac agtgtgtgta tatatgtgtt tatgtgtata tatgtatat   182100 atataacatt aatgtgataa aagtgtatgt gcatatatgt gtatttgtgt ttttgtacat   182160
actcatgacc acatttaaag aataccattg taaaagctga ccatataatc gtctatgcgc   182220
atatatatat gcagcaaaaa tgccatcatc ttcattaata aatgccttct ttattaataa   182280
atatacattg gttcacaata tcaacctcag cattatatac atttcaacaa acatgctcat   182340
tgttttaagc atacattatt aattcatatt tatttgttt taagttgaga ttgttataac   182400
tccctctttt ttcaaatttt tagctaatgg tacttttaa aaagaatgac tttattgtat   182460
tcaaattatc actagtggga taaataatgt aatgatggga aaaagcttcc tttgttccag   182520
ctataattat ctgtagttgt ttatttgttt tattcaactt aacattcatg ttttattcaa   182580
atcatcaata tataatgatt ttgttctgtt accaaagatc ttattgggaa ttctaaagta   182640
ataaattatt ttgaagaggt atcgatacta ttacactctt gattatacc tggatcaatg   182700 aatgttttta aatatgtaag cgttctttta tgtttcttgt tatttatat attttatgta   182760 acatgtgctg tacacttctt agagttattg ctagaacatt tatcatgaat gtgcaaagaa   182820
ttttttcaaa tatatttatg tgcatatata tgacaaatca ttttgtgtta attttataca   182880
attctaaata ataagtgact cattctaaat tatttagctg attctctaga ttctcttcct   182940
```

```
cttgttggat agtcatatgc aggagtgact ttattttgtc tccttctttc tgatattttc 183000
agttctcaat acttttaat aaaaacatat aggcttcgag tctgtagaag tatcttgaaa 183060
tatgatggtg atgatgaaca tcattgccct gtttatactt ttagtgaaaa ttcacttagt 183120
gcaacatttc ttttcctatt tgttgataag attaaaaagg atttcctgcc aaaataaata 183180
ttccatgtac tctacttttt aaattaaata cattaatagt accagatact atttgccatc 183240
tttcaaatag ctttttctc ctttgatctt tccctcagct atcacctgac ttctttcctt 183300
caactgtgaa tgagacaaag caaaacaccc tacttcttcc cattgaacca tcttactgta 183360
tttgtagagt caacctaatt ccttattagg tcactgcata gtttttttt aatttaatat 183420 tttacgctat ttattataat gatcattgga ggaataatca gaacgtgtta agattcttta 183480
caagtaactt ttacatttta gtgttcttgg cctttgaact gcgttttgga tgaagaactt 183540
ttaggatttt ctgtgcttgg gggtgctaaa ggtgtttaca cctgagtgaa tgcccagaat 183600
ttgatcatat agatttttct attgacagtc tcaccttctt atggttattc tcttgtaaat 183660
tatctttacc tcaagaccaa gatttgcaaa tatattgatt ttcagtagat gcagtgttca 183720
catagtatct cctgaaacaa tcacttttg cagtgtcttt tgtatatcac tggttgcgtc 183780
cctttactca gatctaaggt acatctgttt ctgtattttt ccttatgagt ggtctggatt 183840
ttaattcttt caatacactt tatattttat tggagtatgc tttgccaacg catcctttt 183900 atctcagact gttcttatgt ctctgtaata aagaaactgc atcttatttt actccatgaa 183960
aaatcacaaa tgattcccta agtgttcctt tagagtgttc ctgagaggac tgtggttgtc 184020
ttttattcta cattgtgtgt ctttttaag actttattag cgcagtttta ggttcacaac 184080
aaaatagagg ggaacgtaca gagagttctc atatatcccc tgcccccata catggacggt 184140
cttccctatt ttccacatca cccaccagag gggtgtgttt gttacaatcc atgaacttac 184200
actgacatct tcatcaccca aagtccgtcc tttacagtag gctacagtct tggtggtggt 184260
gtacattctg tgggttcaga caaatccgta ataacataaa tccaccatta cagtatcaca 184320
cagtatagtt ctgcaaccct aaaaatcttc cataaaaaaa cctccacaat tttagcagtt 184380
tgtaacaaca aaggcttatt tcctttttct gaagttcatg tcggttgtgg gtggacttgc 184440
ttgttactta ggtagactga tattagaagg tgggaaaaga ataataccctc tccaggaaag 184500 gataggaact atttttgaacc aataatacag ctcactacac aaaatgagtg aacacagtca 184560
cactgaaaga gagatgagtg acatatgctt aagttatgct tatgttgaca aggtctcact 184620 cacctaaaact ggagtgcagt gccacaatta tagctcactg cagcctgcaa tccctggact 184680
caagcagtcc tcccacctca gcctcctgag cagctgggac tacaggcaca cacctgtgtg 184740
attttgttat ttatttattt atttatttat ttattttaa tagaaacagg ttctcattat 184800
gttcctagac tggtctcaaa cttcagcgtt caagcagtcc tcttgccttg gcctctcaga 184860
gtgctggaat tacaggcatg agccactgcg cccagcctcc tttagtgttt aactgaacag 184920
aataaagaac ctcttcatta tggtgaattg gctaagttca aaagagtagc aaaagccttc 184980
gtgggcagta ataattactc tatcttccaa atacttgagt gaccttatgc ttcttaaaat 185040
atatatttta gggctcttaa ttgaaatcaa ttgcctttat agcctctatt acagcatact 185100
cagaaattga agagcgggat gattttgtat aaatctagac taattttgtt tttctggaat 185160
gactagaacc atttaccatg tcaggtacac acacaagaaa cgctaagggc gagttgtgaa 185220
tgatttgact aggaacaata gttgggctgc ttttagatgt ctccttttgc tacatagaca 185280
```

```
gcaaaaggag aattcaccaa aggtgccagc ccttcagaat ccttgtccca caccaccaaa   185340
aagtcctgtg acagaaattc cacctattaa tcagctgctg tgtcctgact acggagaaaa   185400
gtatgatgca acagaacgca aacttttcca caatctcata acaaggaaaa aatatatgta   185460
tgtataatat gtgtacatat ataagaaaat gtatattaca tatatagtaa atacatacaa   185520
atacacgtat gtgtgtatgt atatatacac acatattttg ttttgttagg tattttttat   185580
gactatttat ttaaaaaagt cacattgaaa ataaaattga cttttatttg ccctaagtta   185640
cctcttgaaa tattgtgtta aaaacctaat aacttctgac aggtatatat atacctgtag   185700
aggttaatat atatacgtgt gtttgtgtgt gtgtgtgtgt gtgtgtgtat gcgcgtgcat   185760
agaagttatt aggttttgtt tgtttgatgg ttttgttgtt gttttttgag atggaatctc   185820
actctgtcgt gcaggctaga gtgcagtggc gtgatcttgg ctcactgcag cctccgcctc   185880
ctggattcta gtgattcttg tgcctcagtc tcccaagtag ctgtgattac aggcatgtga   185940
caccatgtct ggctattttt tgtattttta gtaaagatgg gatttcacca tgttggccag   186000
acttgtcttg aactcctggc ctcaggtgat ctgcctgccc tggcctccca aagtgccagg   186060
attacaggcg tgagccactg cgccaggcat tattaggttt ctagtacaac atttcaagag   186120
ttatatgtat agatatgtgt acgtgtgtgt gtatatatat atatatatat atatatatat   186180
atatatatat atatataaaa cctctatggg tatgttaggt ttttaataca catttcaac    186240 aagcatctta ggacaaatga aagtcaatta tgttctcaac atgacttttc ttaataaaca   186300
tacatttaaa aatacctagc aaaatacatt atttagtacc tatttttaaa cacactgtgg   186360
tttaatctca agctcataga ttcttcgaga taatattgtc tatcagctga aaattctaaa   186420
aaaaaaatgg gaaaggctca tgtaaatata ataggatttg tatttcattt ctgaggacag   186480
aaacatttca atagtaaaat ttgcaacaaa aagtgcttat ggaaagttag acaatgctct   186540
aggactctaa tagtaagcac aggaatatgt cagagaccca taaaatcttt agatttattt   186600
tgattcctac ctgtaaaagt gtgaaatcaa ttattgctaa atccagcaaa acagcaaagg   186660
aaaattacta ttcaccttt tctctcagtc tgtcttccaa agctactaag agaaaaacaa    186720
gaaaaataca gaaaatccta cttccattat tacaatgaag cattttgag ctagtagaaa    186780 attagaatta gaccttgctt ttactggcat cacaaaagca tttcatcctg ttttttgaaa   186840
tgacaaatgg cagaattctt atatacaata tgctaaccaa aatcatgtta ttgccacgtc   186900
atgaattata atttaatttc tactctcaaa gttaaataag aagatacaat attgcatttc   186960
cctgcttgaa gaggagaatt agttacactt gttacgtaaa ggctgtattc atcactggtt   187020
gtcatagctg ttatgactgt gactcttata atagaggtgg gcttgcagcc aaaaatatat   187080
gattcatcca aaagatattt accatgtaac ttatattata tgtgctgaat attttggtag   187140
tcattgcaaa ttaaggaata tggtgttgaa aaatcacagg taacaccttt tcttgttgc    187200 taacaatcta acagggagac cttatttaac aagatatcat attacacatt acaattcatc   187260
ttgtgaagaa aaatgccaac tacagtgaat aattgaggaa cccaagttca tttacgaatg   187320
gaaggttggg atgaacaggg aatgcctttc tgaggaaatg gaatttaagc tgatcagtaa   187380
aaatgaatct tccaggagca tatgggcttt gcagatggga gaaacagcag gaatgcccca   187440
aaagttctaa aggaaacctg atgatgaaat gagttaagcc atgttcctgg tagtgtatca   187500
gttagctttt gctacataag gaaccatctc aaagccgagc atctcaaacc acctttattt   187560
agctaagcat ctcaaacaac ctctatttag gttatgattc ttggctggac atctgggctg   187620
tgctcagctg ggaggctctt cagtctagag tcagcttcca ggtctgttgg gtgctcattg   187680
```

```
gccaagcact atcttaacag ggtgcttgac agtgctccat gtggaatatc atcctctaac   187740
aggctagtat agactcttca tggaagcttg tcagggttgc atgtaggtgt gttcaagtcc   187800
tcttataatg aaagctaaga ataaggacag tgtgtcaccc cccacatccg gaatgtccaa   187860
ataagcaaat ccagaaagac acagatgaat gggtagtttc caggggctga gagtgaccac   187920
taaatggtac cataatttttt tgggggggat catgaaaatg ttctgccatt agatattgtc   187980
aattattgca cagatccatg aatatattaa aaaccattgg attgcatact ttgacacggt   188040
gatgtgtatg gtatattaat tatatctcaa ttaagcaatt atatctgtct atcatttatc   188100
tgtaaaccag ataaaataag acaggctagg tatatagaaa aatagaacag aacaaggtag   188160
gcagaaacag aatctagcag atataaaact tggcatgtaa gtaaagagct gtaataccta   188220
tgtagctgaa aatggaactg ttctctaagg aaataattaa aataatctct atgctctagc   188280
atccagataa ataaattcca ggtgagttat gacccagatg tgaaataaaa ccttaaaact   188340
gttaggagaa tatgtaagca aataaaatgt ctttatgttt ctggattaag taatcctttt   188400
tttttaaaaa aagcagaaat tatagagaaa atagtgataa attataatac ttatgcattt   188460
taaagcatta gtttagataa ttaaaaatca ataaaatggt taaagacaac agactagata   188520
tcaccaatgc tcaactgtgt aaacttgggc aaattattta atatctgtat acctaatttt   188580
cctcagctat aaaatgatat tagttacaca tctcataagg tatttatgaa gattgcatat   188640
tcggagctgg acacagtggc tcacacctgt aatacagcac tttgggaggc tgaggtggga   188700
gacttgcttg aggccaagag ttcaagacta gcctgcacaa catagtgaga ctttatctct   188760
acaagaaata gaacaaaatt aaccaggtgt ggtggtgcac acctgtagtc ccagctactc   188820
gggaggctga ggtcgaagaa tcactggagc ccttgagttg gaggctgcgg taagctacag   188880
ttgtgtgact gcactccagc ctgtgtgaca gagcaagact ttgtctctaa aaaacaaaca   188940
aacaaaatgc atattcaaca tgcataaagc ccttagaacc atacgcagca ctgctatgca   189000
ctgttaaatg tttgctttta catgctcaaa aagaggccag catccatgaa tataaagatt   189060
tcctacaaat caataacaga cattcagcca gtcaaaaatt ggattgctat tcaagatggg   189120
aatttagaat gggaatatag aaatgcatct gtactagttt taaggaacat gcaaattgaa   189180
atataaactg ttaatatttt atactcatca agtggcaaa tgtattgtct gataatgtca    189240
agtgttggca acagggtaag ggccaggaaa ttttcttacc tgctagtggg tgtatagcat   189300
aatacaactt gtttggaaag aaatatgcca gtatctactg aagataaaat tagtattacc   189360
ctatgtatca gttagctact gctgcataac aaaggactct aaaagtcaat gccttaagac   189420
aataagcgcc tattactgct tatgagcctc tgcatcttgt tagctggaaa tttattttgg   189480
tcttggctgg gctcattcat gtgtatgcat tgttgatttg gagtgagttc tcttaggtaa   189540
ttgggggttg ctggaggtaa ttttgcctag gttagggcca atgggttctt ctctatgaga   189600
tcttttgttg tgcaacctgc tagtctgatt tttcacagga cagtggcaga atttcaagag   189660
agtaagaata ggtacagggg atttgagtcc cagtcttgga aacagcacat cattatattt   189720
tttcttttga aaaatgcaa tcttaaagcc actcaagatt caagggtga aagtacagac    189780 tctctatgta tgaggaatag taaattcatg gggaggatta tagaactggg aaccttttgc   189840
ctgtcagtgg actacaccct gtaattcaac aattgtctat ctagtagtta tgtgccctgg   189900 aactgggtc ttcaaactgg cagatgtctt ttcaaaattt ttcaaagtat gactctgctg     189960
atgattttaa agaaactaat tttcaggtac tcagcccca gatgttctcc tttctaagcc    190020
```

```
ttcctggtca ccaaaagctt cttcccacat cacaaaagga tgaccttcag taggcatgac   190080
actttgttac caacctttc tgccagggtt tataatacaa gaaatatctt tttgaatgct   190140
gctttctgga aagccccttt gctgaaggct ccataaaata agcctcctat cttatacata   190200
tttccattaa gagtgaagtt tggtcctgtt caggtgttct gatttcagaa aaagaaaaaa   190260
gaagccatag gtcagctatg gcagttcttt caaatgcaga aactgaactt ttctgttgct   190320
aaccaatttt tcaaggtgca tatacattgg gtgaagccca tcggtaaatg atccaatccg   190380
aaaatcatct gaaggtcatc tttcaaattc attgtggtag tgttattcaa gtggaggctc   190440
aaatatattt caagtgtatg catggaatat ttccccagc tagagtctgt tctccaggtg   190500
tatggaggaa agaggagttg tccaggttgt gtacctgttc ttctcatctt tctgggcta   190560
ttcatgtcct ttctgtgccc tcagcctcca acccatgctt ctgctcagag cagcctgttt   190620
tctttgctcc cataaatgta ttcctggccc cagatcttct gtgcatattt agaagcccta   190680
acccacttcc tcaccagcca cccctctatc cccagactct cctaccagga acagcagagg   190740
atcctaaatt catgcatgca ttttcctgcc ccgttggaat gatctgtgtg catgtctgtc   190800
tctgatgttc atctccttct tcagtgtggg tgtgtcatta cctcttttag ccaggactgc   190860
atggcattac ctgtcttagt cgggactgca tgttaaaagg gtcaacacat atttgtagaa   190920
ggaattggct tctgagtgaa tgaacccatg tgtcatgggc agtctgtgag gacataccag   190980
tcacttcctt gctgccgaga gctggggata ttgcattgga ttagaagatt aagcccatat   191040
tactctatgg ccaagtgaca aaataatcaa tcacatccac atctgtgata gccaggaaaa   191100
catttctttc cgtgcccctc ccccaccccc cgccgtatgc aactttccct gtgtggaaat   191160
aatgtactta gcttaaaaag tctctttctc tacttaacaa gactaagttg aaaattaacc   191220
ttgcccactt aaaagaaaac gaatatgcag taaactatga actactaata cagttcaata   191280
tgatatctca tgcagaacaa taatgctgaa ggttcttttt ggttctatta tttccttata   191340
ttcttgctta gataagatca catttgtatc tattgacttt ctatgatgat ttagatacat   191400
aagtggcaat aattaatata tattaaaaat acagatttaa attgtttttc tgacttgtaa   191460
tgttaacagc agtatatgtg actgtgaggt tttccttga tgttaatttt cactttgaca   191520
atagtcttcg tttccaatt ttttttaatt ttttattttt tattttatt tttttttgtg   191580
ataaggtctg gctgtttcac ccaggctgga gtgcagcagg gcgatctcag ctcactgcaa   191640
cctccacctc ccaggctcaa gtgatcctgc cacctcagtc tcccgaatag ctgggactac   191700
aggcatgcac caccatgtct ggctaatttt ttgtaatttt catacagaag aggtttcacc   191760
atgttggtca gtctgttcca gaactcctga cctccgccca cctcgacgtc ccaaagtgtt   191820
gggattacag gcatgagcca ccgcgcccat atcattttcc aaattcttta caagttttt   191880
ctcttacatt cataacataa agtgctattt taaatagact aacttttgaa aataacatag   191940
ataaagcact aaatggggac atcagaggaa caggctaaaa aaaagctgga atattcttca   192000
ggattaggga cattgagatt ttatttataa aatgatattt aaattttaat aatagaattg   192060
ttgtactttt gcttggagta tttaaatctt ctctttaata tttaaagcca gttctgcaca   192120
gaggttttac ggagatgcta attgttgtat gaaaaggaat attattctgg aattttgagg   192180
aagggtagac atagagaaga taaaggaaac tcacagccta cctaggtttt atttgggctg   192240
tgtgtgtgtg tgtgtgtgtg tgtgtgtgtg tgcgccagcc acaagctggg tttattcttg   192300
aataaactgt agacaaattg ttttttcctga atcttctaaa acctgcattt acatagtcca   192360
tggttgtgtc taaactagat actcaagaga acttggtttg ttttaaaggc atttaattag   192420
```

```
ttatatttac atggacaaat agagcagcag tttattaaaa aagaatgaaa ggataaacaa  192480
attaaatata cgtagaacag gaaagacagc atctaattat gtttctgggt caggctctga  192540
tatacaagat taatttaaaa ttgggatttg gcaagtaatt tctatcgaaa tctcagcagg  192600
agtttttatt gcaactaaca agctgatttg gaaagtttca tggaaaggca aaggatctag  192660
agcaatcaaa aagaccttgg aaaaggggaa gaaagttgga gggcttccat ttctctattt  192720
taaaaggtac tataaagata tagtaatcaa gatagcaggc aactcacatg ggtataaatt  192780
tagaccaatg aaatataatt aattacagtt ggcccttgaa caacgtgaag gttagaaccc  192840
ctgcacagtc gaaaattcac ttaaaacttt ttaccccccc aacacttaac aaccaatagt  192900
ctactgttga ctggaagcct taccaataac ataaacagct aattatcaca tcttttgtat  192960
gttatatata caatgcactg tattctcaca ataaactaag ttagagaaaa gaaaatacca  193020
ttaagaaaat cataaggaag agaacatata tttaccactc attaaataga agtggatctt  193080
cttaaagatc ttcatcctca tcttcaggtt gaataggctg aggaggacga gggagaggag  193140
aggttggtct tgcagtctca ggggtggcag aggcagaaga aaatccacat ataagtggat  193200
ctgcacagtt cagaactgtg ttgttcaagc gtcaattata agggtttaga aataaatcct  193260
tcaatttgta gtcaatagat ttttaacaat ggtgccaaaa caattaaagg aggcaaggat  193320
agtcttttca ataaatggtg ctgagacaat tggatattca tatgtaaaaa gatcaatttc  193380
aactcttacc tcttattgta cccaaaaatt aactcgaacg acaggtggca atataagaat  193440
taaagctctt aaacttttag gaaacttcag caacacagga gaaggtcttc agggccatgg  193500
attgggaaag atttcataaa tatgacctca aaagtacaat ccttaaaaga attgatcaag  193560
tgaaactcat caaaattaaa aacttttaca cttcaaaagg cactattgag aacataaagt  193620
gctatttgtt gagaaaacca aaagacaagc ataaactgg gagaggagat ttgccaacca  193680
tattcccaat aaaagacttt tatttagaaa atatgtaaac aaaccactta ctattcaata  193740
ataagaagga aagaaattat ttttttaatgg gcaaaaataa attaatagac atttctgcaa  193800
agacagtgta catgagaaga tatttaatat cattagttac taaacattag ctaaatgcaa  193860
atgaaaacta caatgaggcc aggtgcagtg gctcatgctt gtaatcccag cactttagga  193920
ggccaagatg agtggatcgc ttgaggcagg agttcaagac caacctggcc aacagggcaa  193980
gacccatgtc tactaaaaat acaaaaatta aacaggaata gtggtgcatg cctgtagtcc  194040
cagccacttg agaggctgag gcacgagaat tgcttaaacc caggaggtgg aggttgtcgt  194100
gagccgagat cgtaccactg cactctagcc tgggcaacag agcaagactt tgaaaaaaaa  194160
aaaaaaaaaa cctatgatga gacaccattt cacatccatt agtatggtta taacaaaaaa  194220
ggatattagc aagtgttggc taggtattag agaaatagag acccttata ccaccgttgg  194280 tgagaatgcc aggtattgca gctgatttgg aaaatagtct gtcagtttat taaaacatta  194340
agcataaatt tgccttatga aacagcaatt tcacccctag gtatctatgc aatagagatg  194400
aaaacatata tccatgcaaa aaatagtaca caaatgttca tagcagcttt attaataata  194460
atcaacaagt agaaataaac caaatgtcac tcaacaaata aatggattta aaagatgtgg  194520
tatacccata caatggaaaa taatttagcc ataaaaagga atgaagtatt gatgcatgct  194580
acagtatgaa aggacattga aaacatatgc taagtaaaag aaaccagaca caaataccg  194640 catattatat gagttcattt atatgaaatg cctagaaag gcaaatctta taagacaga  194700 aagtggatca gcaaggctat cacacccacg caccacccag gtctggtttt aaaaggtatt  194760
```

```
aagcccccat gaaatggaca ttacttgact tttgtttgat atatggaaac agcattatca   194820
agtcttggtt tcaaaatatg tttaagctct tctgagttat gtagaacaga ggagtgtttt   194880
ccattcacaa gtgttggaga tgacagtatt ttccctttgc cttaatccgc ttatcctaga   194940
accctatagg aaggcaaaga ctgtcttgat tgattgacgc agttaaagtt attgatagtg   195000
ggatatgcac atatgggctg catctgtcta tgagaaggaa gcaatggagc caattaatta   195060
attcaagcaa aattaaatgt tcacaccttt taaatgtgga aactataaaa accaaaatgg   195120
tgctctgtgc actaagagca taagctagtt ttttgctatc cttaagggcc tcttcctgca   195180
ttttgcctat attaaaattc ctatgcagat cttattgagg tgatcaaggt agatgacttc   195240 gattttatt ttcttcaaca aattcacgta ccaataactt tcaaatgata tttagtaact   195300 atttaaaca cagaggacat gatcttcaaa cgatatttaa tagctatttt acacacagag   195360
ggcataactt tcaaatgata tttaataact attttaaaca cataggacat ggtctataat   195420
gttttgtcct gacttaaata tttattgcat gtagtagatt ttaatagaag aaaacaagag   195480
tgaatagtgg gtagtgcttc tctaaacaca gagtagaggt aaatcttagt gatttaaatt   195540
agtcacaatt ctgactttt gagattgcat gtttataagt ttttaatgca tgaaattaat   195600
gtcaattata taatattttg aataaagtcc ttccatgttt actgtgtttt tgcttgcctt   195660
atgaaaattt ctaaccataa tgtgtcagta acatttcaaa aatttattta aattacaaca   195720
tgttaacatc agaggaccat tgaatacgcc ataagcattt cttaaagaa tgtgggaaat   195780 gtcttttcta ataatttaat ttttctttt tttaaaacaa ctcacgttag cattttttt   195840 tttgcagtag catcatttta acccccaact gcatattcac aggatatcta atattttg    195900 caagtaacat tttgaatttg ttcttcttga catctttatg tttatatgca ttttgcattt   195960
ccctatctca ttttttgaa atccaaatgt aacaaatttc aacttttgt gttacattct    196020 tttctttt tcttttctg ggtagcatct ctctctttc tgaattttt gaaaacctgt       196080 tgttttgaa ttctctttt tcccttatt ttccttctca atatgacccc aggagccaac     196140
acaaagaaaa acgcagatga tataacgagt aatgaccgtg gtgaagacga aggtatttt    196200 tgttttca aagctcaacc ccagtgcatg attttatatc tatctatctc tctttttt       196260 tttcatttca atctgttttt tctcccctta tttaaaacta gtacactttg gtgtgcttcc   196320
ttaattattt tcttccttgta tagaaaccac tgtcattttt taatcccagt taccatgtac   196380
aggaaacaaa tcactgtgag aagtataaac attgtttcta aacatgaaaa gagtaatgaa   196440
ctactgttta cagagaagcc ctttttttt tttttttggc ttggtcgcaa gaagagaaaa    196500
tggaatttta aaacatgcat gtatagtcta ttttctccct tccaaatgtt attttgtaag   196560
ttaatatact actttggagc tttggtcttc ttaattattt ttatgaacta caaaactgta   196620
cagcacctta gaagaatttt ttttgggggg ggggggctg aaatatcagt tttttttc      196680 ttcacaaaca tattgattcc aacatagatt tctgataatc tgctcacagt gaagtacacc   196740 aaaagtgtt ttaatgagat gctgttgtta acgagccctg atgcattcag gactgccttt    196800
tacagcattt aagggggggt ggggaagata agagtatctc agaactgaaa aaggacaaaa   196860
agctagctat gttcatcttt cttttcacac cacggctttt ttgaaaacgt ttttctcctt   196920
aaaatgtttt gttgctgtga agtttcttct taaggctacc aaattgctca acacattgtc   196980
taccagaagt gaaaggattt ttttttaaaa gatggtaggt ctgaggtact catgcagaca   197040
actcgcatgc tgttttctg cccctttctgc acaagaaatg attttttttt ttttaaaga    197100 ggagaagcaa caaaaaaagt actcaagcaa gcccttcttc attggtaagg ctctatagga   197160
```

```
ttagctaaaa gcacattttt cccatctggg tagcaaaatg catggaactc cattaaggtc  197220
ctggctggac ctttgggtct ctgtctgaaa ggcaatttaa agcccaaaag tgagtcctga  197280
attatccttg ctggtcaagc ccaacgtcca tgacagggtc ttttgaccaa ttcttgtagt  197340
tgctcccctc cttgcttatc ttcataaatc aactgttctc caagaaaaga aatcttgcca  197400
acacccttgc tgtgcccagt cttcccttaa cattttgagt attgttactt ttactgagct  197460
catagagctg tcactgtctc aagtagctct ctgagagatc tccattctga tggccatagg  197520
agatcaaaat ctacacctgc ttcaggtagc cccttctttg ataagggctt ctgaatgcct  197580
gacattttat cagtattgag caaatacata aaaatgaaat aaacttttgt ctcatatctt  197640
atactgctct aatttgtatc ctgtttggcc ttctcttttt aatacatttc ctctcgataa  197700
ttagaatctg ttttcacagt gttcccagtg aatctttatt accattaaaa tgccatctaa  197760
ttttcatttc atattgttaa gttatgattt tttgactttg cattaatata acagctggtt  197820
attacttcca caagttcaag agagtcttgt tctatatttt atgaaaggta agagatgtta  197880
atctcacata ttttccaagg gagcacttta aagcagccct tcaaaatctc tacttactct  197940
tttttccaca atttactagg caaccgctgg taatggtaaa agaaatgagg ccaaaaacag  198000
caaattagga accagaaaga agcagtggat catgagaaaa gccatttctt attcatatag  198060
cagaagacat ttcccgtagt gtatgatgaa taaatgatta atagaagatt tttacttcat  198120
atttgaattt tatatgagaa aacaaaagac acttttctgc cgtggattaa atatctgcaa  198180
ataaatactt gggtaacttg acactctttt gtgtgcttta ctgtgaccaa tgggtatgtc  198240
gtgtcttctg tatgcaccca gtaaaattgt gatcataatt cattcaaatt ggagccacca  198300
tccaaacgat ggtaattcat atcctcagaa ttcctttgtg gtatttcaaa agtgtccctg  198360
tggattatga ggaaaaaaaa actttattga tgaagaaatt gaaataaat atgcataaat  198420 acttgagttt tcttttagtt acaaagatat ttaaattgta cacacacaca cacacacaca  198480
cacacacata tctgtatcca gaaatattta tacgtgaggt cagtcttcca aagattaaat  198540
gcagccctaa tggctgatta atgttataaa acaggtcttt ttcacaaagc aggccctaca  198600
gatggtctcc aactttctat catcacagat cattgttttt acatcattgt taatttaaat  198660
aataaagtaa attaccaaga ggaatcattg gttgcaagtc acaatgggag tttatattcc  198720
ctgtgaaaat ataaagcatt taaatagttt ggattctttt gccatttttt attacatctc  198780 ttttatttt gtcacctaag tatgttagta tgttactgta atcactggaa caaagacatt  198840
tgcttggaca tcttttcttt tttttcccta tttctgttca gttaataatt tttaactgtt  198900
gattttgctt tcttgtcatt atctgtccct tattgatagt ttatagcttc actactactt  198960
ttatgttttt attgttaaat tgaagatgaa tctgtacact cacctgcgaa ttaagatgca  199020
actatattaa aattaattat aattttgaag ttgattttat acttaattag aagataaaat  199080
atatttcatc aagggtccca tgtgtttatt caatttaaat cacattttag ggtttgagca  199140
aaatttagga aatgtgtact ttacctaaaa ccatttcttt tagtgcttta gatatatata  199200
gaagcttaga tgagcagagt acgctaaatg tctgtatgct tcttaaaata ccatttccat  199260
aaatagaaaa cgtaatagca ttgatcattt tccttagaca ctcttatcaa gggtcatatc  199320
atccataaaa ataaatgtgc ttaattcaag tcaaaatagg gaaatcagtg aatctccttt  199380
tttcttaatt tagcattggt gagtcagtgt gattcttat tgtgtttcct tacttggctt  199440 tttttccag atattcatga tcagaacagt aagaagcccg tcatggtcta tatccatggg  199500
```

```
ggatcttaca tggagggcac cggcaacatg attgacggca gcattttggc aagctacgga   199560
aacgtcatcg tgatcaccat taactaccgt ctgggaatac taggtaagtg atttcatcat   199620
gtgaatgact gagcaagagg aaacatgaaa agtccacttc tcgttttgac ggggctcgtg   199680
gatttgaatc ctgttattcc agttcctggt taattccact tcacggtatt tactttatgt   199740
gattggatat gtttattcct tttactacct tgtgcaaca tggtcatgaa tcccttctca   199800
aaccaatgca gactttaaga tcttaaagat gaaatgaaat tttatttata gcatgtttct   199860
cccttggagt tcaatgaatg tatgtttgtc tacatagacc tgtacaatga acacatattt   199920
ggtgatatta tagttgggaa tggccataga tcttagcttt cttttctgat tgtgtcattg   199980
tatgaatcag tatattgtgt ggaggaaaag attttatcca attctctaac tgattatgtt   200040
gagcctttgg aagatctgtt gttttggttc cattgcattt gcatgcaggg aaacttagct   200100
gttagttgac ttttgtccat tgatgatcta cgattaaagg ctaaatacat ggaaattcaa   200160
gtttagttcc tccttgtttt gatgtttcat ttcttttctt tctttctttt ttttttttt    200220
cttgagatg gaatctcact ctgtcgccca ggctggagtg cagtggtgcg atcttggctc    200280
actacaacct ctgcctcccg ggttcaagtg attcttctgc ctcagcctcc caagtagctg   200340
ggactacagg cgcatgccac cacactcagc taattttgt gttttaata gagacagggt    200400
ttcaccatat tgaccaggct ggtctcgaac tcctgacctc gtgatccgcc tgcctcggcc   200460
ttccaaagtg ctgggattac aggtgtgagc cactacgccc ggccatcatt catcttcttc   200520
taattgtagg ttggaaaatt atacatcttc agagtcagat ttcagtacct tctgagatgg   200580
cctttcctgg tgttggttag tttgtgaata atattcctaa gacctatgta aaaacatttg   200640
ttttccaggc aaaaatgcat taaaatggta tagaagataa agttttaac aagttagcca    200700
tgagagagat gtgtatattg gttccagtgt gattatgata caatatgaaa tacaaaacaa   200760
aatgaaggcc aggtgtggtg gctctcgcct ataatcccag cactttggga ggcccaggca   200820
ggcagatcac ttgaggtcag gaattagaaa acagcctgac caaagtggtg aaaccctgtc   200880
tctactaaaa atacaaaaat taactgggcc tgatggcagg cgcctgtaat cccagctact   200940
caggaggctg aggcgggaga atctctggaa cccagtaggt cgaggttgca atgagcagag   201000
atagcgccat tgcactccag cctgggtgac cgagtgagac ttttctcaaa aaaaaaaaa    201060
taataataat actagtaata aattaattaa aataaaagc aaaataagat ggactaaagg    201120
aggtctgtca aacaagaaat atgactgaaa atgttttctt caaatatggc caagaatatt   201180
ttcttttcaa tcagatgact tcatttcatt ttgagtgggt tttttttttt cctatgtgaa   201240
aacattaacc tgtaagaagc cctaaaaggt ggtgaattgc tgagaaaccc taagaggtgt   201300
tgtaagaaac cctaagagaa atgcatttct tactttgaaa tgcaaatcag tcacaggtgt   201360
tgctaaagtt gtatcttttg aaacattgat aaagaactca aaattccagg ttggtttctg   201420
cattaaagaa aataaacacc accaaaaaac cttttagtgt caaaaaactt attatgtcgt   201480
tggctttatt tcctatattt tttgtagttt tctgtgagcc acatcttggc ggaataatgt   201540
ctctgaactt ttgcatagca gtaattgcac gcttcactga atagttttca gaggcgctgg   201600
atagttgctt tggctactag tgttggaaac aggaaattgt gcttcttgat gttttacaaa   201660
aggttcattc tgacaaagag gtggaaggag gaaagtatgt gtgagggcat tgcacaggcc   201720
ctcttcaaag ggagcagtgt gtgcactgcc tgtagcacgg ccacacgaa gaaagcttgg    201780
gcatgctttt ctgagggaag cagtgggcat caagaaaatt cttgctttgc tggaaccaca   201840
caatattctg ttgcatgcgt gatgaattga tgtgtctgat aagatagagt ttcaaaataa   201900
```

```
attgatctcc ttttccccct aaagctcagt tgtatcaagc aactctacac tatgattttt   201960
tttttatcag ttttgtccct tcgtgaatca attgcacatc ttgcaaatta gcctggaaag   202020
tatacacact tttttagag gaaaaaaaaa ctaattgaaa aattgttaag tctacttttt    202080
gttatggaga gtttttaaaa gtcataagat aacagagagc tgtaaaattg gtggggaaga   202140
aataaaagaa gcgatttagc atctctatgc cggtctattt acattcctcc aatgagctag   202200
tgtggaacag ccaagcacac tacagacccc ctttcatttg atggaatgaa atgtgccaag   202260
tttgccgatt ttacaggacg atagagactt taaaatgtga ctgcgttggt ttttatcatg   202320
gatcttgcat ttactattgt cctcttgaaa acagctaggc ggcatttact ttttgcttgc   202380
aggaaactcc tattatcggt cttgaaaaaa tgtttttaaa cctttggcat ccagatattt   202440
aaaaagatga tcaaataaaa tacacagcag gcactgcaat gatcatttca gtgagtgcat   202500
ttcatacaag tagatacaat tttaggcaaa aagttgaaat attctttgag ttctttttct   202560
tccagtaaaa gtcataaatg cataaatgtt atcttcctac ctgaggaatg gaaaaatatt   202620
gttttaagat ttttttttt taatggagta acaaatgcta ttctctgtta cccaaaagag    202680
aggattaaaa agatgaaaca tgcccataat ggaagcggaa tgctggcatt ggaaagaatg   202740
tagatcgcag ccagagacag acaggagcta acaactttcc tctacctctg ccttgagaaa   202800
gtcagctagc gtttcctcag actctttcct tagatgtaga aggcagtggt ctctcccttg   202860
caaggttgtt gtacagtata aaagttccat ggttcaaaat accacacttt acctcattaa   202920
tatataatct gcttgtcaat aaaaaaataa cttttttctt ttctttttt tttttttga    202980 gatggagtct cgcttttatt gcccaggctg gagggcagtg gcatgatctc ggctcactgc   203040
aacctctgcc tcccgggtcc aagcgcttct cctgcctcag cctccgcagt agctgggatt   203100
acaggcgcct gccaccacgc cccgctaatt tttgtatttt tagtagagac ggggttttgc   203160
cattttggcc aggctggtct caaactcctg acctcaggag atccacctgc cttggcctcc   203220
caaagtgctg ggattatcag catgagctac tgtgcctggc caaaaaataa cctttaaaa    203280 aagatttaat ggactcatgt agatgaagtt tcataggctc tcagcagcaa ccattatacc   203340
cagtcacact acaatttcta gtgttattaa taccattatg cattgtatta atactactgt   203400
ttatccacag taagaattgt agctgaccca acctgtaatg gctaactaat atctatcaaa   203460
tattggcatc cagactgaac catgttaatt taaaataaca ttacaagaca cttgtagaca   203520
ttaaataaat cagaagatca tcatgtttgc tatttttta aaaataatca gaactgtgct    203580
acacaatctt gctagccatt ggccatataa tttatgatcc aatccaggac atgtttgaga   203640
gttgctcatg tgctatgaat aaactgggat tgtcccaggc aaattgagat gtatcattat   203700
agctataaag taattattta tatctacatg aagtgtcttc tgattgaatt ggtgttcagt   203760
ttgtttttaa agaagctgca cttctataaa cagatttcct atgtgttctg ctatacaccc   203820
ttgtcactag gaaggtgtat atgttaccag aaagggatcc taatccagac cctaagagag   203880
ggttcttgat tctcgtgcaa gaaggaattg gaggcaaatc cgtaaagtga agtaagttt    203940 attaggaaag taaaggaata aagaatgact gctccataag cagagcagcc cgagggctgc   204000
tagttggcta tttttatgat tatttcttga ttatatgcta agcaagggt tggttattca    204060 tgagatttcc gggaaagggg tggcaattat tggaactaag ggttcctccc cttttttagac  204120 catatagggt aacttcctga cattgtcatg gcatttgtaa gctgtcatgg tgcttgtgga   204180
agggtctttt agcatgctaa tgcattgtaa ttagtgtata attagcgtat aatgagtagt   204240
```

```
gaggatgacc agacatcact ctagttgcca tcttggtttt ggtgggtttc ggctgttttt   204300
ttttactgca tccttttatc agcaaggtct ttgtggcctg tatcttgtgc tgacctcctg   204360
tctcatcctg tggctaagaa tgcctaactt cttgggaatg cagcccagta ggtcccagcc   204420
ttacgttacc cagcccttat tcaagatgga ggtgctctgg ttcaaacgtc tctgacatat   204480
atattcaaga atttggaaaa cctcaagttc accaatgcct ctcagattag tcattgccag   204540
ggtgtgtggt gttcctatct gctcagaagc cagaagccag caaaatcctt gctgagctgt   204600
acgtgccagg gcatttgcct ggtctcacct acccacttga gtacctatgc cctatcaccc   204660
attcacctca caacatccat acgtatcatt taccccctaag aagattagac attaatccag   204720
gtaataaact ttcagaacaa tcacctccag acagaaactg cagaggataa tctgataaat   204780
ctgaatccct gtaaggccat tactgaatca ataaatactc ttttctccat cttagttcct   204840
tactttagta taacttgagt tctccccaat ctgtttttttt tttgttgttg ttgttcatga   204900
tagtccaaag accttcgatg taaaagagaa tgcatcttgc tcatgctttt tgatggaaat   204960
acctggaact tatttattcc ttccccttt cagttgtctc caagtgcaag tctgtctgta   205020
cctgcagtgg atttcatcta cctccatta aatatgtatt tccgtttagc tcacatggta   205080
ctatcacctt tttggtgatc ctatgacttc atgcttcatg tatgctgaaa ttaattgttg   205140
cttcaaaaga gtcccaacta tgtaacatca actcattgtg tgcctctatg tggctggcag   205200
atattacttc atttaatctt cgtaaactcc cttggaagag ttaaccttat gtcctaccta   205260
tgaggagatg aatgctttga ggtaatggga tttactcatg gcatcacacc ttctagcagt   205320
cagagcaggg actgaaaccc gggtgtaact gaagccagag ctctgactta ccactcagaa   205380
ctcatccaca gccttcttaa ttaatgtcaa gtatgaatta gtaaaccatg gaatgagtga   205440
agaaattgag tatcacttta gcatcagatg tagcttttat cattatgcaa aaagttctt    205500 actgctgatc aagatacaca attgtgataa gatgcttaca gtgtatttt aagttcctca    205560 aagtgggtcc ttgaaggctg attcatttcc attcaatcga tactggtttg ctttggttca   205620
cggtgatggt ggcattaacc acaacaatgg catttgtcac atcaaagctc ttcggtgcag   205680
tagaactagt gtttcatcag gaaatttggt gtcctacccc cagttcccat gtcattgctg   205740
gcttgctgtg tcgtgtgcat aaattgagtc aaatgatcat ttcggtgcat ttcttacaat   205800
ctttcacata ttatagctat cctgaaaatt ttcatctgag ggtagattgc gtcatggtct   205860
tctgaagttg tctttctctt taagaccatt cattgaataa acctattaga cgctttggag   205920
tcataattga atataagaca gaaatggttt gatataaaag caaccaacat gcatagcaga   205980
aacagcattt gtagtcataa tttgggtgac ttaacccata tgcacgtgct cagcctaata   206040
atgtggtcac tttccctgtt ctggtgtccc ttgtagggtt ttcctctgaa attgagggag   206100
ggtgggctga gctctgaagc attcttgcaa catcggccag agtggtctca cctttatgct   206160
tttgtgatat gtgtgagcca tgtaatattc cactcaacaa aagaagcctg gaaatcatta   206220
gaagagagga ccaatacgtt cttcccaaga gttacagcct caattccatg ggtgtgcatt   206280
tatgtgacat gcatctgaca ttagtgggag ttcaatgggt cactataatt tccctgaagc   206340
acacctgctg aaaaatgtca agctatctta taaatgacct gtatgttctt ctccccttttg   206400 gaagttagag gagttgctct atttttggta catttgctat tttatttctt tttttctaac   206460
aatatttctt tcttttaatg ctttatgaag gatttatttt gaaatgataa atggaacaca   206520
tcttatgtat caagtcaaaa gttcataagc gtatatatta aaaagaaag catcatttcc    206580 ttttttcgaga atcaacacac cttgatgcca gtctcctggt ttcattagaa tccctctctt   206640
```

```
ctcttcctct aaccaaaatg tctcagattc ccccgatttg atttctgtaa atggcctact 206700
ttgactggaa gaattgcctc tctctgtcta aaacaggacc caggcgttac taaaacaaaa 206760
cactgcaaaa agttaaatga ggagaaagga aagttaagca ttgtacttag tgagaaatac 206820
ataaacaaaa gtagagacgt aaaagaagca tgagagaagg gtgagaaagt gaaatcctga 206880
gacaagatga atggtgtgtg agcactcaaa cccaggaagt agcaaaaggt ggaaggaaga 206940
atgggagcct ttagaataag attctttgtg ggctgggtgg cagatgttat cggtaaagcc 207000
agcctgggga gttggcaggg gtccatgcag tagataacac agcaatagag tgaacacatt 207060
gcagaagata gggcaacctc taatccagaa attatcagat aaagaaaaac caagacactt 207120
tgcaaaacaa aaaaaaaac aaacaaaaaa acacaacaca atgtcttgtt tttcatcatc 207180
atcttcttta taatgaggtt tccatgcatt gaatacacac ttggaaacac tgtaatccca 207240
tggttgttgt ggctgcagat tgataggtgt ggacaggtct ttggtggggc aaacaaaacc 207300
aggatcatgt ttttgctct cagaatgatc gtttgcttgg actttcctct tctgcctcct 207360
agtggctcaa aatgcccact gcattcattg gatttattca ggatgtgaag aaggtcaggg 207420
gaaattaagg atgagtgctt tgtcattagg acctgagagg caaatggagc agagatgggg 207480
acgactgcag tgggataagg actctctcac caggaaggtg ccattgatgt aatagttgat 207540
gggaacagca gagcaaagag gctccctcgt cctcagctga ctcaacaaca agcgagacat 207600
cagatggaac ggtatttatt gggcaaggaa aatcagggga aggctaggtg cagtggctct 207660
cacctgtaat cccagcactg tgggaggcca aggtgggagg attccttgag gccaggagtt 207720
ccagatcagc ctggacaacc tagtgagacc ctgtctcaga aagaaagaaa gaaagagaga 207780 gggagaggg gagagagaga gaggggagg gagggaggga gggagggagg gagggagaga 207840
gagagagaga gagagagaga gagagagaga gagagagaga aaagaaggaa ggaaaaagaa 207900
aaaattagcc agatgtggtg atgtatgcct ggtgtctcag ctacttgaaa agctgaggca 207960
ggaggattgc ttgagcctag gagttcgagg ctgcagtgtg ctgtgattgc actccagtct 208020
cagcaacaga gtgaaatcct gtctcaaatt tttaaaaaag actcaaaaga aaatcaaggg 208080
agggagtgga gacaaggtag aaaagaattt tttttatttt gtgctttttt ccctaatgta 208140
ttcatttaat catcaaataa aaattgaata tattgatcat gtacaaagtg atgttttgaa 208200
atatgtatcc attgagaaat ggctaaatcg agctaattca caagtgcatt acttcaaatg 208260 cttattttc tggtgcaaac acttaaaatc tactttctta gagatgttca aatattcaat 208320
tccttgtgat tcaactttgt ttgccatatt gaacagatct tttgaacttt ttcctgccaa 208380
ctgaaacttt gtaaccttg gccaacatct cccgtttcct ctccacctcc agcttcaagt 208440
tctgtaagag aacattctac tctctgcttc tgtaagcttg acttttttt agattccaca 208500 tataagtaag aacatgtgat atttgtcttt ctgtgtctgg cttgtatcac ttaacataat 208560
gtcctctggt tcatccatgt agtcccaaat gacacaactt cttttctttt ttttgaggta 208620
gaataatagt cccttgtgtg tataaacccc atttttcttta ttcattcatc taatgatgga 208680
cattcaggtt gattccatat ttcagctgtt gtgattagtg ctgcaatgaa catgggagtg 208740
cagatttctc ttcaaagact tcttttttcc aatcccaaat acacaaaatt atcatctggc 208800
atctgtcatg ctatggagac tctccttgat ctatttataa acgattcagg atttcttaa 208860 agaagctgaa attttatttt tacatgcata accatattta gaaatcaaaa tattcaaaca 208920
gaaatcacag aagaatctat tccatcaata tataattccc agttaattga ttatataatg 208980
```

```
tcatttaagc atgagttagt agtcacagag aatatgcctt aaaaatgttc tgtctttgaa   209040
agttttacat tcaaaacagt ctcttaagat tattaattct aaaagacacc atcccttttct  209100 ctcttcagcc tgttttcttc attttgcttc tcatccagta tgtgaaaggt tgatgatttt   209160
tagttgatga ggttgacgtg ccctcttcct ccttggggac agaaggacat aagttgtgct   209220
ttaaatgaaa ataagagtat gatgagtatc ccaagggatg atggaaagtt ccagggagaa   209280
gcattgaaat tgagagccaa attcaagtac attggaatta gggttctggt gataattctg   209340
tcagtatcta catatattca aggaaattag tcctttcgag taggataatg gaaaaatctc   209400
taaaaggcaa tctgagcggg atgtttaaag actacgtgat tattatgcag tgcatgcctg   209460
taccaaaaca tctcaagtac cccacaaatg tatacactta ctatgtaccc ataaagttta   209520
aaaaaatgta agactactac acatattctg gcctgcagct ttttttcccc tgacatttgc   209580
ctacccgcct gtaatagcac aggcaattct acaagaagca tgaatatgca catatgtaca   209640
tgcatgacag cagtgataca aagacagatg tgttgtgttc tagtataatt gtcttatttt   209700
tgtccattcc aacgttaata agtcattagc tttatgaaaa tgaaccctag gggatgaaac   209760
atacaggtgc aaagtaaatt tcctagggac taaattataa ccaaattatg gcaggtacac   209820
cctgcattta gcgatataaa tatatgtttc aaataaaatt gtaacatatt gattggcacg   209880
tccagccata ttcttaagat actttatcct tggactaaaa ataataataa tcgcttttt    209940 gaatgaagtg tttaattttc agtgtaaaaa gtcaggaata ttttagaatg ctcaacgcaa   210000
cattgcttca atgagctagg gcctttatga agataagtca ctagaaagtc tgtgttgatt   210060
cggttaatta tttgagattg tatgcactga ttttcactgt gttaagtata gtggcattta   210120
ttagaggctc agatgttata gagagaaggc tgtgtccagt tatagggctg tagtcataaa   210180
cagatgggta aaatcaacac atcattgtaa atcataaaca ggcaggtatg ataaacacat   210240
aatgataagc atttcagcac tgggtgcagt gttgcatgcc tgtagtctca gctactcgcg   210300
aggctgacga tctttggagc ttaggagttc aagagcagcc tgggcaacat agtgagaacc   210360 catcttttaaa cattaaaaag aacaacaaaa aaacatcatt tcagtgtaga caggcataac   210420
atgatctcac agagaaacac tacgatttgt acacaagaaa actaagcttt gcactggtgt   210480
tgggagaaca ttttggaatg ataaactatt tcctgtttgt tttaagaaat atttggtaag   210540
gtttaaagta gtgtctgcct ctttactaaa atattccagt atctgtttag atgtcccagt   210600
tggtcttaga tacttggtgg taaacatata tatacacata tatagcgcat atatgtgtat   210660
atatgtgggt gtgggtgcat atgggtgtgt ataatctatg tgtgtataca tacatatatg   210720
tgtacataca tacatatgtg tgtatacata tacatgtatc agttgtttgc ccttgtgatg   210780
cacacacaga tctatatgtg tgtatatata tgtgtctata tatgtataca tgctaatgtg   210840
tatgtataca tatataaaat atgttccttg attcacagtg ggattatatc ccaataaacc   210900
cgttgtaaat gtaagatgtc attagttgaa aatgcatcaa tacatctaac ctaccaaaca   210960
tcatagctta gcttggctga cattgaacat acttataaca cttacattag cctacagttg   211020
ggtgacatca tctaacacaa atcctatttt ataaataaag tgttgaatgt ttcatgtaca   211080
ctgcagagta gcagttgttt gcccttgtga ttgtgtggct gactgggagc tacagaccgc   211140
tgcctggcat ccaaagagac tatggtactg catattgcta gcttgggaat atatcaaaat   211200 tcaaatatg atttctactg actgaatatc attttttgtat catcttaaga tcaaaaatca   211260
taaatcaaac cattgtaagt ccgggaatgt ctgtgtaata atttggctat agtcttaaac   211320
aggtgggtag aataaacaca ttattataaa tccatcctgt gcttttgaac acatggaggc   211380
```

```
taccccacca aaatgcctgt gttcaatata ttgcgaacct ctaggtatct ttttccttca   211440
ttgctgttta attttccctt ctaagcatga acttacaaga ttacttagga atagcattca   211500
tccttcttca ttcctctttg tttaaaacat gcttagcatt tctcatcttg aaagaaatga   211560
gtagctttct tcttttcaat catatttcat cagaactatt ctcttgaggg ccacagaaat   211620
gtcataagca ttttctctgg cacttctgat acttttaatg gcttttgata catcttcatg   211680
tttcttaatc ttcttgtgat ccttaccatg taagtgaccc gttgagctta tctccaactc   211740 ctattttttca ttgtctcctt cctttatttg aaacaactta catccagcgt gcacgtttga   211800
agtgtgcaat tcaatggcct ttagtatatg cacaacattg tgacaccagc aacaccatct   211860 aattttttgaa cattgacgtc attccaaaga gaaatcccat acctcttctc tcccaggtcc   211920
ccaggagata ggcttccact aactatctac ctgtctatat agatttgcct tttgggggca   211980
tttcatgtaa attaaatcat ataatacatg cttttttgtg tgtctgactt cattcccctta  212040 atgttttttga ggctcatcca tgttgtagca tgcatctcta ctcttttatt ttttatggtt   212100
cggtaatatt tcattttatg gatataccac actttgttta tccatccatc tgttgctaga   212160
cattgggatc atttccagtt tctggctgtt ctcaataatt gtgccatgaa cgttcatgtg   212220 caagttttttg tatggacata tatttcattt ttcttgattg gggatatagg agccgaatcg   212280
ataggtcata tcatgaactc tgtgtttaaa tatttgagaa tctttcaaat tattttccaa   212340
aataggtgta ccatttttaca ttttcaccat caatgcacaa aagttttaac ttctccacat   212400
cctcactcac acttgttctc atctgtcttt ttaattatag ccatcctaat gggtgtaaag   212460
tgatatcatg tttgggggtt tatttttgaa tatttacatc attccaaaaa gaagtcccgt   212520
atctcttctc tcctacatcc ccaaaaagta ggcaagaggt aatctactca agaaatgata   212580
ccagcttaaa ccagggcagt accagtgaga atgcaaagaa aataaaaaag aagaggttgt   212640
tctgcgtgtc ttacagatgc aacaggattt gctgatggat tggatgcaag gtggcagaga   212700
atgagaatgc attttttcctg atgactaatg atgttgaaca cctattcatg tgcttattgg   212760
acatgtgtgt aaatcctttg gaaaaatatc tattcagatc ctttgcctat tttaattgga   212820
ttatcttttc attactgagg tttaggaggg gtacttttaa gtagtataat gtggatacat   212880
gttccttacc acatgtggga ttcacaaaca ctcccattct gtgtcttcca cctccacttt   212940
cttgatggca cattcttatt actcatgttt ctgaaaacat aatcttcagc ctcattgacc   213000
aatgactctg aatattgact catatatgtt taagcaggct tgtccactta ctatatctca   213060
caagtcccat ggttatcgtg acagtccact gctatcccgt cccttgtggc tgtctcatca   213120
ttgtatggag acaatataag gatgccggga cagataaagg gtattaggat agagtgccat   213180
caatgtgtct gtgaagaagg gttcgtttca atcagttcac catgactggg gatttgattc   213240
tgtcaattgc tgactcagga atgtaaatgc tgagtaaggc aggacttgat cagtctattg   213300
ggggaaggca tcattgacca aagtgcagtg caaatttatt cattgactat gaggcatata   213360
actctttata actgtcaata gaaaatggac aaggcatccc tccgttcctt acaaggtttt   213420
gtaatgagcc ctggatttaa aaaaatacta gtaataataa gagaaagaga gggagacaga   213480
gagagagaga gtgagataga gtttctagtt taagtgaagt taaaatgttt tttctatata   213540
tacaaaacta gctttgccaa ggaagatgta gtagtggttt tcattcattc attcttcttt   213600
cattcaagaa acagatattg acaacctgct gtttgacaca tggtataaca acttccattg   213660
aaaatggagt agcaaacaaa acagagaaaa aatcccccaat cctacagcat ttctatccag   213720
```

```
tagggggaaaa aacaacgaca gacaagtatc gtaaaataca cagtagaata tgatatcaca    213780
agtgctatgg agaaatattt agtagagaag ggtgctaaat tagaaatttt gtgccaaaat    213840
tttgactaag gtggttatgg aaagtttcac agataaggca aaactgatgt gagggagtga    213900
tccatacagt tacctggagg aacagcatct tgggctaagg aaagatccag tgcaaaggcc    213960
ctgtggccac agagtccctg agaatatcag tgcagctgga aagtagtggt gaagggata    214020 gtagcacctg atttcagaga tgtcagcatg agccacattt tatatgcctt taaaggacta    214080
gtgtattgtt cttagtgaga aggaaatgg ctgtctatgt aaaggggcat taggttagaa    214140
ggttgttgca taatccaccc aagaaataaa aggcatttcg atcagaattt agctcttcta    214200
ctccatgaaa ctacttatca gttccattaa tgccttccac tctgcactct cagggttcga    214260
ttttctggaa aattttgaat tttgattttg attttccaga acatttagag ttctcgatga    214320
ctctctcctt cacgaaaaac attccttact tggtatctat atttgtttct ttcctattgc    214380
tgctaaaaca aggtatcaca acttgttata actctaatgt taactctagg gaattaaaag    214440
caatgcagat ttattatctc acagttctgg gtgctaaaag tcccaaatgt gttcacattc    214500
aaagagagaa tccatttcct tggtttgtct gtttgtcttc ttttgaagac tggctacata    214560
tcttagatct cattctctgt ttctaacctt ccatttttaaa aaacaaacaa acaaaaaaca    214620
ttatgattac ctagattcat ccagatgaac cgggttaagt tctcatctta agatcctcac    214680
tttttttttt ttttctctct ctgagatgga gtcttgctct gttgccaggc tggagtgcaa    214740
tggcgcgatc tcagctcact gcaacctccc cctcccgggt tcaagtgatt cccttgcctc    214800
agcctcccga gtagctggga ctacaggccc gcaccaccat gcctggctaa ttttttttgta    214860 ttttactaga gacgggtttt caccatgttg gccaggatgg tgttgatctc ctgacctcgt    214920
gatccgctct ccttggcctc ttaaagtgct gggattacag gcgtgagtca ccgtgcctgg    214980
ccaggatgtt cacttttaa aattgattta ttcttatttt attttagaga tgaggttttg    215040
ctctctcaga taggttggag tgcagtgtca taatcatagc tcactgaagt cccagcctct    215100
tgggtcaatt gatcctccta tctcaccctc ctgagaagct gggactacag acatgcacca    215160
ccacgcccag ctaagtttta tatttgttta cagaggggg ttcaccatgt tgcccaggct    215220
ggtcgtgaac ccctaggctc aagtgatcca ccggcctcag cctcccaaaa tgctgggatt    215280
ataggtgtgc ttcctgacac cagtttctga ggtccttgac ggctgtggtc atagctcata    215340
ctacctctct ctccctagtg tctaccggac aataagcagt ttctgaatga ttagccgttg    215400
cagggttttt gactccaaat tgcaaaatgc aagctaatta aaaaaggagt gaatctattt    215460
actcattttt ttttttttttt agtttgagtg aactgattct caaaatcagt gaatgcccag    215520
tttcatgtaa accgtgttta tttccactgt ttacactcag cagctgtttc ttttttcacaa    215580 acactggaga ttccatgttc cccgaaatat ctatgtatac ctgtatcata attcattaca    215640
cataggttag ctggaatgga gatattttat atttgtggca tgcatttgat cttgaattga    215700
aacctgtagt ttagaaaaat ctacatatct ttatattttt aacagatttt gagaattata    215760
aaagcaaaac agtagagctc tacggtagaa tttttttttc tttaggtctt tccatgggta    215820
ttttaaatgt ctcattatga aaagaccata aaccatggtt ttctaagagt tctgctgaat    215880
tttgcaattg gctggcacat tttctaaatg atcctgtaat ctccatgtat tagttttcta    215940
gagcggccat aacaaatgac cacaaatgtg atggctttaa aagagagaaa tttactcttt    216000
ctcatagttt gggaaccag atgttcaaaa taaacgtgtt ggcagggctg cctttccctg    216060
ggtggttcca gaaaaagatc cttccttgcc ttttcagctc tggtggcctc ggtgtttgtc    216120
```

```
tctatcttcc caaggctgtc ttccctctat tgtatgtgtc gtctccttt  cttataaaga  216180
taccagtcat tggatttagg gttatacccct caattcagga taattttatc tgcagatcct  216240
taactaatta tatctgcaaa gaccctattt tcaaataggg tcacattctg agtttccagg  216300
tggacatgta tttttggagg atattacgca acccactcca cccaacacat cattattgca  216360
atatatatgt atgaatatag gtgtttcaga tatttacact acacatgtgt gtacaaccaa  216420
tgtattcagg atgccacctg gctttctcct tactaggcca cactctggca agaagatcta  216480
aggacaatct gggattcttc atctccttct tgcatcctct ttgcttccaa ataatgtagt  216540
catgcagtat ctgaaagttt atttcctgag cctttaaaac ttctccatca gtttgacaag  216600
gagtaaaagc gttttcccc  gttggccaca aaacttgtgc ttttgctcca gcaatacgca  216660
aagctatatt tcacacttcc ttcttaaatt acaggctata aatataaagc aaaacctttt  216720
accttggata ttctttctgt cttttccctc tgtgattaaa tctgattaca aatgctcatt  216780
aatgctctgc cttggaattg caatttgggc atgtgccatg tgaaaatgga ggttcctaaa  216840
aattaaaatc aaagattaat gcaggtttta aaaaagggtc ttattcaaat atatctcaag  216900
ttttaaaacg actcatggac ttttaatgaa atcaatggcc ttgtaatgcc tcattttttt  216960
tttcaaactc aactgtttca tagccttctc tttagaacat atctgattta ccagaaccca  217020
agatttgtga gatggtgtta ttttttatct ttacttttc  ctcacccac  ggtaccatga  217080
agagatcgtg taacatcctt tcctggtttt aaagacaggt gagtaacgat tacataacgt  217140
tcaaacaagt caggtgttct ccagaagatg gtgttaatgg tgtctgattc acagatgctg  217200
ccttgacccc tggcggtggt aggacctata ttctggtgaa agccaatttt aggccatgga  217260
ttataggacc tagtggagaa aaacgatac  ctaaacctca tgagatctta attcactgat  217320
cggtggagag atatttttct ttcagatggt atcatcttat tgcatctcca gcagagtgtt  217380
tggccggtga aaataaaaat ggccattata agaagttct  ttagactttt aaaaattta   217440
ctaggatcat gccagaaatt cctgctgtag aagtagatat gtatgtgtgt atacatatat  217500
atatatatat atatatttct gaatttgaga tgttgggtat tggtagagat tcattcattt  217560
gaatggaaat acgcttgctt tacttttggc cagcatgaat gctctcattt gccacaggtt  217620
ggcaagctta ttggtttaaa tataaaggat cttgtgggta agactaacag caggttttca  217680
tagtgccaac atttctttct tttttattat catatttagg aaagtctctt gactctgaga  217740
tactttatat tgtgaaataa tagttctggt gcaagtatag attaatagat tattaaacac  217800
tttaagatat ggatggaaga gtacaactag gatattatta atgagtccca tttactattc  217860
tttaatttgc agtggaattt tcatttaact tttgaatata ccaatgatag gaagttagta  217920
gtgtttgcct gtaatttatc ctgagctcat ttatttgaag ttcaaatttg aaagcttcct  217980
tttgttgttt ggtaaataga gattattgtg attcaaaatg agtaatccct aaattgatgt  218040
agaaaaagat atttgaggct gggcacagtg actcacgcct gttatcccag cacgttggga  218100
ggctatggga ggtggatcac ttgaccagga gtttgagacc agcctggcca acatggcaat  218160
accccgtctc tactatgaat acaaaaatta gctgggcatg gtctcacaaa catgtaatcc  218220
cagctacttg ggaggctgag acccaagaat cgctggagcc tgggaggcgg aggttgtaat  218280
gagctgagat tgtaccactg cactccaccc tgggcgacag agcaagactt cgtctaaaat  218340
aataataata ataataataa taataataaa ataaaaagaa ctttgagata ttcatattgt  218400
ccaaaaagta taattcaaat acttaatgca gaaggcagta ggatcactaa actacagact  218460
```

```
cattcatcaa ttataacaga tggaagggtc tttgttagag tcctggaggc tgattgagca 218520
ttttaaatgg caggttcata ggggagatcc aggaggtcta aaggtgaggg tctacaagca 218580
ggaagcaccc ccactcccac ccccaaattc atgacaacaa cactaactag gcagcaaagg 218640
gatatttcct gatgtcagca gtcagcagaa tggtactgaa ggttgctaga taaatgcaag 218700
ttttgtagtc actcacctgc aagttatagg caagatattt atctgtactc ctacaggaaa 218760
ttagccctaa ttgactgctc ttaatcagaa caagacattc taacctctta ttcatggtta 218820
gcagtatatc ccacttgctt cactttgtga ttctccatca cattggaata actggacgtg 218880
ggatacattt ggaattgagt ctcaaattca aatcgccata gaacctgaaa agaaaatgta 218940
agaagagaca aaacagaaga aaaatgcagg atagagagtt atgatttaga tgtgttcatt 219000
ctgtgaacag agagcagatt ctcttggatc tggctgaaac aggggccccc tgtgttgtga 219060
aagtggtgta tgtcttcata cgtgttccca cgggcctgga caaccaacca catttgaaaa 219120
atgaagaaat gaaagcttgt ggtcagggtc acaaaacttg acagtggcag aagtggatcc 219180
aatttccagt caaatctatg actcgttcca tcttggccac aattatactg caactcaatt 219240
gcttttcttc cagtcagtac ccacccaccg aaatgtcagc tcttcaaggg cattaattgt 219300
tgtttgtttc attcattgtt gagtcttagg agcctgggac agtacattga aaatctcaat 219360
tgttgacatt ctcaataata cacaagaaat catgttttca gatcatggaa atcatatcca 219420
ttaggatggc tgttaataaa gtaaacgtaa aataagaagt tgtaatgag atgtggagaa 219480 actggaactc tttcacattg ctggtgggaa tgtaagatgg tacagtcatt gtggaaaact 219540 cttttggctgt tcctcaaaaa agtaaacatg gaactaccat atgtgatcca acaattctac 219600
ctccgggtat atactccaat tctacctctg gtatatact caaaagaatt gaaagcagga 219660
attccaggag atatttgtat acgcagtcct taaccatgtt attcacaata gctaaaaact 219720
gaacttttga actagccaac tatccattga tggatgaatg gataaacaag tgatatatat 219780
gtatatattt atgcgtgtac acacacacac acacactgct gaaatggaat attattcagc 219840
ccttaaaaga aaggaaattc tgatacatgc tacaacataa ataaaccttg aggacatcat 219900
tctaagagaa ataagctaca tgctagtcac aaaaggacaa aagctgtatg attttaccaa 219960
tatgaggtac gtagagttgt caaattcaca gaggcaaaaa gttgaatggt gtttgtgtgc 220020
ggctgagagg cggagagaat ggaaaattat ttcctaatgg atagagtttc agtttggaaa 220080
ggtacaaaat gttctgaaga tagatggtgg ggacagttgg acaataatgt gactgttctt 220140
aaggccactc aattatacac caaaaaatag tttaaatgat caatttcata ttctctatat 220200
cacagtaaaa taaaacatta tggtatctgt gatttaattg actatttgta atcatcacca 220260
tgttagagca tgttcagtat ctcatatcct gcaatattgg aatggacatg gtaattttg 220320 agtggtagaa aataaagtaa cttttaaaaa cccatctcta tgtattcaca taatcttaca 220380
tttcatataa gtgaaatcat acactctata tctcatttct ttctcctaat aaaatgttta 220440
caaggtttac aaggttcatc cacattgtag catgtatcaa tcagtaccgc atgctggttt 220500
atggctggat actattccat tgtatgatag accgcattct gttatgttta tctatttttc 220560
atttgatgga tatttggatt caattcatag agacagaaag tagattagtg gttgctggtg 220620
cttggaagag gactataggg aattagcgtg tcatggttac agagtttcag tttgcgaaca 220680
tgaaaaattt ctagagatag attcacaaaa atgcaaatat actaaatgac attgaacaga 220740
acagtacact ttaaaatggt tcactttatg ttacgtgaat ttcctcttaa atagaagaaa 220800
aataaagtct gaagttgtca tatccttcac tgggatgctc tctttaaaag tgtagaaagg 220860
```

```
tcctgaaagg agcatataaa caaactaaac aacaatcaaa caaaacatgt catcgtaccc   220920
cacagcatcc tgacatggaa gactaaaaac tgtcccaggg ctctcttctt ccttatctgt   220980
tactttcagg ggcattttag cttaggattt aatttgacta ttgacaaccc cagtgtctcc   221040
atttgatctc agagcaaact tgaattgata attaaatttc catgcttttg accagggaaa   221100
gactttagga aatgtctttg aaactgtgaa cttgcagaaa ggagaaaatt ttatatgtat   221160
ctagcttcta tccattccat ttgtcatatg gtcagaactt acatgatgca agcaggccat   221220
ttacagggcc ctgggctgac agctacatgc tatattttgt atttgcttcc actattttgt   221280
tagcaaatgt atgtacttac taacaaaata cgtgttttaa gaaataaaat tattttaaga   221340
acaaaataat acaatgtttt aagaaaacct gcttttattt gcttttttatt ttttatttaa   221400 aaatgtttat aaatttatgg gtgttacaaa ttcagttttg ttatatgggt atattcatag   221460
tggtgatgtc ggggctttta gtgtactcat cacccgaata gtggaacctt tatccagtag   221520
gtagtatttc atccttcatg ccccttcctc ctccttccac ctcctgacac tttatagtct   221580
ccagtgtcta ttattctacc ctgtatgtta atgtgcacct gttgtttagc tcccacttat   221640
aagtaaaaac atgcagtgtt ggactttctg agttatttca cttaggataa tggcctccac   221700
ccagtttcat acatgttgct gcaaaagaca taatttcatt ctttttttatg actactactg   221760 agttgtattc catggatata taaaccatgg tatatataaa catttatata tccagtcatc   221820
tgttgatgga cacttaagtt gatttcatga ctttgctgtt gtgaatagtg tagtgataaa   221880
catatgagtg gaggtgtctt tttgatagaa ccatttcttt tcctttgagt agaaacccac   221940
aagtgggatt gctgggccaa atgatacttc tatcttaagt catttgggaa atctccatac   222000
tattttccat agaggttgta ttaatttacc ttcccaccaa cagtgtataa ctgtaccctt   222060
ttctcagcat ctttgccaac atgtgctgct ttttgacgtt tttcaaaatg tcattcattt   222120 tcattttttat tataattact taaaaatgat gacttttaac agagaaggga aaaataaagt   222180
tggtaatctt ttgtagtgcc atataatttc tagttacaag accacagata agtcccatgc   222240
tgaagagagg tgggtaaaat agctcgtttg aaatgaagca catttgggaa gataaaattg   222300
tttttaggat gataacgatg tttgatgtct aactttggtc tagttttttct aatgttaagt   222360 gtattcttaa catctgccca aattattcac tctttaaacc acatgccaaa acattactta   222420
catttacttg gttataata aaatttggga ctattagtgg atgatattta ctgcaagaat   222480
tgttaatctg gcgtttggat ctagtattta gattacttta tattttcagc tgcatatgca   222540
actattagat atctgcccac acttttttcct tcccactgtg gaaaatacac actgtattaa   222600
ggtgacaggt tttcctattt tcacccctta gacttgagtt attttctcat cattattaac   222660
tcatagaacc tgtgctttgt tcctggcttc agcttgagca ctgtgcaaaa atttatctta   222720
taagatttgg tcaaaactgt tggctgtgta ggcacttccc ctagtagaaa cttccccttt   222780
cccctctgag ggttcactga aaatcaact taaaaaggca gattaattga agaaaaggca   222840
tgcaaatttc ctttaatgtg gatagcttgg caggaaggat taggagactg attacccaat   222900
atcttaatgg agtagatatg cttatatact ctacttccta gaggaaaggg aggtgaggac   222960
tcctggatga tacttagggg gatagtaaat gatttttagg ggaattaagt gggcttgaag   223020
aacatacagt ggcttagaac aaagtctgtt gggcttgcag agcagacagt ggtttgtcac   223080
aaaagtctgt ccaggtgtgt tgacagactt cattctttct tcctgcgata tgagtccagt   223140
tactagaatc tcggggaagg gaccagaggt cattgttttc ttctttgatg ggtccagact   223200
```

```
ttaggcagat aaacaacttc agaaaacaac ttcctcctgt gctttggggg tcacagaggg 223260
ttgagagaca agagggagtg ggagaagatg agagagacgt tgaggcttct tcttcagttc 223320
agcacatcaa agtgccatat tttgctgtat gggtttatga gtcccaacaa ctgggtagtg 223380
aagacaaccc agggctgtgt gttgatggtt ccgctgcaga cagtcaaggc tcacttctct 223440
gggaggaagc taaatgccac tcagagacac atccccatct cagatgtctt tgttatattg 223500
atgacagttg gcacccagat ggcatgtatc ccttgtggtt tcaaccattg gttgacatga 223560
ccttaaaggc ccaaggtatg tattcgttgg tccattttt ggaggaatgc cattttactt 223620
ccacaatgca gcatagctgt taaccattca tcatgccagt aagagaatcc ccgggatctg 223680
cattgggaca gaatccccat tcactgcctt gtctcacttt tgtagtttgt tttgttttgt 223740
ttgaatttgt tttagttttt aacaaataat ctgaaggtaa aatacaattg aaagaagcac 223800
ttatcttatg atatcaggat aagtaaacta gtgcagtttc agaaacatct aaccaagtgt 223860
tgttttcttg ctggattgca atattgatag gcacatggga taatatctca tgtaaattct 223920
gaaacatcta attgcatctt gatccttcat cttgaccctc ttctcagtgg gctgcattta 223980
tccctaaaca gcaacattct gtcaattctt aggaacgtga aacgttacag tctgcagagc 224040
aaattaccag caggagaaaa tattactgaa tattcaaaag catgccttt gtgtgaatga 224100 tcttgaagcc ccagggaatg ggggaaacag ggttgggagt acataagcca agaaccttat 224160
ttgatccagc agtttccggc ttctaaaacc ctacccatgc agttccaaga agaaaataac 224220
aaattggcat cacttaatgt ttagtgatag aagaagaaaa gcatgccttt gttcattttc 224280
tactcttctc atttcctgct tcaccattcc tatcaaatga aacatttcgt tttcatttcc 224340
tctctataac ttgtactatt tctgtgaata gatgatgtgc ttaacatatt gatgtttgtg 224400
agtaaagata ctcttgctat catcaaaaga aatagtatcc atttgagaag catctagtat 224460
atgaggaaaa gttttgtttt cattttttccc ttatgttgtt ttttatattt taaatgtagt 224520
tgtaaaatga cagaacatgg gatcacaaag aaacacaaaa ttcgtaatta ataaatgtga 224580
ttttgtattt atttttaggta tgcaagggc acgtttgtgt gggagttcaa aagcatttaa 224640
atattttaaa tctcctttca ttcatttaat aagtgtcttt tgaggtcaga tgtaaacaga 224700
caacttgtta cacatgtttc ttgttttag ggaacttcca ccccaacatg ggaaataaac 224760 agagaccta ctagttcttt aacagtttct taatgaaaca ggatatttcc ctgaccccc tt 224820 cacaggtggg aactggagtg cactggtgct ggaactagcc ggctgcttcc aggccagcgg 224880
gggtgaaccc tgctcactcg ctgctctacc ccttgtggga gggaagcac aggtgagcag 224940 gtacaggagc cagggcgaac aattttgggc accagcaaga atgaactcca taccagcccc 225000
acggcagcat ctagtagagg gtagcccgca acccctgaag acccagagga agtgttacac 225060
tgcctgtttg gctttgccat ccgcagagac cgtaagtgtt aacagctcag tggagggtca 225120
atgtgacagc ctttttgcacc cacactcatg gcacgcaagt ttttgtcctg aggtgggaaa 225180
ttaaagaaaa ataaaatcaa aaagaaagag aaataagttt tcctgtatta ggctgacttt 225240
tcccagaggc agcaacaggc acagcccaga cccaggaaaa gtcttgataa tattatctaa 225300
tgtgctctgg agactctccc agcactccct caacatagggg agaaggaaaa caaattttcg 225360
tttgttttat ggaatgagtt tatagattcc tgttctctgt aactaatgac ttcaagtatt 225420
ctgttttatc taaaaagtac aacgaaggtc atgagaagcc tgattaggcc tgaactacag 225480
ctgcttgggc accatagtga aggttatgaa ataaaccagt gcaaggcact ttagagcaaa 225540
acctaggtaa cagacatctg gattgcttgg caatggtcat atgcggtcct gagtttgtcc 225600
```

```
tgcctctgta tccctgcttt cacgccactg taagcttact tcaagctagc ccaccccctt 225660
ttgttaagtg tgtatgaaag acaagtgctg tctttgttcc gggcccagtc gttggacgtt 225720
gagtctgctg ggtctgagtg cactcaataa taaagatatc ctcctgtata cacccgagg 225780 tctctctctg gtcctcctga tcccgcaaca gactgacgtc caggagcaat caggtcacac 225840
gaacaaattg aagatggtaa atgcaggga ttttttattg ctggttgaaa gtagctctca 225900
gcaggaaggg gaactgaaaa cgggatggag caggaagata atcttcccca ggagtcccgt 225960
catccccggc cagaatcttc tccaaagcta tgccatcaag ctgtccctct gaagtcaagc 226020
cacttctctc tgatgtccaa ctataatttc cgatgtccag ctgcttctcc cctttccaag 226080
ctatgcctgg agttttatg ggcacaggat gtggtgcagg gcaggccatg ggtggttttg 226140
gaaaaggcag cagtcgagtg ggaaaacagg aatgtaaatt ctcactttgg gccctggttg 226200 cttttggct tgagggtggg gcacttaccg ggaacccgct ctcttctgcc cagaatttcc 226260
ctgccttctg tccctatcgg ttttgtattt attttaggta tgcaagaggc acgtttgtgt 226320
ggaagttcaa aaacgtttaa ttatttaaaa tctccttta ttaatttaat gaatgtcttt 226380
tgagctcaga tgtaaacagg caagtacagc ttatagctgc agtgaatgct gagaatgaag 226440
tactcaaaca attccagctg aacggggcgg ggaacagctc ttctgagaga gtgctgcccc 226500
aagatccatc cacctgaata tttattgaga gagcttgttt aaactacagt tcagatgaac 226560
aaaagacatc caccaggtgg ctcttttgcgg ttgggtcatg aggcacatat gaccttgtaa 226620
aaaacactca aaccacattc ttaggaggct gtgttcagca ctccttatca cacatactac 226680
tccctgtcct gtttcaggg acaaggagtt ctagtctcat gcacaaacaa catgcacaca 226740
gtgcctcagt atttttccat gcctcgacct cacgtgtctt ctacattagc ttgaatatgt 226800
tgccatgcac cccccacagg aagtcattac acatgtttcc tgattttagg ggagcttcta 226860
ccctaacatg ggaattaaag agagatccta ctagttcttt caagtgtctt aggtaaccaa 226920
ttagatatat tctacacccc ttagtggcaa gtgctcatgt tgtcaaattt gcatttgttt 226980
tcaaatgaga ttaaaacaca acaacaacaa tgtttaaatg tttctactat tagaaaataa 227040
aatcaatgta ttctatcttg gatttttcct ttatttcttt atagagttct ggtttgcaac 227100
aaagttttat cagtagctta tttaccttcc caagagctcg ggcaggattt gatggtgaat 227160
gtacatttag tggtttccat atttaaaaaa aaaaaaaat gactctgaat aagctcccag 227220
gctctcagtt tcttctagtt ctttctgaaa tggtccacaa catgattgtt ttgaaattga 227280
aaaattaaat gcttttattt caaaccccac cgatctaaaa ccagtaggtg tacctttcat 227340
gagcacactt cattctgcag gtgaaaaatt ttcttccaac aattgtctat gatagtgatt 227400
tataagtcag caatttgctc taaagaatgt gtctctttct aagcatcaca agaagtaatt 227460
taaattatgc tgtttcttag taagcatgtt gattgaacct cacatatttc cactgattct 227520
acactaaaca cagactctct tttagttgta ctccatttga cttggtttat acagttcaca 227580
tagtcacttt tgtatgtcta aacttgcctg accattttac tagatggcat ggtgatatgg 227640
tttggctttg tcctcaccca aatgtcatct tgaactgtag ttcccataat ccccatgtgt 227700
catgggaggg agccagtggg aagtaattga atcctgtggt ggttaccctc atgatgttct 227760
catgatagtg agttctcatg agatcagagg attgtgtaag gggcttttcc tccttttgct 227820
cagcacttct ccttgctacc accatgtgat gaaggacata tttgcttccc cttccgccat 227880
gattgtaagt ttcctgagga ctccccagcc atgctgaact gtgagtcaaa cttttttcct 227940
```

```
ttatacatta cccactctcg ggtatgtctt taatagcagc atgataatgg aaattgctac   228000
tgagagtggg gtgctgctgt gaagataccc aaaaatgtgg aagtgacttt ggaactgggg   228060
aacaggcaga aattggaaca gtttgaaggg ctcagaagac agggagatgt gggaaagttt   228120
ggaactttct agagacttgt tgaatggcct tgaccaaaat gctgatagtg atatggacaa   228180
tgaagtccag gctgaggtgg tctcagattg atatgggtaa cttgttagga actagaataa   228240
aggtgactct tgctatgttt taccaaagag actggaggca ttttgcctgg cgttgttgtt   228300
ccatgatttt tttttttatg ttcaacagga cgatggcaca acctagctgc aaggcacaga   228360
ccaactccca gcattgccag ggcttagggt acattaccag gtcagctgct gaccagcagg   228420
ggctgctttt ctcttttgtg agtaactgag aattaaataa actaagtaac atgcctcaaa   228480
tcctgcagag ggttggagat aatactggag tctcaacata gactatatgg gaaagtctag   228540
cccattaatc tccaggcttt tttctaagaa accaaacgcc aatatttat ttgttgcaga    228600 aaagggacat cctgtggtca acacaatctt cagtgggagt taattttaat caggttcttt   228660
agaattcagg aaagctggaa aaaagaggag ttgtgtaact cacatactgg gaggcatctt   228720
ctgtggccag tcagcagata ccatctccat tggagagatg caggcatctt aaggatggga   228780
gaattccatt tatagcctag gacttttgtc catgggcctg gcttggatag ggatggccca   228840
tattaatgtc tttgactctt ggttttattg ttacattctg tatggctgat tcagatttgt   228900
ccacactgat atatttgttc tctgattctg atcattgtgg ccatcttttc ctagaacaaa   228960
gggcttaggt taattttgc ggagtaatga cattttctgt ggcagccaaa ctccgtagaa    229020
caatattgct cctacttctt gttttcttcc aatggtaatt gaacgtgcaa gccacattca   229080
ggagtagggt ctgaaattcc ccaagagcta gccagcgata atagtgcaaa tctaatacat   229140
gcccttgaaa caccaaggga taaactcatg tgcatttgtt cttttggggt ttgaagaacc   229200
agatgacatg caaagaaaa atattgacaa aagatatctc atcgtttact ttcaattatt     229260
gagtttgatt ttcatgcatt caaccttagt ttttttaaga ggtaagtgat tctagtttgt   229320
gagagccaga agcatgcaca aataaacctt attaacaaa ttaatctcat attttcttgg    229380
ttctgatgat tgcatactgc ttattttaaa aaggttgtga gcaagccaaa gttatcatac   229440
ttatttttaa agtgacagca tggctgagct ttcaaaatat gtttaaagat tctaagagaa   229500
acaggttaga aaacaagatg attgacagct ttttgggtta ttagatacag aaaattatac   229560
ttagatttat ttaggttgaa aattaatcct acagcattta aaccagctgg gagagcttgt   229620
gcatgcacaa gagtgttcaa gctgcaactt aaggccattg gcaacagta gaaagaaaaa     229680 aatggttatt tcttctcttt cagaaccaac tgtgactgat taaccacaaa agatcagtgg   229740
gggtattcag gcctaggtcg tcttggtggc aactgggggtt ttagtttgct ttcaggctca   229800
ttgctggaaa aggctgttca gaagcttcct ctacaacaag ggagatgaca gtgcgtgagt   229860
acaaagcaga gaggtgcagt gctttctaca gcaccgagtg ggcaaattgt gcagatttt    229920 cagtagaatc tacttaacac caatccatgc atttgcattt tattaaaatg aaactgtgat   229980
catttcaact gcacattgca gacatgccct ataaaatgtt tgaagtcctg ttttggacaa   230040
aagttttgaa aacatgcacc ccgtatcaat ttctctactt atattttgta tttaatttgt   230100
ctaaagaatg ccacattttc aaagcaagca ggccaagaga atgatctttt tttcctctttt  230160 tttttcccca gtgtttaaaa tgcaactgcc atgggctgt gccattttag ctgttggaaa    230220
aaataatcta ctatgccttg gttgtatgtc tgagtcatca gagcttctgg gaatgattct   230280
ttggcacatt ctaccaacaa tttaacatga cacaaaatca ttttcatatc ttgtgatagt   230340
```

```
gtcagccaag tgtttcatac acatggtgct aggtgctgaa aaaggtgtct gaataaaatt  230400
gttttcttaa aggaaccata ggggacatga taaaaagatg cacaattata tatctttttt  230460 ttttttttt ttgagaagga gtttccctct tgtcgcctag gttggagtgc aatggtgcaa  230520
tcttggctca ctgcaacctc tgcctcccag gttcaagtga ttctcctgcc tcagcctccc  230580
gagtagctgg gattacagga gcctgccacc acacccagct aattttgta ttttagtag  230640 agacgaggtt tcaccatgtt ggcctggctg gtcttgaact cctgacttca ggtgatccac  230700
ccgcctcggc ctcccaaagt gttgggatta caggtgtgag ccactgcgcc cggcctaaag  230760
atgcacaatt acatttcata aattgagaga gtttcctaaa caagagagag catacctgga  230820
aatatcagag aaaaatacaa agggcttaaa gatgttgtat taagcaaagt tagactaagg  230880
cagcttggat gtgcatctcc tccactttat gtttatacct aagtagagat taaaagcaga  230940
ggaatttcaa tttccacatg acttgtatat gagcaacaga tgggagttct aactactgac  231000
cacattggca catcacacaa tgttttcttt caggtttctc tacctatggc aaaaccagtg  231060
ctgtattaga gcctcgtgag ctgtgtgttg ttgattaatt gacttaacct ctctgggcct  231120 cattttctc acctttaaaa taaatgagtc ttatggtgtt ttgaggatca aaagagttac  231180
tgtacaaaca gtgctagtaa gagtccctgc cacatggaaa ggctattata tatatatata  231240
tatacgtgtg tatatatata tatatatgtg tatatatata tgtgtatata tatatacaca  231300
cacacacaca cacacatgta attttatata ttaaatgtgt ataatttata aattttgta  231360 ttataaatgt aaatctgtga tatatattaa aactatgaaa tacagatcat gtaatatata  231420
ctacctattg tttttttttt aattttgtaac catattttga aaattttatt ttgcttatag  231480
gtcttgaaag tcattcccca atcaaccttt attaaaatcc ctttgattca ttggagaata  231540
tcaatacata tgaggtatta atatatataa catatgtaac tcttctgagt ttataaatgt  231600
atgtataaaa cataaaaatt actaactctt catatatatg tttgtatcta tataatttt  231660 atatatatag atatatatac atatttgtat tacatatgaa taatcatcac agtgtgtctg  231720
catttgttaa tctaacctcc tccaacccca cccccaaaaa agcagaaact aaaatagag  231780 gaattttaag ttccacatga tttatatagg agcaacaaat ggaactacta acttccgacc  231840
gcattagcta atcatacaat ttttttcttt cgtgcttttg ttgtaaatat gatttttatt  231900
taagagggta ttattgatta tctacgcaag aattagccat gttctccata cttctacttc  231960
agttttttaa aaaggatga ggatagaccg ggcataagtg gctcatgcct gtaatcccag  232020
cactttggga ggccgaggcc ggcggatcac ttgagggaag gagtacaagt ggcctggcca  232080
acatggtgaa accccatctc tactaaaagt acaaaagtta gctgggcatg gtggcgcatc  232140
cctgtaatcc cagctacttg ggaggctgag gcaggagaat ctcctgaacc cgggaggcag  232200
aggttgcagt gagccaagat cacgccactg tactccagcc tgggtgacag agcaagactc  232260
tgtctcaaaa aaaaaaaaa aggtgaaaag ggtgaggatt gttatttctg tgggcaggcc  232320
cacacagcat cagattcctc agaaactgca ccggtaaatg ggaaagtctt tgagtccctc  232380
tgacagagct tcaaggggct ggctgttcat tatcccacag cctccttgc tctgtgtaag  232440 tggaggctct gtgcctctgt tatcttgcag tccctaggtg accccggcag ggagaaaaat  232500
cagtggaatc aaactcggta gcacagaaaa acgccccaaa ggcaaggatg agaggaaagt  232560
tgtgatccca catatcaaag tcggactctt atctagatgg gcacacctga gccacaggct  232620
ggcaggctga gattctgcaa aggctctgga ccccagataa gcttgactga ttgcattgtg  232680
```

```
atctcttctt ttcatcaggg gaggcgctgc tttgaatgac taagctggat ctgactttcc    232740
agggaatcct ttcagggact gtgaccatcc agctatcttt ggatggcttt gatgccctaa    232800
ttattttca cttggttgag gatactttta ggtatctgtt catgtgtcat cttgtacaga    232860
aatgtgtgtt ctgggcttat aaaaaaagtt taattgtaag acaaagggct ctaggtttca    232920
tatttattca cagtctgatg aatggcactt atggatacgt acgtgtatac agtaagtgct    232980
cactgaattt ctcttgagtg ataaactggg atacaaaatg tcagaaaaga aagagtgagg    233040
atgggcactg gatccagatg tcagtgaact ctgagggtct cttgctggtt aaaagaacag    233100
ggtacttta ttttcattct aaaccctgcc tgacccttgc ccttatatca gtgaatcacc     233160
atctcgatgg cccctcaaac atggcatctt tgaagtagag cctcattgag aaggactcct    233220
tagaagtctg tcatggctac taaaattcat atctgtgctt tgtgcctgag cactagtaca    233280
tgtgtcagct gtttcttaag cctacattga accattaggt aaagcccagt gtgctcccag    233340
ttcctaaaat ctggtcaagt cttgatgttg gtcaacatct tgcctggccc cagtcagatg    233400
tctccagcta tctgtaacag gactcagtgt cttgtttaca aaatgcatta gtcatatggc    233460
ttcgttgctg gctttgctgt ataggtcagg aataagtcag aaataaccaa aatgctccaa    233520
atcaagttct agctgttttg ataccaacat cttccatcaa cttcgcttct ccctgactca    233580
tctgtctgtc tgttcctgtg ctcttcgcac acagaggcaa ttttgtgtat aaagctcccc    233640
aagggaagaa gaggacagtg ccttcatggg aaactccttt ctcttaaata ggatttgcat    233700
acttaaccag agcatttgct tcagttaacc aagtgagagg tggagaaatt cttgcaaaac    233760
tatagctaca ttgagaggga ttattaaaag tattgactca ttcattagag gagctgttac    233820
aaagattgta gcaaccaaag caaaataaaa atattgcca aaagtattct caaacgtatt      233880
ttaaaatgtc caaatattg ggcaagacta acatcaaaga aggtatatgt tttgacattg      233940
atttactaac tacttatcag tgtaagtaaa tacaccttca agcacttatt taggattaag    234000
gtagtcaagt tatatgagtt gtatgagtat gtgcaggcca caagggttgc aaaacatagt    234060
gaattcaata tccctctgcc atattgaata tccttctgcc gaacttctgc atcacagttg    234120
tggcctgcaa acaggtaaca gttgtctgcc aatcccttag ggatcactgc attctatagg    234180
gcttgaccag gaagtaagag gctcttccca ataagcgata tcgttatggt ccttgtggtt    234240
ctgctaagaa tctcagagaa gaaatgaaag atacatgaaa ttgtttgcat gctactagct    234300
ctagtgggta ggttggtagc gtagttcttc atggcaaaag acagaatata tccaaaattt    234360
tcaccattt gccctggtt tgagggatgc atattccttt agaccattat gttgaaaaga     234420
aagttaaaaa taacataaga agagacctcc taagttgttt aatccaagcc ctcaatctta    234480
gcaagtgcct ggtgtaaaat gtctcattag gtaattaccc atctcctgtc tacccactaa    234540
gaggttctag taaagtacat actggctgga ttcaataaag cacaaatagg cagcaaatgc    234600
ttcttacatc tcaatctaat cggtagcctt ctttatcctc acccttggct gactaacgtg    234660
cataaagcat aggaattctg gccactcaag gatcttaacc atccagttca gtctgttgca    234720
atttctcctc cattacaaat ttttttcact ttcctttcct gggaaagcca cagacaggac    234780
aaccattcag tgagaaagga gtgtgaagct gacgtctttc ctcactaaga ggagagggc     234840
catgagagga aaaggcaact tcttgcgtgg ctggtggtag agttaaagtc tgatgctact    234900
gtcttctggg agcagcagct gtacacagtt gaactttact ttggaggcat atatgatttc    234960
cagggttct gtggcaagtt ccacccactg cagttcattt gacttgggtt gaatctcttt     235020
cctccctcca tcacttcagc tgaacctctt ctgtgatcct cacctgttct ctagaggtga    235080
```

```
gaccagggca cagtcccttt ctagatgacc aaagagcact tctttctatg tggttcacat   235140
ttggctccat caccatcgta gctgacaggg ccaaccctcc ggcatcttca tccttcacca   235200
ctgtctttgc tgtgccccat aaggcctgaa caaggctgat gggccaagta tggtgtggcc   235260
agccccacag tctgttacta ggccttgctt tggtagacac acttcttgat ttagaaccat   235320
ggctctcagt catgggcagt tgtgccctgc ttggcaatgt aaggagacat tccagttgt    235380
cagagtgagt ttgaagggtg ttaatgcact tagttggtgg agaccacggt tactgttcaa   235440
catcctacaa ttcgtaggac actcatccat aacaatgatc tgattccaaa tgtcattgat   235500
gctgacatta ataaaccctg ctctaagtta atgttttttt cttactcata tttaaaatgc   235560
ttcctctagc taaaccatta gccccagtg aggtataagt tttcctctcc aagggacatt    235620
tgactatgca tgtacatact tcgggttgtt acagctggag attggtgatg cttctggcat   235680
ctaatggata taagtccaag atgttgctca atatactgca atgcagagga cagcccacga   235740
gaacaaggaa ttatcccatt cataatgcca ctagtattaa ggttgaaaaa ccttggttta   235800
gaatatgggg atacttattg gtgctcccta aggtgctatc tgaaagcagc tttgaagaca   235860
agcagaggct ttgaagacat actcacaggg tatgatatag tttggatatt tgtcttctcc   235920
aaatctcacg ttgaaaactg atccccagtg ttggaggtgt gacttggtgg gaggcatttg   235980
ggtcattggc cggatccctc atgaatgact tggtgcagtc ttccaggtga tgcctgagtt   236040
cttgctctat tatttctcag gagatcaggt tgttaaaaag agcctggcac cttcctctcc   236100
tctctctctt gcttcctctc tcaccatatg atctgcgcac acagcagctc cccttcctct   236160
tccaccataa gtggaagctc cctgaggcct caccagaagc agatgctggt accatgcttc   236220
ttgtacaccc cgaagaactg tgagccaaat aaacctcttt tcttttcttt tttatttttc   236280
taattagaga caaggtcttg ctctgttaga ctggagtaca gtggtgcaat catagctcac   236340
tgcagcctca aactcctagg ctcaagccac cctcccacct caacctcccg agtagctagg   236400
actacaggtg catgcctcca tgcccagtta attaaaaaaa ttgtagggac agtcttgctg   236460
agtttcccag gctggtctca aactcctgac ctcaagcggt cctcctgctt cagcctccta   236520
aagtgctggg attacagatg tgagccacca tgcctggacc gtcttttctt tataaattgc   236580
tcagcttcag gtattccgtt atagcaatgc atatggagta agacattgta caagtcccac   236640
tttgggcacg tctagatctg tctgtgatcc tagacaagtt atgtaatctc tcttgtgtc    236700
taaacctgtt gtttgtttct gtctttattc ctcattaggt ccaactctaa agatagtaaa   236760
attataggta taaatggagt taagagggggt gccttaccaa gagtaaaccc tccaggagtg   236820
ttattctgtc agtatgactt ggttttagc tttgaaactt ttagcatgaa actaacatgg    236880
caggaaaagg cctaaattag aattcttcac acacaaaact ccttctatca ggaggcagcc   236940
catctgttgt caaataatcc tactcgtaga aatgtattaa attttcttt tccttcccctt   237000
ttccccttc attaaatgga attagattgt gacactatga ggaaattaaa gtgaaggtaa    237060
aataaaacaa acaggaagaa gtctgtcttc agattggata tgcaattatc ctgtctttac   237120
tgctgatttc aattataact cattggtgtt accagcccac gatagatgtc ccctgcctat   237180
gtggtgttta aatcaagtgt tggcatcatt cacacttgtt tactgttatt agcactgatg   237240
gatgtaatct tcatgtcttc ctctgaacac tgcatgctga gaaagggggcc ttatttcctc   237300
gtggattttc taggcaagag aatgtcaggc cctcacctgt cctatttcca tctcactcag   237360
cagaaaacac actggctcat ggaaactgca agcatcgttg tcagctgcac ctgcaggcac   237420
```

```
catggggttg caagtcagca tccccttcca gaaatgagga tggaattaga ggtggaaaga    237480
aaattctcca cagtcctctc acttctctgg gcttagacag ggaggtttct gctatgtttt    237540
cattgattat gctgtggggg aagggagag gaggaatccc ctaagaagaa caatgtctca    237600
ttggatattg ttcctttggg ggaaaaaaaa aaggaaagg aaatattttc attttttctt    237660
acttttctta ccctagaatc tcaatgccac cttcaaacat ttgaatctca cagggagaag    237720
gcggccacat atttcacccc caaatgctag gccatgtctt ctcatgtcag aaatgcccta    237780
ttgtgcgtgt gtccttgttg caagccatct tagacttgtt gtttcaggga tagggaaacc    237840
attctgcaat ccaaataagg ttgcatttct tgcaattcaa aataaaaggt gtgcatgcac    237900
acacgcatgt gctggtatta ttgtacagct tgcgtggtgc aaggctgaag gctaagggac    237960
taatggaggc tgaaatttag ccctagatac actctgcaag ctgagtacct gtggggccgt    238020
attacctggc tagaggtgtg cctatttctc atgcatccag tatcaggtac ttttctgact    238080
tagagggtcc ctcaaccctc tcctccttcc cctccaccta tcgtacttag catactgtat    238140 atttgcccctt agtctgtttc atccaacttg atcacttggt agcctgtctt tatccccact    238200
gtctaaatca gtatttggaa tgtagtaggg acacaaaaaa aattagttga ataaaggaat    238260
aaatgggtga aatagtgaat gcatgaaaaa ggaaaaaatg aatattttgg ctgctgtgta    238320
ttcttgtatt gttgttatat ataattcttc tgcctgtctt tcttcataca tacctcatta    238380
ttagtataaa ctaccagcat tcgtgatatg caggtctttg cttttgcaga gagccatggg    238440
tttctctaaa aggcatcttg cagcctcccg cccagggtgt ctctgtgcag ctaacctggt    238500
tgctaatctc tgcaagctcg tactttttct gcagcacgtg attctgttct catttactct    238560
tgtaatcctt ctgtttcctt ctgaccagct tgagcttctg tatctagtgc cttgacgttc    238620 tcttctttc ttggtctttt taacattatt atgtcagtta aatgtttttt cagttgcttt    238680
tagtattcag aaaattcttg aagccttctt attgcccact ggtattttgt cttcgccgct    238740
tgttgtttgg gtggatttag atatagcaga gagagagaga gagagagaga gagagagaga    238800
gagaggaaaa tagagacaga gatatgtaat ccccccaacc aaccccgtt atctgtgatt    238860 tccattaccc atggttaggt tagtacagta cagtgatatt ttgagagaga gaaagagaca    238920
tcacattcac gtaacgtttt attagagtat atattgttac agttgtattt tattttaatt    238980
gttgttaatc tcttactgtg cctaatttat aaaataaacg ttatcatggg catgcaggta    239040
taggaaaaaa cattgcatat atagagtttg gtactgtcca cagcttgagg catccaatgg    239100
gggtcttgga aagcatccct cactgcccct ggtaaggagg agctactcca gttttgagag    239160
gagaaactaa acagatatga aaacataca agttgtaacc taataggaaa attttaaag    239220 tgttattaaa aaccatatct tatatatctc atatattaaa ggacttcaca atggacttta    239280
ggaaattaag atggaagttg caatagcaaa agtttagcaa tgcgtattct tacatatgaa    239340
aatcaaaatt aacctagcag tgttctgagc aacttcactt taagaagtaa aactagtgaa    239400
atgataaagg tatatgggtg ctgactgtta cgtaattagg ctgatataat ttagcaagga    239460
tatcagaaat catatacccca aaatgagctt tattatattc aaattagtca cttcagaggc    239520
agtacactaa ttcaataag gtaagactgc tggaaacttc ttatttctc ctcactttaa    239580 aacgtttcag agcccatagt aatttatttt taatatcttg ctgaggcaag tcttaatcct    239640
taaggaggca tttatatttg gatacagcca gggttctgtt gagtaaggtc agtgaccaca    239700
ttgtataaca caatttttaat tcaaagacaa ggaacagcta taaataaagg tgagcttgtt    239760
tcaactaact cttttttatt tttttttta tttttttat tttttttatt tttttgagac    239820
```

```
agagtctcgc tctgtcgccc aagctggagt gcagtggcat gatcacggct cactataacc   239880
tccacctcac aggttcaagc gattctcctg cctcaacctc ccaagtagcc agaaatacag   239940
gcacgtgcca ccacgcccag ctgattttg tattttttt agtagggacg gagtttcacc    240000
atgttagcca ggctggtctc gaactcttgg cttcaagtgt tctgcccgcc ttggcctccc   240060
aaagtgctgg gattacaggc gggagccaat gcgcccagcc tcaactaaac cttaaggcac   240120
attgaaaaga aaatcaaaat gcattgagct aaatgccagg catatgcctt ccaaatgga    240180
cttgccatga aggatgtcat tcctgtgcag ccaggtgttg tcttctatgt attttagaa    240240
tgcccatcat atagtctcac cttttaaagt ctgtttagtg gaatgttttc taactttccc   240300
atgtacctcc catgtcattt tttgccagtt ctgccttccc taataaccaa tgaaggtact   240360
tgcttcatgt taaattctag gtaatctggt ttctactgaa ttagaacatt cccacccgcc   240420
aatgtctttg aataattaaa ggttttataa tgtggtttcc atacaactaa ctgaatattt   240480
catgtggcta gataaatagg taaattgcag tacagtagca attggtgtag acacttagag   240540
ggtcctaata aattattgca cacgccaatg tgcaatcaga aagaataact gtagtgttaa   240600
gcctcagaca atgctataga cctgaggatg ggcctgtgat ggacggatca atggctcagt   240660
tcctattgga gtttcacatc taggaataag tgaattcacg actattcatc agctgctgct   240720
actgtacgga agtgtgtcca ttgagaagtt gcagaagggg ctgggagatt ggataaggct   240780
tttgcagtac ccctcctttt taaaaaagca gacagggtgt aactctattg caggctggag   240840
tgcagcgttg tgaccatggc tcaccgcagc ctccaactcc tgggctcaag tgatcctcct   240900
gcctcagcct cctgagtagc taggactaca actaggcacc accataccaa gctaattttt   240960
ttaaataaat tcactgagac agagtcttac tatgttgccc aggtgggtct caaactcctg   241020
gcctgaagca gtcctcccat ctcagcctcc cagagtgctg ggagaacagg cgtgagccac   241080
ggtgcccagc ctcaatacct tttaaattaa caggaagtgg aaaacagaaa ttctgcagca   241140
tgttttctc attagcatga atcactctct ggtgatgtgt tcatggtttc taatggtatt    241200
ttcaagatgg acaatataaa gacaaccatt agaaaccaca aataataggg ccatatgaaa   241260
caatataata gatgcatgag gttaactggt caacatttat gctgaactta gatttacact   241320
gattaaaaaa aataatccat ttgaagtgta acacacagaa accaaagttc tgtgtgttct   241380
gttatcttat attatcaatg ctccatgcaa tgtgaaagct taaggcaagt gtttctataa   241440
ccaacaccca tgtgaagaaa tatagttttc atcttcaaag cagtgcatgc tcttttccca   241500
ttctatctcc ttatcctcct ccgtgataac cattattccc ttttactact catttccatg   241560
cttttcttta tattttccca atgataaagg catccctgaa tcacataatt aaattttgct   241620
tgttggaga ctctaaatga atgcaacttt ctattacttt ctggtgtgtt tttttcatgc    241680
ataatactgt tttataaatt tcatatgtgt tgctgtgtat acatccattc cactcatttt   241740
aattgttgta tagtgttcta aagtctgaac ataccacagt ccctatgtcc attttattcc   241800
taatagatat ggttattatt ttgagtttga ggttattata aattcgtgtt attaacattc   241860
tttttcaggc accctccttt ctcacaagca ttggttttct gagacatata ccattatgga   241920
attgctggtt caaatcttca actgtatagt ttatataagg atgaactgtt ttccagtaca   241980
gaaatgcctg ttttcaccag gagtgtgcaa tcttcaacat gtggcagtat aaaagttcta   242040
ttttattttt ctgatctagc gtgtgtacat ggaaacccat tgtgtgttca ctgtgtttac   242100
tctgaggttg agacatttcc atatatctct tggccattca tatgtcctgt ttggtgaagc   242160
```

```
gtctgttttt gatctgtttt tctactgggt tgtgtgtctt attgctgtat ttcgattaga 242220
gtgcttcact gattatatat gttgcaaata tcttctgatt ttccttccat gttttaatg 242280 atttatttaa ataagctaaa gttcttaatg ttagtttata gactttacaa tattttcttt 242340
cagattagtg ctttggaatt tttgtttagg atatcttttc ctaccaagag atatgaagat 242400
ttccttttat tttatctgaa aaaagcttaa tattttatct ttcatattga aaccacacag 242460
ggaatatatt tattgcattc tgtaagaggt ctagtttatt tttccttaga atatcacaat 242520
acaatttatt ttaaacagtt tgatccatgt cactaaagtt caagtgatct ctttgtctac 242580
ctctgtgcca atcatcacat ttttatcttc atgatttat aataatccgc aatttatatt 242640
tttatacttt gtttatttct tgccaatatg cattgcatcc ctgagaaaag tgtttatttt 242700
gcgatggttg gtgcaatgtg ctatatgtct aatatctcaa actgttgaag tatgttgttc 242760
acatactcta tatagttttc caggtggtag tttacatatt ctttcagtaa ctaaaatagg 242820
tctattaaat tttcccacga tgtttatgga tgttttaaaa tcttttcgta tattttccca 242880
aaatttagtt tcttgcattt tatatgctta tgaatttag tggatacagt ctagaatttt 242940
tattgcattg tggcaaatta aggttcttct cattataaag tgatcctctg taagtctgtg 243000
gtgcttcatg ccttaatgtc tgtttagttt gacgttaaca ttacctttgt tttgttagta 243060
atccaattgt gtatagttcc catgtgttta cttcaggcct ttctgttgac tcaggttttg 243120
agtcttttct acatagcgtc tatttgggtc tcataatctt tgattttcaa ccgcagatcc 243180
actgatattt acttttattt ttgatatatt tgtgtttaag tcttctatcc taaattgtgc 243240
tactaatatc ccacttctac atcttgcttg aattgctttt taaaaaatca ttcaggccag 243300
gcacagtggc tcacacctgt aatcctagca ctttgggaga ccaaggcagg aggatcactt 243360
tagaatcctc caggagttca agaccagcct gaggaacata gcaagacctc atctctatga 243420
aacataaaaa aaaataaata aataaaaaaa ataaattagc caggtgtggt ggtgtgcacc 243480
tgtagtccta ggtactccag agataagagt tgacaggaga gtctgatccc atgagttcaa 243540
ggctgcagtg acctatgatg gcaccactgc actgcaacct ggatgacaga acaagatcct 243600
gtctcagaaa ataagaaat aaaagacaaa taacattact ccatttcctt cactcccact 243660
tctccctcta cactagatgt taaaagactg tactagtttt agtaaataac cctagaaatt 243720
acaacacaga tccttaatat aatcactaat tttaattaat acattttcca cttctctgaa 243780
aatacccagt agtcagtgta ttttagctcc atgtttatga cctaacctac ttgctgttag 243840
tacctttcaa tgttttgtgt tttttaggaa tcttttcag atatgattgc ttatcttatt 243900
atttcaatat taattttgat tttctgatga ttacactatt ttatttatgt ttcattactt 243960
tttgtacctc ctacttttat ctgtgattat tgtcttaaaa gaatctatcg gtgatctaaa 244020
atatattttc agagctaaca agctgttgga aactctgttt gcatggctaa atgtgtcttt 244080 atgcatcct cttcttgaac aatattctca ttgaatttta atttgcaatt acttcttcca 244140
gccatctgag aaatcattct cctattctct ggattccatt attggtatgg agaatttagc 244200
tgtcagttta agtgttgctc ctttaaaaat aatatatttt ctgcagatag tttgtctata 244260
tccccctgat acctttaaga tagtttttct ttgagtttct gccgtttcac tgtgatacca 244320
ttaggggttt attaatctga ttggaattcc ttgatgacct tgaaatttgc aatcgtggtt 244380
tcttccattc tgaaaatagt cattacctct tcaaattttg gtgctgtttc tcttgttttc 244440
actctgtttg cacataattt agattttctc cctctggctc cttttttagt ctttttttt 244500 ttgtattttg tattaaattt tactttcaag cttcattctg gattactttt tctcaagacc 244560
```

```
tataatctat ttcattaatt ctcttttcta ctgtatctaa tgcatggtta aaccaatgca    244620
tcaaatcttt atgtttgata tatattttca ttacatttca aggattaatt ttagtttctt    244680
cttatagttt ccacattttc gaagttctca attttatatt ttctggaatg cattcttcct    244740
agttatttta aagtctgcat tttgtatttc tattttttc aatcacccctt ttgtttcttt    244800 ctctttttg cttttggtt tcattgacta atatcttcat ggtctaagta ttataattat    244860
gcatatatta gatattctca tattgttttc cttatttcta actctctatt ttatatttt    244920 tgtatatgac agctccctgt gttgcccagg ctggagaggt tgtgctctgt gcccagtggc    244980
acaatcatag ctcactgtag cttcgatctc ttgggctcat gtgattctcc tgcctcagcc    245040
tcctgagtag ctgggactac agtcacatgc caccatgcct agctactatt ttatacttta    245100
aaattttttt agagactagg tcttgctttg ttgcccaggc tgttctctaa ttcctggcct    245160
caagcaatcc ttctaactca gtcttttgaa tagttgggat tacaggtgtg gccactgca    245220 cccggtttcc cagcttttt cagatttcca cgatactctc tggatcgttt cttctcacct    245280
cttctcaagt ttgtccattt ttctcttcag ctttgtttaa tctgcccctta ggtggaccca    245340 ttcattttct catttttgttt attctctga tctagaagtt tgatttgatt tttatttttt    245400 cattttttaat actttcttat tccctgcaga tgttttccaa cttttttgttt tcaagctttt    245460 tgaacattct tcaaaaaatt ggttatcatg tatatatttt catggcatct taattccttt    245520
gggatttctg ctggctcttg ttggtgactt cttgtttctt tcttcatggg cttggtaatc    245580
attgtgaatt ggccattgta tttgcaaatg gattagtggc atctttctcc aaagcagata    245640
acccatgggt agcgaaattc taggttcttt catccatggg gccatgctct tccctgaatt    245700
gttcatagat gttatgaagg tagactgcaa gcacttgcaa gactgaattt agttttgttt    245760
catgtttgcc ttgagggtga aacccatgaa ggtaggaaaa tgttaaaggc aagtatatta    245820
gattgggacc ttcaggcgtg actagggtct gagagttgcc ccattacatg gtgatgctgc    245880
aagaactccc acagtttctt ccagattgga acagtgcact agggcaaagg ctgctttgtg    245940
tgctgggcat ctagctggat catcatttgg tcgtcagtgt gttttttgttt gtttctttgt    246000 tttttgtttg tttgtattgt gttttgagac agggtcttac tgtgtcatcc aggctggagt    246060
gcagtggcac gaacagggtt cactgcagcc tcgaactcct gggctgaaga cttcctccca    246120 cctcacccctc cccagtagct gggaccacgg gtgtgtgcca ctacgcctgg ccacttttta    246180
aaaaattttt tgtagagaca aggtttcacc atgttgccca ggctgtgata atcagttttg    246240
aagctgtaat cttaaatatg attttagcac taaaatgttt ttaagagact taaaaaaatc    246300
acacatatta caatccatttt tcaataagaa ggttggtttg aataatctac tctgttactg    246360
ctagatgtag gcttctgatt tattctaata tattacagaa atgagtaggt ggaacatgag    246420
tttataaaga taatgcaaat attttattag cactgtattc tcttaagagc agttcagagt    246480
tcaaagaatt gtgactttat ttcacaggca ttaaaataaa ttaaatcagc aatctcattc    246540
ctaacaactc aaacttcaaa gaaatttcag acagttaatc atcacctgac accacagcct    246600
atgcaacttg ggtttaatta ggatttatgt tactggtagc attgtggttg aaagatatt    246660 ttcattaaca tttctctctg aagcactgag tcatactctt gttattcgc aagtttcttt    246720 acactttca atcaatattt gagtgttcct tgggaaatgt atgtttggct attttggtgt    246780
ttttgagagt gtttgatctt tgaaaatgca tgattaaaag ccattttaga aataaacatg    246840
agtgttttaa atacaaatta ctaaagccac tgttttgttt caaatttagg gatttaattt    246900
```

```
ttttaatgaa aatgctcctg tttatatatg catgaggtta tgtaaggtca tcaacttaaa   246960
gattgatgat ggatttagtg ccagctgttg attagtatgt ctgcaatcaa tctacaacat   247020
agcaataacg ctagctacct tggagagtta ctgggagaaa taaataagac acaatgtatg   247080
taattggcct agcaaacttc tttgtatact ataattattc agtaaataat acccttgtga   247140
ttatttatct atcaatcagt cttagagcag tgaatttacc tttaaaatct agacacatta   247200
ggaaagaata atggtagatt ttaagacaaa attaaaattt cttggtgtac tcaaaaatat   247260
atattttctg ttaatgcaaa ttaggctttt atatttatta tttttaatat ttgactctgg   247320
aatgttttca aaatttagtt gagtagatct taatgcaagt ctacttttaa aaaatctcat   247380
tatctagtag gctttactag taattaattt gaatttggta gacatgaaac acaccaattt   247440
cttgtacaca atcataaatc ctgtatacta tgtatactct gtatgcctgt atcttggtga   247500
agtgggaatt aaactttatc aaatttccat tgaaaaactg aagagcaaac taagatgtaa   247560
tcagaatgtt aataaatatt gtagaaatgg aaaagtttca gaatgtttag atttctcaag   247620
gaaatctcaa agcatgacac ttttcattgg tctgtcatgg ataattaggt cttttgctat   247680
ttttattttat ttatttccaa tccgtcacaa acgtactttg gttgatgcat atatcaacta   247740
tagagtagta aatctgacaa agtctatgca ctgaaaacta tactctgtca ctgagggaca   247800
ctgatgaagg cttaagcaac tgggagacag actgtgttca caaacacaac accctcctga   247860
gaagatacaa tattgttaag atattttattt tgtacaaatt aatctacaga ctctttgcaa   247920
tcccaaataa aataacagta gacttttaga aaatacataa attaacaaga taaatttaaa   247980
atttaatga aaatacaaaa gatctacaat aaccaaaaca tttttgtagc agtagaacat   248040
acttggaggg ctcctgctac ctgagctcaa gacttagtat agagctatat taattgaaac   248100
agcgtattat tgcataaaag atgtaaaacc tgatcaatat catagactag agacaccaca   248160
tagaactgta catatatgga caatgaattt tccaaggaga ttcaaaggta attctatgca   248220
ggaatgattt ttttttcaag aaatggtgtt ggaaacatta agtatccata tacaaaagaa   248280
aagaaaaagt aaacaaaaag ctttgatcta taactcacaa tttgtacaaa aaacaactga   248340
aaagtgagtc aaatacctag atgtaaagct taaaattgta aaacttccag agaaaaaaaa   248400
aaaaaaagaa aaattttgtg actttagatt ttggcaaata tttcttactt aaaacaagaa   248460
gcttgatttt taaaggaacc aattaataca ttggactaca tcaaaactta aaaaaatgct   248520
tatgctacat gaaagacatt gctaagggaa tgtaaagaga attcacaaac tgggaggtaa   248580
gataggcaaa ttaaatatcg gatgaaggta ttgtaccagt ataaatgtat gcatacatac   248640
atatatatga tgcagtttcc tataaatata tagtatatat ggtattagac atatatgtat   248700
agacacgtac tggtacaatt atatactata tatacaatat tcatatatag tatatatgat   248760
acagtattgt atactatata taaaatatat catatatta ccatacagta tactacacat   248820
atgtatatat atgatatact gagtatcact attactaaaa attacagaat gtgaactatg   248880
aaaatgtaaa agcctattta aataaaataa atatttaaaa tactgtgttt tttatatata   248940
tagcacatgt agtatactaa attgtataca gtatagtata tatagtatac tgtatcatat   249000
atattgtcaa tatagtatat aatttacccc tgtgtgtgta tagatgtgtg tatatgtgtg   249060
tatatataca catatatatg tatgtgtgta tatatacaca tatatatgta tgtgtgtata   249120
tatacacata tatatgtatg tgtgtatata tacacacata tatatattct aaaaggagaa   249180
ttaaaaagaa accaccccat aacaattgga cagaaaattg aacaggcagt tcacctagga   249240
aaacatacat atgaccaata gcccaatgaa aatgtgctca gcatcattag tcattggata   249300
```

```
aatgcacaaa tgaaaccaca gtgaaatacc actacacatc tgagaatggc tgaagccaca  249360
agactcgcta tgccagggct tggtgaggat ttggaggagc tagagtccac cccaagctgc  249420
tggtggggaa gtgatatgaa accaggactt ttgagaagag tttggcaatt tttttgttgt  249480
taaacctaca agtaccatgt ggttcagcca tttaactcct aggtatttac acaagaaaaa  249540
gaggagcata tgtccatacc aagaccaaga acctgaatgt attcataggc tggaatgctt  249600
ctgagcagta aaaatgaatg aactgttggt gcatgctaca acctgcatga atattaaaat  249660
gattatgcca agcctaagag gccaagcaat gaagagaccg taattctgtt acttcgcttt  249720
taatattttg gaagctgtaa ttcataatgc ctgtctgtaa gcagataact gtttgcctga  249780
gatgaggagg aggagcaaga gatatagatt ataaagggat atgggtaaac tttggggtgt  249840
gatatatata tatgtacatg tatatatatg tgtgtgtgta tatgtgtata aaatacacat  249900
atatgtatat tttaaacaga gtctcactct atcacccagg gtgaagtgca gtggcacaac  249960
ctcggctcac tacaacctcc acctcctggg ttcaagcagt tctcctgcct cagcctcccc  250020
agtagctggg actacaggtg catgccacca cgccctgcta tgtgtgattg atatttctgt  250080
caccttgact gtggtgatgg cttcataact gtatacataa gtcaacattt attatactgt  250140
atactttatg tacagtttat acttttacaa ctataacttc agaaacccac taccctattt  250200 taaaaagtt aataattact ctcagccact gtgagacctc actgtttcct tatgctcatt  250260 tttccctta acaacaatgg ggaactagta ttttatcaga taaaaataat gtttgatagg  250320
attttgtgca aagtctgttt tgcctactaa ttctgcctta tggcatctca gacatgtaaa  250380
ttagacaaga gccttcagta tgtctgatct gttgtcacgt tattttccac tagtttgtgt  250440
gatttagatt atttttaaag agctgataaa ggaaaggaaa ggaagagaga gatgaagaa  250500 agaaaagaga gaagaaagag aaagaaagag aaggaaggga agaaagaaa gaaagaaga  250560 aagaagaaa gaaagaaaga aagaagaaa gaaagaaaga aagaaagaaa aaaagagacg  250620
cctgtctttt taattccagt tggaagcagc tttagttata aaatttccac tctctagaat  250680
attcttgggg aaaaaatgaa gtgtcaatta aattgatttt tttaacttgc atcctatgtc  250740
tctgaacatg attcttttc aatcaggcat gtagttattg aggacccatt tatgagctgt  250800
gcatacatcc catccaattc catccaattc cgtccaatcc tgtccacaga catgttgaaa  250860
gcatgagctt cctgcaagag caatgcacca gccgttttcc tagagatggg tcttcaaaga  250920
gagggttctt tctcggagca cctgctcagg gaacaagact gactttaaac cagtgttagc  250980
aatatgcatg gtacactgaa ccatctgctg gaggacctcc ttgtgtccaa cacagtcctt  251040
ctgttgaatg tcatggaaaa gactgagggt tgaagcaaat cattttatgc agtgaggaga  251100
agaccgtgct catctttcag tttttgagcc acatctacct aatttatagt caggtttggt  251160
agcctcagca ctactgatat ttgctgcata aatctatgct ttgttggggt tgtcctgtgc  251220 atttaaggt attgaatagc atccccagtt cacacccacc agataccagt atataaatat  251280 ataccgttt tgccaattaa aatgaataag aaaaaaatca ttgttacaga ttaataataa  251340
taataataat taataataag tggctggaca cagtggctca tgcctgtaat cctggcattt  251400
gggaaggcca aggcaggagg atcccatgag cctgggaatt tgaggccagt ctgggtaaca  251460
tagtgagacc ccatctctaa aaaaaaatg aaaaattagc caggcatggt gatatgtgcc  251520
tgtagtccaa gctactcagg agactgaggc aataggatca cttgagccca ggtgtttgag  251580
gctccagtga gctagctatt gatggttcca ctgcactcca gcctaggcga cagagcaaga  251640
```

```
cctggtctct aaaaaataaa aataagtaaa taagctaaat gctcttgaac tgaaaaaaag 251700
aatgtattct atgagagata cctgataatc acctactttg accatgtttt tatccttcaa 251760
ggatttcaaa ctgttacaac aaacttctaa acgtgtatct ctttagttca gcttccttac 251820
atgaatttaa tgctccagta tgtgagacca attattgatt taaaaaaggg tagatctgtt 251880
ttaaaattcc tttaccaata ttcctcatgc tcatgagaaa gatatgaggc agtgctgttg 251940
actgcatttg tatttagtta ataccacgag caagtgggaa aaattcagaa gtgacactga 252000
gttggtcatc tctcaattat catcatgaga agtacgcaca atgtgaacat tctgccatag 252060
ggcttgtctc tgtaaactgc tggtcaaggg gcatggacag attctactat ttttaaaaac 252120
atctttctga acagataacg gaggcttaat tgtagtgtaa acacactgat gtacaaatct 252180
cgaaaaacat aaaataaagt gtgttgagat tggaggtgct ctgttcaact ttcgagggat 252240
agaaaatatg cctatcagct gtaaaagcgg tgcatttatt ttcatttttt gagaccaaca 252300
ctagagcaga aagacacatt aacaaaaggg taagagtctt cagagcagat tactcccact 252360
tgaaaaatga gttaagtgat ttcacagcgg gagagaggga tatttgcagc aagaagtttc 252420
attagtcact gaatgaggtt tctctgacat atattttcac agaatgagaa gcatgatctt 252480
tagaagcaag agccataacc tttctatatt tttcttctgt ttattcattt tgctggaaga 252540
ttcccttccc tagccttctg gaaatttcag ccttctagtc tgatttggtg acctttgttc 252600
actaggaaga acatagtccg tttctctttg ccaaaaggta gttgcatgca tttgcaattt 252660
aaacaaggaa catccaaaaa aattagaatg tgtgtttgtt gaaaatattg tgattattaa 252720
agtcagagaa gatagctaaa acagaagatg cccatacttt gaaatcagat gattattaat 252780
agatgctgct ttgtgttgac tggagtttaa ctgccagtcc tttctttttgc caagatattt 252840 tcccaaaaga aacatttcag ttgtaggctc aataaggaga ctggaatctg ctttgtgaat 252900
tggtggcaaa aggaaaaggt ggggaaggta ggagaagaaa agagagatgg agccttcagg 252960
taggagacta ctttttcttc ctttggtgtc tcatcttaat atttaaaaaa ttaaattgaa 253020
gactcagcta aggtatagaa aatatcaggc ttttttcttt tgacatataa ccaacattat 253080
ctcttgtcaa gcaattatt tttttatttt attttttttaa ttttctaata agactaggtt 253140
tattcagtac cctagtaaaa gttttttatta taagtatcca acagtataaa aagtacaaaa 253200
cagacctgta gatttctaat atattaatac aaagtgctta ttttttaaac tgcttttttt 253260
tttttttttt gaaacggagt cttgctttgt cgcccaggct ggagtgcagt ggcgccatct 253320
cagctcactg caacctccat ctcccgggtt caagcaattc tcctgcctca gcctcctgag 253380
tagctgggat tacaggcacc caccactatg cctggctaat ttttttgtat ttttagtaga 253440
gatgaggttt caccaagttg gccagcctgc tctcaaactc ctaaactcaa gtgatccacc 253500
cacctctgcc tcccaaagtg ctaggattac aggtacatgt caccacgccc agctaatttt 253560 tgtacttttta gtagagacag gttttacca tgttggccag gttggtctac atgatgactt 253620
cctaaacaag tgcataactt cgattctaca aaagatgaca gaattcatta gtactactcg 253680
tttgtcctca gttatacttt ctgcagtttc agttatctac ggtcaaccat ggtctgcaga 253740
aaattccaga aataaacaat gcatcagttt tacattgccc ttggttgtga gtagcatgat 253800
gaagtctcca gcagtcctgc tccctcccaa tccatcctgc ccaagaggtg aatcctccct 253860
ctgtctggca ttttcatgct gtagagactg cctgacccct agtcacttag tagtctgctc 253920
agtgaccaga tcatctgtca tggtactgca gtgtttgttc tcaagtaacc cttatttcag 253980
ttaacaatgg ccccaaagtg caagagtagt gatgctggca tagtgttata attcttctat 254040
```

```
tgtattatta gctattattg ttaatttcct gtgactaatt gataaattaa gctttatcat    254100
aggcatctat gtataagaaa atgcacagca catataaggt tcagtactat ctgtgttttc    254160
aggtaaccac tacaggtctt ggtacgtgtc ccccgtgggt aacggaggac tcctattgtc    254220
tgtgttttat ttgaagggat tttgattcat ttgtgatctg tttcacgccc tcttcctttt    254280
ctcctctggc aaatttgagt tggcatgccc tccacttaat cttttaaatg cttgatccat    254340
tctattctgc agaagaatgt taaattttc attatgtcag tcaatatgct tttggaaaaa    254400
gggacactcc tgtttgtgtt tcctctttaa attcatggtt tagagttttc tcctcttcct    254460
ttcgcttgag cctccccaac tgcagtgtct cctcagtcct ctaactccat gactgtggat    254520
gaaactccat cttgttttc ttcaatgtgc tatttctcaa gtttacatct acaaatgtgc    254580
tgcaaatatc tggtactgaa tgatgtttca tttcagtgaa gcgtttgttt ttgtttgttt    254640
tgaaagttaa ttgtgcatgt ggtttaaaaa atccaatata acaaaggca tacagggaca    254700
ccatttgacc atgccattcc ccacccttc attcagttgt ttcagcgacc acctttcttt    254760
gttgtggctt gagaatcctt ccagagacgt gactaaacag ccatggaaat gccagtgcaa    254820
cagagcattc tttacatctt gcttttcca cttaataaca taactttgag gttgtcctat    254880
tttgacacat agacatccac ctcattcttc aggaagcctc tgtcacaggc acatatatgg    254940
acctaccata attcattgat tggactgcca tggttggaca cgaagattgt ttccaaatac    255000
ttgctaccat aaaccctagt gcagtgaaac ttccttcaca caccttttt tttcttttt    255060
gagagggagt ctagctatgt cacccaggct ggagtgcagt ggcacgatct cggctcactg    255120
caagctccgc ctcccgggtt cacgccattc cctgcctca gcctcccgag tagctgggac    255180
tacaggtgcc cgccaccaca cccggctaat tttttgtat ttttagtaga cgggggttt    255240
cgccgtggta gccaggatgg tctccatctc ctgaccttgt gatctgcctg ccttggcctc    255300
ccaaagtgct gggattacag gcatgagccc ttcacacacc tttgagtggg ggtaggattc    255360
catatctatt ttaaatgtat atagatgtta ttgagtttta gaggactaaa caatttagct    255420
tccaagcata acctataaat gcatcttggc cactttcttg ccaacagagt gtgttataaa    255480
gcatgtcatt tttgtctgtc tcaggtcagt gaaactcctg taaaggacca gatagtaaat    255540
gtgagccaca tggtttctgt cctgactact caaatctgcc cttgcagtgt gagagcagca    255600
atagatgatt tgtccatgag tggtgtggct ctcttccaat aaatctgtat ttacaaaagg    255660
aggtcctggc caggtttgct tcctggatca tagtttgctg accctggtc tatctaataa    255720
caacaataat aatctttagt ttgtttcttt tgtatgagtt aggctgttca tctgtttaaa    255780
aatctactta ggtatttttt tcctgttaat tacatccgtt gctcatttg cataatgcag    255840
tttaactttc tcttgttggt ttattaaaag caatctatat atttgaaact taattacttt    255900
tatatattct gaaaataat tgatctgtta gctgttgcaa cagttggctt tctgataaat    255960
ttctatttga catagaacca agtaaaaatt atgttacctt gggttgtaac agttactctt    256020
aaaaacattt agatctgcaa ggcacagtgt ctcatgcctg taatcccagc actcttgaag    256080
ctcctggctt caagagacat ccccgccccc acccgcccc cgcccccac cttgtcttcc    256140
caaagtgttg ggattatagt tgtaaaccag caggcctgac cttgtgtaga catggtaatt    256200
gacaagaatc ttgtagtcac attttcatag actatgcagt agatgcaata gactaacttc    256260
tgtatgaatc tttttcattt tgtattaatt ataatcattt gccaagtttg cttcattcat    256320
ttgtttagta aaagagtatg tgtaaggaat ttggtaggca atttttagaa cttttagtga    256380
```

```
caactttgtt tttgattgtt tcttagtgaa agaaggatta caataagaac ttagccacaa    256440
aatacaagtt tccatgagtc actgcaaaat aacagggata gtttggaaag gcaaggagta    256500
accagaagct ttggggcata gttttcctta gttaaatcag tataataaat ggggtacaca    256560
ttgcaaatta tttattcata gtttggtagt ttgcattggt atgtcttaaa cctgaatact    256620
ttagagtgaa tgaagtaaat aggatgagat gatgggaat  gcacacacac ccacacacat    256680
gcacacacaa acacacatgc atgcatgcat acatacatgc acacacacat atacatatgt    256740
gtgtgtgcct gtgtgtgcac atgtgtgtgt atgtatgtta cgtttacatt atttctgcat    256800
attaaacact ttcccctttc gttagatatt ctttattgag aaaatgcact acactagatt    256860
accattactt aaaagttgct ctcgcagcac aaatcaattc attatcttta aggataagcc    256920
catgtctgga ggtagggaaa tcattttta  aaaattaaag tttctgtctt gaaatattgt    256980
catccttcac tttttctatg cactaggatg ctctttgctt tcaggaaaac acgttatgac    257040
tcatttaata ctgttgtccc tcttatccag aacagaacat accgtggttg cctaacagga    257100
aggctgcata taaaacccag ttttgtctag tatcatttc  cccaagtcca ttatgtgtgt    257160
tattgtgcag tgcatgtcca aatgaggatt tgagcagtag agaagaaatt cattaaagaa    257220
atgtgtcatc tccttgcaaa aaggaaagta ttgttgagga aattgttact gataagacaa    257280
aagtggtgaa tgaacatcta ccatttgaag gcatttctct gaagtgaaaa ttaccttgaa    257340
ttgtcttggg atcagttgtg acttgatcct tctattagga gctgtttcaa actcagaaa     257400 ggggtgatga ttcacactga tgactgaagg tttcttggag ctggtgtgaa taagaaggga    257460
aaagtattgc aaatgcatca ttgtggcttt cactgagact cagtggacag aattcatcat    257520
gatcttcctg ggctccagaa acacaggctt gaaatttagt agccagtctg ccaagcatgg    257580
agttaggcac agatgggatc tgagttagag aactctcctg ggactggtac ccagggaggg    257640
taatgtaggg tgaaatgtca ttgttcaaca tgcttattat tcacctgaac atgggtgaca    257700
ttcctttcct gagaaactct ggtctgacaa atggggtctt acaattattt ctgaaaatag    257760
aaaatgtatt tccaataatt attagttata tctatttatt atttctagtc atattattcc    257820
taataattga gctctatggc tattgggtga ggttcctcag ggaacagcgg attctctgtt    257880
actgaaggag tttaaacagt atctataccg agagtagtca agacatgcag agatgatttc    257940
catattataa gagaagttgg attgaattaa gtctgtgatt ccctgccatt ctgagatttt    258000
aaaagtccag gcctttaatg taccaattcc ctgtcatcat tagtctaatt attggcaact    258060
acattgaatt atacagtata gtatcagttg atgaatatag tatcaattga ttggtacaac    258120
actgtatcag gttgaattta actgagttaa ggtatggccc taccttctaa gagcttacca    258180
gttgacaata aaagcacatg ggtaggcaag agacacccac attattagat ataactatgt    258240
tattcatgtt acctaaagtt ggagagtaag aagaatgaat ttcttgaggt agggatgaaa    258300
gtatatcccc attccaacag tttagatcca gagaagaaaa aatgtttcag agaggagata    258360
tgattttaaa aattgcttca gaggaaaaat tcagattggt aatggcagcc tagaaagatg    258420
ctaaatgagg aattctaagt caaaggcctt gcagaaagct aggaatgaac atgtcactgg    258480
ttctcatgga aaatgcttag agtcctgcag ggaataaatt cctttttttt tcttttctt     258540 ttattattat actttaagtt ctagggtaca tgtgcacaac gtgcaggttt gttacatatg    258600
tatacatgtg ccatgttggt gtgctgcacc cattaactcg tcatttacat taggttatct    258660 ccttttttt  aaatcattat tactattgta tttatttatt tattttttat tatactttta    258720
tgttttaggg tacatgtgca caatgtgcag gttagttaca tatgtataca tgtgccattt    258780
```

```
tggtgtgctg cacccagtaa ctcgtcaatt aacattaggt atatctccaa atgctatccc 258840
tccccctcc ccccacccca caacaggccc cggtgtgtga tgttcccatt cctgtgtcca 258900
tgtgttctca ctgttcaatt cccacctatg agtgagaaca tgcggtgttt ggttgttttt 258960
ccttgtgata gtttgctgag aatgatggtt tccagcttca tccatgtccc tacaaaggac 259020
acgaactcat cattttatg gctgcatagt attccatggt gtatatgtgc cacattttct 259080
taatccagtc tatcattgtt ggacatttgg gttggttcca agtctttgct attacgaata 259140
gtgacgcaat aaacatacgt gtgcatgtgt ctttatagca gcatgattta taatcctttg 259200
ggtatatgat cagtagtggg atggctgggt caaatggtat ttctagttct agatccctga 259260
gaaatcgcca cactgacttc cacaatggtt gaactagttt acagtcccgc caacagtgta 259320
aaagcattcc tatttctcca catcctctcc agcacccgtt gtttcctgac ttttaatga 259380
ttgccattct aactggtgtg acatggtatc tcattgtggt tttgatttgc atttctctgg 259440
tggccagtga tgatgagcat tttttcatgt gtcttttggc tgcataaatg tcttcttttg 259500
agaagtgtct gttcatatcc tttgcccact ttttgatggg gttgttttgt tttttcttgg 259560
aaatttgttg gagttaattg tagattctgg atgttagccc tttgtcagat gagtagattg 259620
caaaaatttt ctcccatttt gtaggttgcc tgttcactct gatggtagtt tcttttgctg 259680
tgcagaagct ctttagttta attagatccc atttgtcaat tttggctttt gttgccattg 259740
cttttggtgt tttagacatg aagtccttgc ccatgcctat gtcctgaatg gtattgccta 259800
ggttttcttc tagggttttt atggttttag gtctaacatt taagtcttta atccatttg 259860
aattaatttt tgtgtaaggt gtaaggaagt tgagactggt agaagactaa gcttcttcca 259920
gactttaatc attgttatct ggaaaggaat tgaaaatagt ttttttctga atcattgtaa 259980
tcatgtgaaa tcactaaatg tcagtgttga attgaccaca aggaccaagc taattatgga 260040
agaaataggt gggggagaca ttgaacacag caatccacag gagtttgagt aagtctggag 260100
tgttgaactg gtgaaagtcc tccctgcaac agctccatcg gggcaattct gttaagtcaa 260160
gactcaagca ctggacggtg aatggtccag aaaaactatg tcattaaaaa tgcacatttg 260220
tttaaaataa ctaactgctc tttcgtggat gattggtact aagatttat aaactgttta 260280
gggaccacca tgattcctca cacacattaa ttaattcatg agagttgatt ttcttttcaa 260340
acacattgat acattattag tagatagcac cccaacacac acacacacac acacacacac 260400
acacacacac acacacacac acacagagag agagagagag agaggggtac ttacaatcaa 260460
agacagccat actagatcca attggtagca acaaagtgag aaaagtacca gaacacacag 260520
gcaaattgaa aatacacaaa gccacatcca cagcatgccc tttaatggag gaagtgggaa 260580
gaaggttcca ttttccactc tgctcatttt cttcccacc acccattaag agtgtcaatt 260640
ctcattcaca ttccttttag agaagaacga accatcgaaa agggagctga gagttgtaat 260700
aaaaatattg cattacggat ttctccagtt tcctttcagt atgaagtatt tgttacttca 260760
ttgaaaaaag tagaagtatt gatcagccgc ttagcttgtg gcttctgctc tcaaggagtc 260820
agcacatagt ctgatgtgga ggaaaatcta taaatggatt tctgcaatct gcaggtaagc 260880
atgggatgaa atgttccttg acatccaacc caggttagaa atcagttttc aagactctaa 260940
atttgaggac ccctaggagc tcaaatgata aagagaagaa ggtttatagt ccatgatggg 261000
ggagggactg cacactacct gcagggtgag cagaaaggat gcaggggctt ggtatcacag 261060
gaccagcatt gtaaatatta caggaagtaa cctttcctgt gtgtccttca tgtgcttttc 261120
```

```
tttgtgcata ttcttgaggc ttaaaggaaa gggagccagt ctgtgtccat acttctctcc   261180
cgtgcacatc atcccggcat ggcactgctg atgcaaatta aaaaaataac ctttgactag   261240
aagcattttc ccagctacca gtttccttct ccccagtgca agacaatgtg acagcaaagg   261300
ttcatgcaca gaagcagaaa ggtagtggaa tgactcagct tctaactaaa ttccttccac   261360
cttccttagc tttgtggtct caggatttta taagaggtct ctcatgtgct gctacagaac   261420
cagcaggaaa aatcagacag ggccaagaca gagagaaaag agaccctttc tcctatatt    261480 gcccctacct agggctccta tccaaagcat gttctagttc ctagatggtt gattccaata   261540
aaataacata aaaataaact gtgcaataaa aatttaaagg gagttgcgct gaccatcatt   261600
tttgaaatat ttaaaaatga gtcctcagta aattttggtg tgaacattag tatttttgtca  261660 tggatagagg cacaagaaag gagtaaatgt gagacctaca ttgcatccaa tgcctgcatc   261720
agtagaatct aatctcttcc ccccatgata aaatggcctc attctgtcaa ctacaggctt   261780
tgctagcttt ttctcagaca acagaccaaa tttatcccca gcctgataag gatctttatt   261840
gcatttgctc ccacccccacc tactgtattt agggtaatgg tgaaaaatgt acattgatgc   261900
tgaattttat agaaatagta gaaatggaaa tgatcttaca gagttgtcat ctactatctg   261960
gtgtaggttt ggttacaaag ctgtatttcc tcttccaagt tttaagtaat caagtttcaa   262020
aacaatcttt cctgacatcc agtttgtgtt aaagccaatt tcccaaatga ttttcatttg   262080
cattctggaa atgcagtgaa gccttgacat tttacaaaat gacctatctt ctactcaagt   262140
caatgaaact acagtaaaca ttttatgtgt agttgcaatg cttgtatctc cctcaagatt   262200
aaacacagaa aagcatcttt ggggaggata tttaaatacg atattaaagc atataacatg   262260
tgtctgtatt ttttcagttt taagtatact tactaataat aacaggcaaa gtggtacgag   262320
gtaaaacact acttttcatt gttcagttta cagtagtcat tgactattct acatatgcgc   262380
ttagcataat atttacagac tatgtaatac aaatcacact ctgtgaattc tcatgtcctg   262440
tgagacacag gaacagaaga gctttgtaaa aaaacagcaa agtacaactt gaaaagttaa   262500
gccatatgag taagaaatca aagtgatgaa tttactaagt gtttattaat atttaagcta   262560
agtttacaca tgactcaaca tcatattcat actcatagtc tgttactgta ctttgccaaa   262620
ctgtctgtac tattttgtga gaggatatta tctttaatat tgctctcact gcaatgaagc   262680
ataaataaag tatatgtcat gttctacctt ttcaggagct ccaatgaaca catgctatgg   262740 ttttttaatga ctgtaaagaa aatttcaaag ccatatctta tctgtttcta tggagaagtt   262800
gatcaatgat caataccatt tgcaaggacc ccgatgtgtg acttgtttct ctttatactg   262860
tgacatgttt ccctgaaggt ggaacgtcaa tgagacattc attttctact aaatgaaaat   262920
gatgttaaag ttgcagtcta gtgataaagt taccaagatc tgcttcttgg atttttttatg   262980 gggtttgggc aacacataaa gaaactttcc tctcattcaa gttgaacata tccaaccact   263040
tatatatatg ttgcccagtg aggtcagtgt tacatgaagt tgtagaacat ttactttgaa   263100
atgaggtttt ctcatttaat aaaagtgtca ccttgtgtca gtggcttagc tagttccagc   263160
ttctatttta tctcttatcc aatgagaata tgcctatcac ataaggagtg tggctgggaa   263220
gaatggtggt ctgtccttat ctcctgggtt tctctggttc agaacctgca cagcggacag   263280
ttccaaacac tgcattccac catcatttca tcagcattcc tcttggaata aatgtgtctt   263340
gacagtctct cttagaagtg ctttctctga agctactgag gaccatgcca tgtgtaggca   263400
taactgaagc gtgcacattc tatagagtgc ctcgaagatg tgcacattct atagagtgcc   263460
tccaaggttt tcaagaagaa tggagcccaa cttggccaca ttggttacac acttgtgcat   263520
```

```
ggtccattta ttgactatcc caccttccaa gtaatttacc tgcacccgac ttcttgtctc 263580
atgtggggcc tttagagtaa ctccaaataa gaccaggtgg atgtgcagat gaaacgtttg 263640
atgcttgcat gtgcttgcct gattatgact gttaatcacc aggtgtgtca aactactcta 263700
gatgctcatt gtgtgtgtat gacaggtttt ggtgctcttt ctgcttttga taagccattc 263760
aatttaatag ggtgttctct gaatgcccag cttttcttta aacttagcat gtatattcac 263820
taccccacga tccacctaag acagttgcgt atcatttctt tatgcctgtt ccgtgttcta 263880
tgtatattag atgatttcat atagataagg agggaaagct catattttat acattttaac 263940
tattatgatg aaaaccttat ctagaagagg ttctcttctt tttgaagttg catagcatta 264000
gtaaagctat aggagctatc tcttgtatct gactagaaac gatacacatt taagataaaa 264060
agcatgggcc aggtggtggc atatgcctgt aatcccagta cttttggagg ccaaggcagg 264120
aggatcattt gaggccagga gttcaagact agcttggacc acatagcaag ccctccctcc 264180
ccaccctgtc tctacaaaaa gtgaaaaaat tagccagtca tggtggcatg tgcctatagt 264240
cacagctgct cgagaggcta agttgggagg attgctggag tccaggagtt caaagatacg 264300
ctgagctatg atcatgccac tgcagttcag cctgggtgac agagtgagac catgtttcag 264360
aaaacaagtg agtaaaataa aataaaaagc aataacaaga ttgcattatg ctttgagggc 264420
attaattttc aaatttaact ttacttgcat tttttttcctg tcattctttc tgtgtcggct 264480
agttcttatt ttagttgtaa tctttttta gaatacttat gaatagaata ataccactg 264540 tattcacata gtatatttac tattatttt gtctccttgc attgtatttt aattatctat 264600
gtcagacact ttcctcagtc aaatgtacta ctagccatct aaatggagaa tttatcttag 264660
gaggagaatt cttctcattt attttttgcat acccagcaaa ttattcggga gtgagtgcac 264720
tgtttcatcc tgttgatagt cttccctgaa catttataac ccaccctga ctggctccag 264780 tcttacacc ttcctcaaga cctaacttaa atacactgaa ctgcctgaag tcgtctttga 264840
attttacatc cttttctctta actctcatac actttgcatt gttttcccat acaggggcat 264900
caagaaatag accatattat aatgaatgta caataaagta ctaagagtaa taaaagtaaa 264960
tatattccga agcaggaaag agcaaatgct tgggttttt atagaaggag agaaacgata 265020
atttgagaat gtttcatgga aactcttgca tttgagcaga actttacaaa ttaggcttag 265080
gcttcaatag ttaaaaatta gtgaagagaa catctctgca aagttgaatg ttctggtctc 265140 cttttctgttt gtttagtgag cagaattgat aatcgacatg caagtggctt ttaaactttt 265200
ccaaggacca gtcattgggg aattagtgtg gttcctctga acctttctag taatcccagg 265260
atttgagtat taagaacagt tagttgtgtt agccttaaga tgaaattctc ctaccttgtt 265320
gttttgaaga tgttacttag agggaaggag atgttttggt ctgttcgggc tgctaataca 265380 tcttttttctt ctcaaatttt actttaagca gtcaggagga accaagccat ccttcaaca 265440 ctttttcttag aaatagcttc agctaaatct acttttatca ctcacacgat ctgccttcca 265500
caaattacta aaacatgaac acagttcagc caagttcttt gccactttgt agcaaagatc 265560
acctttcttt cattgtgcaa tggcatattt ctcatttgcc tctgacagct cataaaaatg 265620
gagcttcctg tccatatttc tagtgtcatt ctgttcaaaa ttgcatagat tttccctaag 265680
atgattgagg ctttctgtac agctcttctc tttttttttc tgagccctcc cctcactaga 265740
atcaccttca aaggtctatt catggcaacg taggctgtgt ctagcataca cttcaaaact 265800
tttctggctt ctacttatta cccagttcca gagctgcttc tgcattttta ggtatttgtt 265860
```

```
atcttaacac cacactctca gtaccaattt ctgtcttagt ccactcagac tgctataaca 265920
aaataccata gtctgggggt gggggtgggg ggggtaata aacaacagac atttatttct 265980
cacagttctg gaggctggaa gcccaagatc aaggcagcag aagattcagt ctctgttgac 266040
aacccacttc ctggtccaca gacagtgact tctccctgtg tcctcacatg gaaaagggg 266100
gagggagctc tttgagatct tttcttgaag gacactaacc tcattcacga gtactccatc 266160
ctcatgatct aacaacctct taaagatgcc acctcctaat accatctcct ggggaaggg 266220
agtttaggat ttcaaggttg aattttggga gaatgccaac attcagccca taaaggaga 266280
tagtatagga aaactacaga aatcaataaa ctcttctact gttttgatta aaatatagca 266340
agtgcatttt tggtgtacat attttacttt atctttgtta ttattcatct agaaaacaaa 266400
cgtacatagt gatagttaat tcttccatga cttttttgca aaagtgttgg tatgcattgg 266460
ctataagtct cctctctgac ttcataagac cttggaaagc tgccaaatat ctcagaactt 266520
gttgtcttga gtcttaaagt gactaaaatg accttagctc tacctgcctt ataggatgct 266580
ctgcccaatg atgcatgcag tatgcatgtt ctttaacaga gtatgttttg agactgcagg 266640
tttaggcgtt attagaatcc atttgactcc atagccctt tatggaaac atacatacat 266700
acttaatgtc aaatagttta tatctttta ctagctaata tggataagta ctgtctcttc 266760
ccatttgact gtgtgtaact gccttctctt agaactcaac acaaaatgag ctttatgatt 266820
cacatttaca gtaacatgga gacagaacca cctcattcaa aacaggaaaa agcaggtata 266880
agatgccatg aagggaaatg agactgaatg tgttcaattt ttctttgttt ggcttatcac 266940
atatcgtaga gagatgtcct cttacatgca gtagaaataa gaacatcctt gaaaactcgg 267000
tttgagcagt tcaaaatcat atattttta atgttgtatg agtttcaggt gataaatcct 267060
cttcaggata cctcagggggt tcgcaaaaat gtaaaaatat gtttaaagtt tgaaatgact 267120
cacatttttt agtatccacg gcaaagaact gcttttccaa ccttaatagg atttcaaatt 267180
gacattgaca ttttagtaaa tcagaattag cttttttcttt ttaagctcct gtgtcttatg 267240
taaatggctg tgctgacttt tatggaattg aatattccag aaaatgtcat ggaacctaat 267300
ataaaacaag ttaacattct cattttttaga tcttaaaggg atatggtgtt aaaatatagc 267360
ttttgatacc catccaacct gtgcaaggtt ttctgtgtat atgcgaattt caaatttgag 267420
aacttagcat gtcgatgaag gcaaatctat atacctgttg aaaacaaaat tgaaattctg 267480
aaggaattat tgtaatttac ttaaataaga actgtaagaa gtcagactgt taatggagtg 267540
tcaatagatt tcttctgaga gcttcaaaat cttttcactg cctttattac aagtctacca 267600
aaatatctgt tagattctga aagccaatct ctcattacaa aaagcattat tcacaatttt 267660
aacttatttc cacaatgaac attctacaga attattgtat ctttgtttaa agataaaaaa 267720
ttctccctcg ggaggctgag gcaggagaat ggcgtgaacc cgggaaggcg gagcttgcag 267780
tgagccgaga tcgcgccact gcactccagc ctgggcgaca gagggagact ccgtctcaaa 267840
taaataaata aataaataaa aataaaataa agtaaataaa taagtaaatg aataaataaa 267900
ttctcccccc gaggtctgaa atttattatt aatgtgaata ttttaagcat ttttagaaga 267960
aaataatttt gtaaaaaata ttgtaagtta tggaaaatat ggtggtgaag tataacattc 268020
acgaacttgc tagaaccttg ccctaaaaat gaactaatta ttggatcata tggcaaactg 268080
attaagaaga ataaggaact actttatatc atgaaaaaat acatgactat ccacctgcct 268140
tcctaaaact tcttcctctc atgtgccgct attttactta gagttttctt tcgggttaag 268200
gaacaatatc tttagaaggc tattcattaa agtactaatt agaaaaggta gttaattaag 268260
```

```
cttgtcacac acaatttata tattttctta tgatgtgtaa gagaaaacag cataaaaaag 268320
ataaattatt tattttcagt caaaataggg cacttttttt gctttcctgc agctcattat 268380
acctaaattc ctttgtgaaa gtatttaagt aagttctttg aaatattgct tttaaaatat 268440
gtttactctt taaagtttta aaataagga aatgtataat atagtgaaat ttccccatca 268500
gtgtgttctg tgtattttct ccagctcttt cttgaattac aaacagcagt tctacaactt 268560
taccacccac acacacacat ttattcattt gcacatattt cttttagtg ttttttttt 268620
tttgcaaaat tggcatcata ttaattatac tactctgcaa cttgctttat ttactgtttt 268680
taatatggaa attgactgaa gttaattttc aagcagttgt gtaatattga ttgaacttaa 268740
ttgatatact ataactgatt aaactacctc actgttattt ggaacactta tcgacaacac 268800
tgcagtgtaa aaccctcttt ctactttgc agctttatga taattctata aataatcaga 268860
caccgattgt gatgcaatcg tatcacaaat tcaaagacac attataatgt cagtggaata 268920
agttagacat acagtgccaa ttaactcagg gttccagggg taattctttt cgtattgatg 268980
aaacgcaaat gcatcttact cattcagagt tgccagggcc ctggtgtaga aatctaaatc 269040
ataaccaaaa caaacagcat caccacgaag aaatcaacaa aaacaatttc atgagggttt 269100
tgagtatttg aataatattt cagtaattaa attttaaagc aagaactgac aggtttgccc 269160
accccatcca tcctgtgatg tcaaatgcac ggtatgtatc tggctgacag ggaaattgag 269220
gtaggaaaat agaatagata atatgctatt atgtacctgc gcttcagttt gaggaggata 269280
aaattgtttt aaccttatgt ccacattcct ggagtggttt gctagacctg catcagaaaa 269340
tccacatctt agttcttcag ctgttcacat ctcaatccac acagccttt gtcattagca 269400
tgccagaaat gcactacatt catgaaagga attactagtt acatcatggt gaatgttagc 269460
atgaactctc attggcccat aacattaaaa tattcaaaac atacaaattg ctaaaatcg 269520
tttagagaaa atgttcacaa tggcatgatg aaggtataaa aatccagaaa tgcctatgcc 269580
tttgacctgc tccagtgccc ataacttgaa gtctctttag tcctacgctc agccatggac 269640
taaggaaaat ttctcattac ctgatgctga ctgagaaaga taaaagaaca ccacttgttt 269700
tgtccttaaa gacttgagag gcaaagagct acatgataga agttgtacct ctcacaagtt 269760
tatggaagga gacatatgaa ctgttttctg tctgctgtgg aagtcagatg aatgactgcc 269820
tatatgtgta acacatttgg gcctgagaca cacatgatga ggggaggaat tacaaactat 269880
cactggtctc cttctttttc tgcgattact gttaccttac ctaacagtag gtaactgtaa 269940
tctaaaatga acctaaaaat tgtgcatgaa caaattagct caggtagctt gcaacattga 270000
ctttacagtt tgacctaggg gagccccacg ggctgaacct aatgaaactc agccaggtta 270060
tattaaaact gcgatagcct gtatctctac attttctgca acctggtttc tacataggga 270120
aatgctgctt gtgtttgctg taggcaaatc ttaaataaac catgactcag caagaagaag 270180
agaatgatgt gcagagatat tttagggaag ggataagatg gcagttttga atgggagccc 270240
acatggtaca agtactcata ttccattacc aacttcagga gcttttact ttggaaaacc 270300
attttttcacc ttatttcagt aatatgtcaa gcatttcagg tggtctgcaa aagccacata 270360
gctcagaggc ttagcaaacc tcctcagaca tcaggcagaa acactttcta aaccccttaa 270420
tgagtgtcaa gcaggaaatt gtgagtatat agtattaagg agatggactt gctattctta 270480
aatttacaga aaaaaattct ggattttctt cctcagtctc cacttaatga cagattttt 270540
tttaacaaaa agatgcatga cagtacctat ttaaacttac tctgataaat ttgatgaaat 270600
```

```
attcttttttt taatccagac atctctatga gtttcagaat tattacccttt gtcaaattca   270660
tctatgcttt ttttgtggaa atgttcaact tttgttctca ctgctccctg ccttccccca   270720
tcaacaaacc ctgaatatct gggaatttct caccagctat tatttaactc cattccacat   270780
gtccatcaga tgtcctacac aagattggtt aaatagaagt ttgttcgctg ggagaagatg   270840
acaacttttt atattaaatg cataaaaatt ttctcaatac tgcagggtga taaagacaaa   270900
gaaaaggcca atttaaaagg aagtctttag aaaaaataca ataaagcaga aatgcttcac   270960
tttcctacac aatagggaaa aaattttaat gcttttgcaa aaattaaact ctaatgatgg   271020
aacaaagttt attttatact gggtaaattt atgttaggca tgaaactaca taaaaatatg   271080
tggacaacaa agagtgattc agggctgctt aatcgctgtt gctcttggtg tggtttttag   271140
gggattgcat aattggtgag ttccttacac gttgatttct cagattcacc aggcaataca   271200
taccagctgt cttggtaaat gcatgaaatg ttgcaatctt tgcaagtcct gcaattttac   271260
ttcaccagta actttccctg gtcaactaac agtatctaga gatcaggcag agggtgacca   271320
atggctgctc tgacgtacac atggagatac tgaaagatgt ggagttaagg atatttgaat   271380
aaatatttca tataatgaca actgtctttg ttagcaagca gaaatatcca ctgtgatgca   271440
aaggcatatc cttatgtcat atatatttgc tgtgaaaggt actgattcgt gcttatgtga   271500
aaacctctta aatcccgaat ctggggtctc ctctccccgt tttttctgga actcagatgc   271560
taaagttgat acaggaggag tggactgtcc caaataaagc agtcggggaa aggaggatcc   271620
attgcaaata aagggtaaaa aaggtacata tgaatagtat atctatttgc acgtaatgca   271680
ggttattctg gagggtatta aatatctatc agtaactatc atttgttaaa aaccagggat   271740
tcccaaggat gttagtggat gtatgagaaa gagtttctgg agatatatgt ttgggtgtcc   271800
actacgattg ttgcatttct ttcttctttt gtctctctct gtctctgact gtctctctct   271860
ctcagtttgc ttctctttcc ctttaaacac acacaaacac acacacacac acacagac   271920
accacacaga atattcccaa cttcttaaca cacaacacca ataaaaaatg ccaataatca   271980
gattgtaaaa ctggcagttc ttttctttca atgtggcttt ctattctatt gtctctcaca   272040
tatcaaagaa acaagaggac aacagatcag gatacatttt gtcatgttta cattatgtag   272100
taacctgaaa caaatgccca gtgagtggag ggtttcttag cttcctgtca gttttcaaat   272160
gttttccctc ctcctgcctc cctggctttg ggttggtgat gcacgtgctg gtgctcagag   272220
atgccgtgcg ccctgacaag agattttgaa ctggggcata gatgattgtc cccaaagtga   272280
tctgctcagt tcccataatt ctacacattt caggcaatgg aaacaaatg agagagatag   272340
tttgggtggt ttttggattg caaacttagg cagccacagt ttcaaccagc aatactgatt   272400
tttctcagcc tttccatttc tacccagtgc ataacttata taaattttct tccaaaactt   272460
cacaattaaa ctattcctta ttttatgaag ttatcaatgt gtgtatgtct tagaatataa   272520
ttggtgtcat acaaaccagt ttatgcctct ttaactttag tgctatgatc ttaaaaattt   272580
tgactcccag gcaaatatag atataaatat aaatatacat gcatttttt cttgagagtc   272640
aaaattatat atttatatat atgtgtgtat attatatata tgtgtgtata tacacacata   272700
tagattaaat atatatattt catattatat attacagatt aaatatatat tatctatatt   272760
taatttcatt agtcatattg ttttctacag tttgatttcc agttttgcag gactttgtat   272820
tcatattcct gatatcagga aagggtgcat attgacacta cagctcaggt ggaatattta   272880
gaagacacat ggttgtaatt agttacttgc attttttcctg aatgcttttt atggtgttga   272940
ctgtttaaga atatcttgca ttgctttcca aacaaatata ctacacaagc agcatttctt   273000
```

```
gaatctcgtt gatctgtgtg gtgtgttggt gtggtcttat acaggatttt gtcttttttt   273060 ttttttagt gtggttgttt ctccttttt cctttaatct aacaaatatt gaagtacttt      273120 aaaatttta atactggttt ttatggagaa tgagagtttc ctatcatttt cctggggtaa     273180
tgtcatacaa tgcatttctg aaaaaaaaat acttcttaaa ttttgttaat gttctgatta   273240
tttttctgtc attattttgc cactttgtat tatgttacat tactattcca taacctcctt   273300
tgattccagc attgggaatt ggttttcatt tccatggact cattactgag gtccttgttt   273360
ctttcgagat attaaacctg accctgaatt ttttttcttc cctgtgagag tggaaattat   273420
aattcttttc tactggttca ggaaaaaaag aaacttttact ttctaaagaa tatatttctt   273480
tttatggtca gatacgtttt aaataaaacg aaagctttca atatctgtct gtaaaagagc   273540
agggtttgga attctcattg gtgatggata tgtttatttt cttacctgac acgtcagcta   273600
ctgcagctaa agccagtgaa ctatttctat atcacttact gatgaagaaa taagggctc    273660 tctcatgata ctaagtgtat tgctgttcca ccatccggat attttggct taaaccctga    273720 ggtgttacca gatggtaagg attttagaaa tgctaaaatg ataatagtag ggactacttt   273780
cgatattgtg aagtcagata tatcattgca agttttaaaa aaatggaata ttttatattt   273840
ttaagtatct gatttacctt aataaacact ttcatcaatt tcaagagcat ctacatgcta   273900
cattctggtc ctgaattttc atggttaaaa taaagcccca cccagagact agctaataac   273960
tatggtgatc aacagtggac agaaattcag agatactagt tatggtaaca tccttttaatg  274020 ctggagcctt actgtcatag aaacatgtga atgtcaaact aaaagtttaa agccagata    274080 tttcaaaaga gtggggagtg ggagagtata aattaccccc aaggaccctg gaagtgctag   274140
attctgggca agatccagat atttgcaatt tgtttaactc ccagttgacc atctgagaaa   274200
tattgagcaa gagagacaga gagagagaga gagagagaga gagagagaca gagacagaga   274260
gagacagaga cagagacaga gacagagatt gccaggacc aagggatgat gctagtgaac    274320
catttagcta caaagtgtca atgtatgagg ctggcgtggt ggctcatccc tgtaatccca   274380
gcacttttgg gaggtcgagg caggaggatt acttgagccc aggactttga gaccagcctg   274440
ggcaacatag tgagacctca tctcttaaaa aaaaaaaaa aaaaaaaaa agttagccaa     274500 gcatgctggt gcctgcctgt agtcccagct acttgagagg ctgaggctgg aggatcattg   274560
agtcctgcag ttggaggctg aaatgagctg tgattgcacc actgcactcc agcctgggtg   274620
acagaacaag accctgtctc taaataaata aataagtact atgtatatgc tgactctcca   274680
gccttgccta gtccccagaa gccttgcaac cttccaaaac ttgattgttt ttctcctaaa   274740
tttctcagat aattgagggg aaaatagagc tcagaatttg acaacagctg tccacatctc   274800
ctggaatccc tggcagaatg ctggtgctgt ctcttctctg ggtttcacag ggcgggcata   274860
aattataact ttattaggtt gagcacatat ggcctttagc cccaggagac cctccatggg   274920
gctagtctgt tggcagaggc agcttctgca ctttcattca aattcacaat ccataaggaa   274980
aaagaggcct tcaaggctgc agcctgcctt gggcttccgt ggggcatctc ctatcattgc   275040
caataatgct gtggtgaaac ccaggccaaa tattccaaca tctttttgct gcttgtatga   275100
acacgatgca tattgcagtt caaaactagg aaaaagaag agcatattac aggcgaacac    275160
gaatgcatca gaatatggta cctttaaatt aaaagagaag gctcttgatt ttgaattctc   275220
aagtgtttct cttcaaatac acacaatgat gtctttcact ttaattttaa ctattatgga   275280
tacataatag atgtatatat gtatggggca catgcagtgt tttcctacag gcatacaatg   275340
```

```
tgtaataatc aagttagggt aattggggca ttcatcacct caagtattta tcccttctct 275400
gtgttaagaa cattccaaat ccactcttta gttattttaa aatatacaac agattatttt 275460
tgactatagt cactctggtg tgctatcaaa tagtagattt ttttttcgag gcagggtctt 275520
gctttgttac ccaggctgga gtgcagtttt gtgatgatag ctcactgccg cctcaatctc 275580
ctgggctcaa gcaatcctcc cacctcagcc tcctgagtag ctgaggccac aggcacatgc 275640
taccacagct ggctaattat tattttttta attttgtgta gattaggtct cactgtgttg 275700
cccaggctgg tctcaaactc ccgagctcaa atgatccccc tgccttgtcc tcccacagtg 275760
caacgattac aggtgtgaac ctgtgcccgg ctgataggaa tttttgatgg agtttcccaa 275820
tatctgggct ttcaaagatt tggatagtg aacgagatac tgcaaagatc tctctaaata 275880
tcaccagcct gaccagggac cttgtgttac ctatatgaat acactgaggt tgctgtctgt 275940
ttctctgtta atgtataagc agagaaagtt acattgatgc tcatcagatt ttcagtttaa 276000
tatcagagca ttgcaaatta aaatataagg tgcgggacat gtacaatttt actgcgggc 276060
atgcaaaacc tgagggcccc caaagcagaa gaaggcattc ggcctctagt ctgcatttcc 276120
tccctcctga gttgccagcc agccagccag cctgtcttac agattccaga cttgccagct 276180
cccacattgc atgagccaat tccttaaaat agatcaattt aataaattta acctatattg 276240
gtgaacaaat ttagcagaga actttgtat acattagtac cacttattat tttagaaaa 276300
attggaattc gaataactaa cactaaagtc taattcgtca tctggtgtgt atgttataaa 276360
tgcacaccca ctcaccgaga cctattcaca gccacagcct catataaaaa taggcaatag 276420
atacaggaaa tgagaagcag ccatagaggg tcttacgtaa gaaacccat ccttctcaca 276480
cctactcaag aacgttgttc ccaacatcta catcttttgt agtttatatc cactgggcgc 276540
acctaacatc acatccacat tcttttgttt atcccgtttg gaaatacgtg cctgaccttc 276600
actttctctg cctgatgtgg ctgcatgttt ttgtttctct ggcaaccatc tcctcgtctt 276660
ccaagagtcc tcaccgatca catctcaact cctctccacc tatcctttct taaattcact 276720
ccaatcagta tatagcctca ccacttcacc agactcctct tgccaattat accattgcat 276780
cctaggcccc acaaaagtgg agttgctatt cctaatgttt ctaaaaaatg gccattctgc 276840
attttccctc gaatctccac tgcctctatt tttggaaaag agtttcatct ttgaaaaagc 276900
atttaagacc aactttttc ccactctgga gggaaatgaa atattgctga atgcagagga 276960
tatctccaag gcttcatact acttgctctg gcaatatttc cagatcctta tcctgcagca 277020
tttgcggtag ttgtcccct agaaatcata gttgaaacct actcctcaac tgtgtaggta 277080
tttggaagtg gggctttgga aggtatttgg agagtggagc ctcatgagtg gaattcctac 277140
cattataaaa gggaccccag agggcacccct cgtccctttt atcatgtgag gacacagcaa 277200
gaaggcgctg tctatgaccc agaaagtggg tcctcaccag ccactgaatc tgccatgcct 277260
tgatcttgga cttccggtct ccagaactgt gagcaatttt ttttacaagc cgtggggtct 277320
gcagtctttt gttttagcag ccaaaagagg taagataggg catgttggga aggaatggag 277380
atgtccacaa acaccctgaa tcatatactg ctccccaacc ccccgtcctc ccagcagaga 277440
gagcaggaaa gagaaggctt acttcctcca ggttcgatgc tcttctacac acagttatga 277500
cagacagatt gccttatatt tttattcttt ttagttcatc tgaccaattg tcaaattgct 277560
caaatgtcag aaaatggct caagggccg ctatggattt ctgcagtaga aaagaaaag 277620
acagaagact agatcccaat gtgttcctgg actggaagaa agttcttatt ttatggagcc 277680
ataaataaat atgacatttc ttgtgcctga gaatttgagg caggtagtac tcctgtgaag 277740
```

```
taagataatg tcttctgtaa aagaataaat tcattaaaaa ccatgggaat cattgtaagt    277800
ttcattgtca agaaagaaac agacatgatt ttggatgtag gtgaatgtta attattgaag    277860
atgattattg ttctcagaac aagtttattc tgattcgtag ccacagcagt tcaagagaaa    277920
agcaataaag gaaccacaac catatgaccc ttcttataat catgttgtgg tggggatgtt    277980
tcttctccgt cctacttcct gagaatgaca gaagggtttt gcaagagtga aggcagctgg    278040
gaatatattc cagccgcttc catagttcat gctgtggtaa ggagtttcaa ggtcacagtg    278100
aggcaaggag tttcaaggtc acagtgattg aacactagaa cttgtgcctc tgttctctgc    278160
tgaacgtctt ccatgactgc tacatcaggg cttggggttc ccactgacgt ggtgtttaag    278220
taacatttag agtccttatg gttatacact ttcatctcct tgtacagaaa gtttctggaa    278280
actgcccact attatatgac acatattaac ctgttgaatt tggttattta tgtgaggaaa    278340
ccacagaaaa ccataacaaa tcaaaatacc taagagccac aaatttcctc cagtgcagcc    278400
acatcccata gacaggtaat gtgcactaca tgtgtaattt taagttttct agtagttgca    278460
ttcaagagtg cccgaagaaa ccattgatac caattttaaa aatacattta atgtatccca    278520
atatttataa agtactaagt cagcagacaa tagagacaaa atatagtttg catatttttt    278580
actacatatt tgatattcag agtacatttt acacttacaa cacatctcgg tttgaacaag    278640
ccacatttta tgtgctcaat agccacatgt ggttattggc tagcattttg gaaaacacag    278700
tgctagaaaa tgcattcttc ctgccatgat caaccattgt ctctcactta ctcctgggca    278760
actgtgttct aattgatttc cgggcattga ttattgcctt tcagggagaa caactgatca    278820
ccgtattata gtaggtcatt cctacacatg gccttcaggt cccaaacccg tctgatttgc    278880
taagccgttt ttccctcttg tcatgccatc ttcccttcat ttgctacatt ccaggttttc    278940
tagtctaatg cagtcactcc aggcactctg tacttgtact cagcatttac tgggtggtgt    279000
atatctgtcg taggctgttg gttgtaagtt tcatgacagc atacactatg cctcccttt    279060 tccacatgca ccaatccatc aaacctcatt gaggacataa aacacagcat ataaagcact    279120
ccatcgattg aattgaatta atgtgtgaac aattgcacct gcaagtgtaa ctgagggctc    279180
acgtggttgt catgtatcat tttttaaaatg tttaaataat gcgagttttc atctatattc    279240
ttattacttc tgtagaaatt aatctataat atttcaacag taacatggtt gaaattgagg    279300
ccttatgtaa tgtttgaaca caaatgataa cttgattctg aatcaacact gtatgtgcga    279360
tttgatgtct gatgtatgat ttggggcagt ttgagggtca gtcatttatt tgtactgagc    279420
ctctcaaatt ccctgtatgt gaagggaaca gttgagaata agtgtcttca gtggataaga    279480
cagtcgtctt tatccctgga aggcatcacc aactgatcac agcagtctgt ttttctgagt    279540
caagaggcaa cttcccctct atgtaggata ctacttttag tgtagtgtgc tcttccatat    279600
ctattggaat cattacacct gatcaatcag gtttaagata aagggtgtga tagatagaaa    279660
tggatgcaga tgctcttgca aattgagttg aaccctttgt cttgcatct tgtgctggcc    279720 tcagtgactg tcttcttgaa tagaatgttc tgggagtaaa gcactgggac ttccagggct    279780
ggatcataag aagctattaa gcttccattt agggcacttg gagtactgac cctcagggca    279840
ttctctcttg gaaccacat ctcatgttgc aaagtgttca agcccatgg agaggctatg    279900 catggtgctc cagtcagtag ctttagcttc actcccggtt gacaaccatt agtaccgcca    279960
tgtgagtcac ccattgtgga catcccagct gattgaggac tcctgtctct tcctatccct    280020
tagctgacta aggagatctc aagagagaac ttctcagcta agcccagtca gctcacagaa    280080
```

```
tcatgggaga tcctcataaa aggttgtttg aagccccaca ttatgggcat gtttgttaca    280140
caacattagc taaccagagc aggcactgaa actggaagtg aggttctgtt tcaacagaaa    280200
cctaaagtac atggtgttgg tgttggaccc tccatagggc aagactaaag gcttgaagaa    280260
caagggaaga aaattggagg ctggggaaat ggaatggaca aagagaactc tttgaatgac    280320
tcactcacag ccttacagga cgagaagtaa cttttagcac tgtgcaactg caagcaaact    280380
ggattttgtc ctttaaaata gaaagatggc atctcaaaga acacatttgt catgagtagt    280440
tcctaataag cataatactt aacataaagt tcactgcgt atgttattta taatcttact      280500
atagtataat ttccattgga tagcaaaagg tcaaggatat aattacagaa atatattctt    280560
ttaaaatttc ttttggttac acttaaatgt aaattgtgaa caccatttta ttttctattg    280620
tatcccatga cttttctatt gtttgggtca tattaaatct attttacag tataaatttt      280680
gcagcatata ttcccacagg aaagaacaaa ttataaaaca cacagtttgt atatgtcttt    280740
cctttaaaag tgaaatttta actagttttt ctttttttc tgttactatg tctttccatt      280800
ctttggttca atacattccc acctactctt gaacgttttt tggaaagttg gcaatgaccc    280860
tttaaattct tttcagtctc tatctgccta acatatattt aggttccgta tatatttata    280920
tcatttccta cttaaataca catatttcca tttttgtgct catgctattc tgcaaatgcc    280980
tgcattttaa ggatgagaca tacatttaaa aagggcatct atgccttctt tcagaatttt    281040
ttttctaaat atctattact ttgatatttg aaattttgta cccacaaaca tacacataca    281100
cccatgtgtg cataatatac atctcacaga aatgccagcc atgtcgggaa aatgacagct    281160
ccatcagaaa tgtctttaca tccacgtaat atatcttatt tccttgtata aggcacagat    281220
cctctgttac caatatcaac ttatccccag gctctaaatc acttgaagct acttttgatt    281280
ctctggagaa tttcagaata tattttttc ctcaaaattt catgaacttg tatgcatttt      281340
gtgcctcaga ctttgaacgc cttggacaaa ttcctttatc cctgtgaatt tttaacgaat    281400
tctaaacaaa atacctgact ccactttccc cccaaatttc ctgaccttgc gtgcattttg    281460
aactgcagac ttgaaaacac ttgtgcaaac gttccttcat ccctatgaat ctttaatcct    281520
aaacaaaatg cctgtatcaa tgctggcaag gttgtggaga aaagggaatc cttatacact    281580
attggtggaa gtgtaaattg gttcagccat tgtggaaagc agtgtggcca ttccgtaaaa    281640
agctaaaagc agaactacca ttagacccag caatcccatc cattactggg tatatactca    281700
aaggattata agttgttcca tcataaagac acatgcgcac atatgttcat tgtagcacta    281760
ttcacaatag caaagacaca gagtcaactt aaatgtccct cagtggtaga ctggataaag    281820
aaaatgtggt acatatacag aatggaaaac tatgcagcca taaaaagag caagatcatg      281880
tcttttgcag gaacatgaat agagctggag gccattatgc ttaaccaact atgtcggtaa    281940
cagagaatca aatactgcat gttctcactt ataagtggga gctaaagatg agaacacatg    282000
atcacatagt agggaacaac agacactggg gcctgctgga gggtggaggg taggagaggg    282060
agaggatcag gaaaaataac tattgagtac ttggcttagt acctgggtca tgaaataatc    282120
tgtacaacaa acccccatga cactagttta cctgcataac aaacctgcac atgcacccct    282180
gaacctaaaa taaagttttt aaagaatgcc agtatccact acatttatgg gcggtctttc    282240
tgagtttcac ctcagagaaa cactcctaaa attcaagtta tgactattta gactatttgt    282300
taatgatagc tctgtgtgtg tgtcttagcc ccctctctgt ttcctatgtg ttctacttga    282360
tttttaaata aactatagga gctccacata ctaatttgat tctctacata aaatggtgcc    282420
atattctctt atttttcctt taggatttgt acagagactg tacaaaatat tttttgagtt    282480
```

```
gtgtaatggt atccaatatg gacaataaat gataagtaaa ttttggaaaa atcagttaaa  282540
agaagtgtaa tagatacata ggtgtcttaa ttgttttccg tcctcaagta tggacgtttt  282600
tgcaaagaca cgagcttttt acttcaggag acatttgtcg acgtctggaa aaaattttgg  282660
ttgccacagc tagatcatgg gggtgggtat cacttgcatc tagaggacag aggccaggga  282720
tgcttttaag ggacccacaa ggcacagaac agccccccat gacaaagagt ctttcatcta  282780
catgtgtcaa tatcgatgag attgagcaac ccaggtatag agtaatactg atgagcacaa  282840
agtatagctt gaagcctctt tttccatatg gctgtgatag attgttttaa atgatcattg  282900
gaagaaataa acccttggtt ctatggaagt catgaggaat attctgccca tgtgcttgtg  282960
aaacctcagc ttggagcaaa gaggcgaata tcatgcaagt ggcttcctag aatcatgggg  283020
ttttgtacag attatttcat catccaggta ttgagccaag tacgcattag ttattttttt  283080
gatcctctcc ctaccccccac ccttcaccct caagtaggcc ccagtgtgtg ttgttcccct  283140
ctatgtgtgc atgtgttctc atactttagc ttccgtttat aagagaggac acgcagtatt  283200
tggttttctg agctggaggc cattatcctt agaatcttct atgttaaaaa caacagagca  283260
cctcctggct ttcctgggaa tccttgtttc ctgattccag acaagcgcca tggctgtgaa  283320
atcatgtatt tatgtgtatg ctgttggatt ttaatgtgaa ataccttttc actgcgccaa  283380
gttcgcttcc aaatgtgatc ccgccaggct gaccaacaag gcattcagtc agcctacttt  283440
cttatgccgg gacctttcac aaaatgaatc atatgtcact tttcttttca gaagcatatg  283500
ccattttatt ttattctggg agtttgaatc acaccatgca tctgttttag tgttgttttt  283560
agtaagttca ctatcagtgc ttcctgagca tggtttctcg tatggggtac tcactgacct  283620
gtcccatcca tcttttcttc ctataaagcc tttactgcta tacttgtcta cttgcagaac  283680
ctccacactt tttatgagct cccatttttc tctcttcttg gtatttatca ttacttattg  283740
tgactcttgc atattggatg gtcaaaagag atccccagtg gttacactac aacaagataa  283800
atgtaggtat acttttctta attgttatta gtgttactta ttattttgtt ttattagaca  283860
ctactttcaa aggctttaca gcactgggta tgtgttctac ctttttcttt catttatcc  283920 tccacaacag ttctgtgatg aaagtactat tattaacttc atagtttaca cgacaaagca  283980
tggtttcata acttgtcagg atttcttagc cattatttga taaaattagg gatctaaatt  284040
ctgtcttcta gctccaaaca gatggttctt tccatgctat ttgctattat cttgtcaaaa  284100
gtaatgacaa aatagaactc aaatagtatt tttcttttgg ctgatttctt ctttcagacc  284160
agagaggttt ccaaggttaa agtagttcat taatttcaat ttcttcttct tttttttttt  284220
tttttttttt ttgagacaga gtcttctggt tcttttgccc aggttgaagc acagtgacac  284280
catcatagca cactgcagcc ttggcctcct aggctcaagc agtcctcctc tcttggcctc  284340
ccaaagtgct ggaatacagg ggtatgccac catgtcaggc tactttttat ttttattttt  284400
ttaagagaca gtcttgatct gttgcccatg ctggtctcga actcctgggc ttgaacattc  284460
ctccctcctt gacttcccaa agtgctgaga ttacagacat gggccaccat gcctggcctt  284520
aatttgggta tcttctaatt gatgtggact cttatgccct attcatttgt gttttgaagt  284580
gaactgactc tgaatgtcag tgatagggca ctgcttagtg ttgggggtgg ttaggaagat  284640
atgcaagttt cttagagaat aaagcagctt gctgttcaca gcagaggggg tgtaactgtt  284700
tcaagaattt tagaatacta ctgtctgtga gttctgcaag aagttaggga agcctcccac  284760
tcctggttag actggcagca acttttttgca ttataacaca acagacattt catgtccaag  284820
```

```
ccaggtaatc tgagctaccc ttgttcattc cagatccagg gttggtgagg caaaaagggt  284880
gtccccaaaa tagatgggtc tctttattga acttctgggt tatctccatc atgtacagag  284940
atacagaatc atgcatttat aaactttatg gttgaagatg gcacccacag ttacagtttc  285000
ctcccaaacc tccctggcct atctcagttc ttaaagatgt ctggggattc ccagttaggc  285060
atagagtaac aaggcagctc tatccttaaa tgatcatggc aagctgccat atggctggta  285120
ttcatcctca gttaatgtgg atattctagt aggagggcac agtgacatag gaagaaatgg  285180
tcactctgtg ttcaaattat ccctttaact tagaaggcaa gtttaccacc ctgtgggtac  285240
tgagcattgc agacttcatg taagcatatt tttgagcatt ttctacaaac cctcatttct  285300
ccaaatccca tccttttgcaa cctcaagttt atccagggga ttcacactgc ctgcatgtcc  285360
ttgtatgcgt ttcttattgt tcctgtaaca aattatccaa cctgtagtgg cttaaaacac  285420
acgcatttgt tatctcacca ttctgaagct ctgaagtgtg agtagctcgg atggtttctc  285480
ttcatcatca cccaagggtg atttctgtgt gttggcagaa aggctgtgtt tcttcctcca  285540
gactccaggg atgcatccac ttccaggaac atttgggttg atggctacat ccagttccat  285600
ggggttgagg ttcctgcttc cttgcaggct attggctgag ggcaaatttt ggcttcttga  285660
gaaccgtagc attccttgac tcctggcctc cttcctcccc cttcaaagcc agcagtggca  285720
gcttctaatg cactgaatct ctccgacttc cttttctacc tcttgtctcc tttcccaagt  285780
tgcatggctt gtctggactg attgttccat taccatttc ctgcttctca gtatcatgga  285840
cccacttgga tattctagga taatcagctt atcttgacat cagctgccta gtaaccttaa  285900
ttatatctgc aaagacaatt cacaacagta cctagattca tgtttgattt aataaccagg  285960
ggaacgagaa tcttgggtgg atgactttat aattctgctt accacattcc tgtctataaa  286020
ctaatcttaa ggttggtgga caggcccctt acaactgact tgagtaccc agaacactgg  286080
cttcctatct ttactcaacc agtgggctcc tccaggaaaa gcccaatcaa ggaagataac  286140
gccattattc tcatgctttt cctttcccct tccctcccct tctctcccct cccctcttct  286200
cccctttcct ttccttctct ttcattttga acagagtct ttctctgtct cccaggcagg  286260
agtgcagtgg catgatctcg gcccaatgca acctctgcct cagcttcccg agtagctgag  286320
actacaggac catgccacca caccacctaa tttttctatt tttagtagag acgaggtttc  286380
gccatgttgg ccaggctggt ctaacctcag gtgatccacc tgcctcagcc tcccaaagtg  286440
ctgggattcc aggcatgaat caccatgccc agcatgtcat gcccttcga agtctgggta  286500
ataatcctca gatggtagtg cacatagtta tggagaatta gtgaaccact cctccctgat  286560
gtggctcgcc cccactgcaa ataatttgtc tattttatt tttattttta tttatttatt  286620
cttttttgag acagggtctt actctgtcgc ccagtcttga atgcagtggt gcaatcatag  286680
cccactgcag cctctacctc ccaggctcac gtgatcctcc cacctcagcc tcccgagtag  286740
ctgggactac aggtgcatgt caccctcgcat gactaatttt taaatttttt gttgacgcag  286800
gatgttgtta tgctgcccag gctggtctta aacttttagg ctcaagcagt tctcccacct  286860
aagcctccca aagtgctgaa attaacaggt gtgagccacc cagcctggcc tatttgtcct  286920
ttttaattta aaagactcaa catgtagaaa ccatttttacc ccttcacctt gtgcattaag  286980
agcttccttt ttcttaacat cctgctcctt gaaatcaacc cactctactt gtatggcagt  287040
tgttatttta atatttctaa ttaagataca gttttcattt taccttacag agacagtgag  287100
cgggtgctct tgaattccag tctggctttc tccattcctt tgggtaatca caggttaact  287160
ttttccttc atcagttttc agcagtcagt gaaaggtgca ttcatttca taaatcagcc  287220
```

```
atttggcaac atttgaatgt ttaatcagtt tgcgatcaca tcaaagaaca agggaagttc  287280
ttgggagatt tattacctcc tttggaatct gtgttcttag ctacaaaggt gcaatgactt  287340
tttctagttc tctgcccag atgtctgaac tgttaatatt tacagtgctc ctttcctgaa  287400
attcagagtc agcacctcat tttatcctat ttgtatccca acttacttta ttcaaagaga  287460
ttttacaacc tgagatagct ccgtaggaag agttcagttg tcagaagcaa tctgatccat  287520
ggaaattttc tggtgtttgt ttttccttga attaatttgc aggtttaaat tcttgcttag  287580
gccactctag gacttttaat tgctatttct taggaaatat tccttagaac atgaagcagt  287640
ctgtctttca acacacacac acacacacac acacacacac acacacacac acacacacac  287700 acccctagc atacgatcca gaacaacgtt ttatctttt tttttttttt tgtaggaggg  287760
agtgtctcac tctgtcaccc acgctggagt gcagtggtgc cctcatagct cactgcagcc  287820
tcgacctcct gaacccaagt gatcctccag cctcagcttc caagtagct gggactagag  287880 gcacacacca tcacacccag ctaatttaat tttgaaaaaa cttttttttt tgtggagaca  287940
aggtctccat gttgctttgg ttggtcttga attcctgggc tcaagtgatt cttctgcttc  288000
agcctcccaa agtgctgaga tttctggcgt gagccaccac acccagccct aacatttat   288060 tcttttactg actgtgagat tttcattgac ttacgctatg tcaggcagac ttttcaagcc  288120
ataacctggc tttggtgatt tattatttta gctcttcatg ttttaacagc ttctctgcta  288180
ccatgatagg ttataataag tgatagaaga aaggcatttt aaagtaattt atgaatgtgg  288240
atctcatttt gcttagctaa aaaaaaaaaa gttttttttt tttctagaga atagaaccaa  288300
acagtgttca ctgtatcaca tattcctttt agtgtattga gcattaatgg ggtatttttg  288360
cagcatcaga tcttcacaag gctggggttc atcagcagca cagtagctat taggtgattt  288420
tactcaaggc agcaaaattc gtttcttata acacagtctc tattgaagac acactctaag  288480
gcagtttgcc tcatctattt agcttttccaa aattctctct taaattgcag tttaatgaat  288540
agactaaaac acaaattta agaaaaatgt agttataaga tatgaagtgt cttttaaatc   288600
tgccagtggt ttaagggata gtatacattt aaaataaagt tataggcact gatttagtcc  288660
tggaaaataa tggcttttat tcaataagcc agtatcagaa attagttttt gttttctttt  288720 ttttttttccg tgatgaaatg tggtttctag tactggataa gaaatgcatg agaaataatg  288780
tatcccagca tatttaatat gcaacagtgt gatctcagta gccttgcaga tggctgagct  288840
gaggcactaa aagtgatgag atgacatttt gtattttcc acacgttctt gcccattctc   288900
aggtgagtct gggctctcat cagtatttaa atgctgtttt accttggcaa gacatttagg  288960
tccagaaaat agtttaaaaa attaacatct acgcagaaag aacctccagg tagttaaaaa  289020
tagggcaatt gcggataca ccacatcctg aagactagt gttgctaagt aaaccacatt    289080
attttaggtg tttcttcctg acatttttat tttttcttg tgttatttta attctggaac   289140
ataactggga actgagaata ctacatggga cccttatctc ttttctttgt tatgactgaa  289200
aatcataatt tgaaagatgc ttggaaaagg gaaagcttaa tatcttacac atatttttat  289260
aagacaaaaa tatggaaaga tatgaaccat aaaatcagtt tagaatggga agggttagta  289320
aaacattttt tttgagcaga aaaggaatca tggaatggac actttataat atagtaattc  289380
agccaattta tttgatggaa ttcaaatgtc atgtcctctt tgtagctaag agtgcacatt  289440
agcattaacc ctaaaccaga ccacttggag ccaaagagat gtgtatgtgt gtgtgtgcat  289500
ctgcttctgt gtgtgtgtgt ttgccccatc tgagtgattt gattttcac catctctcta   289560
```

```
tttttccact tccaaaattt aagcatttag acatttatta tattaaatat gtttgcattc  289620
tccctccctc cacatgcagt gttttacaaa tttcctatca gactgttccc atcctgcaaa  289680
cccccagagc tctatggctg aggtactcct ctttctgttc ccttctccat gcagatggaa  289740
tgtctgctgg gaactatctt caatctatat gtttcccatt cgtagaggtg gctaaatctg  289800
tgacatgcat ccatcctcat ccaatagtgt ctccacatga gtgagctgga taatgcaaaa  289860
ccaagcttcg acatcagtgg tatgaagtac acacacacac acacacacac acacgcac    289920
acacacaaat acaaacacac ataatctctg tagctcagat tgggattgtc tagggttaat  289980
atcttttgtg ctaaaaatat ccctgtgcca cattgaagct tattataata attattaatt  290040
actgatatat ttcaactgtt atgtctccta aaaatatgca tagattatta agttttccct  290100
tctccttgtg tttttctgat tatgattttc tatcataaag gtgaaagtga taagggtccc  290160
atgtagtgtt ctaactctaa acctaatact gaccctaaac agaattgaac gctttaaact  290220
aacccatggc ctttgaccat tgcttcttga ccgttgagtt aacccataac cctgaacaga  290280
gaatgagaaa ttgaacccaa atttgaaccc aaaccctaac tagtgactgg atatgaaacc  290340
taatcctacc caactttgaa aaagaactca attctaaact caaaagcaaa gccaaccgaa  290400
cacctaatct aactttaatg taaaccttttg aacttaccct taacttttgc cagtagccct  290460
tgactcttga cccctgatct gaacactgaa ggcatccccc aaattctccg acccatggcc  290520
tttgatccta atcttgactt tgatcactg tccctaataa tgaatataat cccttgatca  290580
taacattgaa ctttgctcct accctgacat tcaattagtg atctaaccat accacaacct  290640
gaacttgaac ccaaatccta acatgaacct tcctccatac ctgaaagcta tcctaaccct  290700
tgacctttga tctttatttt tctccttgac tcctgactgt gagatcccag cctggactaa  290760
aatgtataca cacactcaaa atctttttg ttctgaatcg ttacccaaac ctgaacttga  290820
acccaaaccc tgaccctacc caattacaaa tctgaataca aaacctatcc ctattctaaa  290880
gttggggatt tgagtctctt agtcccgtag ggtagatgtg gtgtttgcag ccctgcagcc  290940
actatggaca ccacagactt ggacaaaatc tccaacgtat ttttgggaaa aaaggatgca  291000
accattagag aacaagatgt tgaaactttc atccataatc tctgtttgta cagacttcag  291060
ggtgaaatac atgtggttgg aattgtgata tttccagcca caaaattgta ttatgttgag  291120
ataatgtggg tttccctatc cctgaaaatg tgttcatcca accaatagtt acttgtacca  291180
gcagtgcacc agggaccatt ttgggttcct ggaggcagcc gtaagcaaaa gcatcccaga  291240
tccctgcttc tggaatccct gactatgaaa ttggcatcct cataatgaat gtaataaaga  291300
aataaggtaa ataaagaaat aatctagact caaatgtgaa ctttagtcgc tctggaagtc  291360
caaaccctgt ccaaacatgt ccgccgatta ctttcagagg atgggtgatg actcaggtta  291420
atatggttat ttttggagcc cgtcttacct attgtccttt atagatgatg tgttttccac  291480
ctcagatatc aacatgaaag actgggtcac ttctcaattc agaaatccac tcaaggttag  291540
gcactttggg aggtcgaagt gggaggatcg cttgagccca ggtgttcaag accagcctgg  291600
ccaaatggtt aaatcctgtc tctacaaaaa atagaaaaaa attagctggg tgtggtacca  291660
cctgcctgta gtcctggctg cttgggaggc tgaggctgga ggatacctga tcccaggagt  291720
ttgaggctgc agtgagctgt gatcatgcca ctacactcca gcctgggcaa cagagtgaga  291780
ccctgcttaa aaaaaaaatt cattcaacta tgtgtaagag agagagagag gtgtttatta  291840
gatttaactg aggatttggg gagaaacttg ggggcatttt atcctatggg ataagaggga  291900
aaaataaacc ttttaaatta aacatctcgc ccttttgctg actacctttt ggctatccta  291960
```

```
acatgaaata ttcttctgga tgctacaact ctcagctcca ctgatcggct agagcagatt 292020
caccatcact tcttgttttt ggatttcacc ctctgccact cgtgatttaa caaataattc 292080
tctgaaaggc agttctcttt tgaaaaagag ttttgcttct ctgtgttaaa ataatgtgtg 292140
ctgctgttaa aatagttttg tatacacgag ggaactcctt tagaagcttt atcacgtctc 292200
ttagctgtgc gtgcaatttg agtaattact atgtaccaat tccagtaaca tagccaatac 292260
atcagaactc tcaggggacg tagctgggaa ctttcttgca aaacaactcc cacgtgttca 292320
ttcctgtctg gaaaccacca gtaaaattta aatcagtaa taatttctcc aggcacagca 292380
actgagaatg gtagaacatt agttttaaaa accatttaa taaaatgcct ttataaatat 292440
tgagacttaa ttatttagat taatttgttc cagttaatga aagatctctt agcacaagac 292500
tgggaaaaat tagaacacgt ataatttct tcattccaga taaacaatta ttttaatgtt 292560
tatctggtat ttgaccacaa acttaaattc ctgggtttcg taggattaga aattttaagg 292620
ttagtaatca ctcccgttgt taaactgctg gattttacct aaaattactg caaggatgta 292680
tcattttttt atacctcaag ctgttttgtg cagttctgct tccaacttcc atagacaatt 292740
ttaatcattt ttttttgttt tttcttatca gataatgttt cataacatgg atgtgaagaa 292800
ttaaatgaac atccttctgt gcacaaatta agattagaac acgaagattt tgggattccc 292860
ctcagttcct tttataaatt gtatttcttt ggacctgtcc taaggataac cactttgtg 292920
aatctgattc attatttcct tcttttatta agttttattt ctgcaaaatt gtcatgacca 292980
gcataaccca aagaatatat tgttcgctct gcttttgatc tttataaat aggatcatcc 293040
tatgttcttc ttgacctggc atttcccttt tcattgaata gtatgttttt gattttaacc 293100
atgaagatgc ttggagctgt agtttatttg tgttcactga tatatggaac ctcacccgat 293160
ggttatacca caagatattt aactctttca gaagctggaa atttgaattg gccttatgta 293220
aagagttcag ctattaggat tctgtgcgtg tctcttgttg aaaaaaaatg cagaagtttc 293280
tccaactaga aatgtattta ctggaccata ttttatgtgc atatttggat atacactctc 293340
aggttaaaaa ctgtttaagt ggttggacag ttttattcac ccaagaacag tatcagagtt 293400
ccctgtcctc tctgcattca ctgcactgaa tccaaaattg aatagaaatg aaattagctg 293460
tctttgattt gttctctctt tagacaaaag gcttccaatg ttgtatcatt atgtataatg 293520
tttgaagtaa gatataaata aactaccatt ttcagataaa gaaatgttta tttctttcct 293580
taatttgata acatacaatc ataaattggt tcaaggcatt tttctttatc ttgtaagatt 293640
atccttgctt tgcatttaat tttttcatgt agcaaattaa ataacttaac tttcaaatgt 293700
taaacttagc ttgatattca gtatcttctt taatactgtt tttgtatttg tgttagata 293760
ttaatcattt ttttctatct ctgtacaaaa caagatagac tataattttt ctttgttgag 293820
cttccctggt tttagcatcg actaatagta gctgtgtaga aagagtaaga gaacatttgt 293880
ttatgcttc tgggagagtt catataaaaa cacaaattat tcattcatta ataggtggta 293940
gacttgccat tcagtccacc ttggacagat tatttctttg ttgtacttaa aaccatcatt 294000
tatttcctcc ttgatttgtg gactacatta catattgact tcttgtatat atgaagaaaa 294060
acatgtttgt atgtctgcac atgtctgtta tcactctatt atgttccctt tctgcatttg 294120
tctgtctgct atatacattt tgctaaactg tcataacaaa ttatgagaaa tttagcagca 294180
taaacgaata gccatttatt acatcaggga tctgtaggtc agaaatcctg gtgcagtgga 294240
gcctagcttg gtcctcttct tagggtctcc catggctgaa atcaagagat tggcagggct 294300
```

```
gcattccttt ctgggtgctg tagggatgaa tatatcacaa catatagatt tttaaaatct   294360
aattatttgc actaacttct gattttacca cattagattc atagggtgaa ttcctgtcat   294420
attgatcatt cgagtcttat ggaagctttc tttctatctt acaacatcgt cagattgtta   294480
caggttttca tatgtattta ttcttatgct ttaaacaagg ggttttctct gttttatgta   294540
aagtttgacc taatattttc atcatatctg tgttatactt gagatgtata ttgtgaatat   294600
ataagcacac acaatgaact attcttcagc cttaaaaaag aaggaaataa gaaggaattc   294660
atgtaatttg tgacaagatg gatgtacctg gaggacatta tgttaagtga aataagccag   294720
gcacagaaag gtaaacactg catgatctca attatatgtg gaatctaaag aagtcaaact   294780
cagagaaaca gagagtagac tcatggttgt cagggactgg aagttgggtt catggggaa    294840 ttttggtcaa gaggcataga catctttctt cttcttataa tattatgttc ctatgttcta   294900 gttttttgagc tattaggatt tccatatcag cattttaggt cttatttatg cttgcatttt   294960
ttatattctt gataattttta gtctttctat atcttttggg tttaaatttg tctcttgagt   295020
tggatgcatt cttcatctta ggttttgtta caaacatgag attgtctgga aattttttta   295080
aattcatgag tttaaaccat ttatgtttgt tgaacgttaa ttttaccgat gcttatttct   295140
gccatcttgt tttatatgtt caattagtt acttcaggat aagcgtaact gtacattttg    295200
tttttgaaaa cataagtttc tacctgtcat ttaatagata tttaaataca tagttattta   295260
aaactctgtt atctattttt tatccttact atggttaacc ataactgatc acagggaatg   295320
ctgtttattt ttcccagttg tttttataaa tttaacaaca taatattggt ttataccaat   295380
tttgttcaat ttctatatga aaatcaaaaa tatatagaat acatcaagga attcattgac   295440
agatctggga atttctaaca agataaactt ttttcaaaca tgcatctttt ttagtcccac   295500
ccctagtgct atttaagtag atatttccaa gaatttaagt tctgggctat tatccatata   295560 tgattttttgt cttccttttt ctacccattt tagccaaata gaaattatag ttattggttg   295620
tgcttgcatt tcatatattt ttcagaattc ttaccaaatt agttatattc tttgataagt   295680
attttctcaa agataatttt cagtctttaa atctttgctt agcaaaatga ttgaatctct   295740
ttttgatctt tttttttaac ttggcctata gtattaaatt ttttaaatt cagagttatt    295800 tttcttcaaa ctttcaaata tgactcctgt gtctgctaat gtcttgtgct atgactggga   295860
agtttgatgt caatctgatt cctattcatt catagctcac ccattttct ctctgaaggc    295920 tattagaatt ttctgtttgt ctttgatgtt cttaaatttc ttagtaatat atctattcag   295980
ggcactcttt gagcccattc aaaataaggt ttttgttctt tttgtttgtt tcaagtgtat   296040
tttcattctt tcatcaactt agttcttcct ctgtatttt ttttctcttt ctgttacctg    296100
atcctggtat ctctaacaaa gtcatccatt tttccaagga tgcctttctc tccttattc    296160 tttcctgatg ctttctggga atttcttcca tctgatcttc caatttggta attcattcta   296220
tgatttatct taactattag gttcttgttc atctttacta ttatttattc tatacctact   296280
atatttacca agttctcttt tacttcttat tataatctcc tatttgaaat atattccctt   296340
aggtgatcga atatatttat tttgtctatt gtaatttctt cattgatctg ttccaatcat   296400
tatatttaac gtagaagaat ttttttttct gttgagagag agcgtttggt acctttgtaa   296460
atgttcaggt atatagctct tgttaaaaca tttagcctgt gttctcctta ggtgagtgga   296520
aactcatcca tcactctggt ttgtaattac gcatgtgatg ggacctaagg gcagacccaa   296580
gtctatgttt cttctatgag attaacattc aacaaacact tttagatcac tctggcgcac   296640
tgaagaagtt tgaaatttga gatttggctt taaactctct aaaggagcca gcattaggaa   296700
```

```
gaaacagcct ctttagcttc attcctgggg gtgtggaggg gaaggggtg  aaacaggaaa 296760 agcccatagt ggccataagt gactggtggc cctgaaagtt tttaaccagc tcctcaacgc 296820
agctgagttt tccgtgggct tgccagagtc ccactacctg atggctgccc tcgagttcta 296880
agttgtatgg agaagagaag atgggaggga gattagacaa tgattaactc aaggcattct 296940
ttataagaga caagagtgaa cttaatactt tgtttttaaa ccagcatctt tctattacca 297000
cttccaccct ctgccagaag gtgcagccac tcccattcac catatataca tgattcatca 297060
gcttgtaatc tcctcgggat ggcttatagc ttactgattt catgttctat tattgctctt 297120
tccgcagatt gatgcctcgt cttatcctct gtagttttc  aaaagtagat ttctgtggag 297180 gaagggcat  tatgttctat tcaccatctc aaaagaagca taactctctt tcttggatat 297240
attactattt ttcccacgtt gtgtatgctt ctcattaaag gtaggattct aaaccatcca 297300
aatgaatctg tgccaccacc tgcccctgga ctttggactg aagaggattg agaaatggtg 297360
aaatacttaa ctatttgata gcttccttca ttcccacaga ccacatcaga tgtagttagc 297420
taatatacca attaacaaaa ttacccagga aatgcaacat atatacttat ttcattactt 297480
gtcaaaactt tctaaatggc tttcatctat ttctaaaaag aatcccaaat gttccaggaa 297540
caatttccta atgttctggt tttgaatatc acagctcatt tatcagcgta tatcatagct 297600
atgactatag acgccaaaat attaagtaat tcataatgac aatttggaca atgaagggta 297660
tattagaact tctttgagta ttttttattg caatatgaat ttttaaccaa agacttgtat 297720
gagctccaga gagcaaatcc actacatttc cccactctgc ctcccaaccc atcactatat 297780
agatccattg tggagctttt ttacttcttt gtggtgtatt aaaacaaagg atataatatc 297840
ccctgattat ggatgaaagt gatggaacat ttactgccat gagagtccct tatgataagt 297900
ggtagctgaa ctggaagttt aaagaactgt ggcagacagg atgggtaaa  tcaataggat 297960 ccaggaccta ggaatgcatc aggaaagaca gcaacaggga aggatgagct agagcaattg 298020
aaagggtgat acatatattt ggagccaatt cttttttatgc tatcatcaag ataaaaccag 298080
tattcctcac ctggtagata tttctctttg caaaggtgga tattccacag ttcacttcca 298140
cagacctcat gcaaatgtca gattcagcgg ggagagggag caccccagtt tctttggcag 298200
cacagaatat aatgcatcat gtttatttgc aagcctggag atattcttgc atacatattt 298260
tatctagcag atgacactgg atccaattaa ttggtggctt tgaaatatat ttattggaat 298320
tcattatttt gggttatagt tgtttctgtg atccatgcaa tctaccagga tactcttcat 298380
gcttttgcat ttaaaagaat gacaccaagg gcttgtgaaa ggcacattct ggggtccatc 298440
ccccacaatt tgtgttctgt tgctttaggg gagggtgtga ggatttgtgc atctacctgc 298500
tttccacaaa gtagggtccc tgctggtata agggcacacc gtttaagtgc tactgcacag 298560
aagcatcaga tgtcattaag attgtgtgtt atctacattt cttattgttg ctcaactgcc 298620
agttactctt ttcataaaat atgtatctgt cctatatagg gctaagaatt aatttatccc 298680
agtctataac tacagagaga agcctactta atgagcattc ttgatggggc ataccaccca 298740
taaatatggc accttagcat ttgaaaaaac agaagaagca ggaaagttct ctctgacctt 298800
ctccccatcc ttctccccta aagccaggtc ataagaccct cctatgagag gtgactctct 298860
ataccaagag gaatagaaca ttcttatctc tgaggacaaa aggacacaga ggagaatctg 298920
aacacacagg ccttgctaag ttctccccag ttttttccca ttagataata aacattttta 298980
cttcaatcat actttccaat gactgtccac tctttatcaa acctaagtat ctaagcacaa 299040
```

-continued

```
aaatccacag gtttccctgt ttcttttggg tcttcattgc cttatgaagg ctcctgtgtc   299100
atataaaact gttattaaat gaagtgcact ctttgcttaa tctgtctttt gtcatagggg   299160
cctcagccat gaaactaaga taggaagaaa agatatttct tttcccttat attattcaac   299220
aatattctag ttatacatgt aagcttaacc aaaagcttct agaatatcaa agtaataagt   299280
gtgaaatatg tgtgtgtgca cacatgtgtg catgcatata tatacacaca ctacattgta   299340
ggtgtgtata tatatgtata tacatataca catatatatt ttataagatg cgtatacaca   299400
tatacatttt tgtatgtgtg tgtgtgtgac agagtcttgc tctgttgtcc aggctggact   299460
gcagtggcgc tcactgcaac ctccacctcc tgggttcaag tgattctcct gtctcagcct   299520
ctggagtagc tgagattaca gccatgtgcc accatgcccg gctaattttt gtattttctt   299580
ttagtagaga tggggtttca ccatgttggc caggctggtc tcgaactcct gacctcaggt   299640
gatcttccca cctcggcctc ccaaagtgct gggattacag aggtgagcca ccacgccaag   299700
ccggcacata atacatcttg taaaatatat ttagcaaagt ctatttaaaa ataattaata   299760
gtttattaaa tcttatgtag atttttttt caaaatgaac aagcttctgt ctttccaaca   299820
aagctttgga aataataatc attgcatttt cctctaacag gttaatcagc agatcaacta   299880
aaaccaaaat gagtctttct ctgggcacgg tggtgcatgt ctatagtccc agctactcag   299940
gagactgagg caggaggatc acttgagccc aggagttcaa ggaccagctt gggcaacata   300000
gcaagatacc atctctaaaa aaaactaaa aattaaaaaa aaaataagt cttcctataa    300060
ctgtatgaca gggctaaggt gattttattt gacagaggaa ttaaatttca atgtaccaag   300120
ttctatccgt atgatatctt ttctgatggt tggaagggca ccaaggggct tccatgaagc   300180
tcagtgacag cattttcaca tggaagtcac tgcagcggaa agtagggtac acattcttgg   300240
taaataatat atgattgcac tattgatgaa tagcatttca aaagctctgc tatttattgt   300300
ctattgaaag ataaatgaat ccagcaagta aactgcctaa atatttgta cactgttata   300360
aaatgtaaac acctctatca tactataaat ctccctcccc tccgctggaa aagacttcaa   300420
gctgagatca tcctcgtcct catcacatga ttgcttggaa tagagttgtc cctgaggcca   300480
cctgtcacct aagaggactt gtattcattt attcagtgtc catgtaatga agaataaga   300540
cagacatact gtgaatataa gaacacagag ttcaaaagac tattctgatt gagcagaagg   300600
aagatactaa acaaatatta gatgaacaaa gcttgtgtgt atggctttgg aagataagcc   300660
taggatctta atcttgttta taacacaa ctattaaacc ttcctgcgta aaatacattt     300720
taattgagac ttagcatgaa gatagaacac caagtctggg cattctgaaa agtttagacg   300780
cagaggaata actggcaggc agtgatttaa agtggataca gattttgcc ctggagttgc    300840
agatgcgtgt aggaatgaaa aggaagtaat gggtgtgata accgatttaa acactaatca   300900
gtgagcccca atattaacc atatactggg attctacaaa gagatgccat ggtaaaaata   300960
tgaattcaag tgttttaacc tgtatagctg gatacattct tgtgatatta acacgggaaa   301020
taagaaaaga gacgagtttg aatgagaaaa agatgtttag ctcaatatag cacacactga   301080
gctttaggct cgaataagac atctgagtgg tggaagactt agtcaagcat gggagaagtt   301140
agagctgaaa cccaggtaaa atccttcaag ttacaggcag aaatcattac cagatgtgtg   301200
gtggagtcac acggggatg tgagtcctaa tgcctgtgca gatgcatggg gaatgcagtg     301260
tcttttgaa ggactggttt tagcgctgca agaagtaaag taaattctct tttacctgca   301320
ttcttgttcc ctctggtgct tttatgagga cctaggcaag aatagtattg aaccacttat   301380
accatccatc tgttagaaga acctataata cagaaatatt tgctttgggc tgaactccaa   301440
```

```
acgtaatact taatgatttc tcttcaagtt tgttgacaca ttctacatct ccacatacaa   301500
tttgctccca gtcgtttctg agatatgcta cagaaagtac aattgatcaa acgttggctg   301560
tagggattca agaacagtcc tgtgactgca ttttcgttcc ttcctgaaac tattccaagg   301620
ccataaaaca cctttttttgt gtgaactgtc tttctgtatc ccatttcaga tgatatcttt   301680
tttcctttaa atacagtctt ttatatttt ctaattgtct gattgccaaa acaatatatc   301740
tgcattgcta taaatttaca gtatcaaaga tcatacagaa gaaaaatctt ttttaacaaa   301800
agaaaaccat tgttgataat ttagtttaca tacatacata tgtacataca tgtatcctct   301860
tagcactctg gggcccggag tagagagcaa acctgtgaaa cagatagata gatagataga   301920
tagatagata gatagataga tagatagaag atatagagat atgttagagc tatagagata   301980
tagtctctag atagatagat aagaaatatct gtattctctc tctctagaca aatgattagg   302040
aaacagtcta taagaacgtg tgtgtgtgtg tgtgtgtgtg tgtgtgtgtg tgtatgctct   302100
ctagaggtag aatatatctc tctgtaggga gagagactta tgcatgtgta tgtatgtata   302160
aaacaaagaa acaataaaaa cacaaaggcc caaatatcaa ccagaagaaa ctgaccagct   302220
gtaatgggac aattgaaaca tctgtaagaa tatttgtact ggatttaaaa tgataaagac   302280
ataaaagttc atgtattcat catgacaccc agaataaaac tcactggtta tattactagg   302340
ccacgatcgc attttcctga atcttgatca ataaaagaat catgattttt tcccactttt   302400
cctatatata ttgaatttca gagtaactaa aaaattggtg attacaagta aaatttcaga   302460
taatatatgc agaaagaaca atactatctg aaaatcatta ttttgtgaaa ctccaaatta   302520
agtaagtata ttaatctgtc ctcacactga tctaaagaac tgctggacac taggtaattt   302580
attaaggaaa gaggtttact tgacttgcag ttccacatgg ctggggaggc ctcaggaagc   302640
ttacaattgt ggcagaaagg gcagcaaacg tgtctttctt cacatggtgg tggcaggaga   302700
gagaaatgag tgcccattga aaggggaaat cccttataaa accatcagat cttgtgaaaa   302760
ctgactcact accacgagaa caccatgggg gaaactgccc ccatgattca attatctcca   302820
cctggttcct cccacaacat gtggccatgg aactacaatt caagatggga tttgggtggg   302880
gacacagcca aaccatatca ataagagatc taggaaatta tctctgatta tttgaaaagc   302940
ttcgcaggtt tatatatata tatatatata tatatatata tatatatata tatatatata   303000
tgtgtgtatg tatatatata tatatatata tgtgtatgta tatatatata tatatatggt   303060
gggattcatt accaactgaa tgtaattatc aaccactctt aagataatta aaagtaacac   303120
tagcaggtat catgtaagtc cttattaaat tcagtataaa gtacagagca gttcctgggt   303180
gcgttgtttc ctacaaaggg caccataacc ctaaggaaga aaacaagat gtgattagga    303240 aacattctgt taattctaga acatgggtg ttccttcagca gtaatgttca aaatgtggtt   303300
cacaaagcag caacttgtta gaaatgcaaa atttaagatc ctatacctgg gaggaggctt   303360
cctgaatcta aaattgaggg tgtgggttgc aaactattat ttctttccca aacccatctg   303420
tgatgtttat gcttgataaa atttgatggg acggttcatt gatttccata aggaattaac   303480
gatgtaagaa aatgagaaga agaattgtat tatggaaaag agggtgtcaa tattttcact   303540
tgctttctct ttaaatgtgt ggatcacaag atttgctttt cattaaaagt attcagatat   303600
atatacgtat ttgaaataca tgtgcctata cactaacccc aaaacagctc attaagaatc   303660
tcttccactg ggacataggc atcagtattt gttaaaatat cactaagtgt ttagtgtggt   303720
tgatgagtgt agaaagaata tattttcacc aagcttatga gatgggcagt ttggggccag   303780
```

```
gagaagaagg cagtgaaaga acttgggtga taagcagctg tctacttgca aaacaactta  303840
ttattaatga attgggactt taaatttttt tttttatttt cataggtttt aggggaacaa  303900
gtggtatttg cttacatgag tcacttcttt agtggtgatt tgtgagattt tggtgcaccc  303960
attacccaag cagtatacac tgaacccaat ttgtagtatt ttatccccca accccctccc  304020 acccttccc tctgagtccc cagagtccat tgtgtcattc ttatgccttt gcatcctcat  304080
agctcagctc ccacttatga atgagaacat aagatgtttg gttttccatt cctgagttac  304140
ttcacttcca ataatagtct ccagtcccat ccaggtagct gtgaatgcca ttaattcatt  304200
tctttgtatg gctgagtagc attccatcat atatttatgt accacagttt ctttatccgc  304260
tcgttgattg atgggcattg ggttggttcc acattgtgac ccaatgcttt taaaataatg  304320
tgtgtgtttg gccacgaaca taagccagaa cactagaaaa attgtttact gaaagccatc  304380
ttagtttcag gaacacaaag gaaatgaggt aatgtgtgaa aagaaccttta aaaattgtaa  304440 ggcattttgc ataaagatgt taggtgcttt ttgaagtttc tatttaaatg tggtcaatta  304500
gagaggtttt ttttttttca ttttatgttt gccttgaaag catttagaag tatgagaata  304560
tataatttca ttttgtaaaa cacaatatgt tgaacctaat aggatctttc ttggaaactg  304620
aacattgtcc tgggttttgg aggcatccca ttgaaattta gccatgattc catattcagc  304680
aaattgctgt ggacccagat acatcttcgc tgaccagaag tctttccaga gtggaagatt  304740
ttagtaaatg tacaagtcaa tcttgtagaa ttagataaaa tgcattctgt tttccatcac  304800
ttgccgatat cccccccactg ctaattaaag gaaacacaat ccacaattga tttacttatg  304860
taaatgtaga ttacaaacca acaacatgat tttaagagtc ttaagaagtt gagggctatt  304920
ttgaatgttt actcttggag acatgtatat ttaggtgtcc tggtcaacaa gatcaattgt  304980
aggaatggtt ggtgcaatca cattggtcat taaatacaga catcacacat aatcaagcag  305040
atttagctca gggtatgggt aactcaacat atgaacacca ttcaaagtat ttccccaaaa  305100
ggctggcatg gtggctgaca tggtttggtt gtgtccccac ccaaatctcg tcttgaattc  305160
ttgtgagagg gacccagcgg gaggcaagtg aatcatgggg gcaggccctt cctgtgctgt  305220
tctcatgata gtgaataagt ctcatgagat ctgatggttt taaaagggg agtttccctg  305280 cataagctct cttctgttgt ctgctgccat gtgagacatg ccttttacct tccaccatga  305340
ttgtgaggcc tccccaggca cgtggaactg ttaagtccat taaacctgtt tcttttgtaa  305400
attgcccagt ctcaggcatg tctctatgag cagtgtgaaa atggactgat atagtggctt  305460
acgcctgtaa tcctagcact tgggagggc aaggcaggca gatcgcttga gctttgcagt  305520
ttgagaccag cctgggcaac atggtgaaac cctgtctcta taaaaatac aaaaattagc  305580 tgggtgcagt ggcacaagtg tgtattccca gctacttggg gacactgggt caggaggatt  305640
gcttgagcac aggattgctt gagctagaga tgcccaatgc atctcaaggg tgcagtgagc  305700
cgagatggcg ccacttcagc ctgggtgaca aagtgagatc ctgtctcaaa aataaaaaa   305760 atatttcccc aatggggaca tatggcttaa tagttagggt tattgtttgt agtgatgaat  305820
aggtttggaa ataggtagtg gtgataatta taccacattg tgaatgtaat gaatcccact  305880
gaattgtaca ttttaaaatg atcaaaatgg caaacttatc ccacacacaa ataaatagat  305940
atagatatac atagatatct tcatatggtt tttcttgttt tttaattttt tatttttta   306000 ttttatttat ttatttattt gagatggtgc ctccctctgt cgcccaggct ggtgtgcagt  306060
ggcatgatct cggctcactg caacctcctc ctcccaggtt caagcgattc tcctgcctca  306120
gcctctcaag tagctggtat tacaggcctg tgccaccatg ctctgctaat ttttgtattt  306180
```

```
ttagtagaga cgaggtttca ccatgttggc caggatgatc tcgaactcct gacctcaggt   306240
gatccgcctg cctcagcctc ccaaagtgct gggattacag gtgtgagcca ctgcgccctg   306300
ccttcatata ggttttaata ttagttttgc ttaatttaaa gacagtttga ggcagtacag   306360
cataaagtac tccccacatt tcatttattt agttttaatt gacaagtaat aattgtacat   306420
atttacgggg tgcatactga tgttccaata catgtaatat acagtgatca gatctaagta   306480
attagcatat ccattatcta aaacatttat catttctttg tgttgggaac attcaatttc   306540
ctccttctag ctatttgaaa ctacatatta tattatttt aactacagtc accctgcagt    306600
gctatggaac acgagaacct atttctcctg tttccccccc tccccacgaa gaaataaaag   306660
aggtgaaatc tgacacacaa agcaaaagga acaaagacat tcaggtactg gagttgagca   306720
taaattttac ctcacaattt ctggcagata aagcaaaaag agagagaaaa acaattggtt   306780
ctgggattag tatttccggc aagagaaacc ttctcccttt tccctctgat tcttggtgaa   306840
gagcagttat gatgttggag ataaaaggag aagatggcag tgatggttcc ttgttctttc   306900
cttctgcagt ggctgtcagc ttcgcctgtg atattaacag taagacagga aagcctgaga   306960
ccgcctcact aaagacagac ccttcccatt atgtgtcacg gcagccttca cccttgaatc   307020
tagaaaatac tacctgggcc gtgctaagtt tattcttaaa agcctaacac cgtgtagcta   307080
ccgctgccca atgcatctgc ccaaaacagc actcccaaa tcctgaatat gcatagaaat    307140
aacttttcag ttttcatgcc tactgctgaa ttgtaccaac agagattctg atttggaagt   307200
cagcggagga gtctatgcag tttaaatttt tacagacaac tcaaggtttt gtggatatat   307260
cctgagacag ctcagccctc ccaggctgtt ggtaccatag gggctgggag agattgccct   307320
cacttacccc gcaaacacct tgcaggatgc agaacagctc ttaataaata tgtgttatgg   307380
aaataaagga atgcccctgt gcttggaagt attaggctgc ctctctctct ctctgtctct   307440
gtctctcctc tctctctctc tctctctctc tctctctctc tctctctctc tggttcattt   307500
tcaatgccgc tgagtcatac agtgagaagc agcttagggt cattaagaga ttgaaacatc   307560
ggagaaaaaa agtgaatatg ttttcatttg aatctctatt tttaactctt tctgaccttg   307620
tctgtcaaat ttggctacct tgagactgtt gcagtgataa tgaaataagc ctatgctgtt   307680
ctttggaatc attttagaca tatacatgtc taatatatat atatatatat atatgtatat   307740
atatatataa aaaatactta ccatatgtga tcttgtttga catgcctttt ttctatacaa   307800
aagcacatga atcaccatgc ttcagcaatg aagatgttgt gttttggact aaaggcagtg   307860
taaacacaac atgctattag cgttttctt aatcatcact accacccagc cgttgtcttc    307920
ttgcacaaga taataatagc atctcacatt tccatggagc tttataatgc atgaaggtct   307980
ttcacattca tcgtttttgtt caatgtcata gggagaggga gcttcagtaa cctcaaagcc   308040
cagtgtgcag aaagagaaac tgggattgat tcaatcattt ggccacagtc ctaggactct   308100
tgaatgtgtg tgtaactcag gcagggtgaa aatcccagaa gatacgtccc catcccaagg   308160
gcacctaccc aggttcaata acttggttac aactgacact ctttggatga tgctgcactc   308220
ttcacaaaca cgtatccaaa cctatcatga acccaaacca gagcaaacat caaatcccca   308280
ctcctaccac atattcacat cttgtattaa caccaaagcc tgaagcaccc tgacaacatg   308340
tgtccagaag atgttgaatg tcttccaccc tgactgccac taacctggtt aaagccagga   308400
ccaactttca cctggacaac tgcagtggac ttcttccaaa tgcacgctcc tgcagtcctg   308460
tccaccagtg gctcctgtga gctttacgaa accataaatc ctatcacatc cctgccatgt   308520
```

```
tccaactctt atgccttgtc attgctttac aataaattcc aacattttac tctctctttc  308580
aagtgtgaac tcactttgcc tactactgga ataacgttct ttcacatttc cttgctaatt  308640
atgagtcagc tacaccggga ctccttctgt tctcctcacc ctttaaacat atttcccatt  308700
tgaaacttcg caactcgtaa ttcttttcag gaatgtttcc cttt catcat cttgtagctg  308760
cttcgttgtc atcatttcct ttcatttcca cctcttcaga gaggctttgt ttagaagaaa  308820
acataggagc aaatatttgc cagctagggt tatgcaaaag tttcttacat agaacacaaa  308880
atgtaagaac cgcaagagaa tgtattgacg gggccttcca gacaccatga agaactcaga  308940
gagcaagctt cagattgaga gaaaacattt acaactaata tagcagagaa ttgacttgta  309000
actagaatat ataaaaatat ctcccaactc aatgataagt caggcaacct gcagagcagc  309060
agtcctcaac acttttggca ccagggacta atttcacgga agataatttt ttccaagtag  309120
gggaacggtt tcagtatgaa acttccacct cagatcatca ggcattagat tctcataagg  309180
agcaggcaac ctagatccct cacatgtgca gttcacagta gggttcacac tcctatgaga  309240
atctaatgcc accgctgaac tgacgagagg tggagctcag gtggtaatgt gagtggtagg  309300
gagtggctgt aaatacagat gaagcttccc tcgcttgccc accactcacc tcctgctggc  309360
ccagtcccta accaaaactg gtccatggcc tggggcttgg ggacccctgc tgtagaggac  309420
agaataacag cccc ctacat atgttcacat cctaccttat gcagtaacac ggacttgact  309480
gacgtgataa agattttgag atggggagag tatcttcaag tatctaagtg agctcagtgt  309540
aataaaaata tccttataag acagaaactg gaagcttgga acaatagaag agctgaaggt  309600
gaaacagacg tcagacagag attaagatgc tatgctacat atatatatat attgcccagg  309660
aggattgctt tgttggagcc tataaaggtt tgtgagataa aagttctgaa gtggagaatt  309720
gttactatga tggttgctta aaatctagtt tttagaacag agatgagttt gactgtagct  309780
actctggtat gtgatccatt taatcatttt tttgtttaat taattctcag agagaaatct  309840
tagccccagc tatttaaatc tctccgtaaa taaagacttc caagcaccac tgggacagtt  309900
accaaaaatg acaaatcatt ggcaattcta acaataaact tcagtatagt aagagatata  309960
atggaactct gtaactgctc tcaaatcaaa catccctcct gcttagtgaa aacagaattg  310020
cactaatttc tctgatgcag tctcaaaatc gagccaccat ttcaggtttt gtaagaaaag  310080
ttgcggactt caggcttaga aaagacatcc cagttatgca ttgtggctga ggataacagg  310140
aagatgagaa ttaggatgta gctatcttca aaaagaaaag tggcaaaaag aaaagaaaaa  310200
ccttaatgtt agaacatata aaaatagtat aaataattaa gaacttaaag aggcagagag  310260
tttggttaaa gcggcaagcc agcaggacaa ttttagtgtg tagcttaagg tacaatacat  310320
gcataatttg cccttcctca attctagaaa atattgtctg tcttcttcaa taacctttct  310380
attcctgaaa ctaagcattc cactgggatt ttagctattt tatgtgctgt catatttact  310440
ttgctagcgt gcatgtgatt acacctaagt tctaattcgt ctaatatatg tgcattactt  310500
tttcattcat ctaatatgaa ttctagttca tctaatatag tgttgtataa gttgtctttt  310560
tacttatgtg cattttacag tgccctgaat agcactgaag tacaaaaatg tatcttaata  310620
tgtgttttat ctccatactt tgatggtgaa aaatattact ttccattcaa atgagtttta  310680
aaatagtctc attaaaaaca aatgaaaacg taaataaaaa aaaaaaaacc ttttctgtaa  310740
ttttttcaaga tatctatgga aatgcactga actaccgcat cattttcccc cagattttgc  310800
ttgggtcatc atggctactt catacattgt tgaatgagca tttgccgtaa atctcatagc  310860
ataagtaaaa gctatgatgt gttttttgcc ttgtctttct cttttcactt taaacacata  310920
```

```
ataaacactt agtaagcaga ttgaataaat acatacccccc tttatgcaaa attattcaca   310980
aataaatggt atctaattca ttctttaaaa taccatcaga gaacacacaa tctcgcttta   311040
ccatctgtat aattttagag tcagagtcta atttgaccag cagtcaattt tttcccttttg  311100 gactcctttc atatatttga aggacatttc tttgttccta gtatgtgtag atgaagcaaa   311160
actaaactgc atggcttctg atattcatga aagcaggcta gtaggtaacc attttttgaac 311220 acattccaca ccaagcgcaa tgctgtttct tgtgcattgt ccagttgagt tcctcagctt   311280
gctatgggag ggctactatt ctcctcccca tttcacatat aaagaaagtg ggactttgaa   311340
atcttaagtc atgtgcttaa ggcttttgcaa tagattccac cacaaggatg tccaactgaa   311400
tccactgcaa gcaataactc caaaagcagt caccaagcaa atgcccttgg tgtaaagtga   311460
tacgttctgt aacagaaatt cattgaaagc catttactgt gccgagagaa taagataat    311520 cacacaggac acttttggaa aggggcccac attggtagaa agagatggcc aggttctacc   311580
tgagtatgca ggtgaccccct gcggaagatg cagagactga ccttcaggtc acactgacct  311640
ttcaaatggt gctgggtcca tgagctagcc gtgcagcttt gtgtgcggcc atagcccaca   311700
ggaaggtgtg ctcaggcaag gtgttcaggg caatttatgg tcgcccagca gccctgcaga   311760
gggcgcccta gatcttgggg atttttatata aaaaggcaag catatcaaaa tgcaaggcat   311820
attctggaaa tagctagcaa gtgttgtggt ggatttgcag gctccagaac ataagtaggg   311880
catcccttga gaaggtcaca tgggcccaca cagaatgacc cttggattcc cagtaatgaa   311940
tttgtttctc caacacattc actttattgt gtgggtgtga ttgttgttgc taaaaaggga   312000
gatttaaatt atgaactaaa tataaacaga tattagcaat aaaacgtgaa tattccctat   312060
agtcacatgc ttcgaaataa tcaccctcca ctgtttgaat tccttccaga tttttatttt   312120
taataaaaca aatgggctgg acgcagtggt tcatgcctta atcccaggac tttgggaggc   312180
cgaggcgggt ggatcacttg aagtcaggag ttcaagacta gcctggacaa cattgcaaaa   312240
ccccatctct acaaaatata caaaaattag cagcaaatgg tggcacattc ctgtaatccc   312300
agctatttgg tgggctgagg caggagagtc gcttgaatcc aggaggcaga ggttgtagtg   312360
agctgagatt gcaccactgc actccagtct gggaagcaga gcgaaactct gtctcaaaaa   312420
aaatacataa aaatataaaa taaaataaat gatatgtagt attcagtagc ccactatttt   312480
ttcttgagat accttagatg tgtttctgtg tccatgagtg taaatactcc ttagcactt    312540 atgcagacaa acagcatctc ataatatgga tccaaccaag acaatccatt caaatctctg   312600
acttgtgaac attcagcttg ctgctattgt ttgtttttaa aattacaatc cgtgtgaatt   312660
gtggagcctt gggtggctat ttttatgcat cagaataaag attttcatag aaagcattca   312720
aagaattagg actcctgggt cagaagtttc caattttcat tttcctgggt tttacccatt   312780
ctcttacact ggagaccatc atgatgatgt tgatggtgtg gaaattcaga ggaagctaaa   312840
aggacgtagc acccaaatga gcaggtcctg gggaactgta gttctcatct cagacactag   312900
gatgcagacc cagggaggga caagatgtac aagctctttg aaaactaaaa ccaaaggatg   312960
tgacagccaa ttgaatgaga gtcagcagca aatctggaga aatatctaag gagaaagtgt   313020
tcagttgaaa atactcaaag ttggctgggc atggtggttc acacctgtaa tcccagcact   313080
ttttggaggc tgaggcaggg agatcacttg agctcaggag ttcgagacca gcctggccaa   313140
catgatgaaa ccccgtctct actaaacata caaaaatcag ctgggtgtgg tggcgtgtgc   313200
ctgtaatccc agctactctt gaggctgagg caggagaatt gcttgaatcc aggaagtgga   313260
```

```
ggttgcagtg agccaagatc acactgctgc actccagctt aggcgacaga gcgagagtct  313320
gtctcaaaaa caaaaaaaga ctcaaagttg actcaaagag atttgtttcc aggctggcta  313380
ttcccaaatt ttcatttgca tgaaactcat gtatcaatta tcttcagatt ttgatgtttt  313440
attatttaat aaacaagctg tatttattat tttatatttt gttcctaaaa tatgatcaat  313500
ttcagttttt ttttatttca tgtaatttaa actaaagcac ttaaaaaata cctatgcagc  313560
ttaattctag ataaatgtgt ggagatatta tcttttatga aaatactgca aggaatctca  313620
gtagtagttc ataggcccca gagtttggaa acctgtggta taaaaatcat ttgtctctta  313680
taattgtttt agattttctc tactgatatt ggaaatagac tttggttctg tgcaatactg  313740
ctgtgataac atgatacaaa tggagaatgg tctgctagta ctcattccat ttttaagtaa  313800
aaactaaaaa taaaggcac tgaatttcaa gcagccctgc ctatcaggca acagaatttg   313860
aatgcagtgc atcagcttcc ctcccttcca gcccatcctg tgcaatgtgt gcttctgtgt  313920
taaatcctac atgttttcag tcagaaagtt aaaggttcac cttgtaataa atgcatttca  313980
tgaatgattt cctataaccg tcaaagatta gttttgcatc tgtttgactg attttgtttt  314040
tttatgcttc tgcttcatt ctaaccaaac agatttcttt ttgacctcat ttgcatgatc   314100
taacacaaat tctgtttatt ctcactgaag aattttatt taaacatttt ctgtttggtg   314160
tcacttcttt agtttaaagg tgcacaaatg tatgtctgtg tacatataca tttatagtca  314220
cacatgcata tatatggtta tatatgcata tatatatata tatacataca tatattatat  314280
atatatacat acacacatat caggtgaatt acacacactg aaatggtgaa agatatttaa  314340
cttctgtatt cacttaatta tctcctggtt acttgtctcc aaaaaatgcc tactgtgttt  314400
atgcaaggaa tgatctccta aaagaaaatg gattgcagct ttaacgtcat gtaacaatgt  314460
cttttgttaa ttgaaagaaa aacaatatct gaccccattg ggttccttac catttacttg  314520
cagtgcatgg agaaacaaaa gacctgcagt cattctccta agccctgtga tgtaattcaa  314580
aatgagagga aacatctaca ttattatcta taataaaaat tggaaacttt tctgttgtga  314640
caacaatatt aagcctgaat agaaatattc atgtttatat gatattcact tcagtcaaca  314700
tgcagcagga aaaactgtga ttcctatttt tagtcatctt ttccatgaaa cctgttttcta 314760
aataaccata ctaactaaat gtactagtct gttctcatgc tgctaataaa gacatacctg  314820
agactgggta atgtataaag aaaagaagtt taatggactc acagttccac atggctgggg  314880
aggcctcacg atcatggcag aagacaaagg agaagcaaag tcacatctta catggtggca  314940
ggcaagagaa tgtgtccagg ggaactgcca tttataaaac catcagattt catgacactt  315000
attcactatc atgagaacag catgacaaaa acccacccc atgattcagt tacctcctac   315060
tgggtccctc ccatgacaca tgggattat gggagctaca gttcaagatg agatttgggt   315120
gaggagacag ccaaaccaga tcactgaacg tatctattga tatctcttgt gtgtgtatat  315180
ttgttattgt tgttccttcc aggaccctgg atgaaacttg gcatcaatgt agccattaac  315240
atggattcat tcacatggtc tcttttgcat ctttctttcg ttgttcaatt attggaggag  315300
aggttgctga ttacaagctt catattaggg agagtaaagc tcagaaacca aaatttcatc  315360
ggctaaaatg cttagagagt ttgtagccta aaggacctgt cagttaaagg agccatttgt  315420
tgtaaatctc tggttttaga caatcaagta gcttgttctc ttcattcacc ttgaacatat  315480
atttaaagtt aagtgatcta tccgaggaat gacttctcag gagcagcact catctttggt  315540
atcatgtgtg gctcttttcca agttgatgag ctaccatcat tttgctttct acaatcagga  315600
ggcaaaaccc agtggtttag gtttgcagga ttcctaaaaa tattaatttt aatttgctac  315660
```

```
aataaatacc aggattcctg gtgtcaaaaa gcttgcaaaa aatcacacca ttagaatttt  315720
ttaagatcac tctttattta cacttaagaa gatagctttg ccaggaaaat gcctgccttc  315780
cttctttcct tccctccttc cttccttcct ttcttccttc cttccttcct tccctccctc  315840
cctcccacct tccttacttc cttccctccc tccctcctac cttccttcct tccttcctcc  315900
tgctctccct ccctccctcc ttccctccct ccctccttcc ctccctccct ccttccctcc  315960
ctccctcctt ccctccctcc ctcctgcctt ccttccttcc ttccttcctc cctcctgctc  316020
tccctccctc cctccttccc tccttccctc tccctgctcc atcacatcac agagctgtag  316080
tgtgctgcct gttccttgcc tccagtctta ttcacaggaa aacctggcca ggtgctgatg  316140
aataaagaag aagacagatt gatagtgaga tctaattttc acagatcagg cgacttggga  316200
aaacaggtct ttttattttc aaatgctaac tttctgggct catagaattc tgtatcagta  316260
agcccacatg cttttaagt ctgatttata gaaaacatga tttggccctc aaaacaatgt  316320
aacctcccaa cagattcatc tttaccacta cacagataga gctgattagt caagacagaa  316380
gaattgcaat agataaaggg tttaattcct gcagagctgg ctaaatggga gactggagtt  316440
ttattgttac tcaaatcagc cttcccaaaa atttggaggc ttgggttttt ccagaatact  316500
ttggcagaca ggggctaggg aatgagtgct gctgattggt tgaggatgca atgataggg  316560 tgtggaaaac agccctggtg cacccagtcg gcctctatgt ggggacacag aggagtcact  316620
ggtcctagta ggaccaatca gttgtcagaa atgcaaaagc ctgaaaagac atcttaaaag  316680
gccaatctgt actatgctta ttacctgggt aatgagataa cctgtacatc aaaccctgt  316740 gacatgcagt tcacctacat aataaaccta caggtatacc cctgaaccta aaataaaagt  316800
tttaaaaagg caaattttag cttctagtga ttggggaagt tgcaaatctt gtgacctctg  316860
gaataatggc tggtaatcat tcaactaagc ttacatctta gcagaattca ggcctctctc  316920
attctttaac ctggtggcct ttcattactt ttacaaaggt ggtttagttt taagagggc  316980 tattatcatt taaactacaa gttcaatttc tcccaaagtt agcttggccc gtgcccagga  317040
atgatcaaga acagtatgga ggttaaaggc aagatggagt tggttaggtc agatctcttt  317100
cactgtcata attgtctgac tattgtaagt tttgcaaagg tggtttcaag gtgaaaggac  317160
tatactctta aagagcataa aattattgca ttcattgtgt acctgaaaca ggcactcccc  317220
cttgttgata gtttaaaaag aaaaaaataa taatccctgg atgttgcaat aaatgaaaat  317280
gccatggcag aaactgtgga aacaccagcc tcaaaacacc acattgattt gttaaacttc  317340
agagatccat ggattgtcgt ttccctcagc cagcctgtag gatatttgga agaatttcag  317400
aacctcaaag atcaaaccat ccaataggat gctgttagaa gaactaagat ttttgaaggc  317460
aggggatatt cattagcctg cttttggaaa ggttaaaaca ctctgatttt gctagggagg  317520
aagagtttat ggtggaagaa aggccaatga tttcctgcgt gttgaaaatc ttcatactcc  317580
tccacagaaa caaataagt caacaagtca ttctgcagaa ttgagaaaga gaacagtg  317640 agtgaagaaa agacgtgctg aagacagaat cgttctgtta gaaaattgct cgtgccttag  317700
gaattaatca cctctttctt taatagggga agaaagcatt gccctgtggt attataggc  317760 acctaaactg acatgattcg tcattgtcat ataaggatct tcgatctttt ctcccaagca  317820
aagcctgatg ccttttatga acgatcgtgt caaagatata gtgatggaga caggtgttgc  317880
agaacatttt tggcatgaag cactaattag taattgctaa ttaaatgggg gaggaggctt  317940
gggtaatgtc tgatcgcacc cactaatcgt agctaatctc ccgtcacatc cctctgaact  318000
```

```
ttaaagaaga tcacattggt aggatgtgtc ttaagtatcc aacctcgcag ttgcgacgct 318060
gcctctcttt gaagctgcag gagatagtga ctcccgattc aggcttggag tttttattgt 318120
cattgttgaa cgaaaatcgt cctgtgactt tctttggagc caggccattt cctcctttcc 318180
agctcagagc attttccac aggtgctcag gaaagctcat ggaagaaatg ctggttgact 318240
caattggtat gcagcctcat cctctactct ttttgtttta aaagtagaag ccggcactca 318300
gtcactcctt ggaatgccgt caactttggt tagggacgtg ctttgaggga attggtttga 318360
tgttatttta gggcttaaag cagcctgtct tcatacaaac atgactgcag gtggccataa 318420
taatgtgctg agcatccctt gaatgagtg aatgacatgg ctcttggaaa aagaaattg 318480 tatagaaggg gcaaatatca tagttgggta gttggggaag gctcaaataa ggacgtgaaa 318540
atggttaaaa aaaaaaactt ttaaaaattc tttgtctttt tggaaggcat atccagtaca 318600
gatttggaca taaagttgga ttaaagttta tgcaatgaac taaacttgca ggaggcctta 318660
gaaaatattc ctagttttga atctgagtag gagagtgtat gtcttcccaa acttgacttc 318720
aaaacatcag aagaaagcag tttttccagg tcaagctatt tttcaataca gaggaacaa 318780 aaaataaaat agattaactc ataactttgc tatcattaat accaaaattg ccattttca 318840 actactaagg agaaattaag aatcgtatgc cttgagtaaa atctagatcc tcaactcaca 318900
gaatccttct ttttaaaata aggaaggcca gttcctgata ttttgggaac agttggggag 318960
atgtgaatat tcattagctt tgggtgagg ttcaataatt acattttttt gtatgtgact 319020
aatattttcg ctatgtagga aaatagaggt gtatactatt tacgagtcgg atctagtgga 319080
gtctgtaact tacgttgttt cttaagcatt gaaaggagtt aaaacaaaat gttaataact 319140
aattcagtga gaaagacagg cgcacactgc ctttgtatac atgcacatat tcttagacac 319200
agacacacat gtgcacttac gcccctccc cccccacac acgtactgtt ttccctgaaa 319260
aatttcttgt aggagtctgt tgcatttttc aaaaagaaa atgaaaatgt gcacagaaat 319320
gataccttga acctagtaaa atttacgacg tcttctggga ttgcttcatg ttattaatat 319380
tttagattca ttttgccttc tctattagcc acatatatac acaaagatgc catggtatca 319440
taacatcaac ctaaataac cattatttat ataattattt ctgccacaaa attttttctc 319500
ctgttcttcc tctaattggt gggggtgaga gttgaggaga gagagaatga agaagacaag 319560
ctatgagata tcttttcaaa tagcagagac acgtatgcac ttttctatt tggccaccaa 319620 aaatatcttg tgttcttttg tagggttttt aagtaccggt gaccaggcag caaaaggcaa 319680
ctatgggctc ctggatcaga ttcaagcact gcggtggatt gaggagaatg tgggagcctt 319740
tggcggggac cccaagagag tgaccatctt tggctcgggg gctggggcct cctgtgtcag 319800
cctgttgacc ctgtcccact actcagaagg taataatggc accccaggg tgggcgggca 319860 aatacctga accaagaaat gaatggtcag agttcatatc tcagatgcat gtcctggtta 319920
ccagaagtca ctctgcaac agaaaatgcc caaagatca aatgaatcca tcttcatgtc 319980
ttttaactca gcttttgttc catttgctct gtcacccagg ctggagtgca gtggtatgat 320040
catagctcat tgtagcttcc aactcctggg cttaaggctt ctcccatctc agtctcctga 320100
atacctggga ctactggctg cttttttaaaa ttttttatag agaagtggtc ttgctatgtt 320160
tgcctgggct ggtctcaaac tccaggactc aagcgatcct cctgccttgg cctctcaaag 320220
tgctgggatg acagatgtga gccaccatgc ttgatcagta atattttct cctaatttaa 320280 atgtgtgaca attaggtgtt ggttacaatg attggaacaa aataactact ttagaagtcc 320340
tgacactttt gttttttttt gccattctga ctgtatttga ctatttgaaa tttttattaac 320400
```

```
ttctagctac aacttagtaa aagtagtatg gaagagagac agtatgtcga taagggatgc    320460
gggtgtatag attttgtaac catcagggct tttagccaca tgtttttttaa gaagtcgctc   320520 ctctctctaa ttcatattaa ttctttaaat cttctggaaa tattgaaaca cgtctggtgc    320580
attcatttag aagtagattc tgggtagaag tagattctac ccagaggaat agtgtctctc    320640
tccctgatgg tctccctccc tcccttgctc ttccctccc attcttctct ttccctctct     320700
cgtcctctct gtctctctcc ctctctatgt cctcctccct ctacctctct cctgctccct    320760
ctctctcttt tgctctgtct ctcaccctct ctctccccct ccttccactg tctctcctcc    320820
ctccctctct ctctccccct cacactgtcc cccactctc cctgtctttc tccctctctc     320880
tctcttcctc tctctccttt tctctgtctc cccactctct tactcactat ctcctttcct    320940
ctctctcttt ccccccttttc cctctgtccc tctctctctt tgtttctttc tctctctctc   321000
cctccctttc ttcttctcct gcaaatatga ctttcaccaa aggacctcct tcctggtcag    321060
gtcagcatgc agcactaggg agtgtccaga gtttgctttc cctctccct tcctctctct     321120 ctctcctgca aatatgactt tcacgaagga cctccttgct gggccagtca gcacgaggtc    321180
ctctgcttgt ccccgtggga gctccaaacc ctccctgggg cctgctatt aacctggaaa     321240 aagctgatgt tggcaaagtg gagaaagagg aaaccacaaa aacacatgtg catcatgtta    321300
cctcaaccag atgtgcactt gaacgtgtag tcagcatagg cacccgtacc caaccagatg    321360
tgcacttgga cgcctaagca gtagatggtt atgctgccta agtaatggtc agcataggca    321420
gccacacccc tgagccctgc tggagtgcct gaggctttcc ccggaggctc actcagtgga    321480
ttcccagctg tcccttttgtg aaggaggctc cctgcagtat ccgatgagag acttcaaaga   321540
ggagtccaca ggaatttgag gcaattggtt ctggaagcag gatcacaaat tcctggctgt    321600
ggcctaaaag gaagaggcag gaaaatctgc agtgcagatc cagccctggg ttgcctggcc    321660
acacgcaagt gaatattcct aatagccgtc tcagtcatca agacagcttt gtaatttgtt    321720
ctgtgttgtc agtggtcttc agaatggcac cacactgact gaacctgaag ttctcaaaac    321780
cttcatggaa ttttttttttt tttttcaggga gtctcactct gtctcccagg caggagtgca   321840
gtggcacaat cttggcttac cgcaacatcc accttctgga ttcaaagcga ttctcctgcc    321900
tcagcctccc gagttgctgg gattacaggc gcccaccact gtgcccggct aattttttgta   321960 tttttagtag agatgggctt tcaccgtgtt ggccaggcta gtctcgaact tcctgacctc    322020
aagtggccca cccacctcga cctcccgaat gattattttt aaagttatca gctggatatg    322080
gtggctcatg gctgttatcc cagcactttg ggaggctgag cggggaggat ggcttgagcc    322140
caggagtttg agaccagcct ggtcaacata gcgagacccc gtttgtacaa aaatgaaaat    322200
aaaaaccagc tgggcctggt ggcgcatgct tgtggtccca gttacttggg gggctgaggt    322260
gggaggatcg cttgagccag ggatgtcgag gctgcagtga gctgtgaggt tccactccag    322320
cctgggtgac agagtgagac cctgtctcaa catacataca tacatacata aaattaaaaa    322380
gtatctttct ttagagtaac tgcaggactt tcttcacttc ggcaccgtct ggacaagttt    322440
ctggatcgct gtgctcctca gtgtcttcat tggcaagata ggacagatga gggtttcctg    322500
aaatcctcca aactctgaat tccttgagtt tttagttcat aatgtttttgc ccatgagacc    322560 aaatggcctt tgatttctta ctagtgctaa tgagaggaaa ggctcatatt tgtattaact    322620
ttatttcaaa aacacgataa gtgaagaatc tgatgaacca tttggtagag agatttctat    322680 ggcattttg aaaatacctc gattttcact tttctcaatt gatataatca caattgtaga    322740
```

```
tttagaaagc agtcagaacc aacttcagga gtaatcaaac acatgtaagc cacattaatt  322800
ggagggaggt gttaattatt taagtcaata ggttggaaat tattatactt ttgcatcggt  322860
catttctgca aggcatgctt ctaaacagcc catcaatata atcacgaatt atgaaaaata  322920
caagccaggc actgaggctc ctgcctgtct atcatcccag caatttggga ggccaaggtg  322980
ggcagattgc ttgagtccag gagttcaaga caagcctgaa caacatggcg aaaccccgtc  323040
tctacaaaaa agagacgcat ctgttgtccc agctacttgg gaggctgagg tggaaggatc  323100
atttgagcct ggaaggcaga ggctccagcg agccaagatc ccgccactgc actccagcct  323160
gggtagcaga gtgataccct tgtctaaaata aaaataaata tagccagact gttttgcctta  323220 ggaattcctt gcctggttat atggtctaat gaagacaaag tacacgtgga aagtgatagt  323280
tttatgaaga tgttcaccac agtattagta tcgtagcaaa gaatgaaatg aaaagctaca  323340
agatcaaaag gagaggaaaa ttataatgaa ccatatgtat ttactcaata ataatttaag  323400
aatttaccta agatatacat cagctggaaa aacagtttag acagctatat aaatattggg  323460
ctcagctatg caaaacagac atttgaatgg agggaaagag ctaagaatta tgtgaactcc  323520
tagcatactc attacgctaa ggtgagttgt gtttaaagta tgaattctgg gtgattttt  323580 tcattatcca actattttag tcttatcagg agttctgtta cttccctaac atacaaataa  323640
atgttttatg tatgttactt tatatacact actgcctaaa ttattgccag tacttatgag  323700
aagggcggga aaggaacttc tcacagcatt tttttccaatt ctgaatgttt taactaatga  323760
aagtatccaa tagaatacat attgactttc tcttttggtt tttttttttt tggacatttt  323820
aaaataatct tcagagccaa gcactcaagt caatacttgc acatttctga cagaaacgtt  323880
cccaggatgg ctttgatgac atactggtca aagccatatt ggtttcaagt tgcggtcctg  323940
tgtgtcatct ttgggcaatc ctccagtctt taaaatcacg tcttcctgat dacagttata  324000
ttttcctcat atttgattgc ttctgtgacc ttaaaaatcg cagggcatg aacttctgga  324060 ctcacaactg aatgccttat tctttagtgc ccgactcggg ctgggattca cggaaatggc  324120
aggaagcaag tgtaaatgga atgctgattt ttacagcgca cctctcttgt cctatcgtag  324180
ttaaaaatac agattttata cttctggaca tccgtgtagt agactgaact catggagaat  324240
tttaagctac acagaatttt actcctaaaa ttgcccatgc ttttcaagt ttctcagcaa  324300 gtggagcatt tttatatgtg gcaaaataaa atatacacat ctctgagttt ccaatggatg  324360
tagttttgaa agaagtgacc taaaaaatac tccttacttg ggcaccagt tgaggatttc  324420 tttaagcata gctagctgaa tgtatttatt ttaattggca aatcttaata tcttcattag  324480
actcaaggta gaagtagaaa tgcgctcctg aattagcact ctgaagttga ttcaagtgga  324540
tttctttttt tcccataatg aagagatacc tagttttgct tgtgagacaa gagggccttt  324600
gaactggtac tagcttaaag catttttttt cttggaaatg gggaatgcag ttgctcttgg  324660 agttttata tatggcatct ggaggcaagg aagcaaaaac gacactaaat tgtggaagga  324720
aaaagaaatc acatgtattt taccagtgca ggagaagtgt caatgtggtt tcatttcctt  324780
aaactcgtgt gtgtgtgtgt gtgtgtagaa taacattccc taaaatgaat gttcaggagg  324840
aggggtgaag ggggaatgga aatgaaaatg ggtaaagggg cccctgacag agctgaatgc  324900
tactacatcc agaaactcac atgcctgaga gacaatcaca gccttcattg ctcagtaaaa  324960
gctgcatttc tgtcctgtgg gttttcattt gcatgtccac aattttgcac ctgcaggtct  325020
cttccagaag gccatcattc agagcggcac cgccctgtcc agctgggcag tgaactacca  325080
gccggccaag tacactcgga tattggcaga caaggtcggc tgcaacatgc tggacaccac  325140
```

```
ggacatggta gaatgcctgc ggaacaagaa ctacaaggag ctcatccagc agaccatcac 325200
cccggccacc taccacatag ccttcgggcc ggtgatcgac ggcgacgtca tcccagacga 325260
cccccagatc ctgatggagc aaggcgagtt cctcaactac gacatcatgc tgggcgtcaa 325320
ccaaggggaa ggcctgaagt tcgtggacgg catcgtggat aacgaggacg tgtgacgcc  325380
caacgacttt gacttctccg tgtccaactt cgtggacaac ctttacggct accctgaagg 325440
gaaagacact ttgcgggaga ctatcaagtt catgtacaca gactgggccg ataaggaaaa 325500
cccggagacg cggcggaaaa ccctggtggc tctctttact gaccaccagt gggtggcccc 325560
cgccgtggcc accgccgacc tgcacgcgca gtacggctcc cccacctact tctatgcctt 325620
ctatcatcac tgccaaagcg aaatgaagcc cagctgggca gattcggccc atggtgatga 325680
ggtcccctat gtcttcggca tccccatgat cggtcccacc gagctcttca gttgtaactt 325740
ttccaagaac gacgtcatgc tcagcgccgt ggtcatgacc tactggacga acttcgccaa 325800
aactgggtac gttcatcttc gtgttggggt atcactatcc ttgccacttg tttgtgtcct 325860
caatataggt gttgcttcta ctgccacgtg caggagcaca cacgcataca cacacataca 325920
catgcatgca cacacataca cacagacaca cgcttacaca cacagcagta acaggcagct 325980
tctcccccaa catctatggc aactcatttt tttctttact cctaaagtgt tataggagta 326040
aaacacttaa ctgtcaaacc agattttac tagagttcta attgcccatt gggaattcca  326100
gagttcctac ctgcaggtgc aggactcata catatatgat ggttctgtta acagctgatt 326160
aaacggtttt gttttgtcc ttgttgtttt agagacacag tctcactctg ttgcccacac   326220
tggagtgcag tggtgcaaca gtagctcact acagcctcct gaactccta ggctcaagcc   326280
atcctcctgc ctcagcctcc tgagtagctg ggactacagg tgcctgccac catgcctggc 326340
taatttttaa tttttttttt ttggtagaaa gagggtctca ctctgttgcc taggctggag 326400
tatagtggcg caatcatagc tcactgaagc ctcgagctca tgggttcatg tgatcctccc 326460
atctcagcct cttgagtagc tgggactaca ggcgtgcacc accatgccct tacatggatt 326520
tttgtagaca caggtttgc tatgttgccc aggcttctct caaactcctg ggctcaaggg   326580
atcctcccac atcagcctc tgaatagctg ggactacagg tgcacaccac cttactcagc   326640
taattttatt ttgttagaga cagggttttg ctgtgtcacc cgagctggtc tcaaactctt 326700
gggctcaagt gatcttccca cctcagcctc caaaagtgct gagattacag gtgtgagcca 326760
tcacaccagc cctcattaca gagttttaag tctaatttca accatatctc ttttgttaat  326820
ttgcaaggat atcacagcac atgtaccact tggggaactg tgttgattgc ctggccatag 326880
gaatgaaaac aaatatcata ataattataa agaaatataa atatatattc ctatatatat 326940
ttaatgtcta tataaaaata tagatattcc tatttgtata atatagtaca tttatatttg 327000
tatttgtata tatatacaca caaatatatt tgtatataca aatacaaata tatatacaaa 327060
tactatatat atacaatata tatacaaata caaatatata tatacacaaa tacgtttgta 327120
ttttctctgc tatataaata actagagaga gaaaatgaaa atatatgata tttgtatcat 327180
attgctatat gtcatgcata cataaacaca cacacacaaa cacacataca tgtgtatctc 327240
acaggaaagc tcatttattg gcctaaatat agtagaaaat ataaaatata caaaaagcat 327300
atatacaaca gagtctgcca atattctgct gagcggattc tctgcaaacc atgggagaaa 327360
agaacccaaa acaacctaaa tagctccaaa cattgtggca ttttttcatt ttctcttgtc 327420
taataatgta actgtggaaa tggatggggt gtcattctgt tctaccagtg tgtgcctcca 327480
```

```
tcatcaccct gagcctcttt acactgaatg agagagaaag atgtgcctgt cgcccaggga   327540
gggtaaatct tcccgtgcgg aatgaggctc tgagactgca gtggccctgc cacacatgag   327600
ttatgcacag taatccttag aagatctggg gatgctggtg gtttcaatgc ctacgtgttt   327660
agcagctggc atactgtaca aagattccaa agtggtttgg gtagggagtg gtttgagaat   327720
gttttgtgcc cttggcgaaa gtacagcatg ttttggagt ggaaaaggta tcacctggat   327780
accacctttc aataatcaga cttttgtagat ttggtctgag aaaggctacc cagaggagaa   327840
gagaggaggg acccacattt gatgcaaatg cttgtctatc actcaacggt tcttttttgt   327900
gtgaagaaat gattgaaatc aaattaatac ttttttttaaa gtaaaccttg tttattagtt   327960
tgttgggact gctgttatca gagtatccaa aactgtatgg ctatgctggg cgcagtggct   328020
catgcctgta accccagcac tttgggaggc cgaggcagga ggatcacctg aggaggccaa   328080
gagtttaaga ccagcctagg caacatagtg agagtccgtc tctacaaaac aaatgaaaaa   328140
atttagctgt gcatggtagc atatgccgag agtctcagct tctcaggagg ctgaggcaga   328200
gggatcactt gagctcagga ggtcaaggct gcagtgggcc atgtttgcac cactgcactc   328260
caacctgggt gacagaccga aacctttatc tttaaaaaaa aaaaaaaaaa aaaaaaaaa   328320 aagcaccaaa aacggtgtgt cttataacaa cagaaatgta tcggttcacg cttttctaagg   328380 ccagaagttg caaatgaagg tgcttgcagg gccaagttcc ctccaaatct gtaggggggag   328440 ggtatttcct tgctccttct tagttactgg tgtttgggtg cagtctttgg cattcctacc   328500
ttgcaggtgc accatcccac tctgtgtctt tgtcatctta cggcctccct gtgtgtctct   328560
gtctccacat ggccgtcttc atataagagc atctgccaag gtgcattaga agctcaccct   328620
actctagtat gacctcaact taacataaat agtcatatct gcagttaccc tatttccaaa   328680
taagctcaca tactgagata ctgggggttat gacttcagcg tatcttaatt tatggggaga   328740
cagtattcaa tctctaatac cctgtgaaat cagggccagg ccctcttttg tgacagcact   328800
gagataggcg gtgtctgccc ttgcagagaa tttcatcctc ttgaagccta aagacttcca   328860
tgagagtttc ccaacatggc tatactcatt caatcttcgc tacattggca tccaaacgta   328920
ttaccgactt ggtctgcaaa cactctcttt acttactctc attaaaaaca tatgcttttt   328980
cttttcctcc ttacatgatt tgaaaataaa ctttatatga ttatcttaag tggaaagcta   329040
gaatcattcc tcatacattt tatggaacca ttaaaacaat agtgaaatct aaataatgct   329100
gttaaattct cattagctct tcctgacttc caaaggctat gagactgagg ctggctctct   329160
cattattaaa aaaaaataaa aaaaaaaaaa aaggaaaaaa gacagaaaaa gataaaggaa   329220
gttaattagt tccatgaggt gatcgttatc actgctgaca ccaaatggac gcttttacca   329280
agacatcacg aaggtctgag agagccgtga gaagagaata ccacaatgat ctctctgtta   329340
ttgagtgctt ttaatgccat gaatctgttt cttaaaatca cttggcttag agcctgtgat   329400
ttccaccctg catttaggga atacattcac gttgccattc atggtctgtg ttgagggtgc   329460
ttctagcttt catgaaggcc ctgacatggc tggaagagat gaggaaggaa taactgctag   329520
aacttggaga gacgctctga tgctactgaa atcaaaagct gcaggtagag agagttcatt   329580
gaggtaccca gagctcgaat gtcagtccgt ctgaagcctc tattttttgtt tcttccgccc   329640 atgggaaaca tccctgaaat aacactgagt gtattaatgc agtgagctct tttaattcat   329700
tggaaaggta ttagaatgac tcaaatgatt cctcaaggaa gttactcaga acttacatct   329760
catgtgaaat gcaacgtgtg gattcaaata caaatagttt aagtgatcac acctccatgg   329820
cagccccata aaagaaggaa atggggaatt tcactgtcgg gcacagtctg gtgagctagg   329880
```

```
tattcgtcag tggatgacaa ggacttcagt tgcagttggt agttatttgt ttattgtaaa  329940
ttgggtggtg gcccgatcac tccagggcag agaaggattc cctggtcacc aggtgcagag  330000
aatgaaccaa actgatgccc gcaaggagaa agtatgggat gcaccttatc tgctgtcatg  330060
gtgtgagctg ccaagtttaa cgccattttg cagagcacac actcagatga tgactcacag  330120
aacaggaggg catatttctg cataccatca ctgttccctt ccagcactgg aggtgacagg  330180
aggaaacaag aatagctccc agcgtgtctg tcactacacg gtgccgtgga gaaggatcg   330240
cattgtgcca ggacatactt caccactctc agtgggcgtt aagtcaagcg ttctaaacct  330300
gcaggcacac ccagtctctc gatggcgcat gtgtttgcca agatgaagtg gatgggtct   330360
ggatgcttct atatagacat ctcaaagtag atggttctga cctttagtct aggtttgaag  330420
gcacatatac ctggtataca taaacctttg gttttgggat gagcacagaa aaatgatgtt  330480
gggatgtgca tggcggagaa aaggaaggaa ggagggaggg aatggaggaa agagagttca  330540
gacaaaggaa cgaagggagg gaaggaggga ggagggaggg aaaagaaaag gagggcggga  330600
gggaatcaag aaaggagtaa aggaagggag gaagggagga agaaagaggg taagggggga  330660
ggagaggaag gaaagaagaa gggaaggaag gaggagggga aggtgaaagg aagaaaggga  330720
ggaaggaaga aaagatggaa ggaaggaaag gaaagagaga aaagagggaa gagaggaagg  330780
gagaaggggag aaagaagaga ggaaggaagg aaagtagcga gggaaggaag gaaaaaatgg  330840
agggagagag aaagaaggaa gggagggagg aaggaagagg gaggaaaaag ggaatggagg  330900
aggagaggaa gaagggaggg agggaaagaa ggaaaacagg gaaaaggagg gtaagagaga  330960
gaaagagggg aagggggaga ggaggaagga agaaggagg gagggaggga caattggatc  331020
tttgcttata aattatgtca cctgtatatt ttcatggtag cattaggtga gagggctctc  331080
ccatcttaga aaggcggagt cagcgagtac gcatagtaga aatgaggagg aagtccctac  331140
ggaggctcta aattatgaaa accttgatca agaaaggatg ttgaaatcat tgaatgccag  331200
ggcctcaagt aatccttgct atttcttttt tattattatt ttgaataggg aagcagttgc  331260
ccaggcctgt gcctgagggg gatcctcccc tgtagcaagg aggtgtttca atgttagtcc  331320
aggtcagagg actaaaatca tgctggaaga gaaccgtgtg agcccaaaca tgcagaggca  331380
ttgtagaaat aaggtagatt gagaccgttt ttggaaatca gctgcagtgt caaggagaag  331440
tgaaaactaa ctctaaagtt tcaaaagggt tctagagcat taaagtcctt ttcctggaaa  331500
attactttgg gaataggaga aaaagggttc gtccaagctg atcaatgaaa ttcaggtgct  331560
cagtgatcca ggattctttc attttgagct ctgtgtggaa agagatggac aaaaaggagt  331620
ggggaatctt ggtttattta aaggtatga caaagaacag tgctttaaag taaccaaaca  331680
atgcattata atatagaata gaagaccta tgtgctattg gaagtcagat atgagaagag  331740
agttttgtaa tggaaaatca gatcaacaca tattttgatt tttttatgtt gttccatcga  331800
gtctggggtt tgtacggcag attgatttct gtcctgtttg catcagctac catcactgct  331860
tttgaatgtg ctggtatcct atgattaatt tacgttcaac tattgttaaa tctttgggaa  331920
aaaaagaag ttccaatgag gtatttagtg gggatgggtt acagagagtt gcagcgtaat   331980
tctggctgta aaggcgacct ttattaccaa aaaggaattt taagctgaat gaatgaacat  332040
ccccacctgg tgtggaagag gagtcactga atgcataata aactagtccg gtaataatcg  332100
ttaactgcga acaatgtttt gggtatgagg aaaacctgta ctacttaaag gaacagctga  332160
gaggattcac agatattttt agagagatca tagtactata tccatctcca gctaaagaaa  332220
```

```
tgaactagac cttagaaagg cacttgagtc tctgctgcca agatgacatc tcaaataaaa   332280
caggacaggt ggaaatggct gtgttaggtg ctgggggata aggaggaaga catgcattga   332340
gtcttttact agagagacca acttgtgttt ctgtcctcaa tcattatagt ctttaatttt   332400
actcacagga gtttaaacac ttcttaggct gaataaagtc taaaaaacaa aacactgata   332460
ccccacatct agacctcact gtctggaggg tttggtaagg gagaatgact tgggctatca   332520
taatctccac aagtttatct ggctttaaga attctggctg tgcatctccg agatctttaa   332580
tagacagacg gtatcaggtg gcagctcatt tatatggatt ttccaaatcc tctgctttat   332640
tcttcaagaa caaatataaa tgtgttttct ttaccttttca aatatacccct gagttccttc   332700 gaaaatagcc ttgtacccaa catgaacaga atactccttt tcctagatgc tcactgctta   332760
atagatgagg tagccacaca tctaatagat ccaattcagt aaaattggat ccatggaaaa   332820
aaaggtagaa tcttcacttc catttgtttc tttagaatat taaaaatcaa taactaatat   332880
tagtggattt ttttcctaaa atattcattc acttattttt ctttcagtac acgttaaata   332940
actgaaaatt ttaaaattat ttcagaggac ttaaagagca aaagaaacat gagttgctgc   333000
attgaatcca acattttttc aaaccatgt aagaatacat gcataataaa taaaaaaagc   333060
agaagacttt tcaaatatat tgtttatcag taaataagaa aactcatggt attagaacct   333120
atgagattat atatatttgt tctcacccta ttagtaaagt gaaaacacag cagttagtgt   333180
gcattcaact aaagggtaga ggtcaacttt ctttttctcc tgtattatgt tatacatcta   333240
atatctatat ctatagatag atatacacat acacatatat acacatgaca tacatatata   333300
tactgcatat agtatatagt tagtatgcag tataaactgt ggtatgcagt atacttgtat   333360
atagtatgta atatacaata tacttttatg cactctacaa tgtatacaat atagaaattc   333420
agtatgtact ctgatataca gtatatcact ccctacttct ccctcccttg caatattata   333480
ggtgttctat tttttatatt ggaagagagg gggtaatatt tcctgaattc ttaccatatg   333540
ccagacatct tgtcattatc tttcaacctt catcacttac ctccaaccct gatattttca   333600
tcagccatgt agaggagtaa gttaaggcca atactggctg gaaaacttgc ttaagatttc   333660
acagctctta actagccaga gctgcagaaa gttgaataca gggaaatgat ttattttatc   333720
accaccacag actcagactg agggataaa atcttccttc agcaagtgtg gcgcctctgg   333780
ctcaagtata ttgtttgaat cctgcacagt gtctggtaat ggctacagat acatgatctt   333840
ccttggtcct gcagccttct gccatgcagg ccatgcaatg actggaggca gtttcacaga   333900
agtcccgcca aggagaagtt acctggaaga tagcccttag ctcacacctg gagccattga   333960
tcaggatgtt gcaactccct gcttgcctgg ttctgcacat cacatctcaa tgctcagtgc   334020
taactagtac ataacatttt gccatgcata atctcaaatc gttttataa caaataaacc   334080 ttaagacgta attgtttttt agcttacttt acaagccata aaaaaatgg aagaaatgag   334140 catttggtaa tttatttttt gaaggggaag tgttatccta aaagagtcag ttgcaaagat   334200
gtttattaaa ggcccctatgt tttatgaatt atctccaaat ttttatgatt ctccttctac   334260
ctgtgaccac ttgtgcaaat aataagaaga taattctttg gctcatagtt tccaagcaca   334320
acttagcatc tgtaacagcc cttgacttgt ttctgggtgt cttttttatc ttaaacatgt   334380
taacctcatc ataactatat gtaccatttt agcaaacttc ttacagctaa catagcgtgc   334440
tttcatcttt ttaccttcaa atagagagca aacacatggt gcatatgtct atttacaaac   334500
actttgtaat tataaagcct attttattt ctactgttaa tatcaatttt cattgctaaa   334560
actgcaacat ttattcattt acttcaaaag caattcttga gcaagaaaga gaatacccat   334620
```

```
ttcttggaca atagcttctt aatcagaatt tctcaacctc agtactgtta acatttgggt   334680
ccagataact tctttgctgt gggggtctct cctgtgcacc agagggtatt tagtagcatc   334740
cctcacctcc acccttcata gaacaaccct tcgtctacgg aaaccaaaag tgtctccaga   334800
tactgccaaa tatcccttg gagcaaatca gtcctggatg agttttacag ttcgacaaga    334860
gtgaaacttg aaatactgaa attttccta gagacactta gttttccttc tttcccttta    334920
ttttgaaga tcatttgatg ccttaaaaaa tagtaaacat gttataaaaa ttgcataatg     334980
ctgctatcag gatttatatt taaaagaaaa ataagagcaa tttttaaagg aaaagacaac   335040
atggtagaca ggtctaggat taaagcagaa tgtacctttg ctgcttgggt attttgtgct   335100
cattgataaa tatatatgaa gagcagattg taacttcctg atttattggt ttaagataat   335160
ttcacgtcac atgtggaaga gtatgacctt tcttttttc ttccttctat cctcagtgat    335220
ccaaatcaac cagttcctca ggataccaag ttcattcaca caaacccaa ccgctttgaa    335280
gaagtggcct ggtccaagta taatcccaaa gaccagctct atctgcatat tggcttgaaa   335340
cccagagtga gagatcacta ccgggcaacg aaagtggctt tctggttgga actcgttcct   335400
catttgcaca acttgaacga gatattccag tatgtttcaa caaccacaaa ggttcctcca   335460
ccagacatga catcatttcc ctatggcacc cggcgatctc ccgccaagat atggccaacc   335520
accaaacgcc cagcaatcac tcctgccaac aatcccaaac actctaagga ccctcacaaa   335580
acagggcctg aggacacaac tgtcctcatt gaaaccaaac gagattattc caccgaatta   335640
agtgtccacc ttgccgtcgg ggcgtcgctc ctcttcctca acatcttagc ttttgcggcg   335700
ctgtactaca aaaaggacaa gaggcgccat gagactcaca ggcgcccag tccccagaga    335760
aacaccacaa atgatatcgc tcacatccag aacgaagaga tcatgtctct gcagatgaag   335820
cagctggaac acgatcacga gtgtgagtcg ctgcaggcac acgacacact gaggctcacc   335880
tgcccgccag actacaccct cacgctgcgc cggtcgccag atgacatccc acttatgacg   335940
ccaaacacca tcaccatgat tccaaacaca ctgacgggga tgcagccttt gcacactttt   336000
aacaccttca gtggaggaca aaacagtaca aatttacccc acggacattc caccactaga   336060
gtatagcttt gccctatttc ccttcctatc cctctgccct acccgctcag caacatagaa   336120
gagggaagga aagagagaag gaaagagaga gagaaagaaa gtctccagac caggaatgtt   336180
tttgtcccac tgacttaaga caaaatgca aaaaggcagt catcccatcc cggcagaccc    336240
ttatcgttgg tgttttccag tattacaaga tcaacttctg accctgtgaa atgtgagaag   336300
tacacatttc tgttaaaata actgcttaa gatctctacc actccaatcg atgtttagtg    336360
tgataggaca tcaccatttc aaggccccgg gtgtttccaa cgtcatggaa gcagctgaca   336420
cttctgaaac tcagccaagg acacttgata tttttaatt acaatggaag tttaaacatt     336480
tctttctgtg ccacacaatg gatggctctc cttaagtgaa gaaagagtca atgagatttt   336540
gcccagcaca tggagctgta atccagagag aaggaaacgt agaaatttat tattaaaaga   336600
atggactgtg cagcgaaatc tgtacggttc tgtgcaaaga ggtgttttgc cagcctgaac   336660
tatatttaag agactttgta aaaagaaaa atgtatatag ctgtgagttt aaacaaaaac    336720
cacaaacaga caaacaagaa aaaagcttt tattggtgtt ttcactttga aagagctttt    336780
agcaaggttg tgcttttcat tgtgctctgt acgtatataa atatatatat atatacacac   336840
acacacacac attagtcata tcacctctgt ttcctcccca acaaaagagg cttttcttct   336900
taattacttg tggtaaacaa agacatggga ttttcttaca tgagattctc atttgtagga   336960
```

-continued

```
ggatgtgatg tcccacagaa gacccagacg gtctgtgtgg cctatttccc ccgtcaggtt  337020
gcacaggtgc atgcaagagc attcttagga gaccactgtt ttgaaaaact tttgacttgt  337080
acgtgttagc cttcatgaaa ttgcagtaca gagatgggtc cccaaagtgg agtgtattta  337140
cagcttgtta aattagagac atgcacacac aaagaatcag tagggagaaa caaaaataca  337200
agtcccgttc tgtagctctg gcccttttgaa tatgtttagg aagagttgct tcccatttca  337260
gggccctgcc aaaaaagaa gaaagcttgc cttttggtggg gctatgcccc ttggagtaaa  337320
tacggctctg tgttccctag cagctgcggg agggtttggc cgatgaagta cctgctcagc  337380
ttagctaatc agattgaagg aagacatgtg tctttccttt ttgtttaagc actcggtccc  337440
ttatttatca gtaagcaggt ttttaaaaat cttttatatc atttatggga tcaaacatat  337500
gattgtctga aaacatcact ttttgtggat ttgtgtatcc ggtcaccaaa cggtgaatat  337560
tatagaagaa tgggggaaga aaggatagaa tattaaaact gctttgcatg ggttttctgg  337620
gaaattagga taacttcact gagaagacat tgaatggaaa ttattcaccc attttaaatt  337680
ggtgacctag ggatcagaga tttgtctttc caacagcttg tcattttttc atttctcttc  337740
tcatttttca ggaaagtttt gagtgttata aggtggaagg aaacatagta gcaatggata  337800
cttttttgaa aaattattgc attaccaaga aacagtagcc aaagatattt gaagatcatg  337860
ttcctcggct ccattgtggg ttattctaga aatccagtct taaatctctc cgctaaagtg  337920
gacattcccc ataaaaattg tccagctgcc tggctctttt gcaataacaa cctttgatta  337980
ctgaatccct acactcaaac tatagtgata tatcagtgtt tgagagtgac ctctagaaaa  338040
aagaaaagtg ttttttagaaa tgcgtacaag tcaccccccaa atcctattgc ttatcttggg  338100
ttaaatttga gagtgattct ctgtatataa atatgtgaaa tattattatc tcaacttagc  338160
acacgtgaag caacatttct ttcctacaga gaggtgtcat ggtaagattt cattccgaat  338220
tcattgtttc atagagctat gatcaggcca tttctgcaag caatgtatga ccccacctga  338280
gcaaccacaa ataggctctc tgtgaaacta caaaggaagt tatgtgtggc atccatgttg  338340
gtttcgtctg tctgtaatgt gaattccagt atttgtttag tatttccagt tgtctcctgc  338400
tagcaatatg tacagtaacg cgtcaggctt gtgacatttg aataaggaaa aacagagttc  338460
ctgttaagtg ataaacttta gcttttacag gggattatga tcaaaagtga ttttagtaca  338520
tcttaaatga tatcttattt ctacatggaa agaagttata gaatcttcat agagttctat  338580
gagaaaaaat atacttgcta tctataaaaa agagaaaaaa gaaaaaaaat gagaaaaaag  338640
taagaaaaaa aaaatcctg tcctaggctt ttactcttga tcttcaaagg cacgcagggt  338700
ttaatggttc cttgggttat tattttgcag ttttgttttt tattttgcct taagtaatga  338760
tagaagatat atatggccgg acacatatgt ataaacttttt cagcagcatt tttaataata  338820
aaatatcaca gtattttcta atgctttgtg caaataa                           338857
```

<210> SEQ ID NO 2
<211> LENGTH: 5672
<212> TYPE: DNA
<213> ORGANISM: Homo sapiens

<400> SEQUENCE: 2

```
agaaggggaa ggctcctggg ctttcaatac atcctcctga atcatacctc gtttcgggtt   60
ccctagaaaa atctggacgt gtaaaaagaa ctcttaacgg ccgatgcagc tcttccaaag  120
ctaaggctgc cttggagttt tcataagaaa ttgtccctgg aggtgttgga tgatcacagc  180
ttccttggag cattgcagtt gctggaatcc agtttcagga ttaagggagg gctgcctcct  240
```

-continued

```
tgcaatgggc tgccaagaaa acggctgtgc ttgttcttaa cctcaggctc tgtctgtgat    300
cagtctgaga gtctctccca ggtctactgc tccctggaaa gccctatctc tctgcaggct    360
cgcctctggg ctttgtctcc ttggagccac atcactggga cagctgtgga tgtggatgca    420
gatttgaacc atgtcacggc cccagggact gctatggctt cctttgttgt tcaccccggt    480
ctgcgtcatg ttaaactcca atgtcctcct gtggttaact gctcttgcca tcaagttcac    540
cctcattgac agccaagcac agtatccagt tgtcaacaca aattatggca aaatccgggg    600
cctaagaaca ccgttaccca atgagatctt gggtccagtg gagcagtact tagggtccc    660 ctatgcctca cccccactg gagagaggcg gtttcagccc ccagaacccc cgtcctcctg    720
gactggcatc cgaaatacta ctcagtttgc tgctgtgtgc ccccagcacc tggatgagag    780
atccttactg catgacatgc tgcccatctg gtttaccgcc aatttggata ctttgatgac    840
ctatgttcaa gatcaaaatg aagactgcct ttacttaaac atctacgtgc ccacggaaga    900
tgatattcat gatcagaaca gtaagaagcc cgtcatggtc tatatccatg ggggatctta    960
catggagggc accggcaaca tgattgacgg cagcattttg gcaagctacg aaacgtcat    1020 cgtgatcacc attaactacc gtctgggaat actagggttt ttaagtaccg gtgaccaggc    1080
agcaaaaggc aactatgggc tcctggatca gattcaagca ctgcggtgga ttgaggagaa    1140
tgtgggagcc tttggcgggg accccaagag agtgaccatc tttggctcgg gggctggggc    1200
ctcctgtgtc agcctgttga ccctgtccca ctactcagaa ggtctcttcc agaaggccat    1260
cattcagagc ggcaccgccc tgtccagctg ggcagtgaac taccagccgg ccaagtacac    1320
tcggatattg gcagacaagg tcggctgcaa catgctggac accacggaca tggtagaatg    1380
cctgcggaac aagaactaca aggagctcat ccagcagacc atcaccccgg ccacctacca    1440
catagccttc gggccggtga tcgacggcga cgtcatccca gacgaccccc agatcctgat    1500
ggagcaaggc gagttcctca actacgacat catgctgggc gtcaaccaag gggaaggcct    1560
gaagttcgtg gacggcatcg tggataacga ggacggtgtg acgcccaacg actttgactt    1620
ctccgtgtcc aacttcgtgg acaaccttta cggctaccct gaaggggaag acactttgcg    1680
ggagactatc aagttcatgt acacagactg ggccgataag gaaaacccgg agacgcggcg    1740
gaaaaccctg gtggctctct ttactgacca ccagtgggtg gccccgccg tggccaccgc    1800 cgacctgcac gcgcagtacg gctcccccac ctacttctat gccttctatc atcactgcca    1860
aagcgaaatg aagcccagct gggcagattc ggcccatggt gatgaggtcc cctatgtctt    1920
cggcatcccc atgatcggtc ccaccgagct cttcagttgt aacttttcca gaacgacgt    1980 catgctcagc gccgtggtca tgacctactg gacgaacttc gccaaaactg gtgatccaaa    2040
tcaaccagtt cctcaggata ccaagttcat tcacacaaaa cccaaccgct ttgaagaagt    2100
ggcctggtcc aagtataatc ccaaagacca gctctatctg catattggct gaaacccag    2160 agtgagagat cactaccggg caacgaaagt ggctttctgg ttggaactcg ttcctcattt    2220
gcacaacttg aacgagatat ccagtatgt ttcaacaacc acaaaggttc ctccaccaga    2280
catgacatca tttccctatg caccggcg atctcccgcc aagatatggc caaccaccaa    2340
acgcccagca atcactcctg ccaacaatcc caaacactct aaggaccctc acaaaacagg    2400
gcctgaggac acaactgtcc tcattgaaac caaacgagat tattccaccg aattaagtgt    2460
caccattgcc gtcggggcgt cgctcctctt cctcaacatc ttagcttttg cggcgctgta    2520
ctacaaaaag gacaagaggc gccatgagac tcacaggcgc cccagtcccc agagaaacac    2580
```

```
cacaaatgat atcgctcaca tccagaacga agagatcatg tctctgcaga tgaagcagct    2640
ggaacacgat cacagtgtg agtcgctgca ggcacacgac acactgaggc tcacctgccc     2700
gccagactac accctcacgc tgcgccggtc gccagatgac atcccactta tgacgccaaa    2760
caccatcacc atgattccaa acacactgac ggggatgcag cctttgcaca cttttaacac    2820
cttcagtgga ggacaaaaca gtacaaattt accccacgga cattccacca ctagagtata    2880
gctttgccct atttcccttc ctatccctct gccctacccg ctcagcaaca tagaagaggg    2940
aaggaaagag agaaggaaag agagagagaa agaaagtctc cagaccagga atgtttttgt    3000
cccactgact taagacaaaa atgcaaaaag gcagtcatcc catcccggca gacccttatc    3060
gttggtgttt tccagtatta caagatcaac ttctgaccct gtgaaatgtg agaagtacac    3120
atttctgtta aaataactgc tttaagatct ctaccactcc aatcgatgtt tagtgtgata    3180
ggacatcacc atttcaaggc cccgggtgtt tccaacgtca tggaagcagc tgacacttct    3240
gaaactcagc caaggacact tgatattttt taattacaat ggaagtttaa acatttcttt    3300
ctgtgccaca caatggatgg ctctccttaa gtgaagaaag agtcaatgag attttgccca    3360
gcacatggag ctgtaatcca gagagaagga aacgtagaaa tttattatta aaagaatgga    3420
ctgtgcagcg aaatctgtac ggttctgtgc aaagaggtgt tttgccagcc tgaactatat    3480
ttaagagact ttgtaaaaaa gaaaaatgta tatagctgtg agtttaaaca aaaaccacaa    3540
acagacaaac aagaaaaaaa gcttttattg gtgttttcac tttgaaagag cttttagcaa    3600
ggttgtgctt ttcattgtgc tctgtacgta tataaatata tatatatata cacacacaca    3660
cacacattag tcatatcacc tctgtttcct ccccaacaaa agaggctttt cttcttaatt    3720
acttgtggta aacaaagaca tgggattttc ttacatgaga ttctcatttg taggaggatg    3780
tgatgtccca cagaagaccc agacggtctg tgtggcctat ttccccgtc aggttgcaca    3840 ggtgcatgca agagcattct taggagacca ctgttttgaa aaacttttga cttgtacgtg    3900
ttagccttca tgaaattgca gtacagagat gggtccccaa agtggagtgt atttacagct    3960
tgttaaatta gagacatgca cacacaaaga atcagtaggg agaaacaaaa atacaagtcc    4020
cgttctgtag ctctggccct ttgaatatgt ttaggaagag ttgcttccca tttcagggcc    4080
ctgccaaaaa agaagaaag cttgcctttg gtggggctat gcccttgga gtaaatacgg      4140 ctctgtgttc cctagcagct gcgggagggt ttggccgatg aagtacctgc tcagcttagc    4200
taatcagatt gaaggaagac atgtgtcttt ccttttgtt taagcactcg gtcccttatt     4260
tatcagtaag caggttttta aaatctttt atatcattta tgggatcaaa catatgattg     4320
tctgaaaaca tcactttttg tggatttgtg tatccggtca ccaaacggtg aatattatag    4380
aagaatgggg gaagaaagga tagaatatta aaactgcttt gcatgggttt tctgggaaat    4440
taggataact tcactgagaa gacattgaat ggaaattatt cacccatttt aaattggtga    4500
cctagggatc agagatttgt ctttccaaca gcttgtcatt ttttcatttc tcttctcatt    4560
tttcaggaaa gttttgagtg ttataaggtg gaaggaaaca tagtagcaat ggatactttt    4620
ttgaaaaatt attgcattac caagaaacag tagccaaaga tatttgaaga tcatgttcct    4680
cggctccatt gtgggttatt ctagaaatcc agtcttaaat ctctccgcta aagtggacat    4740
tccccataaa aattgtccag ctgcctggct cttttgcaat aacaaccttt gattactgaa    4800
tccctacact caaactatag tgatatatca gtgtttgaga gtgacctcta gaaaaaagaa    4860
aagtgttttt agaaatgcgt acaagtcacc cccaaatcct attgcttatc ttgggttaaa    4920
tttgagagtg attctctgta tataaatatg tgaaatatta ttatctcaac ttagcacacg    4980
```

```
tgaagcaaca tttctttcct acagagaggt gtcatggtaa gatttcattc cgaattcatt    5040
gtttcataga gctatgatca ggccatttct gcaagcaatg tatgacccca cctgagcaac    5100
cacaaatagg ctctctgtga aactacaaag gaagttatgt gtggcatcca tgttggtttc    5160
gtctgtctgt aatgtgaatt ccagtatttg tttagtattt ccagttgtct cctgctagca    5220
atatgtacag taacgcgtca ggcttgtgac atttgaataa ggaaaaacag agttcctgtt    5280
aagtgaataa ctttagcttt tacaggggat tatgatcaaa agtgatttta gtacatctta    5340
aatgatatct tatttctaca tggaaagaag ttatagaatc ttcatagagt tctatgagaa    5400
aaaatatact tgctatctat aaaaaagaga aaaaagaaaa aaaatgagaa aaaagtaaga    5460
aaaaaaaaaa tcctgtccta ggcttttact cttgatcttc aaaggcacgc agggtttaat    5520
ggttccttgg gttattattt tgcagttttg ttttttattt tgccttaagt aatgatagaa    5580
gatatatatg gccggacaca tatgtataaa cttttcagca gcattttaa taataaaata    5640 tcacagtatt ttctaaaaaa aaaaaaaaaa aa                                  5672
```

```
<210> SEQ ID NO 3
<211> LENGTH: 21
<212> TYPE: DNA
<213> ORGANISM: Artificial sequence
<220> FEATURE:
<223> OTHER INFORMATION: polynucleotide

<400> SEQUENCE: 3
cggctgcaac ttctcgcgca a                                              21

<210> SEQ ID NO 4
<211> LENGTH: 816
<212> TYPE: PRT
<213> ORGANISM: Homo sapiens

<400> SEQUENCE: 4
```

Met Ser Arg Pro Gln Gly Leu Leu Trp Leu Pro Leu Leu Phe Thr Pro
1               5                   10                  15

Val Cys Val Met Leu Asn Ser Asn Val Leu Leu Trp Leu Thr Ala Leu
            20                  25                  30

Ala Ile Lys Phe Thr Leu Ile Asp Ser Gln Ala Gln Tyr Pro Val Val
        35                  40                  45

Asn Thr Asn Tyr Gly Lys Ile Arg Gly Leu Arg Thr Pro Leu Pro Asn
    50                  55                  60

Glu Ile Leu Gly Pro Val Glu Gln Tyr Leu Gly Val Pro Tyr Ala Ser
65                  70                  75                  80

Pro Pro Thr Gly Glu Arg Arg Phe Gln Pro Pro Glu Pro Pro Ser Ser
                85                  90                  95

Trp Thr Gly Ile Arg Asn Thr Thr Gln Phe Ala Ala Val Cys Pro Gln
            100                 105                 110

His Leu Asp Glu Arg Ser Leu Leu His Asp Met Leu Pro Ile Trp Phe
        115                 120                 125

Thr Ala Asn Leu Asp Thr Leu Met Thr Tyr Val Gln Asp Gln Asn Glu
    130                 135                 140

Asp Cys Leu Tyr Leu Asn Ile Tyr Val Pro Thr Glu Asp Asp Ile His
145                 150                 155                 160

Asp Gln Asn Ser Lys Lys Pro Val Met Val Tyr Ile His Gly Gly Ser
                165                 170                 175

Tyr Met Glu Gly Thr Gly Asn Met Ile Asp Gly Ser Ile Leu Ala Ser

```
                180                 185                 190
Tyr Gly Asn Val Ile Val Ile Thr Ile Asn Tyr Arg Leu Gly Ile Leu
            195                 200                 205
Gly Phe Leu Ser Thr Gly Asp Gln Ala Ala Lys Gly Asn Tyr Gly Leu
            210                 215                 220
Leu Asp Gln Ile Gln Ala Leu Arg Trp Ile Glu Asn Val Gly Ala
225                 230                 235                 240
Phe Gly Gly Asp Pro Lys Arg Val Thr Ile Phe Gly Ser Gly Ala Gly
                245                 250                 255
Ala Ser Cys Val Ser Leu Leu Thr Leu Ser His Tyr Ser Glu Gly Leu
            260                 265                 270
Phe Gln Lys Ala Ile Ile Gln Ser Gly Thr Ala Leu Ser Ser Trp Ala
            275                 280                 285
Val Asn Tyr Gln Pro Ala Lys Tyr Thr Arg Ile Leu Ala Asp Lys Val
            290                 295                 300
Gly Cys Asn Met Leu Asp Thr Thr Asp Met Val Glu Cys Leu Arg Asn
305                 310                 315                 320
Lys Asn Tyr Lys Glu Leu Ile Gln Gln Thr Ile Thr Pro Ala Thr Tyr
                325                 330                 335
His Ile Ala Phe Gly Pro Val Ile Asp Gly Asp Val Ile Pro Asp Asp
                340                 345                 350
Pro Gln Ile Leu Met Glu Gln Gly Glu Phe Leu Asn Tyr Asp Ile Met
                355                 360                 365
Leu Gly Val Asn Gln Gly Glu Gly Leu Lys Phe Val Asp Gly Ile Val
            370                 375                 380
Asp Asn Glu Asp Gly Val Thr Pro Asn Asp Phe Asp Phe Ser Val Ser
385                 390                 395                 400
Asn Phe Val Asp Asn Leu Tyr Gly Tyr Pro Glu Gly Lys Asp Thr Leu
                405                 410                 415
Arg Glu Thr Ile Lys Phe Met Tyr Thr Asp Trp Ala Asp Lys Glu Asn
                420                 425                 430
Pro Glu Thr Arg Arg Lys Thr Leu Val Ala Leu Phe Thr Asp His Gln
                435                 440                 445
Trp Val Ala Pro Ala Val Ala Thr Ala Asp Leu His Ala Gln Tyr Gly
            450                 455                 460
Ser Pro Thr Tyr Phe Tyr Ala Phe Tyr His His Cys Gln Ser Glu Met
465                 470                 475                 480
Lys Pro Ser Trp Ala Asp Ser Ala His Gly Asp Glu Val Pro Tyr Val
                485                 490                 495
Phe Gly Ile Pro Met Ile Gly Pro Thr Glu Leu Phe Ser Cys Asn Phe
                500                 505                 510
Ser Lys Asn Asp Val Met Leu Ser Ala Val Val Met Thr Tyr Trp Thr
            515                 520                 525
Asn Phe Ala Lys Thr Gly Asp Pro Asn Gln Pro Val Pro Gln Asp Thr
            530                 535                 540
Lys Phe Ile His Thr Lys Pro Asn Arg Phe Glu Glu Val Ala Trp Ser
545                 550                 555                 560
Lys Tyr Asn Pro Lys Asp Gln Leu Tyr Leu His Ile Gly Leu Lys Pro
                565                 570                 575
Arg Val Arg Asp His Tyr Arg Ala Thr Lys Val Ala Phe Trp Leu Glu
                580                 585                 590
Leu Val Pro His Leu His Asn Leu Asn Glu Ile Phe Gln Tyr Val Ser
            595                 600                 605
```

```
Thr Thr Thr Lys Val Pro Pro Asp Met Thr Ser Phe Pro Tyr Gly
    610             615                 620

Thr Arg Arg Ser Pro Ala Lys Ile Trp Pro Thr Lys Arg Pro Ala
625             630                 635                 640

Ile Thr Pro Ala Asn Asn Pro Lys His Ser Lys Asp Pro His Lys Thr
                645                 650                 655

Gly Pro Glu Asp Thr Thr Val Leu Ile Glu Thr Lys Arg Asp Tyr Ser
            660                 665                 670

Thr Glu Leu Ser Val Thr Ile Ala Val Gly Ala Ser Leu Leu Phe Leu
        675                 680                 685

Asn Ile Leu Ala Phe Ala Ala Leu Tyr Tyr Lys Lys Asp Lys Arg Arg
    690                 695                 700

His Glu Thr His Arg Arg Pro Ser Pro Gln Arg Asn Thr Thr Asn Asp
705             710                 715                 720

Ile Ala His Ile Gln Asn Glu Glu Ile Met Ser Leu Gln Met Lys Gln
                725                 730                 735

Leu Glu His Asp His Glu Cys Glu Ser Leu Gln Ala His Asp Thr Leu
            740                 745                 750

Arg Leu Thr Cys Pro Pro Asp Tyr Thr Leu Thr Leu Arg Arg Ser Pro
        755                 760                 765

Asp Asp Ile Pro Leu Met Thr Pro Asn Thr Ile Thr Met Ile Pro Asn
770                 775                 780

Thr Leu Thr Gly Met Gln Pro Leu His Thr Phe Asn Thr Phe Ser Gly
785             790                 795                 800

Gly Gln Asn Ser Thr Asn Leu Pro His Gly His Ser Thr Thr Arg Val
                805                 810                 815

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
aaagccctat ctctctgcag g                                         21

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
tgagtagtat ttcggatgcc ag                                        22

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
aagaacaccg ttacccaatg ag                                        22

<210> SEQ ID NO 8
<211> LENGTH: 23
```

```
<212> TYPE: DNA
<213> ORGANISM: Artificial sequence
<220> FEATURE:
<223> OTHER INFORMATION: Primer

<400> SEQUENCE: 8
gagacattat aaaaccctcc tag                                          23

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
ttagcattgg tgagtcagtg tg                                           22

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
ccgtcaaaac gagaagtgga ct                                           22

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11 cttttctat ttggccacca                                               20

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
ttcttggttc agggtatttg c                                            21

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
agctgcattt ctgtcctgtg                                              20

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
```
tctcccgcaa agtgtctttc                                              20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
ccaacttcgt ggacaacctt                                              20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
accccaacac gaagatgaac                                              20

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
cacgtcacat gtggaagagt                                              20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
gacggcaatg gtgacactta                                              20

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
tcctcattga aaccaaacga                                              20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
aacattcctg gtctggagac                                              20

MODULATION OF NLGN4 EXPRESSION, NK CELL ACTIVITY IN NON-ALCOHOLIC FATTY LIVER DISEASE (NAFLD)

CROSS REFERENCE TO RELATED APPLICATIONS

This application claims priority from U.S. Provisional application Ser. No. 61/884,153 filed on Sep. 30, 2013.

FIELD OF THE INVENTION

The present invention relates to the involvement of NK cells in Nonalcoholic-Fatty-Liver-Disease (NAFLD), mediated by a novel Neuroligin-4 (NLGn4) synaptic pathway. The present invention provides compositions and methods for modulating the action of NLGn4 to attenuate Nonalcoholic-Fatty-Liver-Disease (NAFLD).

BACKGROUND OF THE INVENTION

Nonalcoholic fatty-liver disease (NAFLD) is one of the most prevalent liver diseases in western countries. The full pathophysiology of NAFLD is still unknown. Both obesity and insulin resistance are considered to play a strong role in the disease process. Indeed, the rising rates of obesity and diabetes mellitus correlate with the increasing incidence of NAFLD, which is the hepatic and early manifestation of metabolic syndrome. Estimates suggest that about 20% to 30% of adults in developed countries have excess fat accumulation in the liver, 50% among people with diabetes, and about 80% in the obese and morbidly obese individuals.

Non-alcoholic steatohepatitis (NASH) is the most severe form of NAFLD, and can progress to more severe forms of liver disease, including fibrosis progression, cirrhosis, and even hepatocellular carcinoma.

The disease begins with the aberrant accumulation of triglycerides in the liver, resulting in simple steatosis; most patients who develop steatosis are stable and further disease does not develop. However, some individuals progress to NASH, the severe form of NAFLD. In NASH, up to 20% of patients' progress into cirrhosis.

The normal liver is composed of hepatocytes and non-parenchymal cells, which include kupffer cells, sinusoidal endothelial cells, and myofibroblasts known as Hepatic Stellate Cells (HSCs). HSCs are considered to be involved in the pathogenesis of liver fibrosis from any etiology, including NASH-related hepatic fibrosis. In normal liver, HSCs are described as being in a quiescent state and serve to store retinoids (vitamin A). Quiescent stellate cells represent 5-8% of the total number of liver cells. When the liver is damaged, HSCs can change into an activated state characterized by contractions, loss of lipid droplets and enhanced of proliferation, cell migration as well as cellular adhesion. HSCs are also unequivocally the main cells involved in the production of excessive ECM seen in liver fibrosis. Since activated HSCs themselves secrete inflammatory chemokines, a vicious cycle is formed, whereby fibrogenic and inflammatory cells stimulate each other and perpetuate a process of liver damage and repair.

Natural killer (NK) cells are a key component of the innate immune system, and play a critical role in the early stages of the immune response against tumor cells, as well as those infected by viral and microbial pathogens.

In humans, two NK-cell subsets have been characterized according to the cell-surface density of CD56 and expression of CD16. $CD56^{dim}CD16^{bright}$ NK cells (hereinafter $CD56^{dim}$) compose approximately 90% of circulating NK cells; $CD56^{bright}CD16^{dim}$ NK cells (hereinafter $CD56^{bright}$) constitute approximately 10%. $CD56^{bright}$ NK cells proliferate and produce interferon in response to stimulation with interleukin-12 (IL-12), whereas $CD56^{dim}$ NK cells are more cytolytic and produce significant amounts of cytokine when their activating receptors are engaged.

In a paper published by some of the inventors it was found that, as opposed to CD8 immune cells, NK cells have anti-fibrotic activity through stimulation of HSC killing. (Melhhem et al., J. Hepatology; 2006; 45: 60-71). It has also been reported that the function of NK cells decreases when the liver disease progresses into cirrhosis, suggesting that attenuating NK function is a prerequisite for the progression of the disease (Seki et al.; Clin Dev Immunol.; 2011; Article ID 868345).

Human neuroligin-4 (NLG4, NLGn4, NLGn4X) encodes a member of a family of neuronal cell surface proteins called the Neuroligins. FIG. 1 illustrates the neuroligins and their interactions. Members of this family may act as splice site-specific ligands for beta-neurexins and may be involved in the formation and remodeling of central nervous system synapses. The encoded protein interacts with discs, large (Drosophila) homolog 4 (DLG4). Mutations in this gene have been associated with autism and Asperger syndrome. NLGn4 is also detected with high levels of expression in heart and lower in liver, skeletal muscle and pancreas.

The clinical implications of NAFLD are derived mostly from its potential to progress to cirrhosis and liver failure. There is an unmet medical for compositions and methods for treating NAFLD and preventing the progression to cirrhosis. Nowhere in the art has it been suggested that disease progression of NAFLD can be modulated by attenuating NLGn4 expression and thereby NK cell activity.

SUMMARY OF THE INVENTION

The present invention relates to preventing, treating and attenuating liver disease by inhibiting NLGn4 expression and thereby modulating the activity of NK cells. The invention, according to some embodiments relates to attenuation of the progression of NAFLD into cirrhosis and liver failure by modulating the expression of human neuroligin-4 (NLGn4, NLGn4, NLGn4X) and thereby activating cytotoxic NK cells.

There is provided herein according to some embodiments, a method of treating, attenuating and/or preventing progression of a liver disorder in a subject, the method comprising administering to the subject a composition comprising a therapeutically effective amount of an agent capable of inhibiting expression of a NLGn4 gene product, thereby treating, attenuating and/or preventing progression of the liver disorder.

According to some embodiments, the human NLGn4 gene product is encoded by a nucleic acid sequence comprising SEQ ID NO: 1. According to some embodiments, the NLGn4 gene product is encoded by a nucleic acid sequence with the accession number NM_020742. According to some embodiments, the NLGn4 gene product is encoded by a nucleic acid sequence with the accession number NM_181332. According to some embodiments, the NLGn4 gene product is encoded by a nucleic acid sequence with the accession number NM_001282145. According to some embodiments, the NLGn4 gene product is encoded by a nucleic acid sequence with the accession number NM_001282146.

According to some embodiments, the NLGn4 gene product comprises an mRNA sequence set forth in SEQ ID NO: 2. According to some embodiments, the accession number of the NLGn4 mRNA is AY358562. According to some embodiments, the accession number of the NLGn4 mRNA is BC032567. According to some embodiments, the accession number of the NLGn4 mRNA is BC034018.

According to some embodiments, the NLGn4 gene product comprises a peptide sequence set forth in SEQ ID NO: 4. According to some embodiments, the accession number of the NLGn4 polypeptide is NP_001269075.1. According to some embodiments, the accession number of the NLGn4 polypeptide is NP_001269074.1. According to some embodiments, the accession number of the NLGn4 polypeptide is NP_851849.1. According to some embodiments, the accession number of the NLGn4 polypeptide is NP_065793.1.

According to some embodiments, the agent comprises one or more inhibitory nucleic acids complementary to at least a portion of SEQ ID NO: 2.

According to some embodiments, the one or more inhibitory nucleic acids is selected from the group consisting of: an antisense molecule, an siRNA, and an shRNA. Each possibility is a separate embodiment of the invention.

According to some embodiments, the siRNA comprises a sequence set forth in SEQ ID NO: 3. According to some embodiments, the accession number of the siRNA sequence is SI03083395.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the liver disorder is characterized by NLGn4 overexpression. According to some embodiments, NLGn4 overexpression comprises a 2, 3, 4, 5-10 fold or more increase in NLGn4 expression relative to the expression level obtained in normal subjects. According to some embodiments, the overexpression attenuates NK cell activity, inhibits the expression of NLGn4 and modulates and/or activates the function of the NK cell.

According to some embodiments, administering to the subject the composition comprising a therapeutically effective amount of an agent capable of inhibiting expression of a NLGn4 gene product comprises administering the composition to an immune cell population of the subject. According to some embodiments, administering the composition to an immune cell population comprises infecting the immune cell population with a vector comprising the agent capable of inhibiting NLGn4 expression.

According to some embodiments, inhibiting the expression of the NLGn4 gene product reduces the activity of hepatic stellate cells. According to some embodiments, inhibiting the expression of the NLGn4 gene product increases apoptosis of the hepatic stellate cells.

According to some embodiments, the composition further comprises a GLUT4 antagonist. According to some embodiments, NLGn4 expression is regulated by a specific type of ionotropic glutamate receptor N-methyl-D-aspartate (NMDA or GLUT4 receptor; NMDAR). According to some embodiments, NLGn4 is linked to NMDR and both localize and bind PSD-95; a post synaptic density protein (PSD) According to some embodiments, the composition comprises an NMDAR antagonist selected from the group consisting of: Ketamin, Amantadine, Phencyclidine, Nitrous oxide, Dextromethorphan (and dextrorphan), Memantine, Ethanol, Riluzole, Xenon, HU-211, Lead (Pb2+), Conantokins, and Huperzine A.

According to an alternative embodiment, administering an N-methyl D aspartate receptor (NMDAR) agonist can increase NMDAR-mediated NLGn4 expression and as a result attenuate NK cell activity. Non-limiting examples of NMDAR agonists are Aminocyclopropanecarboxylic acid, D-Cycloserine, cis-2,3-Piperidinedicarboxylic acid, L-aspartate, L-alanine, Quinolinate, Homocysterate, D-serine, and ACPL.

There is provided herein according to some embodiments, a pharmaceutical composition for the use in treating, attenuating and/or preventing progression of a liver disorder in a subject, the composition comprising a therapeutically effective amount of an agent capable of inhibiting expression of a NLGn4 gene product, wherein the composition is capable of treating, attenuating and/or preventing progression of the liver disorder.

According to some embodiments, the pharmaceutical composition further comprises a pharmaceutically acceptable carrier.

There is provided herein according to some embodiments, a method of diagnosing and/or monitoring a liver disorder in a subject, the method comprising: isolating an immune cell population from a biological sample of the subject; detecting expression level of an NLGn4 gene product in the immune cell population and diagnosing and/or monitoring the liver disorder according to the NLGn4 gene product expression level.

According to some embodiments, the NLGn4 gene product is encoded by a nucleic acid sequence comprising SEQ ID NO: 1. According to some embodiments, the NLGn4 gene product comprises SEQ ID NO: 2.

According to some embodiments, the agent comprises one or more inhibitory nucleic acids complementary to at least a portion of SEQ ID NO: 2. According to some embodiments, the one or more inhibitory nucleic acids are selected from the group consisting of: an antisense molecule, an siRNA, and an shRNA. Each possibility is a separate embodiment of the invention.

According to some embodiments, the siRNA comprises a sequence set forth in SEQ ID NO: 3.

According to some embodiments, the liver disorder is selected from the group consisting of: non-alcoholic fatty liver disease (NAFLD), non-alcoholic steatohepatitis (NASH), cirrhosis, hepatitis, liver adenoma, insulin hypersensitivity, liver cancer and any combination thereof. Each possibility is a separate embodiment of the invention.

According to some embodiments, the immune cell population is a natural killer (NK) cell population. Additionally or alternatively, the immune cell population is a subpopulation of NK cells According to some embodiments; the NK subpopulation is the $CD56^{dim}$ subpopulation. According to some embodiments; the NK subpopulation is the $CD56^{bright}$ subpopulation. According to some embodiments, the method comprises modulating the activity of the NK cells and/or a subpopulation of NK cells. According to some embodiments, modulating the activity of NK cells comprises enhancing the cytotoxicity of the NK cells. According to some embodiments, enhancing the cytotoxicity of NK cells comprises, but is not limited to, elevating CD107a expression in the NK cell and/or NK subpopulation.

According to some embodiments, the NK cell is a liver NK cell, and the activity of the NK cell is attenuated in patients with a liver disorder. According to yet another embodiment, NK cells from patients with a liver disorder, overexpresses NLGn4.

According to some embodiments, the biological sample comprises a blood sample, a tissue sample, a biological fluid, or any combination thereof.

According to some embodiments, the NLGn4 gene product expression level is detected by Polymerase Chain Reaction (PCR), Reverse-Transcriptase-PCR (RT-PCR), Northern Blot, Real-time PCR, hybridization to an oligonucleotide or any combination thereof. Each possibility is a separate embodiment of the invention.

According to some embodiments, the oligonucleotide comprises deoxyribonucleic acid (DNA), RNA, complementary deoxyribonucleic acid (cDNA), genomic DNA, synthetic oligonucleotide, or any combination thereof. Each possibility is a separate embodiment of the invention.

There is provided herein according to some embodiments, a kit for diagnosing a liver disorder, the kit comprising: means for isolating an immune cell population from a biological sample of a patient; and at least one reagent capable of detecting NLGn4 gene product expression level.

According to some embodiments, the reagent comprises NLGn4 specific primers.

According to some embodiments, the NLGN4 primers were designed to specifically amplify the NLGN4 copy on the X chromosome (Xp22.32-p22.31).

DETAILED DESCRIPTION

Figure 1:
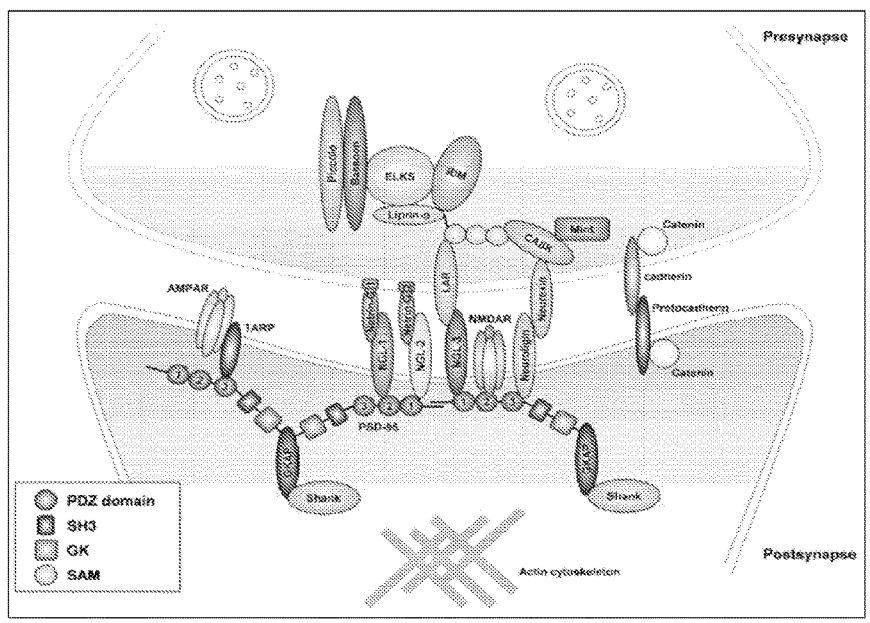
FIG. 1 shows a schematic representation of the Neuroligins and NLG interactions.

The present invention provides methods and compositions for treating and diagnosing liver disorders by activating attenuated natural killer (NK) cells and thereby reducing Hepatic stellate cell (HCSs) induced fibrosis.

In the following description, various aspects of the invention will be described. For the purpose of explanation, specific details are set forth in order to provide a thorough understanding of the invention. However, it will also be apparent to one skilled in the art that the invention may be practiced without specific details being presented herein.

Furthermore, well-known features may be omitted or simplified in order not to obscure the invention.

The following are terms which are used throughout the description and which should be understood in accordance with the various embodiments to mean as follows:

As referred to herein, the terms "liver disorder", "liver disease" and "hepatic disease" are used interchangeably and refer to diseases and disorders that cause the liver to function improperly or stop functioning.

As referred to herein, the term "gene product" refers to a DNA sequence that is transcribed into mRNA that is then translated into a sequence of amino acids characteristic of a specific polypeptide. Hence it is understood by the skilled in the art that the term gene product encompasses non-processed RNA, mRNA, splice variants thereof, corresponding cDNA sequences, polypeptides and proteins.

As used herein the terms "polynucleotide" "polynucleotide molecules", "oligonucleotide", "nucleic acid" and "nucleotide" may interchangeably be used. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules and refers to nucleic acid or ribonucleic acid sequence.

As used herein the term "complementary" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A) forms a base pair with thymine (T) and guanine (G) with cytosine (C). In RNA, thymine is replaced by uracil (U). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

As used herein the term "short hairpin RNA" and "shRNA are used interchangeably and refer to, refer to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

As used herein the term "small interfering RNA" and "siRNA" are used interchangeably and refer to a nucleic acid molecule mediating RNA interference or gene silencing. The siRNA inhibits expression of a target gene and provides effective gene knock-down.

As used herein the term "antisense oligonucleotide" refer to nucleic acids, preferably, DNA, RNA or its derivatives, that are complementary to the nucleotide sequences of a target mRNA, characterized in that they binds to the target mRNA and interfere its translation to protein.

As used herein the term "vector" refers to expression constructs engineered to express shRNAs such as, but not limited to, retroviral and lentiviral vectors. Such expression constructs may include one or more inducible promoters, RNA Pol III promoter systems such as U6 snRNA promoters or H1 RNA polymerase III promoters, or other promoters known in the art.

According to an aspect of the invention, provided is a method of treating, attenuating or preventing a liver disorders such as Non-alcoholic fatty liver disease (NAFLD), and Non-alcoholic steatohepatitis (NASH) in a patient in need thereof. Alternatively other disorders such as cirrhosis, hepatitis, liver adenoma, insulin resistance, and liver cancer, or any NK related inflammatory or neoplastic disorder, can be the subject of treatment as well. The clinical implications of NAFLD are derived mostly from its potential to progress to Non-alcoholic steatohepatitis, cirrhosis and liver failure. In accordance, the invention, addresses the long felt need to attenuate the progression of NAFLD into cirrhosis and liver failure by inhibiting NLGn4 expression and thereby modulating the cytotoxic activity of NK cells. According to some embodiments, the invention provides a method for modulating the activity of a natural killer (NK) cell.

According to some embodiments, the method comprises administering to the patient in need thereof, a composition comprising a therapeutically effective amount of an agent capable of inhibiting the expression of the ribonucleic acid (RNA) encoded by NLGn4 nucleic acid molecule. The agent can for example be one or more polynucleotides, capable of hybridizing with the NLGn4 nucleic acid, such an inhibitory nucleic acid that is complementary and specific to at least a portion of NLGn4. The inhibitory nucleic acid can for example be an antisense molecule, an siRNA, or an shRNA. According to some embodiments, the siRNA comprises the sequence set forth in SEQ ID NO: 3. CGGCTGCAACTCTCGCGCAA.

The NLGn4 mRNA sequence is set forth in the following sequence SEQ ID NO:2:

agaaggggaaggctcctgggctttcaatacatcctcctgaatcataccct gtttcgggttccctagaaaaatctggacgtgtaaaaagaactcttaacgg ccgatgcagctcttccaaagctaaggctgccttggagttttcataagaaa ttgtccctggaggtgttggatgatcacagcttccttggagcattgcagtt gctggaatccagtttcaggattaagggagggctgcctccttgcaatgggc tgccaagaaaacggctgtgcttgttcttaacctcaggctctgtctgtgat cagtctgagagtctctcccaggtctactgctccctggaaagccctatctc tctgcaggctcgcctctgggctttgtctccttggagccacatcactggga cagctgtggatgtggatgcagatttgaaccatgtcacggccccagggact gctatggcttcctttgttgttcacccggtctgcgtcatgttaaactcca atgtcctcctgtggttaactgctcttgccatcaagttcaccctcattgac agccaagcacagtatccagttgtcaacacaaattatggcaaaatccgggg cctaagaacaccgttacccaatgagatcttgggtccagtggagcagtact tagggtcccctatgcctcaccccccactggagagaggcggtttcagccc ccagaaccccgtcctcctggactggcatccgaaatactactcagtttgc tgctgtgtgcccccagcacctggatgagagatccttactgcatgacatgc tgcccatctggtttaccgccaatttggatactttgatgacctatgttcaa gatcaaaatgaagactgcctttacttaaacatctacgtgcccacggaaga tgatattcatgatcagaacagtaagaagcccgtcatggtctatatccatg ggggatcttacatggagggcaccggcaacatgattgacggcagcatttg gcaagctacggaaacgtcatcgtgatcaccattaactaccgtctgggaat actagggttttaagtaccggtgaccaggcagcaaaaggcaactatgggc tcctggatcagattcaagcactgcggtggattgaggagaatgtgggagcc tttggcggggaccccaagagagtgaccatctttggctcgggggctgggc ctcctgtgtcagcctgttgaccctgtcccactactcagaaggtctcttcc agaaggccatcattcagagcggcaccgccctgtccagctgggcagtgaac taccagccggccaagtacactcggatattggcagacaaggtcggctgcaa catgctggacaccacggacatggtagaatgcctgcggaacaagaactaca aggagctcatccagcagaccatcaccccggccacctaccacatagccttc gggccggtgatcgacggcgacgtcatcccagacgaccccagatcctgat ggagcaaggcgagttcctcaactacgacatcatgctgggcgtcaaccaag gggaaggcctgaagttcgtggacggcatcgtggataacgaggacggtgtg acgcccaacgactttgacttctccgtgtccaacttcgtggacaaccttta cggctaccctgaagggaaagacactttgcgggagactatcaagttcatgt acacagactgggccgataaggaaaacccggagacgcggcggaaaaccctg gtggctctctttactgaccaccagtgggtggccccgccgtggccaccgc cgacctgcacgcgcagtacggctcccccacctacttctatgccttctatc atcactgccaaagcgaaatgaagcccagctgggcagattcggcccatggt gatgaggtccctatgtcttcggcatcccatgatcggtcccaccgagct cttcagttgtaacttttccaagaacgacgtcatgctcagcgccgtggtca tgacctactggacgaacttcgccaaaactggtgatccaaatcaaccagtt cctcaggataccaagttcattcacacaaaacccaaccgctttgaagaagt ggcctggtccaagtataatcccaaagaccagctctatctgcatattggct tgaaacccagagtgagagatcactaccgggcaacgaaagtggctttctgg ttggaactcgttcctcatttgcacaacttgaacgagatattccagtatgt ttcaacaaccacaaaggttcctccaccagacatgacatcatttccctatg gcacccggcgatctcccgccaagatatggccaaccaccaaacgcccagca atcactcctgccaacaatcccaaacactctaaggaccctcacaaaacagg gcctgaggacacaactgtcctcattgaaaccaaacgagattattccaccg aattaagtgtcaccattgccgtcggggcgtcgctcctcttcctcaacatc ttagcttttgcggcgtgtactacaaaaaggacaagaggcgccatgagac tcacaggcgccccagtccccagagaaacaccacaaatgatatcgctcaca

```
tccagaacgaagagatcatgtctctgcagatgaagcagctggaacacgat
cacgagtgtgagtcgctgcaggcacacgacacactgaggctcacctgccc
gccagactacaccctcacgctgcgccggtcgccagatgacatcccactta
tgacgccaaacaccatcaccatgattccaaacacactgacggggatgcag
cctttgcacacttttaaccacccttcagtggaggacaaaacagtacaaattt
accccacggacattccaccactagagtatagctttgccctatttcccttc
ctatccctctgccctacccgctcagcaacatagaagagggaaggaaagag
agaaggaaagagagagagaaagaaagtctccagaccaggaatgttttttgt
cccactgacttaagacaaaaatgcaaaaaggcagtcatcccatcccggca
gaccctatcgttggtgttttccagtattacaagatcaacttctgaccct
gtgaaatgtgagaagtacacatttctgttaaaataactgctttaagatct
ctaccactccaatcgatgtttagtgtgataggacatcaccatttcaaggc
cccgggtgtttccaacgtcatggaagcagctgacacttctgaaactcagc
caaggacacttgatatttttaattacaatggaagtttaaacatttctttt
ctgtgccacacaatggatggctctccttaagtgaagaaagagtcaatgag
attttgcccagcacatggagctgtaatccagagagaaggaaacgtagaaa
tttattattaaaagaatggactgtgcagcgaaatctgtacggtctgtgc
aaagaggtgttttgccagcctgaactatatttaagagactttgtaaaaaa
gaaaaatgtatatagctgtgagtttaaacaaaaaccacaaacagacaaac
aagaaaaaaagcttttattggtgttttcacttttgaaagagcttttagcaa
ggttgtgcttttcattgtgctctgtacgtatataaatatatatatata
cacacacacacacattagtcatatcacctctgtttcctccccaacaaa
agaggcttttcttcttaattacttgtggtaaacaaagacatgggattttc
ttacatgagattctcatttgtaggaggatgtgatgtcccacagaagaccc
agacggtctgtgtggcctatttcccccgtcaggttgcacaggtgcatgca
agagcattcttaggagaccactgttttgaaaaacttttgacttgtacgtg
ttagccttcatgaaattgcagtacagagatgggtccccaaagtggagtgt
atttacagcttgttaaattagagacatgcacacacaaagaatcagtaggg
agaaacaaaaatacaagtcccgttctgtagctctggccdttgaatatgtt
taggaagagttgcttcccatttcagggccctgccaaaaaaagaagaaagc
ttgcctttggtggggctatgcccttggagtaaatacggctctgtgttcc
ctagcagctgcgggagggtttggccgatgaagtacctgctcagcttagct
aatcagattgaaggaagacatgtgtctttcctttttgtttaagcactcgg
tcccttatttatcagtaagcaggttttttaaaaatcttttatatcatttat
gggatcaaacatatgattgtctgaaaacatcactttttgtggatttgtgt
atccggtcaccaaacggtgaatattatagaagaatgggggaagaaaggat
agaatattaaaactgctttgcatgggttttctgggaaattaggataactt
cactgagaagacattgaatggaaattattcacccatttttaaattggtgac
ctagggatcagagatttgtctttccaacagcttgtcattttttcatttct
cttctcatttttcaggaaagttttgagtgttataaggtggaaggaaacat
agtagcaatggatacttttttgaaaaattattgcattaccaagaaacagt
agccaaagatatttgaagatcatgttcctcggctccattgtgggttattc
tagaaatccagtcttaaatctctccgctaaagtggacattccccataaaa
attgtccagctgcctggctcttttgcaataacaaccttttgattactgaat
ccctacactcaaactatagtgatatatcagtgtttgagagtgacctctag
aaaaaagaaaagtgtttttagaaatgcgtacaagtcaccccaaatccta
ttgcttatcttgggttaaatttgagagtgattctctgtatataaatatgt
gaaatattattatctcaacttagcacacgtgaagcaacatttctttccta
cagagaggtgtcatggtaagatttcattccgaattcattgtttcatagag
ctatgatcaggccatttctgcaagcaatgtatgaccccacctgagcaacc
acaaataggctctctgtgaaactacaaaggaagttatgtgtggcatccat
gttggtttcgtctgtctgtaatgtgaattccagtatttgtttagtatttc
cagttgtctcctgctagcaatatgtacagtaacgcgtcaggcttgtgaca
tttgaataaggaaaaacagagttcctgttaagtgaataactttagcttt
acagggattatgatcaaaagtgattttagtacatcttaaatgatatctt
atttctacatggaaagaagttatagaatcttcatagagttctatgagaaa
aaatatacttgctatctataaaaaagagaaaaaagaaaaaaaatgagaaa
aaagtaagaaaaaaaaaatcctgtcctaggcttttactcttgatcttca
aaggcacgcagggtttaatggttccttgggttattattttgcagttttgt
ttttttattttgccttaagtaatgatagaagatatatatggccggacacat
atgtataaacttttcagcagcattttttaataataaaatatcacagtattt
tctaaaaaaaaaaaaaaaaa
```

Additionally or alternatively, the method comprises administering to the patient in need thereof, a composition comprising a therapeutically effective amount of an agent (such as for example an antibody) capable of inhibiting the expression and/or function of NLGn4 protein.

The NLGn4 polypeptide sequence is set forth in the following sequence SEQ ID NO: 4:

MSRPQGLLWLPLLFTPVCVMLNSNVLLWLTALAIKFTLIDSQAQYPVVNT
NYGKIRGLRTPLPNEILGPVEQYLGVPYASPPTGERRFQPPEPPSSWTGI
RNTTQFAAVCPQHLDERSLLHDMLPIWFTANLDTLMTYVQDQNEDCLYLN
IYVPTEDDIHDQNSKKPVMVYIHGGSYMEGTGNMIDGSILASYGNVIVIT
INYRLGILGFLSTGDQAAKGNYGLLDQIQALRWIEENVGAFGGDPKRVTI
FGSGAGASCVSLLTLSHYSEGLFQKAIIQSGTALSSWAVNYQPAKYTRIL
ADKVGCNMLDTTDMVECLRNKNYKELIQQTITPATYHIAFGPVIDGDVIP
DDPQILMEQGEFLNYDIMLGVNQGEGLKFVDGIVDNEDGVTPNDFDFSVS
NEVDNLYGYPEGKDTLRETIKFMYTDWADKENPETRRKTLVALFTDHQWV
APAVATADLHAQYGSPTYFYAFYHHCQSEMKPSWADSAHGDEVPYVEGIP
MIGPTELFSCNFSKNDVMLSAVVMTYWTNFAKTGDPNQPVPQDTKFIHTK
PNRFEEVAWSKYNPKDQLYLHIGLKPRVRDHYRATKVAFWLELVPHLHNL
NEIFQYVSTTTKVPPPDMTSFPYGTRRSPAKIWPTTKRPAITPANNPKHS

```
KDPHKTGPEDTTVLIETKRDYSTELSVTIAVGASLLFLNILAFAALYYKK

DKRRHETHRRPSPQRNTTNDIAHIQNEEIMSLQMKQLEHDHECESLQAHD

TLRLTCPPDYTLTLRRSPDDIPLMTPNTITMIPNTLTGMQPLHTENTFSG

GQNSTNLPHGHSTTRV
```

According to some embodiments, the NK cells are liver NK cells which are attenuated in patients having a liver disorder. According to yet another embodiment, the liver disorder is characterized by overexpression of NLGn4 RNA. Such overexpression can attenuate NK cell activity.

According to some embodiments inhibiting the expression of NLGn4 modulates the function of the NK cell for example by activating the NK cell and/or the CD56$^{dim}$ NK cell subset. As a result of NK activation, the activity of hepatic stellate cells (HSCs) and hence fibrosis is reduced. In addition, and according to yet another embodiment, modulating and/or activating the NK cells increases the apoptosis of the HSCs.

According to yet another embodiment there is provided a method for modulating the activity of a natural killer (NK) cell and/or treating, preventing and/or attenuating a liver disorder by administering to a patient a composition comprising a GLUT4 antagonist. Such antagonist can according to the present invention inhibit GLUT4 mediated NLGn4 expression. The antagonist can be selected from the group comprising Ketamine, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A. According to an alternative embodiment administering a NMDAR (also known as GLUT4) agonist can increase GLUT4 mediated NLGn4 expression and as a result attenuate NK cell activity. Examples of a GLUT4 agonists are Aminocyclopropanecarboxylic acid, D-Cycloserine, cis-2,3-Piperidinedicarboxylic acid, L-aspartate, L-alanine, Quinolinate, Homocysterate, D-serine, and ACPL.

According to another aspect of the invention, there is provided a method of modulating the expression of the ribonucleic acid (RNA) encoded by NLGn4 nucleic acid. According to one embodiment, modulating the expression NLGn4 can serve to treat, attenuate or prevent a liver disorder, such as Non-alcoholic fatty liver disease (NAFLD), Non-alcoholic steatohepatitis (NASH), cirrhosis, hepatitis, liver adenoma, insulin resistance, a liver cancer, any NK related inflammatory or neoplastic disorder, or any combination thereof.

According to another embodiment, modulating the expression of NLGn4 comprises contacting the immune cell, such as an NK cell and/or a CD56$^{dim}$ NK cell subset, with a composition comprising an effective amount of an agent that inhibits NLGn4 expression. Such agent can for example be an inhibitory nucleic acid that is complementary and specific to at least a portion of the NLGn4 nucleic acid molecule.

According to yet another embodiment, the inhibitory nucleic acid can for example be an antisense molecule, an siRNA, or an shRNA.

Inhibiting NLGn4 can according to the present invention enhance the cytotoxicity of the NK cells and or specific NK cell subpopulations. According to certain embodiments enhancing the cytotoxicity comprises enhancing the expression of CD107a on said NK cell.

In certain liver disorders NK cell function can be attenuated. According to the present invention such attenuation can be a result of NLGn4 overexpression. In accordance, inhibiting the expression of NLGn4 modulates and/or activates the function of attenuated NK cell. In turn, activating the NK cell may reduce HSC activity and/or increase their apoptosis.

According to yet another aspect of the invention there is provided a method of diagnosing or monitoring a liver disorder and/or the severity of a liver disorder in a patient such as Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The method comprises, according to one embodiment, detecting the expression level of a ribonucleic acid (RNA) encoded by NLGn4 nucleic acid molecule in a biological sample, such as a blood sample, a tissue sample and/or a biological fluid, of a patient.

According to some embodiments, the method further comprises isolating the RNA from the biological sample prior to detecting the NLGn4 RNA expression level. The detection of NLGn4 expression comprises Polymerase Chain Reaction (PCR), Reverse-Transcriptase-PCR (RT-PCR), Northern Blot, Real-time PCR, Flow Cytometry (FACS) or any combination thereof.

Alternatively, the expression level of NLGn4 is detected by hybridization to an oligonucleotide such as a deoxyribonucleic acid (DNA), an RNA, complementary deoxyribonucleic acid (cDNA), a genomic DNA, a synthetic oligonucleotide, or any combination thereof.

According to yet another aspect of the invention, there is provided a pharmaceutical composition comprising a therapeutically effective amount of an agent that inhibits the expression or function of NLGn4.

The agent can be one or more polynucleotides, capable of hybridizing with said nucleic acid. For example the agent can be an inhibitory nucleic acid, such as an antisense molecule, an siRNA, or an shRNA that is complementary and specific to at least a portion of said NLGn4 nucleic acid molecule According to some embodiments, the pharmaceutical composition further comprises a vector capable of expressing the inhibitory nucleic acid molecule. Non-limiting examples of vectors comprise lentiviral vectors, retroviral vectors, plasmids as well as other suitable vectors.

According to another embodiment, the composition comprises or additionally comprises a GLUT4 antagonist. Such antagonist can according to the present invention inhibit GLUT4 mediated NLGn4 expression. The antagonist can be selected from the group consisting of Ketamin, Amantadine, Phencyclidine, Nitrous oxide, Dextromethorphan (and dextrorphan), Memantine, Ethanol, Riluzole (used in ALS), Xenon, HU-211 (also a cannabinoid), Lead (Pb2+), Conantokins, and Huperzine A According to an alternative embodiment administering a GLUT4 agonist can increase GLUT4 mediated NLGn4 expression and as a result attenuate NK cell activity. Examples of a GLUT4 agonists are alanine, Aminocyclopropanecarboxylic acid, D-Cycloserine, cis-2,3-Piperidinedicarboxylic acid, L-aspartate, L-alanine, Quinolinate, Homocysterate, D-serine, and ACPL According to yet another aspect of the invention, there is provided a kit for prevention, treatment or attenuation of a liver disorder such as, but not limited to, Non-alcoholic fatty liver disease (NAFLD), Non-alcoholic steatohepatitis (NASH), cirrhosis, hepatitis, a liver adenoma, insulin resistance, a liver cancer, any NK related inflammatory or neoplastic disorder, or any combination thereof. The kit comprises the pharmaceutical composition as essentially described above and a pharmaceutically acceptable carrier.

According to yet another aspect of the invention, there is provided a kit for diagnosing a liver disorder such as but not limited to Non-alcoholic fatty liver disease (NAFLD), Non-alcoholic steatohepatitis (NASH), cirrhosis, hepatitis, a liver adenoma, insulin hypersensitivity, a liver cancer or any combination thereof. The kit comprises at least one reagent capable of detecting the expression of a nucleic acid in a biological sample such as a blood sample, a tissue sample, and/or a biological fluid.

According to some embodiments, the reagent comprises NLGn4 specific primers. According to some embodiments, the NLGn4 specific primers are selected from the group set forth in table 1 below.

TABLE 1

NLGn4 specific primers

| Exon | Forward | Reverse |
|---|---|---|
| 2.1 | AAAGCCCTATCTCTC TGCAGG (SEQ ID NO: 5) | TGAGTAGTATTTCGG ATGCCAG (SEQ ID NO: 6) |
| 2.2 | AAGAACACCGTTACC CAATGAG (SEQ ID NO: 7) | GAGACATTATAAAC CCTCCTAG (SEQ ID NO: 8) |
| 3 | TTAGCATTGGTGAGT CAGTGTG (SEQ ID NO: 9) | CCGTCAAAACGAGAA GTGGACT (SEQ ID NO: 10) |
| 4 | CTTTTTCTATTTGGC CACCA (SEQ ID NO: 11) | TTCTTGGTTCAGGGT ATTTGC (SEQ ID NO: 12) |
| 5.1 | AGCTGCATTTCTGTC CTGTG (SEQ ID NO: 13) | TCTCCCGCAAAGTGT CTTTC (SEQ ID NO: 14) |
| 5.2 | CCAACTTCGTGGACA ACCTT (SEQ ID NO: 15) | ACCCCAACACGAAGA TGAAC (SEQ ID NO: 16) |
| 6.1 | CACGTCACATGTGGA AGAGT (SEQ ID NO: 17) | GACGGCAATGGTGAC ACTTA (SEQ ID NO: 18) |
| 6.2 | TCCTCATTGAAACCA AACGA (SEQ ID NO: 19) | AACATTCCTGGTCTG GAGAC (SEQ ID NO: 20) |

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1: Methods Used for Evaluating the Role of NLGn4 in NK Activity a) Knockdown of NLGn4: Lentivirus expressing NLGn4 siRNA were used to infect NK cells of either mouse or human origin and thereby inhibiting NLGn4 expression.

b) NLGn4 expression: NLGn4 expression level was evaluated by real-time PCR. In short, RNA was extracted from the cells using Tri Reagent. The extracted RNA was converted to cDNA using random hexamers and reverse transcriptase. NLGn4 expression level was assessed by real time PCR using NLGn4 specific primers. The results were normalized to the expression levels of α-actin using α-actin specific primers.

c) Isolation of NK cells from human blood samples: Blood samples obtained from patients were centrifuged at 4000 rpm for 5 min. After centrifugation, the buffy coat fraction of the blood containing most of the leukocytes was collected and NK cells were isolated using the RosetteSep NK isolation kit according to manufactures instruction.

d) Flow cytometry using FACS analysis of CD107a, NLGn4, α-SMA, annexin.

Example 2: NLGn4 is Overexpressed in Patients with Cirrhosis and in a Non-alcoholic Fatty Liver Disease (NAFLD) Mouse Model Human peripheral blood cells (PBLs) were isolated in accordance with Example 1c from cirrhotic patients and healthy controls, as well as from NAFLD/control mice. RNA was extracted and converted into cDNA and a gene array analysis was performed using an Affymetrix expression array. The results were collated in order to identify the genes having an at least two-fold change in the expression profile. It was found that NLGn4 showed the most significant change in that an approximately 4-fold up-regulation was observed among the cirrhotic patients.

Example 3: NLGn4 Expression can be Reduced Using siRNA

Figure 2:
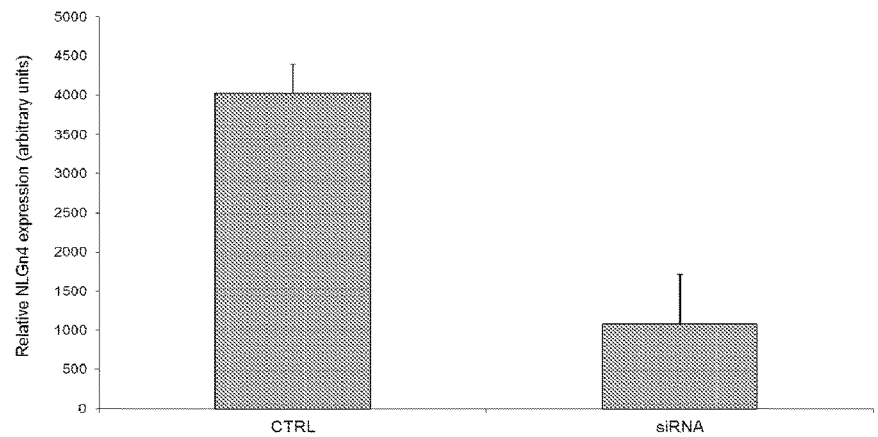
FIG. 2 shows NLGn4 expression upon NLGn4 siRNA expression in mouse NK cells.

Mouse liver NK cells were infected with a lentiviral vector expressing an siRNA against NLGn4 or a scrambled control. 48 hours post infection, the cells were harvested, RNA extracted and converted into cDNA in accordance with example 1b. NLGn4 Expression levels in cells infected with the NLGn4 siRNA or the scrambled control were evaluated using real-time PCR using primes specific for NLGn4. The expression levels obtained were normalized to those obtained for α-actin. As seen in FIG. 2, a significant reduction in NLGn4 expression is observed in cells infected with the siRNA expressing vector, as compared to the control.

Figure 3A:
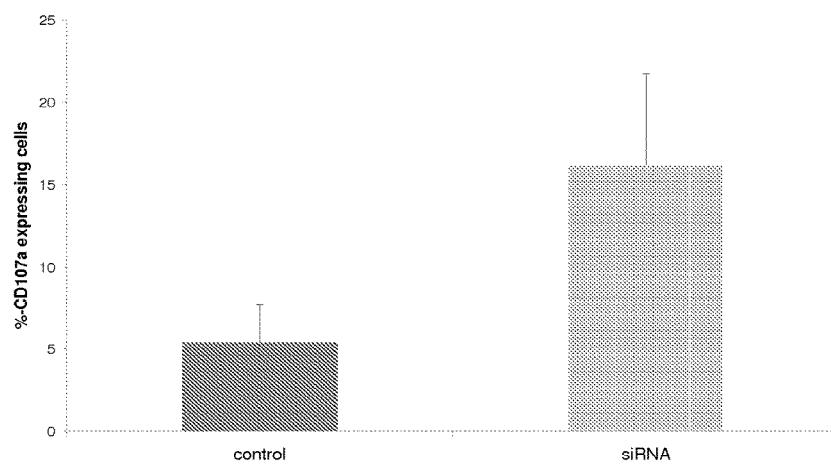
FIG. 3A presents the percentage of viable NK cells expressing CD107a (control or infected with NLGn4 siRNA) co-cultured with HSCs isolated from a WT mouse.

Example 4: NLGn4 Knockdown (KD) Increases NK Activation and Hepatic Stellate Cell (HSC) Apoptosis and Reduces HSC Activity NK cells obtained from mice livers were pre-incubated with IL2 in order to obtain a mature NK cell population. Following infection with the NLGn4 siRNA or with the scrambled control, the cells were co-cultured with freshly isolated HSC from a NAFLD mouse model. The activity of the NK cells was evaluated by the expression of CD107a, a marker of active NK cells. The percentage of viable NK cells expressing CD107a was evaluated by FACS using an anti-CD107a antibody and gating annexin negative cells. As seen in FIG. 3A, as a result of the KD of NLGn4 a significant increase in CD107a positive cells amongst the viable NK cell population was observed.

Figure 3B:
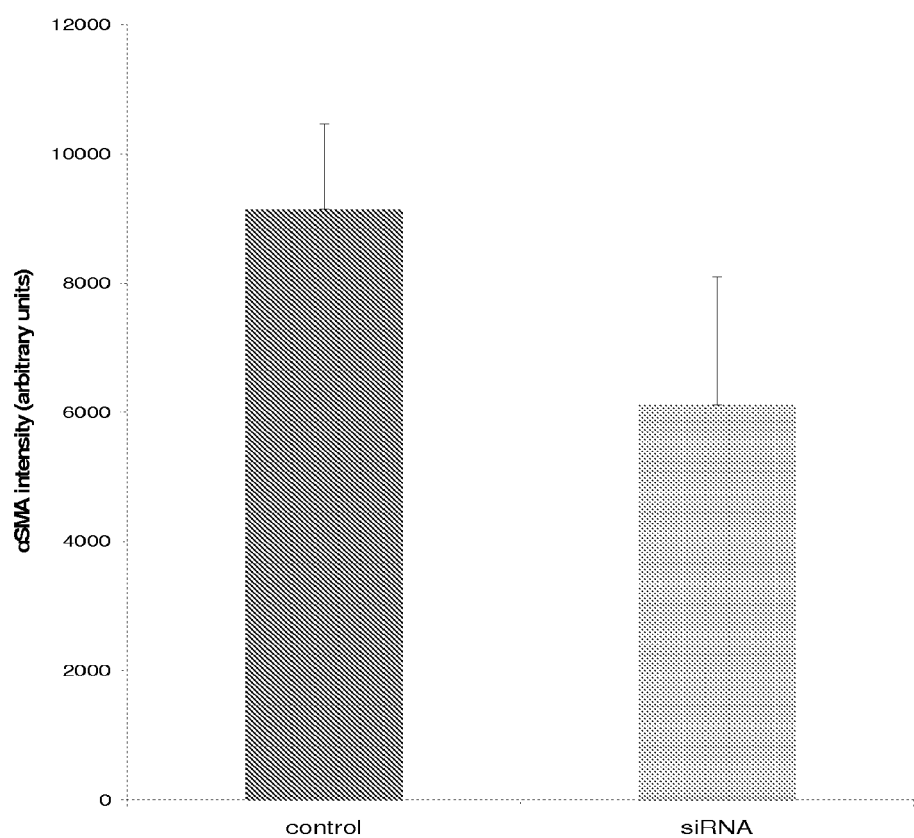
FIG. 3B presents αSMA intensity of HSCs co-cultured with control or NLGn4 siRNA infected NK cells.
Figure 3C:
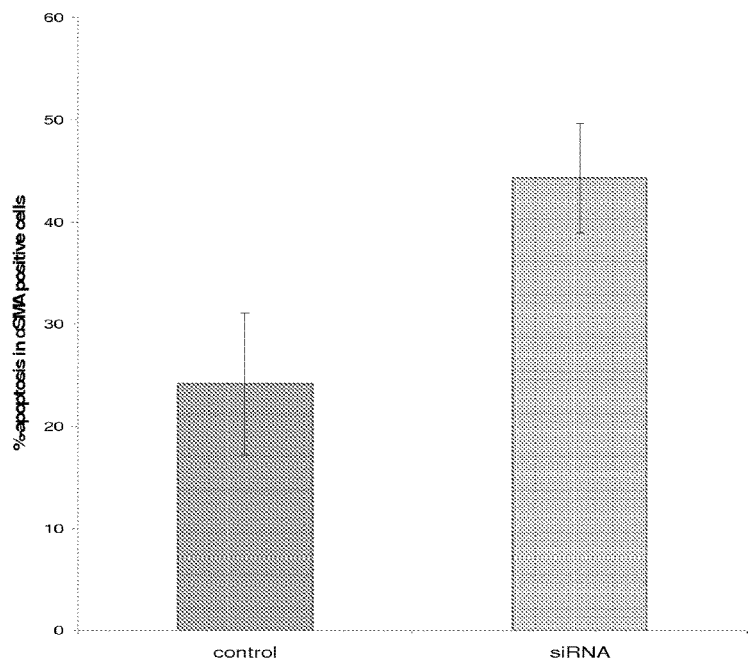
FIG. 3C shows apoptosis of HCS upon co-culturing with control or NLGn4 siRNA infected NK cells.

The impact of NK cell activation by NLGn4 KD on HCSs was evaluated by co-culturing the HSCs with the control or the NLGn4 KD NK cells and assessing αSMA intensity (marker of HSC activation). α-SMA intensity was significantly decreased upon co-culture with NLGn4 KD NK cells (FIG. 3B) and amongst the α-SMA expressing cells an increase in apoptosis was observed (FIG. 3C).

Figure 4:
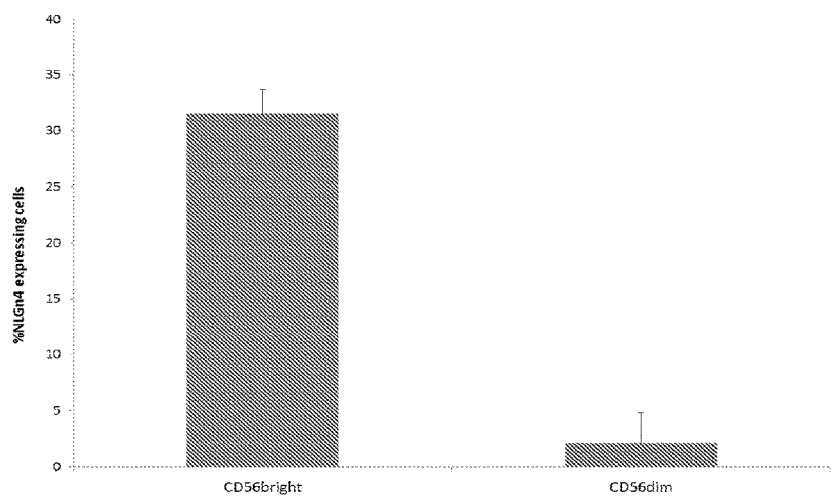
FIG. 4 presents NLGn4 expression in the $CD56^{bright}$ and $CD56^{dim}$ NK subpopulation.

Example 5: NLGn4 is Expression is High in the CD56$^{bright}$ NK Subpopulation and Low in the CD56$^{dim}$ NK Subpopulation Human peripheral blood cells (PBLs) were isolated in accordance with Example 1c. The isolated NK cells were then co-stained with an anti-CD56 antibody and with an anti-NLGn4 antibody. FACS analysis of the cells showed that NLGn4 is significantly more abundant in the CD56$^{bright}$ cell population as compared to the CD56$^{dim}$ cell population (FIG. 4).

Figure 5:
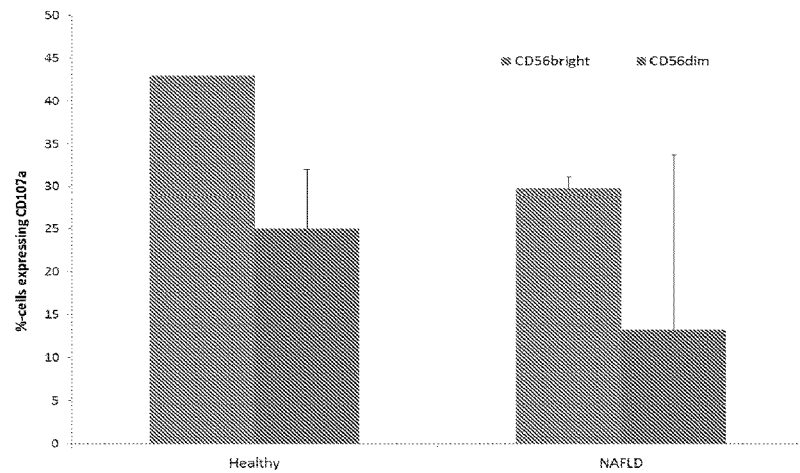
FIG. 5 presents CD107a expression in NAFLD patients and healthy controls.

Example 6: NK Activity as Assessed by CD107a Expression is Attenuated in NAFLD Patients Human peripheral blood cells (PBLs) from NAFLD patients (n=9) and healthy controls (n=3) were isolated in accordance with Example 1c. The isolated NK cells were then co-stained with an anti-CD56 antibody and with an anti-CD107a antibody. FACS analysis showed that CD107a expression was reduced, corresponding to an attenuated NK activity in NAFLD patients (FIG. 5).

Figure 6:
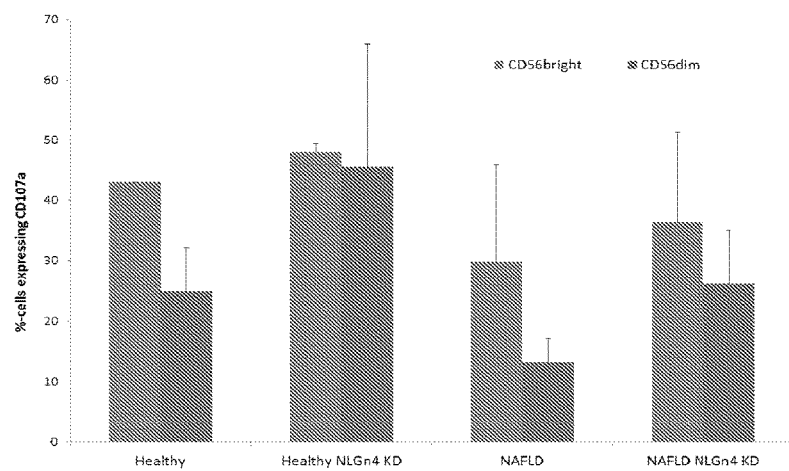
FIG. 6 presents on NK cell activity as assessed by CD107a expression.

Example 7: NLGn4 KD Increases CD56$^{dim}$ NK Cell Activity as Assessed by CD107a Expression Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. NK activity in response to NLGn4 KD was assessed by CD107a expression. That is, the isolated NK cells were co-stained with an anti-CD56 antibody and with an anti-CD107a antibody. As seen from FIG. 6, CD107a expression was significantly elevated in the CD56$^{dim}$ subpopulation. This might suggest that reducing the expression of NLGn4 can effectively enhance NK cytotoxicity. Since NLGn4 is primarily expressed in CD56$^{bright}$ cells it may be suggested that overexpression of NLGn4 by CD56$^{bright}$ cells inhibits the cytotoxicity of CD56$^{dim}$ cells.

Example 8: NLGn4 KD does not Alter NK Viability

Figure 7A:
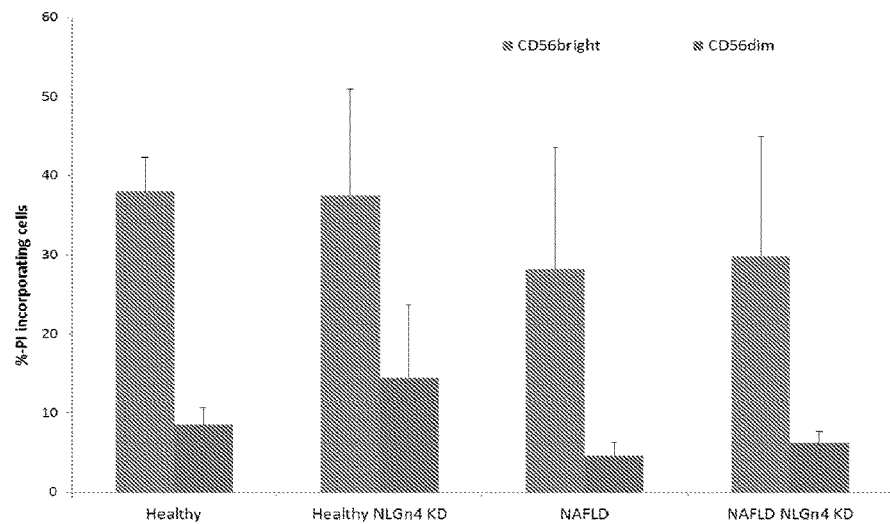
FIG. 7A presents the effects of NLGn4 KD on NK cell viability, as estimated by PI incorporation.
Figure 7B:
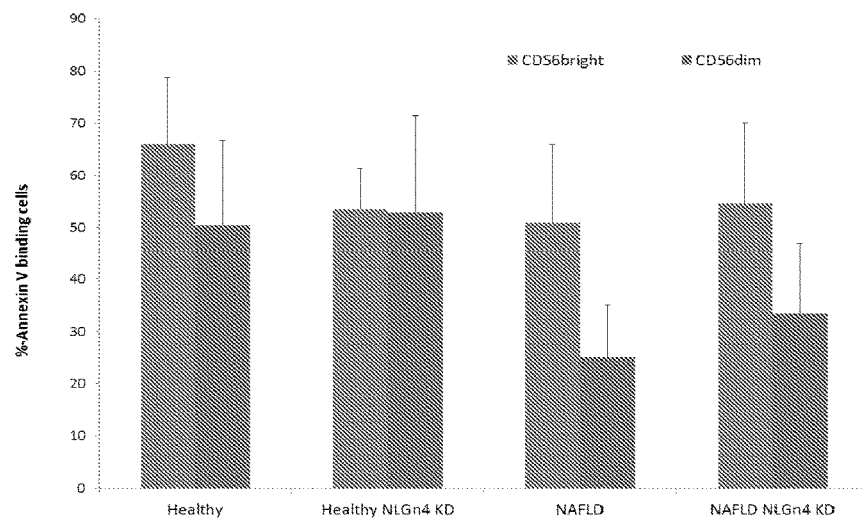
FIG. 7B presents the effects of NLGn4 KD on NK cell viability, as estimated by annexin binding.

Human peripheral blood cells (PBLs) from NAFLD patients (n=9) and healthy controls (n=3) were isolated in accordance with Example 1c. The isolated NK cells were then infected with a lentiviral vector expressing an siRNA against human NLGn4 or a scrambled control. The viability of the NK cells was assessed by FACS analysis estimating annexin binding and PI incorporation. As seen in FIGS. 7A and B, NLGn4 knockdown did not alter cellular viability neither of CD56$^{bright}$ nor of CD56$^{dim}$ NK cells in either NAFLD patients or healthy controls. This indicates that CD56$^{dim}$ cytotoxicity toward foreign cells is elevated without compromising self-recognition.

Example 9: NLGn4 Overexpression Correlates with High Insulin Levels

Figure 8:
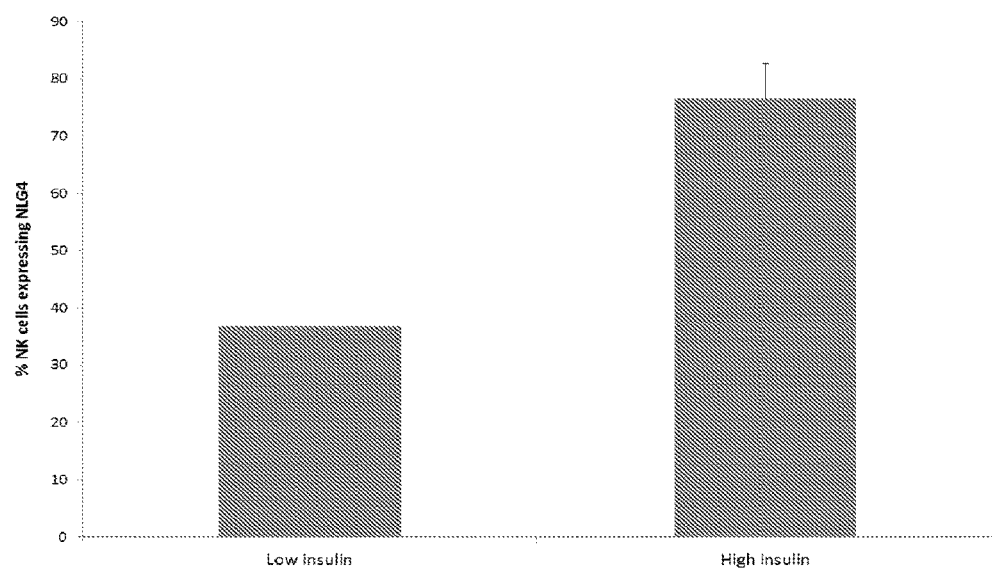
FIG. 8 shows the correlation between insulin and NLGn4 expression.

Human peripheral blood cells (PBLs) from patients with low insulin levels (n=3) and patients with high insulin levels controls (n=3) were isolated in accordance with Example 1c. The isolated NK cells were stained with an anti-NLGn4 antibody. FACS analysis of the cells showed that NLGn4 was significantly higher in NK cells from patients with high insulin levels as compared to those with low insulin levels (FIG. 8). This may suggest that the increased prevalence of NAFLD among insulin resistant subjects may be due to insulin mediated NLGn4 overexpression.

Example 10: Treatment of Mice with a GLUT4 Agonist Elevates NLGn4 Expression NK cells from livers of mice treated with the GLUT4 agonist alanine or control mice are isolated. The isolated NK cells are then co-stained with an anti-CD56 antibody and with an anti-NLGn4 antibody.

Example 11: Treatment of Mice with a GLUT4 Antagonist Reduces NLGn4 Expression NK cells from livers of mice treated with the GLUT4 agonist or control mice are isolated. The isolated NK cells are then co-stained with an anti-CD56 antibody and with an anti-NLGn4 antibody.

---

I claim:

1. A kit comprising (a) means for isolating an immune cell population from a biological sample of a patient; and (b) at least one agent capable of detecting NLGn4 gene product expression level.

2. The kit of claim 1, wherein the immune cell population is a natural killer (NK) cell population.

3. The kit of claim 1, wherein the immune cell population is a subpopulation of NK cells.

4. The kit of claim 3, wherein the NK subpopulation is the $CD56^{dim}$ subpopulation.

5. The kit of claim 3, wherein the NK subpopulation is the $CD56^{bright}$ subpopulation.

6. The kit of claim 1, further comprising at least one agent capable of detecting CD107a.

7. The kit of claim 6, wherein the agent capable of detecting CD107a is an anti-CD107a antibody or an antigen-binding fragment thereof.

8. The kit of claim 1, further comprising at least one agent capable of detecting CD56.

9. The kit of claim 8, wherein the agent capable of detecting CD56 is an anti-CD56 antibody or an antigen-binding fragment thereof.

10. The kit of claim 1, wherein the biological sample is a blood sample, a tissue sample, a biological fluid, or any combination thereof.

11. The kit of claim 10, wherein the biological sample is a blood sample.

12. The kit of claim 1, wherein the at least one agent capable of detecting NLGn4 gene product expression level comprises at least one reagent capable of detecting the expression of a nucleic acid in the biological sample.

13. The kit of claim 1, wherein the at least one agent capable of detecting NLGn4 gene product expression level comprises at least one NLGn4 specific primer or NLGn4 specific probe.

14. The kit of claim 13, wherein the at least one NLGn4 specific primer or NLGn4 specific probe comprises a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20.

15. The kit of claim 1, wherein the NLGn4 gene product is encoded by a nucleic acid sequence comprising SEQ ID NO: 1.

16. The kit of claim 1, wherein the NLGn4 gene product comprises SEQ ID NO: 2.

* * * * *